US011390898B2

(12) United States Patent
Westh et al.

(10) Patent No.: US 11,390,898 B2
(45) Date of Patent: Jul. 19, 2022

(54) POLYPEPTIDES HAVING CELLOBIOHYDROLASE ACTIVITY AND POLYNUCLEOTIDES ENCODING SAME

(71) Applicant: Novozymes A/S, Bagsvaerd (DK)

(72) Inventors: Peter Westh, Copenhagen (DK); Kim Borch, Birkerød (DK); Trine Soerensen, Copenhagen (DK); Michael Windahl, Stenløse (DK); Brett McBrayer, Sacramento, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/508,631

(22) PCT Filed: Sep. 4, 2015

(86) PCT No.: PCT/US2015/048620

§ 371 (c)(1),
(2) Date: Mar. 3, 2017

(87) PCT Pub. No.: WO2016/037096

PCT Pub. Date: Mar. 10, 2016

(65) Prior Publication Data

US 2017/0283843 A1 Oct. 5, 2017

Related U.S. Application Data

(60) Provisional application No. 62/046,344, filed on Sep. 5, 2014.

(51) Int. Cl.

| | |
|---|---|
| ***C12P 19/14*** | (2006.01) |
| ***C12N 9/42*** | (2006.01) |
| ***C12P 7/14*** | (2006.01) |
| ***C12N 15/82*** | (2006.01) |
| ***C12P 5/02*** | (2006.01) |
| ***C12P 7/16*** | (2006.01) |
| ***C12P 7/18*** | (2006.01) |
| ***C12P 7/20*** | (2006.01) |
| ***C12P 19/02*** | (2006.01) |

(52) U.S. Cl.

CPC ............ *C12P 19/14* (2013.01); *C12N 9/2437* (2013.01); *C12N 15/8257* (2013.01); *C12P 5/02* (2013.01); *C12P 7/14* (2013.01); *C12P 7/16* (2013.01); *C12P 7/18* (2013.01); *C12P 7/20* (2013.01); *C12P 19/02* (2013.01); *C12Y 302/01091* (2013.01); *C07K 2319/00* (2013.01); *C12P 2203/00* (2013.01)

(58) Field of Classification Search

CPC .... C12P 19/14; C12P 7/18; C12P 5/02; C12P 7/14; C12P 7/16; C12P 19/02; C12P 7/20; C12P 2203/00; C12N 15/8257; C12N 9/2437; C12Y 302/01091; C07K 2319/00

See application file for complete search history.

(56) References Cited

U.S. PATENT DOCUMENTS

| | | | |
|---|---|---|---|
| 7,375,197 B2 | 5/2008 | Adney et al. | |
| 7,785,853 B2 * | 8/2010 | Lange ................ | C11D 3/38645 424/461 |
| 8,637,293 B2 | 1/2014 | Adney et al. | |
| 2006/0246566 A1 | 11/2006 | Vehmaanpera et al. | |
| 2010/0306879 A1 | 12/2010 | Liu et al. | |
| 2012/0096597 A1 | 4/2012 | Schnorr et al. | |
| 2013/0040346 A1 | 2/2013 | Wogulis | |
| 2014/0065671 A1 | 3/2014 | Stringer et al. | |
| 2014/0106408 A1 | 4/2014 | Mitchinson et al. | |
| 2014/0134677 A1 | 5/2014 | Mitchinson et al. | |
| 2015/0004655 A1 | 1/2015 | Wogulis | |

FOREIGN PATENT DOCUMENTS

| | | |
|---|---|---|
| WO | 2004016760 A2 | 2/2004 |
| WO | 2005001065 A2 | 1/2005 |
| WO | 2005028636 A2 | 3/2005 |
| WO | 2005030926 A2 | 4/2005 |
| WO | 2006117432 A1 | 11/2006 |
| WO | 2007118935 A1 | 10/2007 |
| WO | 2010060056 A2 | 5/2010 |
| WO | 2010096931 A1 | 9/2010 |
| WO | 2011050037 A1 | 4/2011 |
| WO | 2011097713 A1 | 8/2011 |
| WO | 2011098551 A2 | 8/2011 |
| WO | 2011117728 A2 | 9/2011 |
| WO | 2012048171 A2 | 4/2012 |
| WO | 2012051055 A2 | 4/2012 |
| WO | 2012078656 A1 | 6/2012 |
| WO | 2012104239 A2 | 9/2012 |
| WO | 2012135719 A1 | 10/2012 |
| WO | 2013029176 A1 | 3/2013 |
| WO | 2013052831 A1 | 4/2013 |
| WO | 2013091577 A1 | 6/2013 |
| WO | 2013138357 A1 | 9/2013 |

(Continued)

OTHER PUBLICATIONS

Long et al., Gen Bank accession No. AFD50192, Mar. 19, 2012.*
Witkowski et al., Biochemistry 38:11643-11650, 1999.*
Branden et al., Introduction to Protein Structure, Garland Publishing Inc., New York, p. 247, 1991.*
Tang et al., Phil Trans R Soc B 368:20120318, 1-10, 2013.*
Sadowski et al., Current Opinion in Structural Biology 19:357-362, 2009.*
Seffernick et al., J. Bacteriol. 183(8):2405-2410, 2001.*
Birren et al., GenBank accession No. Q0CMT2, Apr. 2013.*

(Continued)

*Primary Examiner* — Delia M Ramirez
(74) *Attorney, Agent, or Firm* — David Fazzolare

(57) ABSTRACT

The present invention relates to cellobiohydrolase variants and carbohydrate binding module variants. The present invention also relates to polynucleotides encoding the variants; nucleic acid constructs, vectors, and host cells comprising the polynucleotides; and methods of using the variants.

14 Claims, 7 Drawing Sheets

Specification includes a Sequence Listing.

(56) References Cited

FOREIGN PATENT DOCUMENTS

| | | | |
|---|---|---|---|
| WO | 2014064115 | A1 | 5/2014 |
| WO | 2014093282 | A1 | 6/2014 |
| WO | 2014093294 | A1 | 6/2014 |
| WO | 2014138672 | A1 | 9/2014 |

OTHER PUBLICATIONS

Takashima et al., GenBank accession No. Q12621, Nov. 1996.*
Kohler et al., GenBank accession No. KIK57628, Jan. 2015.*
Nierman et al., Gen Bank accession No. XP_751044, Feb. 26, 2008.*
Fedorova et al., Gen Bank accession No. A1DNL0, Nov. 28, 2012.*
Guo et al., PNAS 101(25):9205-9210, 2004.*
Long et al, 2012—Uniport Access No. H9C5T0.
Le Costaoueca, 2013, Bioresource Technology, 143, 196-203.
Linder, 1995, Protein Science 4, 1056-1064.
Linder, 1999, FEBS Let 447, 13-16.
Nimols, 2007, Prot Engg Design Selection, 20(4), 179-187.
Pakarinen, 2014, Biotechnol Biofuels 7(27), 1-11.
Takashima, 2007, FEBS Lett 581, 5891-5896.
Varnai, 2013, Biotechnology for Biofuels 6(30), 1-11.
Voutilainen, 2013, Appl Microbiol Biotechnol, 98, 2991-3001.
Le Costaouëc et al. 2013, Bioresource Technology 143, 196-203.
Strobel et al. 2015 Journal of Biological Chemistry, vol. 290, No. 37, pp. 22818-22826.
Strobel et al. 2016, Biotechnol. and Bioengineering, vol. 113, No. 6, 1369-1374.
Devos et al, 2000, Proteins Struc, Func, Genet 41, 98-107.
Tian Et, 2003, J. Mol. Biol. 333, 863-882.
Addou et al, 2009, J. Mol. Biol. 387, 416-430.

* cited by examiner

```
      M  Y  R  K  L  A  V  I  S  A  F  L  A  T  A  R  A  Q  S  A  C  T  L  Q  S  E  T ·
   1  ATGTATCGGAAGTTGGCCGTCATCTCGGCCTTCTTGGCCACAGCTCGTGCTCAGTCGGCCTGCACTCTCCAATCGGAGAC
      ·H  P  P  L  T  W  Q  K  C  S  S  G  G  T  C  T  Q  Q  T  G  S  V  V  I  D  A  N ·
  81  TCACCCGCCTCTGACATGGCAGAAATGCTCGTCTGGTGGCACGTGCACTCAACAGACAGGCTCCGTGGTCATCGACGCCA
      ·  W  R  W  T  H  A  T  N  S  S  T  N  C  Y  D  G  N  T  W  S  S  T  L  C  P  D
 161  ACTGGCGCTGGACTCACGCTACGAACAGCAGCACGAACTGCTACGATGGCAACACTTGGAGCTCGACCCTATGTCCTGAC
      N  E  T  C  A  K  N  C  C  L  D  G  A  A  Y  A  S  T  Y  G  V  T  T  S  G  N  S ·
 241  AACGAGACCTGCGCGAAGAACTGCTGTCTGGACGGTGCCGCCTACGCGTCCACGTACGGAGTTACCACGAGCGGTAACAG
      ·L  S  I  G  F  V  T  Q  S  A  Q  K  N  V  G  A  R  L  Y  L  M  A  S  D  T  T  Y ·
 321  CCTCTCCATTGGCTTTGTCACCCAGTCTGCGCAGAAGAACGTTGGCGCTCGCCTTTACCTTATGGCGAGCGACACGACCT
      ·  Q  E  F  T  L  L  G  N  E  F  S  F  D  V  D  V  S  Q  L  P  C  G  L  N  G  A
 401  ACCAGGAATTCACCCTGCTTGGCAACGAGTTCTCTTTCGATGTTGATGTTTCGCAGCTGCCGTGCGGCTTGAACGGAGCT
      L  Y  F  V  S  M  D  A  D  G  G  V  S  K  Y  P  T  N  T  A  G  A  K  Y  G  T  G ·
 481  CTCTACTTCGTGTCCATGGACGCGGATGGTGGCGTGAGCAAGTATCCCACCAACACCGCTGGCGCCAAGTACGGCACGGG
      ·Y  C  D  S  Q  C  P  R  D  L  K  F  I  N  G  Q  A  N  V  E  G  W  E  P  S  S  N ·
 561  GTACTGTGACAGCCAGTGTCCCCGCGATCTGAAGTTCATCAATGGCCAGGCCAACGTTGAGGGCTGGGAGCCGTCATCCA
      ·  N  A  N  T  G  I  G  G  H  G  S  C  C  S  E  M  D  I  W  E  A  N  S  I  S  E
 641  ACAACGCGAACACGGGCATTGGAGGACACGGAAGCTGCTGCTCTGAGATGGATATCTGGGAGGCCAACTCCATCTCCGAG
      A  L  T  P  H  P  C  T  T  V  G  Q  E  I  C  E  G  D  G  C  G  G  T  Y  S  D  N ·
 721  GCTCTTACCCCCCACCCTTGCACGACTGTCGGCCAGGAGATCTGCGAGGGTGATGGGTGCGGCGGAACTTACTCCGATAA
      ·R  Y  G  G  T  C  D  P  D  G  C  D  W  N  P  Y  R  L  G  N  T  S  F  Y  G  P  G ·
 801  CAGATATGGCGGCACTTGCGATCCCGATGGCTGCGACTGGAACCCATACCGCCTGGGCAACACCAGCTTCTACGGCCCTG
      ·  S  S  F  T  L  D  T  T  K  K  L  T  V  V  T  Q  F  E  T  S  G  A  I  N  R  Y
 881  GCTCAAGCTTTACCCTCGATACCACCAAGAAATTGACCGTTGTCACCCAGTTCGAGACGTCGGGTGCCATCAACCGATAC
      Y  V  Q  N  G  V  T  F  Q  Q  P  N  A  E  L  G  S  Y  S  G  N  E  L  N  D  D  Y ·
 961  TATGTCCAGAATGGCGTCACTTTCCAGCAGCCCAACGCCGAGCTTGGTAGTTACTCTGGCAACGAGCTCAACGATGATTA
      ·C  T  A  E  E  A  E  F  G  G  S  S  F  S  D  K  G  G  L  T  Q  F  K  K  A  T  S ·
1041  CTGCACAGCTGAGGAGGCAGAATTCGGCGGATCCTCTTTCTCAGACAAGGGCGGCCTGACTCAGTTCAAGAAGGCTACCT
      ·  G  G  M  V  L  V  M  S  L  W  D  D  Y  Y  A  N  M  L  W  L  D  S  T  Y  P  T
1121  CTGGCGGCATGGTTCTGGTCATGAGTCTGTGGGATGATTACTACGCCAACATGCTGTGGCTGGACTCCACCTACCCGACA
      N  E  T  S  S  T  P  G  A  V  R  G  S  C  S  T  S  S  G  V  P  A  Q  V  E  S  Q ·
1201  AACGAGACCTCCTCCACACCCGGTGCCGTGCGCGGAAGCTGCTCCACCAGCTCCGGTGTCCCTGCTCAGGTCGAATCTCA
      ·S  P  N  A  K  V  T  F  S  N  I  K  F  G  P  I  G  S  T  G  N  P  S  G  G  N  P ·
1281  GTCTCCCAACGCCAAGGTCACCTTCTCCAACATCAAGTTCGGACCCATTGGCAGCACCGGCAACCCTAGCGGCGGCAACC
      ·  P  G  G  N  P  P  G  T  T  T  T  R  R  P  A  T  T  T  G  S  S  P  G  P  T  Q
1361  CTCCCGGCGGAAACCCGCCTGGCACCACCACCACCCGCCGCCCAGCCACTACCACTGGAAGCTCTCCCGGACCTACCCAG
      S  H  Y  G  Q  C  G  G  I  G  Y  S  G  P  T  V  C  A  S  G  T  T  C  Q  V  L  N ·
1441  TCTCACTACGGCCAGTGCGGCGGTATTGGCTACAGCGGCCCCACGGTCTGCGCCAGCGGCACAACTTGCCAGGTCCTGAA
      ·P  Y  Y  S  Q  C  L  ·
1521  CCCTTACTACTCTCAGTGCCTGTAA
```

Fig. 1

SEQUENCE LISTING

<160> NUMBER OF SEQ ID NOS: 100

<210> SEQ ID NO 1
<211> LENGTH: 1893
<212> TYPE: DNA
<213> ORGANISM: Trichoderma reesei

<400> SEQUENCE: 1

```
caactcagat cctccaggag acttgtacac catcttttga ggcacagaaa cccaatagtc      60
aaccgcggac tgcgcatcat gtatcggaag ttggccgtca tctcggcctt cttggccaca     120
gctcgtgctc agtcggcctg cactctccaa tcggagactc acccgcctct gacatggcag     180
aaatgctcgt ctggtggcac gtgcactcaa cagacaggct ccgtggtcat cgacgccaac     240
tggcgctgga ctcacgctac gaacagcagc acgaactgct acgatggcaa cacttggagc     300
tcgaccctat gtcctgacaa cgagacctgc gcgaagaact gctgtctgga cggtgccgcc     360
tacgcgtcca cgtacggagt taccacgagc ggtaacagcc tctccattgg ctttgtcacc     420
cagtctgcgc agaagaacgt tggcgctcgc ctttacctta tggcgagcga cacgacctac     480
caggaattca ccctgcttgg caacgagttc tctttcgatg ttgatgtttc gcagctgccg     540
tgcggcttga acggagctct ctacttcgtg tccatggacg cggatggtgg cgtgagcaag     600
tatcccacca acaccgctgg cgccaagtac ggcacggggt actgtgacag ccagtgtccc     660
cgcgatctga agttcatcaa tggccaggcc aacgttgagg gctgggagcc gtcatccaac     720
aacgcgaaca cgggcattgg aggacacgga agctgctgct ctgagatgga tatctgggag     780
gccaactcca tctccgaggc tcttaccccc cacccttgca cgactgtcgg ccaggagatc     840
tgcgagggtg atgggtgcgg cggaacttac tccgataaca gatatggcgg cacttgcgat     900
cccgatggct gcgactggaa cccataccgc ctgggcaaca ccagcttcta cggccctggc     960
tcaagcttta ccctcgatac caccaagaaa ttgaccgttg tcacccagtt cgagacgtcg    1020
ggtgccatca accgatacta tgtccagaat ggcgtcactt tccagcagcc caacgccgag    1080
cttggtagtt actctggcaa cgagctcaac gatgattact gcacagctga ggaggcagaa    1140
ttcggcggat cctctttctc agacaagggc ggcctgactc agttcaagaa ggctacctct    1200
ggcggcatgg ttctggtcat gagtctgtgg gatgattact acgccaacat gctgtggctg    1260
gactccacct acccgacaaa cgagacctcc tccacacccg gtgccgtgcg cggaagctgc    1320
tccaccagct ccggtgtccc tgctcaggtc gaatctcagt ctcccaacgc caaggtcacc    1380
ttctccaaca tcaagttcgg acccattggc agcaccggca accctagcgg cggcaaccct    1440
cccggcggaa acccgcctgg caccaccacc acccgccgcc cagccactac cactggaagc    1500
tctcccggac ctacccagtc tcactacggc cagtgcggcg gtattggcta cagcggcccc    1560
acggtctgcg ccagcggcac aacttgccag gtcctgaacc cttactactc tcagtgcctg    1620
taaagctccg tggcgaaagc ctgacgcacc ggtagattct tggtgagccc gtatcatgac    1680
ggcggcggga gctacatggc cccgggtgat ttattttttt tgtatctact tctgaccctt    1740
ttcaaatata cggtcaactc atctttcact ggagatgcgg cctgcttggt attgcgatgt    1800
tgtcagcttg gcaaattgtg gctttcgaaa acacaaaacg attccttagt agccatgcat    1860
tttaagataa cggaatagaa gaaagaggaa att                                 1893
```

<210> SEQ ID NO 2
<211> LENGTH: 514
<212> TYPE: PRT
<213> ORGANISM: Trichoderma reesei

<400> SEQUENCE: 2

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
```

```
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu


<210> SEQ ID NO 3
<211> LENGTH: 108
<212> TYPE: DNA
<213> ORGANISM: Trichoderma reesei

<400> SEQUENCE: 3

acccagtctc actacggcca gtgcggcggt attggctaca gcggccccac ggtctgcgcc      60

agcggcacaa cttgccaggt cctgaaccct tactactctc agtgcctg                  108


<210> SEQ ID NO 4
<211> LENGTH: 36
<212> TYPE: PRT
<213> ORGANISM: Trichoderma reesei

<400> SEQUENCE: 4

Thr Gln Ser His Tyr Gly Gln Cys Gly Gly Ile Gly Tyr Ser Gly Pro
1               5                   10                  15

Thr Val Cys Ala Ser Gly Thr Thr Cys Gln Val Leu Asn Pro Tyr Tyr
            20                  25                  30

Ser Gln Cys Leu
        35


<210> SEQ ID NO 5
<211> LENGTH: 1638
<212> TYPE: DNA
<213> ORGANISM: Humicola insolens

<400> SEQUENCE: 5

atgcgtaccg ccaagttcgc caccctcgcc gcccttgtgg cctcggccgc cgcccagcag      60

gcgtgcagtc tcaccaccga gaggcaccct tccctctctt ggaacaagtg caccgccggc     120

ggccagtgcc agaccgtcca ggcttccatc actctcgact ccaactggcg ctggactcac     180

caggtgtctg gctccaccaa ctgctacacg ggcaacaagt gggatactag catctgcact     240

gatgccaagt cgtgcgctca gaactgctgc gtcgatggtg ccgactacac cagcacctat     300

ggcatcacca ccaacggtga ttccctgagc ctcaagttcg tcaccaaggg ccagcactcg     360

accaacgtcg gctcgcgtac ctacctgatg gacggcgagg acaagtatca gagtacgttc     420

tatcttcagc cttctcgcgc cttgaatcct ggctaacgtt tacacttcac agccttcgag     480

ctcctcggca acgagttcac cttcgatgtc gatgtctcca acatcggctg cggtctcaac     540

ggcgccctgt acttcgtctc catggacgcc gatggtggtc tcagccgcta tcctggcaac     600
```

```
aaggctggtg ccaagtacgg taccggctac tgcgatgctc agtgcccccg tgacatcaag    660

ttcatcaacg gcgaggccaa cattgagggc tggaccggct ccaccaacga ccccaacgcc    720

ggcgcgggcc gctatggtac ctgctgctct gagatggata tctgggaagc caacaacatg    780

gctactgcct tcactcctca cccttgcacc atcattggcc agagccgctg cgagggcgac    840

tcgtgcggtg gcacctacag caacgagcgc tacgccggcg tctgcgaccc cgatggctgc    900

gacttcaact cgtaccgcca gggcaacaag accttctacg gcaagggcat gaccgtcgac    960

accaccaaga agatcactgt cgtcacccag ttcctcaagg atgccaacgg cgatctcggc   1020

gagatcaagc gcttctacgt ccaggatggc aagatcatcc ccaactccga gtccaccatc   1080

cccggcgtcg agggcaattc catcacccag gactggtgcg accgccagaa ggttgccttt   1140

ggcgacattg acgacttcaa ccgcaagggc ggcatgaagc agatgggcaa ggccctcgcc   1200

ggccccatgg tcctggtcat gtccatctgg gatgaccacg cctccaacat gctctggctc   1260

gactcgacct tccctgtcga tgccgctggc aagcccggcg ccgagcgcgg tgcctgcccg   1320

accacctcgg gtgtccctgc tgaggttgag gccgaggccc ccaacagcaa cgtcgtcttc   1380

tccaacatcc gcttcggccc catcggctcg accgttgctg gtctccccgg cgcgggcaac   1440

ggcggcaaca acggcggcaa ccccccgccc cccaccacca ccacctcctc ggctccggcc   1500

accaccacca ccgccagcgc tggccccaag gctggccgct ggcagcagtg cggcggcatc   1560

ggcttcactg gcccgaccca gtgcgaggag ccctacattt gcaccaagct caacgactgg   1620

tactctcagt gcctgtaa                                                 1638
```

<210> SEQ ID NO 6
<211> LENGTH: 525
<212> TYPE: PRT
<213> ORGANISM: Humicola insolens

<400> SEQUENCE: 6

```
Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
                165                 170                 175

Tyr Pro Gly Asn Lys Ala Gly Ala Lys Tyr Gly Thr Gly Tyr Cys Asp
            180                 185                 190
```

```
Ala Gln Cys Pro Arg Asp Ile Lys Phe Ile Asn Gly Glu Ala Asn Ile
        195                 200                 205

Glu Gly Trp Thr Gly Ser Thr Asn Asp Pro Asn Ala Gly Ala Gly Arg
    210                 215                 220

Tyr Gly Thr Cys Cys Ser Glu Met Asp Ile Trp Glu Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asp Ser Cys Gly Gly Thr Tyr Ser Asn Glu Arg Tyr Ala
            260                 265                 270

Gly Val Cys Asp Pro Asp Gly Cys Asp Phe Asn Ser Tyr Arg Gln Gly
        275                 280                 285

Asn Lys Thr Phe Tyr Gly Lys Gly Met Thr Val Asp Thr Thr Lys Lys
    290                 295                 300

Ile Thr Val Val Thr Gln Phe Leu Lys Asp Ala Asn Gly Asp Leu Gly
305                 310                 315                 320

Glu Ile Lys Arg Phe Tyr Val Gln Asp Gly Lys Ile Ile Pro Asn Ser
                325                 330                 335

Glu Ser Thr Ile Pro Gly Val Glu Gly Asn Ser Ile Thr Gln Asp Trp
            340                 345                 350

Cys Asp Arg Gln Lys Val Ala Phe Gly Asp Ile Asp Asp Phe Asn Arg
        355                 360                 365

Lys Gly Gly Met Lys Gln Met Gly Lys Ala Leu Ala Gly Pro Met Val
    370                 375                 380

Leu Val Met Ser Ile Trp Asp Asp His Ala Ser Asn Met Leu Trp Leu
385                 390                 395                 400

Asp Ser Thr Phe Pro Val Asp Ala Ala Gly Lys Pro Gly Ala Glu Arg
                405                 410                 415

Gly Ala Cys Pro Thr Thr Ser Gly Val Pro Ala Glu Val Glu Ala Glu
            420                 425                 430

Ala Pro Asn Ser Asn Val Val Phe Ser Asn Ile Arg Phe Gly Pro Ile
        435                 440                 445

Gly Ser Thr Val Ala Gly Leu Pro Gly Ala Gly Asn Gly Gly Asn Asn
    450                 455                 460

Gly Gly Asn Pro Pro Pro Pro Thr Thr Thr Thr Ser Ser Ala Pro Ala
465                 470                 475                 480

Thr Thr Thr Thr Ala Ser Ala Gly Pro Lys Ala Gly Arg Trp Gln Gln
                485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
        515                 520                 525
```

<210> SEQ ID NO 7
<211> LENGTH: 110
<212> TYPE: DNA
<213> ORGANISM: Humicola insolens

<400> SEQUENCE: 7

```
cccaaggctg gccgctggca gcagtgcggc ggcatcggct tcactggccc gacccagtgc     60

gaggagccct acatttgcac caagctcaac gactggtact ctcagtgcct               110
```

<210> SEQ ID NO 8
<211> LENGTH: 37

<212> TYPE: PRT
<213> ORGANISM: Humicola insolens

<400> SEQUENCE: 8

Pro Lys Ala Gly Arg Trp Gln Gln Cys Gly Gly Ile Gly Phe Thr Gly
1 5 10 15

Pro Thr Gln Cys Glu Glu Pro Tyr Ile Cys Thr Lys Leu Asn Asp Trp
20 25 30

Tyr Ser Gln Cys Leu
35

<210> SEQ ID NO 9
<211> LENGTH: 1593
<212> TYPE: DNA
<213> ORGANISM: Chaetomium thermophilum

<400> SEQUENCE: 9
atgatgtaca agaagttcgc cgctctcgcc gccctcgtgg ctggcgccgc cgcccagcag 60
gcttgctccc tcaccactga gacccacccc agactcactt ggaagcgctg cacctctggc 120
ggcaactgct cgaccgtgaa cggcgccgtc accatcgatg ccaactggcg ctggactcac 180
actgtttccg gctcgaccaa ctgctacacc ggcaacgagt gggatacctc catctgctct 240
gatggcaaga gctgcgccca gacctgctgc gtcgacggcg ctgactactc ttcgacctat 300
ggtatcacca ccagcggtga ctccctgaac ctcaagttcg tcaccaagca ccagcacggc 360
accaatgtcg gctctcgtgt ctacctgatg gagaacgaca ccaagtacca gatgttcgag 420
ctcctcggca acgagttcac cttcgatgtc gatgtctcta acctgggctg cggtctcaac 480
ggcgccctct acttcgtctc catggacgct gatggtggta tgagcaagta ctctggcaac 540
aaggctggcg ccaagtacgg taccggctac tgcgatgctc agtgcccgcg cgaccttaag 600
ttcatcaacg gcgaggccaa cattgagaac tggacccctt cgaccaatga tgccaacgcc 660
ggtttcggcc gctatggcag ctgctgctct gagatggata tctgggatgc caacaacatg 720
gctactgcct tcactcctca cccttgcacc attatcggcc agagccgctg cgagggcaac 780
agctgcggtg gcacctacag ctctgagcgc tatgctggtg tttgcgatcc tgatggctgc 840
gacttcaacg cctaccgcca gggcgacaag accttctacg gcaagggcat gaccgtcgac 900
accaccaaga agatgaccgt cgtcacccag ttccacaaga actcggctgg cgtcctcagc 960
gagatcaagc gcttctacgt tcaggacggc aagatcattg ccaacgccga gtccaagatc 1020
cccggcaacc ccggcaactc catcacccag gagtggtgcg atgcccagaa ggtcgccttc 1080
ggtgacatcg atgacttcaa ccgcaagggc ggtatggctc agatgagcaa ggccctcgag 1140
ggccctatgg tcctggtcat gtccgtctgg gatgaccact acgccaacat gctctggctc 1200
gactcgacct accccattga caaggccggc acccccggcg ccgagcgcgg tgcttgcccg 1260
accacctccg gtgtccctgc cgagattgag gcccaggtcc ccaacagcaa cgttatcttc 1320
tccaacatcc gcttcggccc catcggctcg accgtccctg gcctcgacgg cagcaccccc 1380
agcaacccga ccgccaccgt tgctcctccc acttctacca ccaccagcgt gagaagcagc 1440
actactcaga tttccacccc gactagccag cccggcggct gcaccaccca gaagtggggc 1500
cagtgcggtg gtatcggcta caccggctgc actaactgcg ttgctggcac tacctgcact 1560
gagctcaacc cctggtacag ccagtgcctg taa 1593

<210> SEQ ID NO 10
<211> LENGTH: 530

```
<212> TYPE: PRT
<213> ORGANISM: Chaetomium thermophilum

<400> SEQUENCE: 10

Met Met Tyr Lys Lys Phe Ala Ala Leu Ala Ala Leu Val Ala Gly Ala
1               5                   10                  15

Ala Ala Gln Gln Ala Cys Ser Leu Thr Thr Glu Thr His Pro Arg Leu
            20                  25                  30

Thr Trp Lys Arg Cys Thr Ser Gly Gly Asn Cys Ser Thr Val Asn Gly
        35                  40                  45

Ala Val Thr Ile Asp Ala Asn Trp Arg Trp Thr His Thr Val Ser Gly
    50                  55                  60

Ser Thr Asn Cys Tyr Thr Gly Asn Glu Trp Asp Thr Ser Ile Cys Ser
65                  70                  75                  80

Asp Gly Lys Ser Cys Ala Gln Thr Cys Cys Val Asp Gly Ala Asp Tyr
                85                  90                  95

Ser Ser Thr Tyr Gly Ile Thr Thr Ser Gly Asp Ser Leu Asn Leu Lys
            100                 105                 110

Phe Val Thr Lys His Gln His Gly Thr Asn Val Gly Ser Arg Val Tyr
        115                 120                 125

Leu Met Glu Asn Asp Thr Lys Tyr Gln Met Phe Glu Leu Leu Gly Asn
    130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
            180                 185                 190

Ala Gln Cys Pro Arg Asp Leu Lys Phe Ile Asn Gly Glu Ala Asn Ile
        195                 200                 205

Glu Asn Trp Thr Pro Ser Thr Asn Asp Ala Asn Ala Gly Phe Gly Arg
    210                 215                 220

Tyr Gly Ser Cys Cys Ser Glu Met Asp Ile Trp Asp Ala Asn Asn Met
225                 230                 235                 240

Ala Thr Ala Phe Thr Pro His Pro Cys Thr Ile Ile Gly Gln Ser Arg
                245                 250                 255

Cys Glu Gly Asn Ser Cys Gly Gly Thr Tyr Ser Ser Glu Arg Tyr Ala
            260                 265                 270

Gly Val Cys Asp Pro Asp Gly Cys Asp Phe Asn Ala Tyr Arg Gln Gly
        275                 280                 285

Asp Lys Thr Phe Tyr Gly Lys Gly Met Thr Val Asp Thr Thr Lys Lys
    290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
                325                 330                 335

Glu Ser Lys Ile Pro Gly Asn Pro Gly Asn Ser Ile Thr Gln Glu Trp
            340                 345                 350

Cys Asp Ala Gln Lys Val Ala Phe Gly Asp Ile Asp Asp Phe Asn Arg
        355                 360                 365

Lys Gly Gly Met Ala Gln Met Ser Lys Ala Leu Glu Gly Pro Met Val
    370                 375                 380

Leu Val Met Ser Val Trp Asp Asp His Tyr Ala Asn Met Leu Trp Leu
385                 390                 395                 400
```

```
Asp Ser Thr Tyr Pro Ile Asp Lys Ala Gly Thr Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445

Gly Ser Thr Val Pro Gly Leu Asp Gly Ser Thr Pro Ser Asn Pro Thr
    450                 455                 460

Ala Thr Val Ala Pro Pro Thr Ser Thr Thr Thr Ser Val Arg Ser Ser
465                 470                 475                 480

Thr Thr Gln Ile Ser Thr Pro Thr Ser Gln Pro Gly Gly Cys Thr Thr
                485                 490                 495

Gln Lys Trp Gly Gln Cys Gly Gly Ile Gly Tyr Thr Gly Cys Thr Asn
            500                 505                 510

Cys Val Ala Gly Thr Thr Cys Thr Glu Leu Asn Pro Trp Tyr Ser Gln
        515                 520                 525

Cys Leu
    530


<210> SEQ ID NO 11
<211> LENGTH: 117
<212> TYPE: DNA
<213> ORGANISM: Chaetomium thermophilum

<400> SEQUENCE: 11

ggcggctgca ccacccagaa gtggggccag tgcggtggta tcggctacac cggctgcact     60

aactgcgttg ctggcactac ctgcactgag ctcaacccct ggtacagcca gtgcctg       117


<210> SEQ ID NO 12
<211> LENGTH: 39
<212> TYPE: PRT
<213> ORGANISM: Chaetomium thermophilum

<400> SEQUENCE: 12

Gly Gly Cys Thr Thr Gln Lys Trp Gly Gln Cys Gly Gly Ile Gly Tyr
1               5                   10                  15

Thr Gly Cys Thr Asn Cys Val Ala Gly Thr Thr Cys Thr Glu Leu Asn
            20                  25                  30

Pro Trp Tyr Ser Gln Cys Leu
        35


<210> SEQ ID NO 13
<211> LENGTH: 1614
<212> TYPE: DNA
<213> ORGANISM: Talaromyces byssochlamydoides

<400> SEQUENCE: 13

atgtccgcct ctctttctta cagactctac gaaaatgctc tcattctctg ttccctcgtg     60

gttgctgccc agggccagca gattggcacc ttgcaggctg aggtccaccc ttctctgact    120

tgggagacct gcagcaccgg cggcagttgt accaccatcg acggctctat cgtccttgat    180

gccaactggc gctgggtcca ccaggtcggc accagcacca actgctatac cggcaatacc    240

tgggatacct ccatctgcga taccgatacg acctgtgccc aagaatgcgc tgtcgatggt    300

gctgactacg agagcaccta cggtatcacc accagcggca atgaagttcg tctcaacttt    360

gtcaccgaca actcgaatgg agcgaacgtc ggctcccgtg tctacctaat ggcggatgac    420
```

```
acccactacc agatcttcaa tctgctgaac caggagttta ccttcacagt ggatgtctca    480
aacctgccct gcggtctcaa cggcgccctc tacctcgttg ttatggatgc cgacggtggt    540
gtatccgagt atacgaataa tgcggctggt gctcagtatg gtgtgggcta ctgtgactcg    600
cagtgtcccc gagatctcaa gttcatccaa ggccaggcca acgttgaggg ctggacacct    660
tcctccaata atgccaatac tggtgttggg aacctcgggt cctgctgtgc agaaatagat    720
atctgggaat cgaacagcat ttctcaagcg cttaccgccc atccgtgcaa cactcccaca    780
aatacggtgt gtgatggcaa cgcctgcggt ggcacataca gcactactcg ctatgctggc    840
acttgtgatc ctgatggctg tgatttcaac ccgtaccggt tgggcaacac gactttctat    900
ggtcctggca tgactattga taccacccag ccgatcaccg ttgtcactca gttcatcact    960
gatgatggaa cttccactgg caccttgtct gaaattaagc gctactacat tcagaacgac   1020
gtcgtgtatg cccagcccaa ctccgacatc gctggcatta ctggaaatgt cattgatgcc   1080
gcttactgta ccgctgagaa ttctgtcttc caagaagaag gttccttcgc acaacacggt   1140
ggcatgagtg gtgtcagtga ggctctgtcc gctggtatgg tcttggtcat gagcgtgtgg   1200
gatgactacg acgccaatat gctgtggctc gacagcgact acccaaccaa cgagtctaca   1260
agcacccccg gtgtggcccg aggtagctgt tccacttcct ctggtgttcc cgccaccgtt   1320
gaatcccaga gccctaactc ctatgtgatc tactcgaaca tcaaggttgg tcccatcggc   1380
tcgaccttca gttccggtgg ttctggcagt ggctctggcg gcggttccgg tggctctagc   1440
accactacaa ccaccacttc gtccacgccc acgactacca gctcttccgg ctctggcagt   1500
ggcgtcgctc agcactgggg acagtgcggt ggtgagggct ggactggccc aactacctgt   1560
gcctccccgt acacctgtca ggagcagaac ccttactact cccagtgtct gtaa         1614
```

<210> SEQ ID NO 14
<211> LENGTH: 537
<212> TYPE: PRT
<213> ORGANISM: Talaromyces byssochlamydoides

<400> SEQUENCE: 14

```
Met Ser Ala Ser Leu Ser Tyr Arg Leu Tyr Glu Asn Ala Leu Ile Leu
1               5                   10                  15

Cys Ser Leu Val Val Ala Ala Gln Gly Gln Gln Ile Gly Thr Leu Gln
            20                  25                  30

Ala Glu Val His Pro Ser Leu Thr Trp Glu Thr Cys Ser Thr Gly Gly
        35                  40                  45

Ser Cys Thr Thr Ile Asp Gly Ser Ile Val Leu Asp Ala Asn Trp Arg
    50                  55                  60

Trp Val His Gln Val Gly Thr Ser Thr Asn Cys Tyr Thr Gly Asn Thr
65                  70                  75                  80

Trp Asp Thr Ser Ile Cys Asp Thr Asp Thr Thr Cys Ala Gln Glu Cys
                85                  90                  95

Ala Val Asp Gly Ala Asp Tyr Glu Ser Thr Tyr Gly Ile Thr Thr Ser
            100                 105                 110

Gly Asn Glu Val Arg Leu Asn Phe Val Thr Asp Asn Ser Asn Gly Ala
        115                 120                 125

Asn Val Gly Ser Arg Val Tyr Leu Met Ala Asp Asp Thr His Tyr Gln
    130                 135                 140

Ile Phe Asn Leu Leu Asn Gln Glu Phe Thr Phe Thr Val Asp Val Ser
145                 150                 155                 160

Asn Leu Pro Cys Gly Leu Asn Gly Ala Leu Tyr Leu Val Val Met Asp
```

```
                165                 170                 175

Ala Asp Gly Gly Val Ser Glu Tyr Thr Asn Asn Ala Ala Gly Ala Gln
            180                 185                 190

Tyr Gly Val Gly Tyr Cys Asp Ser Gln Cys Pro Arg Asp Leu Lys Phe
        195                 200                 205

Ile Gln Gly Gln Ala Asn Val Glu Gly Trp Thr Pro Ser Ser Asn Asn
    210                 215                 220

Ala Asn Thr Gly Val Gly Asn Leu Gly Ser Cys Cys Ala Glu Ile Asp
225                 230                 235                 240

Ile Trp Glu Ser Asn Ser Ile Ser Gln Ala Leu Thr Ala His Pro Cys
                245                 250                 255

Asn Thr Pro Thr Asn Thr Val Cys Asp Gly Asn Ala Cys Gly Gly Thr
            260                 265                 270

Tyr Ser Thr Thr Arg Tyr Ala Gly Thr Cys Asp Pro Asp Gly Cys Asp
        275                 280                 285

Phe Asn Pro Tyr Arg Leu Gly Asn Thr Thr Phe Tyr Gly Pro Gly Met
    290                 295                 300

Thr Ile Asp Thr Thr Gln Pro Ile Thr Val Val Thr Gln Phe Ile Thr
305                 310                 315                 320

Asp Asp Gly Thr Ser Thr Gly Thr Leu Ser Glu Ile Lys Arg Tyr Tyr
                325                 330                 335

Ile Gln Asn Asp Val Val Tyr Ala Gln Pro Asn Ser Asp Ile Ala Gly
            340                 345                 350

Ile Thr Gly Asn Val Ile Asp Ala Ala Tyr Cys Thr Ala Glu Asn Ser
        355                 360                 365

Val Phe Gln Glu Glu Gly Ser Phe Ala Gln His Gly Gly Met Ser Gly
    370                 375                 380

Val Ser Glu Ala Leu Ser Ala Gly Met Val Leu Val Met Ser Val Trp
385                 390                 395                 400

Asp Asp Tyr Asp Ala Asn Met Leu Trp Leu Asp Ser Asp Tyr Pro Thr
                405                 410                 415

Asn Glu Ser Thr Ser Thr Pro Gly Val Ala Arg Gly Ser Cys Ser Thr
            420                 425                 430

Ser Ser Gly Val Pro Ala Thr Val Glu Ser Gln Ser Pro Asn Ser Tyr
        435                 440                 445

Val Ile Tyr Ser Asn Ile Lys Val Gly Pro Ile Gly Ser Thr Phe Ser
    450                 455                 460

Ser Gly Gly Ser Gly Ser Gly Ser Gly Gly Gly Ser Gly Gly Ser Ser
465                 470                 475                 480

Thr Thr Thr Thr Thr Thr Ser Ser Thr Pro Thr Thr Thr Ser Ser Ser
                485                 490                 495

Gly Ser Gly Ser Gly Val Ala Gln His Trp Gly Gln Cys Gly Gly Glu
            500                 505                 510

Gly Trp Thr Gly Pro Thr Thr Cys Ala Ser Pro Tyr Thr Cys Gln Glu
        515                 520                 525

Gln Asn Pro Tyr Tyr Ser Gln Cys Leu
    530                 535


<210> SEQ ID NO 15
<211> LENGTH: 108
<212> TYPE: DNA
<213> ORGANISM: Talaromyces byssochlamydoides

<400> SEQUENCE: 15
```

gtcgctcagc actggggaca gtgcggtggt gagggctgga ctggcccaac tacctgtgcc 60
tccccgtaca cctgtcagga gcagaaccct tactactccc agtgtctg 108

<210> SEQ ID NO 16
<211> LENGTH: 36
<212> TYPE: PRT
<213> ORGANISM: Talaromyces byssochlamydoides

<400> SEQUENCE: 16

Val Ala Gln His Trp Gly Gln Cys Gly Gly Glu Gly Trp Thr Gly Pro
1 5 10 15

Thr Thr Cys Ala Ser Pro Tyr Thr Cys Gln Glu Gln Asn Pro Tyr Tyr
20 25 30

Ser Gln Cys Leu
35

<210> SEQ ID NO 17
<211> LENGTH: 1599
<212> TYPE: DNA
<213> ORGANISM: Aspergillus fumigatus

<400> SEQUENCE: 17
atgctggcct ccaccttctc ctaccgcatg tacaagaccg cgctcatcct ggccgccctt 60
ctgggctctg gccaggctca gcaggtcggt acttcccagg cggaagtgca tccgtccatg 120
acctggcaga gctgcacggc tggcggcagc tgcaccacca acaacggcaa ggtggtcatc 180
gacgcgaact ggcgttgggt gcacaaagtc ggcgactaca ccaactgcta caccggcaac 240
acctgggaca cgactatctg ccctgacgat gcgacctgcg catccaactg cgcccttgag 300
ggtgccaact acgaatccac ctatggtgtg accgccagcg gcaattccct ccgcctcaac 360
ttcgtcacca ccagccagca gaagaacatt ggctcgcgtc tgtacatgat gaaggacgac 420
tcgacctacg agatgtttaa gctgctgaac caggagttca ccttcgatgt cgatgtctcc 480
aacctcccct gcggtctcaa cggtgctctg tactttgtcg ccatggacgc cggcggtggc 540
atgtccaagt acccaaccaa caaggccggt gccaagtacg gtactggata ctgtgactcg 600
cagtgccctc gcgacctcaa gttcatcaac ggtcaggcca acgttgaagg gtggcagccc 660
tcctccaacg atgccaatgc gggtaccggc aaccacgggt cctgctgcgc ggagatggat 720
atctgggagg ccaacagcat ctccacggcc ttcacccccc atccgtgcga cacgcccggc 780
caggtgatgt gcaccggtga tgcctgcggt ggcacctaca gctccgaccg ctacggcggc 840
acctgcgacc ccgacggatg tgatttcaac tccttccgcc agggcaacaa gaccttctac 900
ggccctggca tgaccgtcga caccaagagc aagtttaccg tcgtcaccca gttcatcacc 960
gacgacggca cctccagcgg caccctcaag gagatcaagc gcttctacgt gcagaacggc 1020
aaggtgatcc ccaactcgga gtcgacctgg accggcgtca gcggcaactc catcaccacc 1080
gagtactgca ccgcccagaa gagcctgttc caggaccaga acgtcttcga aaagcacggc 1140
ggcctcgagg gcatgggtgc tgccctcgcc cagggcatgg ttctcgtcat gtccctgtgg 1200
gatgatcact cggccaacat gctctggctc gacagcaact acccgaccac tgcctcttcc 1260
accactcccg gcgtcgcccg tggtacctgc gacatctcct ccggcgtccc tgcggatgtc 1320
gaggcgaacc accccgacgc ctacgtcgtc tactccaaca tcaaggtcgg ccccatcggc 1380
tcgaccttca acagcggtgg ctcgaacccc ggtggcggaa ccaccacgac aactaccacc 1440
cagcctacta ccaccacgac cacggctgga aaccctggcg gcaccggagt cgcacagcac 1500

```
tatggccagt gtggtggaat cggatggacc ggacccacaa cctgtgccag cccttatacc   1560

tgccagaagc tgaatgatta ttactctcag tgcctgtag                          1599


<210> SEQ ID NO 18
<211> LENGTH: 532
<212> TYPE: PRT
<213> ORGANISM: Aspergillus fumigatus

<400> SEQUENCE: 18

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Gly Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
```

```
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530


<210> SEQ ID NO 19
<211> LENGTH: 108
<212> TYPE: DNA
<213> ORGANISM: Aspergillus fumigatus

<400> SEQUENCE: 19

gtcgcacagc actatggcca gtgtggtgga atcggatgga ccggacccac aacctgtgcc      60

agcccttata cctgccagaa gctgaatgat tattactctc agtgcctg                 108


<210> SEQ ID NO 20
<211> LENGTH: 36
<212> TYPE: PRT
<213> ORGANISM: Aspergillus fumigatus

<400> SEQUENCE: 20

Val Ala Gln His Tyr Gly Gln Cys Gly Gly Ile Gly Trp Thr Gly Pro
1               5                   10                  15

Thr Thr Cys Ala Ser Pro Tyr Thr Cys Gln Lys Leu Asn Asp Tyr Tyr
            20                  25                  30

Ser Gln Cys Leu
        35


<210> SEQ ID NO 21
<211> LENGTH: 1581
<212> TYPE: DNA
<213> ORGANISM: Thielavia terrestris

<400> SEQUENCE: 21

atgcacgcca agttcgcgac cctcgccgcc cttgtggcgt ccgccgcggc ccagcaggcc      60

tgcacactca cggctgagaa ccaccccacc ctgtcgtggt ccaagtgcac gtccggcggc     120

agctgcacca gcgtctcggg ctccgtcacc atcgatgcca actggcggtg gactcaccag     180

gtctcgagct cgaccaactg ctacacgggc aatgagtggg acacgtccat ctgcaccgac     240
```

```
ggtgcttcgt gcgccgccgc ctgctgcctc gatggcgccg actactcggg cacctatggc    300

atcaccacca gcggcaacgc cctcagcctc cagttcgtca ctcagggccc ctactcgacc    360

aacattggct cgcgtaccta cctgatggcc tcggacacca agtaccagat gttcactctg    420

ctcggcaacg agttcacctt cgacgtggac gtcacaggcc tcggctgcgg tctgaacggc    480

gccctctact tcgtctccat ggacgaggac ggtggtcttt ccaagtactc gggcaacaag    540

gctggcgcca agtacggcac cggctactgc gactcgcagt gcccccgcga cctcaagttc    600

atcaacggcg aggctaacaa cgttggctgg accccgtcgt ccaacgacaa gaacgccggc    660

ttgggcaact acggcagctg ctgctccgag atggatgtct gggaggccaa cagcatctcg    720

gcggcctaca cgccccatcc ttgcactacc atcggccaga cgcgctgcga gggcgacgac    780

tgcggtggta cctacagcac tgaccgctac gccggcgagt gcgaccctga cggatgcgac    840

ttcaactcgt accgcatggg caacacgacc ttctacggca agggcatgac cgtcgacacc    900

agcaagaagt tcacggtggt gacccagttc ctgacggact cgtctggcaa cctgtccgag    960

atcaagcgct tctacgtcca gaacggcgtc gtcattccca actcgaactc caacatcgcg   1020

ggcgtctcgg gcaactccat cacccaggcc ttctgcgatg ctcagaagac cgctttcggc   1080

gacaccaacg tcttcgacca aaagggcggc ctggcccaga tgggcaaggc tcttgcccag   1140

cccatggtcc tcgtcatgtc cctctgggac gaccacgccg tcaacatgct ctggctcgac   1200

tcgacctacc cgaccaacgc ggccggcaag ccgggcgccg cccgcggtac ctgccccacc   1260

acctcgggcg tccccgccga cgtcgagtcc caggcgccca actccaaggt catctactcc   1320

aacatccgct tcggccccat cggctccacc gtctccggcc tgcccggcgg cggcagcaac   1380

cccggcggcg gctccagctc caccaccacc accaccagac ccgccacctc caccacctcc   1440

tcggccagct ccggcccgac cggcggtggc acggctgccc actggggcca gtgcggcggc   1500

atcggctgga ccggcccgac cgtctgcgcc tcgccctaca cctgccagaa gctgaacgac   1560

tggtactacc agtgcctcta a                                             1581
```

<210> SEQ ID NO 22
<211> LENGTH: 526
<212> TYPE: PRT
<213> ORGANISM: Thielavia terrestris

<400> SEQUENCE: 22

```
Met His Ala Lys Phe Ala Thr Leu Ala Ala Leu Val Ala Ser Ala Ala
1               5                   10                  15

Ala Gln Gln Ala Cys Thr Leu Thr Ala Glu Asn His Pro Thr Leu Ser
            20                  25                  30

Trp Ser Lys Cys Thr Ser Gly Gly Ser Cys Thr Ser Val Ser Gly Ser
        35                  40                  45

Val Thr Ile Asp Ala Asn Trp Arg Trp Thr His Gln Val Ser Ser Ser
    50                  55                  60

Thr Asn Cys Tyr Thr Gly Asn Glu Trp Asp Thr Ser Ile Cys Thr Asp
65                  70                  75                  80

Gly Ala Ser Cys Ala Ala Ala Cys Cys Leu Asp Gly Ala Asp Tyr Ser
                85                  90                  95

Gly Thr Tyr Gly Ile Thr Thr Ser Gly Asn Ala Leu Ser Leu Gln Phe
            100                 105                 110

Val Thr Gln Gly Pro Tyr Ser Thr Asn Ile Gly Ser Arg Thr Tyr Leu
        115                 120                 125
```

```
Met Ala Ser Asp Thr Lys Tyr Gln Met Phe Thr Leu Leu Gly Asn Glu
    130                 135                 140

Phe Thr Phe Asp Val Asp Val Thr Gly Leu Gly Cys Gly Leu Asn Gly
145                 150                 155                 160

Ala Leu Tyr Phe Val Ser Met Asp Glu Asp Gly Gly Leu Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Asn Val
        195                 200                 205

Gly Trp Thr Pro Ser Ser Asn Asp Lys Asn Ala Gly Leu Gly Asn Tyr
    210                 215                 220

Gly Ser Cys Cys Ser Glu Met Asp Val Trp Glu Ala Asn Ser Ile Ser
225                 230                 235                 240

Ala Ala Tyr Thr Pro His Pro Cys Thr Thr Ile Gly Gln Thr Arg Cys
                245                 250                 255

Glu Gly Asp Asp Cys Gly Gly Thr Tyr Ser Thr Asp Arg Tyr Ala Gly
            260                 265                 270

Glu Cys Asp Pro Asp Gly Cys Asp Phe Asn Ser Tyr Arg Met Gly Asn
        275                 280                 285

Thr Thr Phe Tyr Gly Lys Gly Met Thr Val Asp Thr Ser Lys Lys Phe
    290                 295                 300

Thr Val Val Thr Gln Phe Leu Thr Asp Ser Ser Gly Asn Leu Ser Glu
305                 310                 315                 320

Ile Lys Arg Phe Tyr Val Gln Asn Gly Val Val Ile Pro Asn Ser Asn
                325                 330                 335

Ser Asn Ile Ala Gly Val Ser Gly Asn Ser Ile Thr Gln Ala Phe Cys
            340                 345                 350

Asp Ala Gln Lys Thr Ala Phe Gly Asp Thr Asn Val Phe Asp Gln Lys
        355                 360                 365

Gly Gly Leu Ala Gln Met Gly Lys Ala Leu Ala Gln Pro Met Val Leu
    370                 375                 380

Val Met Ser Leu Trp Asp Asp His Ala Val Asn Met Leu Trp Leu Asp
385                 390                 395                 400

Ser Thr Tyr Pro Thr Asn Ala Ala Gly Lys Pro Gly Ala Ala Arg Gly
                405                 410                 415

Thr Cys Pro Thr Thr Ser Gly Val Pro Ala Asp Val Glu Ser Gln Ala
            420                 425                 430

Pro Asn Ser Lys Val Ile Tyr Ser Asn Ile Arg Phe Gly Pro Ile Gly
        435                 440                 445

Ser Thr Val Ser Gly Leu Pro Gly Gly Gly Ser Asn Pro Gly Gly Gly
    450                 455                 460

Ser Ser Ser Thr Thr Thr Thr Thr Arg Pro Ala Thr Ser Thr Thr Ser
465                 470                 475                 480

Ser Ala Ser Ser Gly Pro Thr Gly Gly Gly Thr Ala Ala His Trp Gly
                485                 490                 495

Gln Cys Gly Gly Ile Gly Trp Thr Gly Pro Thr Val Cys Ala Ser Pro
            500                 505                 510

Tyr Thr Cys Gln Lys Leu Asn Asp Trp Tyr Tyr Gln Cys Leu
        515                 520                 525
```

<210> SEQ ID NO 23
<211> LENGTH: 108
<212> TYPE: DNA

<213> ORGANISM: Thielavia terrestris

<400> SEQUENCE: 23

```
acggctgccc actggggcca gtgcggcggc atcggctgga ccggcccgac cgtctgcgcc     60

tcgccctaca cctgccagaa gctgaacgac tggtactacc agtgcctc                 108
```

<210> SEQ ID NO 24
<211> LENGTH: 36
<212> TYPE: PRT
<213> ORGANISM: Thielavia terrestris

<400> SEQUENCE: 24

```
Thr Ala Ala His Trp Gly Gln Cys Gly Gly Ile Gly Trp Thr Gly Pro
1               5                   10                  15

Thr Val Cys Ala Ser Pro Tyr Thr Cys Gln Lys Leu Asn Asp Trp Tyr
            20                  25                  30

Tyr Gln Cys Leu
        35
```

<210> SEQ ID NO 25
<211> LENGTH: 1578
<212> TYPE: DNA
<213> ORGANISM: Myceliophthora thermophilum
<220> FEATURE:
<221> NAME/KEY: misc_feature
<222> LOCATION: (1092)..(1092)
<223> OTHER INFORMATION: n is a, c, g, or t

<400> SEQUENCE: 25

```
atgtacgcca agttcgcgac cctcgccgcc cttgtggctg gcgccgctgc tcagaacgcc     60

tgcactctga ccgctgagaa ccacccctcg ctgacgtggt ccaagtgcac gtctggcggc    120

agctgcacca gcgtccaggg ttccatcacc atcgacgcca actggcggtg gactcaccgg    180

accgatagcg ccaccaactg ctacgagggc aacaagtggg atacttcgta ctgcagcgat    240

ggtccttctt gcgcctccaa gtgctgcatc gacggcgctg actactcgag cacctatggc    300

atcaccacga gcggtaactc cctgaacctc aagttcgtca ccaagggcca gtactcgacc    360

aacatcggct cgcgtaccta cctgatggag agcgacacca agtaccagtt ccagctcctc    420

ggcaacgagt tcaccttcga tgtcgacgtc tccaacctcg gctgcggcct caatggcgcc    480

ctctacttcg tgtccatgga tgccgatggt ggcatgtcca agtactcggg caacaaggca    540

ggtgccaagt acggtaccgg ctactgtgat tctcagtgcc cccgcgacct caagttcatc    600

aacggcgagg ccaacgtaga gaactggcag agctcgacca acgatgccaa cgccggcacg    660

ggcaagtacg gcagctgctg ctccgagatg gacgtctggg aggccaacaa catggccgcc    720

gccttcactc cccacccttg caccgtgatc ggccagtcgc gctgcgaggg cgactcgtgc    780

ggcggtacct acagcaccga ccgctatgcc ggcatctgcg accccgacgg atgcgacttc    840

aactcgtacc gccagggcaa caagaccttc tacggcaagg gcatgacggt cgacacgacc    900

aagaagatca cggtcgtcac ccagttcctc aagaactcgg ccggcgagct ctccgagatc    960

aagcggttct acgtccagaa cggcaaggtc atccccaact ccgagtccac catcccgggc   1020

gtcgagggca actccatcac ccaggactgg tgcgaccgcc agaaggccgc cttcggcgac   1080

gtgaccgact tncaggacaa gggcggcatg gtccagatgg gcaaggccct cgcggggccc   1140

atggtcctcg tcatgtccat ctgggacgac cacgccgtca acatgctctg gctcgactcc   1200

acctggccca tcgacggcgc cggcaagccg ggcgccgagc gcggtgcctg ccccaccacc   1260
```

```
tcgggcgtcc ccgctgaggt cgaggccgag gcccccaact ccaacgtcat cttctccaac   1320

atccgcttcg gccccatcgg ctccaccgtc tccggcctgc ccgacggcgg cagcggcaac   1380

cccaacccgc ccgtcagctc gtccaccccg gtcccctcct cgtccaccac atcctccggt   1440

tcctccggcc cgactggcgg cacgggtgtc gctaagcact atgagcaatg cggaggaatc   1500

gggttcactg gccctaccca gtgcgagagc ccctacactt gcaccaagct gaatgactgg   1560

tactcgcagt gcctgtaa                                                 1578


<210> SEQ ID NO 26
<211> LENGTH: 525
<212> TYPE: PRT
<213> ORGANISM: Myceliophthora thermophilum
<220> FEATURE:
<221> NAME/KEY: MISC_FEATURE
<222> LOCATION: (364)..(364)
<223> OTHER INFORMATION: XAA = ANY AMINO ACID

<400> SEQUENCE: 26

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Phe Gln Leu Leu Gly Asn Glu Phe
    130                 135                 140

Thr Phe Asp Val Asp Val Ser Asn Leu Gly Cys Gly Leu Asn Gly Ala
145                 150                 155                 160

Leu Tyr Phe Val Ser Met Asp Ala Asp Gly Gly Met Ser Lys Tyr Ser
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Glu Ala Asn Val Glu Asn
        195                 200                 205

Trp Gln Ser Ser Thr Asn Asp Ala Asn Ala Gly Thr Gly Lys Tyr Gly
    210                 215                 220

Ser Cys Cys Ser Glu Met Asp Val Trp Glu Ala Asn Asn Met Ala Ala
225                 230                 235                 240

Ala Phe Thr Pro His Pro Cys Thr Val Ile Gly Gln Ser Arg Cys Glu
                245                 250                 255

Gly Asp Ser Cys Gly Gly Thr Tyr Ser Thr Asp Arg Tyr Ala Gly Ile
            260                 265                 270

Cys Asp Pro Asp Gly Cys Asp Phe Asn Ser Tyr Arg Gln Gly Asn Lys
        275                 280                 285

Thr Phe Tyr Gly Lys Gly Met Thr Val Asp Thr Thr Lys Lys Ile Thr
```

```
    290                 295                 300

Val Val Thr Gln Phe Leu Lys Asn Ser Ala Gly Glu Leu Ser Glu Ile
305                 310                 315                 320

Lys Arg Phe Tyr Val Gln Asn Gly Lys Val Ile Pro Asn Ser Glu Ser
                325                 330                 335

Thr Ile Pro Gly Val Glu Gly Asn Ser Ile Thr Gln Asp Trp Cys Asp
            340                 345                 350

Arg Gln Lys Ala Ala Phe Gly Asp Val Thr Asp Xaa Gln Asp Lys Gly
        355                 360                 365

Gly Met Val Gln Met Gly Lys Ala Leu Ala Gly Pro Met Val Leu Val
    370                 375                 380

Met Ser Ile Trp Asp Asp His Ala Val Asn Met Leu Trp Leu Asp Ser
385                 390                 395                 400

Thr Trp Pro Ile Asp Gly Ala Gly Lys Pro Gly Ala Glu Arg Gly Ala
                405                 410                 415

Cys Pro Thr Thr Ser Gly Val Pro Ala Glu Val Glu Ala Glu Ala Pro
            420                 425                 430

Asn Ser Asn Val Ile Phe Ser Asn Ile Arg Phe Gly Pro Ile Gly Ser
        435                 440                 445

Thr Val Ser Gly Leu Pro Asp Gly Gly Ser Gly Asn Pro Asn Pro Pro
    450                 455                 460

Val Ser Ser Ser Thr Pro Val Pro Ser Ser Ser Thr Thr Ser Ser Gly
465                 470                 475                 480

Ser Ser Gly Pro Thr Gly Gly Thr Gly Val Ala Lys His Tyr Glu Gln
                485                 490                 495

Cys Gly Gly Ile Gly Phe Thr Gly Pro Thr Gln Cys Glu Ser Pro Tyr
            500                 505                 510

Thr Cys Thr Lys Leu Asn Asp Trp Tyr Ser Gln Cys Leu
        515                 520                 525


<210> SEQ ID NO 27
<211> LENGTH: 111
<212> TYPE: DNA
<213> ORGANISM: Myceliophthora thermophilum

<400> SEQUENCE: 27

gtcgctaagc actatgagca atgcggagga atcgggttca ctggccctac ccagtgcgag     60

agcccctaca cttgcaccaa gctgaatgac tggtactcgc agtgcctgta a            111


<210> SEQ ID NO 28
<211> LENGTH: 36
<212> TYPE: PRT
<213> ORGANISM: Myceliophthora thermophilum

<400> SEQUENCE: 28

Val Ala Lys His Tyr Glu Gln Cys Gly Gly Ile Gly Phe Thr Gly Pro
1               5                   10                  15

Thr Gln Cys Glu Ser Pro Tyr Thr Cys Thr Lys Leu Asn Asp Trp Tyr
            20                  25                  30

Ser Gln Cys Leu
        35


<210> SEQ ID NO 29
<211> LENGTH: 1676
<212> TYPE: DNA
<213> ORGANISM: Trichoderma reesei
<220> FEATURE:
```

```
<221> NAME/KEY: exon
<222> LOCATION: (1)..(461)
<220> FEATURE:
<221> NAME/KEY: sig_peptide
<222> LOCATION: (1)..(17)
<220> FEATURE:
<221> NAME/KEY: CDS
<222> LOCATION: (1)..(461)
<220> FEATURE:
<221> NAME/KEY: mat_peptide
<222> LOCATION: (52)..(1673)
<220> FEATURE:
<221> NAME/KEY: Intron
<222> LOCATION: (462)..(529)
<220> FEATURE:
<221> NAME/KEY: exon
<222> LOCATION: (530)..(1226)
<220> FEATURE:
<221> NAME/KEY: CDS
<222> LOCATION: (530)..(1226)
<220> FEATURE:
<221> NAME/KEY: Intron
<222> LOCATION: (1227)..(1289)
<220> FEATURE:
<221> NAME/KEY: exon
<222> LOCATION: (1290)..(1673)
<220> FEATURE:
<221> NAME/KEY: CDS
<222> LOCATION: (1290)..(1673)

<400> SEQUENCE: 29

atg tat cgg aag ttg gcc gtc atc tcg gcc ttc ttg gcc aca gct cgt       48
Met Tyr Arg Lys Leu Ala Val Ile Ser Ala Phe Leu Ala Thr Ala Arg
        -15                 -10                 -5

gct cag tcg gcc tgc act ctc caa tcg gag act cac ccg cct ctg aca       96
Ala Gln Ser Ala Cys Thr Leu Gln Ser Glu Thr His Pro Pro Leu Thr
-1  1               5                   10                  15

tgg cag aaa tgc tcg tct ggt ggc acg tgc act caa cag aca ggc tcc      144
Trp Gln Lys Cys Ser Ser Gly Gly Thr Cys Thr Gln Gln Thr Gly Ser
                20                  25                  30

gtg gtc atc gac gcc aac tgg cgc tgg act cac gct acg aac agc agc      192
Val Val Ile Asp Ala Asn Trp Arg Trp Thr His Ala Thr Asn Ser Ser
            35                  40                  45

acg aac tgc tac gat ggc aac act tgg agc tcg acc cta tgt cct gac      240
Thr Asn Cys Tyr Asp Gly Asn Thr Trp Ser Ser Thr Leu Cys Pro Asp
        50                  55                  60

aac gag acc tgc gcg aag aac tgc tgt ctg gac ggt gcc gcc tac gcg      288
Asn Glu Thr Cys Ala Lys Asn Cys Cys Leu Asp Gly Ala Ala Tyr Ala
    65                  70                  75

tcc acg tac gga gtt acc acg agc ggt aac agc ctc tcc att ggc ttt      336
Ser Thr Tyr Gly Val Thr Thr Ser Gly Asn Ser Leu Ser Ile Gly Phe
80                  85                  90                  95

gtc acc cag tct gcg cag aag aac gtt ggc gct cgc ctt tac ctt atg      384
Val Thr Gln Ser Ala Gln Lys Asn Val Gly Ala Arg Leu Tyr Leu Met
                100                 105                 110

gcg agc gac acg acc tac cag gaa ttc acc ctg ctt ggc aac gag ttc      432
Ala Ser Asp Thr Thr Tyr Gln Glu Phe Thr Leu Leu Gly Asn Glu Phe
            115                 120                 125

tct ttc gat gtt gat gtt tcg cag ctg cc  gtaagtgact taccatgaac        481
Ser Phe Asp Val Asp Val Ser Gln Leu Pro
        130                 135

ccctgacgct atcttcttgt tggctcccag ctgactggcc aattcaag g tgc ggc       536
                                                       Cys Gly

ttg aac gga gct ctc tac ttc gtg tcc atg gac gcg gat ggt ggc gtg      584
Leu Asn Gly Ala Leu Tyr Phe Val Ser Met Asp Ala Asp Gly Gly Val
140                 145                 150                 155
```

-continued

```
agc aag tat ccc acc aac acc gct ggc gcc aag tac ggc acg ggg tac       632
Ser Lys Tyr Pro Thr Asn Thr Ala Gly Ala Lys Tyr Gly Thr Gly Tyr
                160                 165                 170

tgt gac agc cag tgt ccc cgc gat ctg aag ttc atc aat ggc cag gcc       680
Cys Asp Ser Gln Cys Pro Arg Asp Leu Lys Phe Ile Asn Gly Gln Ala
            175                 180                 185

aac gtt gag ggc tgg gag ccg tca tcc aac aac gcg aac acg ggc att       728
Asn Val Glu Gly Trp Glu Pro Ser Ser Asn Asn Ala Asn Thr Gly Ile
        190                 195                 200

gga gga cac gga agc tgc tgc tct gag atg gat atc tgg gag gcc aac       776
Gly Gly His Gly Ser Cys Cys Ser Glu Met Asp Ile Trp Glu Ala Asn
    205                 210                 215

tcc atc tcc gag gct ctt acc ccc cac cct tgc acg act gtc ggc cag       824
Ser Ile Ser Glu Ala Leu Thr Pro His Pro Cys Thr Thr Val Gly Gln
220                 225                 230                 235

gag atc tgc gag ggt gat ggg tgc ggc gga act tac tcc gat aac aga       872
Glu Ile Cys Glu Gly Asp Gly Cys Gly Gly Thr Tyr Ser Asp Asn Arg
                240                 245                 250

tat ggc ggc act tgc gat ccc gat ggc tgc gac tgg aac cca tac cgc       920
Tyr Gly Gly Thr Cys Asp Pro Asp Gly Cys Asp Trp Asn Pro Tyr Arg
            255                 260                 265

ctg ggc aac acc agc ttc tac ggc cct ggc tca agc ttt acc ctc gat       968
Leu Gly Asn Thr Ser Phe Tyr Gly Pro Gly Ser Ser Phe Thr Leu Asp
        270                 275                 280

acc acc aag aaa ttg acc gtt gtc acc cag ttc gag acg tcg ggt gcc      1016
Thr Thr Lys Lys Leu Thr Val Val Thr Gln Phe Glu Thr Ser Gly Ala
    285                 290                 295

atc aac cga tac tat gtc cag aat ggc gtc act ttc cag cag ccc aac      1064
Ile Asn Arg Tyr Tyr Val Gln Asn Gly Val Thr Phe Gln Gln Pro Asn
300                 305                 310                 315

gcc gag ctt ggt agt tac tct ggc aac gag ctc aac gat gat tac tgc      1112
Ala Glu Leu Gly Ser Tyr Ser Gly Asn Glu Leu Asn Asp Asp Tyr Cys
                320                 325                 330

aca gct gag gag gca gaa ttc ggc gga tcc tct ttc tca gac aag ggc      1160
Thr Ala Glu Glu Ala Glu Phe Gly Gly Ser Ser Phe Ser Asp Lys Gly
            335                 340                 345

ggc ctg act cag ttc aag aag gct acc tct ggc ggc atg gtt ctg gtc      1208
Gly Leu Thr Gln Phe Lys Lys Ala Thr Ser Gly Gly Met Val Leu Val
        350                 355                 360

atg agt ctg tgg gat gat gtgagtttga tggacaaaca tgcgcgttga             1256
Met Ser Leu Trp Asp Asp
    365

caaagagtca agcagctgac tgagatgtta cag tac tac gcc aac atg ctg tgg     1310
                                    Tyr Tyr Ala Asn Met Leu Trp
                                    370                 375

ctg gac tcc acc tac ccg aca aac gag acc tcc tcc aca ccc ggt gcc      1358
Leu Asp Ser Thr Tyr Pro Thr Asn Glu Thr Ser Ser Thr Pro Gly Ala
            380                 385                 390

gtg cgc gga agc tgc tcc acc agc tcc ggt gtc cct gct cag gtc gaa      1406
Val Arg Gly Ser Cys Ser Thr Ser Ser Gly Val Pro Ala Gln Val Glu
        395                 400                 405

tct cag tct ccc aac gcc aag gtc acc ttc tcc aac atc aag ttc gga      1454
Ser Gln Ser Pro Asn Ala Lys Val Thr Phe Ser Asn Ile Lys Phe Gly
    410                 415                 420

ccc att ggc agc acc ggc aac cct agc ggc ggc aac cct ccc ggc gga      1502
Pro Ile Gly Ser Thr Gly Asn Pro Ser Gly Gly Asn Pro Pro Gly Gly
425                 430                 435                 440

aac ccg cct ggc acc acc acc acc cgc cgc cca gcc act acc act gga      1550
Asn Pro Pro Gly Thr Thr Thr Thr Arg Arg Pro Ala Thr Thr Thr Gly
                445                 450                 455
```

```
agc tct ccc gga cct acc cag tct cac tac ggc cag tgc ggc ggt att      1598
Ser Ser Pro Gly Pro Thr Gln Ser His Tyr Gly Gln Cys Gly Gly Ile
            460                 465                 470

ggc tac agc ggc ccc acg gtc tgc gcc agc ggc aca act tgc cag gtc      1646
Gly Tyr Ser Gly Pro Thr Val Cys Ala Ser Gly Thr Thr Cys Gln Val
        475                 480                 485

ctg aac cct tac tac tct cag tgc ctg taa                              1676
Leu Asn Pro Tyr Tyr Ser Gln Cys Leu
    490                 495


<210> SEQ ID NO 30
<211> LENGTH: 514
<212> TYPE: PRT
<213> ORGANISM: Trichoderma reesei

<400> SEQUENCE: 30

Met Tyr Arg Lys Leu Ala Val Ile Ser Ala Phe Leu Ala Thr Ala Arg
        -15                 -10                 -5

Ala Gln Ser Ala Cys Thr Leu Gln Ser Glu Thr His Pro Pro Leu Thr
-1  1               5                   10                  15

Trp Gln Lys Cys Ser Ser Gly Gly Thr Cys Thr Gln Gln Thr Gly Ser
                20                  25                  30

Val Val Ile Asp Ala Asn Trp Arg Trp Thr His Ala Thr Asn Ser Ser
            35                  40                  45

Thr Asn Cys Tyr Asp Gly Asn Thr Trp Ser Ser Thr Leu Cys Pro Asp
        50                  55                  60

Asn Glu Thr Cys Ala Lys Asn Cys Cys Leu Asp Gly Ala Ala Tyr Ala
    65                  70                  75

Ser Thr Tyr Gly Val Thr Thr Ser Gly Asn Ser Leu Ser Ile Gly Phe
80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
        130                 135                 140

Leu Tyr Phe Val Ser Met Asp Ala Asp Gly Gly Val Ser Lys Tyr Pro
    145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190

Trp Glu Pro Ser Ser Asn Asn Ala Asn Thr Gly Ile Gly Gly His Gly
            195                 200                 205

Ser Cys Cys Ser Glu Met Asp Ile Trp Glu Ala Asn Ser Ile Ser Glu
        210                 215                 220

Ala Leu Thr Pro His Pro Cys Thr Thr Val Gly Gln Glu Ile Cys Glu
    225                 230                 235

Gly Asp Gly Cys Gly Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
                260                 265                 270

Ser Phe Tyr Gly Pro Gly Ser Ser Phe Thr Leu Asp Thr Thr Lys Lys
            275                 280                 285

Leu Thr Val Val Thr Gln Phe Glu Thr Ser Gly Ala Ile Asn Arg Tyr
```

```
        290                 295                 300

Tyr Val Gln Asn Gly Val Thr Phe Gln Gln Pro Asn Ala Glu Leu Gly
    305                 310                 315

Ser Tyr Ser Gly Asn Glu Leu Asn Asp Asp Tyr Cys Thr Ala Glu Glu
320                 325                 330                 335

Ala Glu Phe Gly Gly Ser Ser Phe Ser Asp Lys Gly Gly Leu Thr Gln
                340                 345                 350

Phe Lys Lys Ala Thr Ser Gly Gly Met Val Leu Val Met Ser Leu Trp
            355                 360                 365

Asp Asp Tyr Tyr Ala Asn Met Leu Trp Leu Asp Ser Thr Tyr Pro Thr
        370                 375                 380

Asn Glu Thr Ser Ser Thr Pro Gly Ala Val Arg Gly Ser Cys Ser Thr
    385                 390                 395

Ser Ser Gly Val Pro Ala Gln Val Glu Ser Gln Ser Pro Asn Ala Lys
400                 405                 410                 415

Val Thr Phe Ser Asn Ile Lys Phe Gly Pro Ile Gly Ser Thr Gly Asn
                420                 425                 430

Pro Ser Gly Gly Asn Pro Pro Gly Gly Asn Pro Pro Gly Thr Thr Thr
            435                 440                 445

Thr Arg Arg Pro Ala Thr Thr Thr Gly Ser Ser Pro Gly Pro Thr Gln
        450                 455                 460

Ser His Tyr Gly Gln Cys Gly Gly Ile Gly Tyr Ser Gly Pro Thr Val
    465                 470                 475

Cys Ala Ser Gly Thr Thr Cys Gln Val Leu Asn Pro Tyr Tyr Ser Gln
480                 485                 490                 495

Cys Leu
```

<210> SEQ ID NO 31
<211> LENGTH: 1545
<212> TYPE: DNA
<213> ORGANISM: Trichoderma reesei

<400> SEQUENCE: 31

```
atgtatcgga agttggccgt catctcggcc ttcttggcca cagctcgtgc tcagtcggcc     60

tgcactctcc aatcggagac tcacccgcct ctgacatggc agaaatgctc gtctggtggc    120

acgtgcactc aacagacagg ctccgtggtc atcgacgcca actggcgctg gactcacgct    180

acgaacagca gcacgaactg ctacgatggc aacacttgga gctcgaccct atgtcctgac    240

aacgagacct gcgcgaagaa ctgctgtctg gacggtgccg cctacgcgtc cacgtacgga    300

gttaccacga gcggtaacag cctctccatt ggctttgtca cccagtctgc gcagaagaac    360

gttggcgctc gcctttacct tatggcgagc gacacgacct accaggaatt caccctgctt    420

ggcaacgagt tctctttcga tgttgatgtt tcgcagctgc cgtgcggctt gaacggagct    480

ctctacttcg tgtccatgga cgcggatggt ggcgtgagca agtatcccac caacaccgct    540

ggcgccaagt acggcacggg gtactgtgac agccagtgtc cccgcgatct gaagttcatc    600

aatggccagg ccaacgttga gggctgggag ccgtcatcca acaacgcgaa cacgggcatt    660

ggaggacacg gaagctgctg ctctgagatg gatatctggg aggccaactc catctccgag    720

gctcttaccc cccacccttg cacgactgtc ggccaggaga tctgcgaggg tgatgggtgc    780

ggcggaactt actccgataa cagatatggc ggcacttgcg atcccgatgg ctgcgactgg    840

aacccatacc gcctgggcaa caccagcttc tacggccctg gctcaagctt taccctcgat    900

accaccaaga aattgaccgt tgtcacccag ttcgagacgt cgggtgccat caaccgatac    960
```

```
tatgtccaga atggcgtcac tttccagcag cccaacgccg agcttggtag ttactctggc   1020

aacgagctca acgatgatta ctgcacagct gaggaggcag aattcggcgg atcctctttc   1080

tcagacaagg gcggcctgac tcagttcaag aaggctacct ctggcggcat ggttctggtc   1140

atgagtctgt gggatgatta ctacgccaac atgctgtggc tggactccac ctacccgaca   1200

aacgagacct cctccacacc cggtgccgtg cgcggaagct gctccaccag ctccggtgtc   1260

cctgctcagg tcgaatctca gtctcccaac gccaaggtca ccttctccaa catcaagttc   1320

ggacccattg gcagcaccgg caaccctagc ggcggcaacc ctcccggcgg aaacccgcct   1380

ggcaccacca ccacccgccg cccagccact accactggaa gctctcccgg acctacccag   1440

tctcactacg gccagtgcgg cggtattggc tacagcggcc ccacggtctg cgccagcggc   1500

acaacttgcc aggtcctgaa cccttactac tctcagtgcc tgtaa                   1545
```

<210> SEQ ID NO 32
<211> LENGTH: 1545
<212> TYPE: DNA
<213> ORGANISM: Trichoderma reesei

<400> SEQUENCE: 32

```
atgtatcgta agctcgcagt catctccgcg ttcctcgcaa cagcacgagc gcagtccgcc     60

tgtaccttgc agtcggaaac acatcctccc ctcacttggc agaaatgttc gtccggagga    120

acgtgtacgc agcagactgg ctcggtggtc atcgacgcca actggaggtg gacgcatgca    180

accaactcct ccaccaactg ttacgatggc aacacttggt cctccacctt gtgtcccgat    240

aacgaaacct gtgccaagaa ctgttgtttg gatggtgcag cctacgcctc gacatacgga    300

gtcactactt ccggcaactc gctctcgatc ggcttcgtga ctcagtccgc acagaaaaac    360

gtcggagcgc gactctactt gatggcatcc gatacaacct accaggaatt cactctcttg    420

ggcaacgagt tctccttcga cgtcgacgtc tcccagctcc cttgtggcct caacggagca    480

ctctacttcg tgtcgatgga cgcggatgga ggtgtctcca agtacccgac caacacagca    540

ggagcgaaat acggcacggg ttactgtgac tcgcagtgtc ctcgcgatct caagttcatc    600

aacggccagg caaacgtcga aggctgggaa ccctcgtcga acaacgccaa caccggcatt    660

ggaggccatg gctcctgttg ttcggaaatg gatatctggg aggccaactc gatctccgag    720

gcactcacac cccacccctg tacaaccgtc ggccaggaga tttgtgaagg agacggctgt    780

ggcggaactt actccgataa ccgttacggt ggtacctgtg atcccgatgg ctgtgactgg    840

aacccctacc gcctcggtaa cacatcgttc tacggtccgg gttcctcctt caccctcgac    900

actaccaaaa agttgacggt ggtcacgcag ttcgagactt ccggagccat caaccggtac    960

tacgtgcaga acggagtcac attccagcag cccaacgcag aactcggctc gtactcggga   1020

aacgagctca acgatgatta ctgtacagcg gaagaggcag aattcggagg atcgtcgttc   1080

tccgacaagg gtggtttgac ccagttcaag aaggccacat cgggaggaat ggtgttggtc   1140

atgtccttgt gggacgacta ctatgccaac atgctctggc tcgactccac ctaccccacc   1200

aacgagacct cctcgacacc tggcgcagtg aggggctcgt gttccacttc gtcgggagtg   1260

cctgcacagg tggagtccca gtcgccgaac gccaaggtca ctttctccaa cattaagttc   1320

ggacccatcg gttcgaccgg caacccctcc ggtggaaacc ctcctggcgg aaaccctcct   1380

ggcacaacta caacacgacg gcctgcgact acaacgggtt cgtcccctgg accgacccag   1440

tcccactacg gacagtgtgg aggcatcggt tattccggtc cgaccgtctg tgcgtccggc   1500
```

```
acaacctgtc aggtcttgaa cccttactat tcgcagtgtc tctaa                1545


<210> SEQ ID NO 33
<211> LENGTH: 1545
<212> TYPE: DNA
<213> ORGANISM: Trichoderma reesei
<220> FEATURE:
<221> NAME/KEY: sig_peptide
<222> LOCATION: (1)..(51)
<220> FEATURE:
<221> NAME/KEY: CDS
<222> LOCATION: (1)..(1542)
<220> FEATURE:
<221> NAME/KEY: mat_peptide
<222> LOCATION: (52)..(1542)

<400> SEQUENCE: 33

atg tat cgt aag ctc gca gtc atc tcc gcg ttc ctc gca aca gca cga       48
Met Tyr Arg Lys Leu Ala Val Ile Ser Ala Phe Leu Ala Thr Ala Arg
        -15                 -10                 -5

gcg cag tcc gcc tgt acc ttg cag tcg gaa aca cat cct ccc ctc act       96
Ala Gln Ser Ala Cys Thr Leu Gln Ser Glu Thr His Pro Pro Leu Thr
-1  1               5                   10                  15

tgg cag aaa tgt tcg tcc gga gga acg tgt acg cag cag act ggc tcg      144
Trp Gln Lys Cys Ser Ser Gly Gly Thr Cys Thr Gln Gln Thr Gly Ser
                20                  25                  30

gtg gtc atc gac gcc aac tgg agg tgg acg cat gca acc aac tcc tcc      192
Val Val Ile Asp Ala Asn Trp Arg Trp Thr His Ala Thr Asn Ser Ser
            35                  40                  45

acc aac tgt tac gat ggc aac act tgg tcc tcc acc ttg tgt ccc gat      240
Thr Asn Cys Tyr Asp Gly Asn Thr Trp Ser Ser Thr Leu Cys Pro Asp
        50                  55                  60

aac gaa acc tgt gcc aag aac tgt tgt ttg gat ggt gca gcc tac gcc      288
Asn Glu Thr Cys Ala Lys Asn Cys Cys Leu Asp Gly Ala Ala Tyr Ala
    65                  70                  75

tcg aca tac gga gtc act act tcc ggc aac tcg ctc tcg atc ggc ttc      336
Ser Thr Tyr Gly Val Thr Thr Ser Gly Asn Ser Leu Ser Ile Gly Phe
80                  85                  90                  95

gtg act cag tcc gca cag aaa aac gtc gga gcg cga ctc tac ttg atg      384
Val Thr Gln Ser Ala Gln Lys Asn Val Gly Ala Arg Leu Tyr Leu Met
                100                 105                 110

gca tcc gat aca acc tac cag gaa ttc act ctc ttg ggc aac gag ttc      432
Ala Ser Asp Thr Thr Tyr Gln Glu Phe Thr Leu Leu Gly Asn Glu Phe
            115                 120                 125

tcc ttc gac gtc gac gtc tcc cag ctc cct tgt ggc ctc aac gga gca      480
Ser Phe Asp Val Asp Val Ser Gln Leu Pro Cys Gly Leu Asn Gly Ala
        130                 135                 140

ctc tac ttc gtg tcg atg gac gcg gat gga ggt gtc tcc aag tac ccg      528
Leu Tyr Phe Val Ser Met Asp Ala Asp Gly Gly Val Ser Lys Tyr Pro
    145                 150                 155

acc aac aca gca gga gcg aaa tac ggc acg ggt tac tgt gac tcg cag      576
Thr Asn Thr Ala Gly Ala Lys Tyr Gly Thr Gly Tyr Cys Asp Ser Gln
160                 165                 170                 175

tgt cct cgc gat ctc aag ttc atc aac ggc cag gca aac gtc gaa ggc      624
Cys Pro Arg Asp Leu Lys Phe Ile Asn Gly Gln Ala Asn Val Glu Gly
                180                 185                 190

tgg gaa ccc tcg tcg gcc aac gcc gcc acc ggc att gga ggc cat ggc      672
Trp Glu Pro Ser Ser Ala Asn Ala Ala Thr Gly Ile Gly Gly His Gly
            195                 200                 205

tcc tgt tgt tcg gaa atg gat atc tgg gag gcc aac tcg atc tcc gag      720
Ser Cys Cys Ser Glu Met Asp Ile Trp Glu Ala Asn Ser Ile Ser Glu
        210                 215                 220
```

```
gca ctc aca ccc cac ccc tgt aca acc gtc ggc cag gag att tgt gaa      768
Ala Leu Thr Pro His Pro Cys Thr Thr Val Gly Gln Glu Ile Cys Glu
    225                 230                 235

gga gac ggc tgt ggc gga act tac tcc gat aac cgt tac ggt ggt acc      816
Gly Asp Gly Cys Gly Gly Thr Tyr Ser Asp Asn Arg Tyr Gly Gly Thr
240                 245                 250                 255

tgt gat ccc gat ggc tgt gac tgg aac ccc tac cgc ctc ggt aac aca      864
Cys Asp Pro Asp Gly Cys Asp Trp Asn Pro Tyr Arg Leu Gly Asn Thr
                260                 265                 270

tcg ttc tac ggt ccg ggt tcc tcc ttc acc ctc gac act acc aaa aag      912
Ser Phe Tyr Gly Pro Gly Ser Ser Phe Thr Leu Asp Thr Thr Lys Lys
            275                 280                 285

ttg acg gtg gtc acg cag ttc gag act tcc gga gcc atc aac cgg tac      960
Leu Thr Val Val Thr Gln Phe Glu Thr Ser Gly Ala Ile Asn Arg Tyr
        290                 295                 300

tac gtg cag aac gga gtc aca ttc cag cag ccc aac gca gaa ctc ggc     1008
Tyr Val Gln Asn Gly Val Thr Phe Gln Gln Pro Asn Ala Glu Leu Gly
    305                 310                 315

tcg tac tcg gga aac gag ctc aac gat gat tac tgt aca gcg gaa gag     1056
Ser Tyr Ser Gly Asn Glu Leu Asn Asp Asp Tyr Cys Thr Ala Glu Glu
320                 325                 330                 335

gca gaa ttc gga gga tcg tcg ttc tcc gac aag ggt ggt ttg acc cag     1104
Ala Glu Phe Gly Gly Ser Ser Phe Ser Asp Lys Gly Gly Leu Thr Gln
                340                 345                 350

ttc aag aag gcc aca tcg gga gga atg gtg ttg gtc atg tcc ttg tgg     1152
Phe Lys Lys Ala Thr Ser Gly Gly Met Val Leu Val Met Ser Leu Trp
            355                 360                 365

gac gac tac tat gcc aac atg ctc tgg ctc gac tcc acc tac ccc acc     1200
Asp Asp Tyr Tyr Ala Asn Met Leu Trp Leu Asp Ser Thr Tyr Pro Thr
        370                 375                 380

aac gag acc tcc tcg aca cct ggc gca gtg agg ggc tcg tgt tcc act     1248
Asn Glu Thr Ser Ser Thr Pro Gly Ala Val Arg Gly Ser Cys Ser Thr
    385                 390                 395

tcg tcg gga gtg cct gca cag gtg gag tcc cag tcg ccg aac gcc aag     1296
Ser Ser Gly Val Pro Ala Gln Val Glu Ser Gln Ser Pro Asn Ala Lys
400                 405                 410                 415

gtc act ttc tcc aac att aag ttc gga ccc atc ggt tcg acc ggc aac     1344
Val Thr Phe Ser Asn Ile Lys Phe Gly Pro Ile Gly Ser Thr Gly Asn
                420                 425                 430

ccc tcc ggt gga aac cct cct ggc gga aac cct cct ggc aca act aca     1392
Pro Ser Gly Gly Asn Pro Pro Gly Gly Asn Pro Pro Gly Thr Thr Thr
            435                 440                 445

aca cga cgg cct gcg act aca acg ggt tcg tcc cct gga ccg acc cag     1440
Thr Arg Arg Pro Ala Thr Thr Thr Gly Ser Ser Pro Gly Pro Thr Gln
        450                 455                 460

tcc cac tac gga cag tgt gga ggc atc ggt tat tcc ggt ccg acc gtc     1488
Ser His Tyr Gly Gln Cys Gly Gly Ile Gly Tyr Ser Gly Pro Thr Val
    465                 470                 475

tgt gcg tcc ggc aca acc tgt cag gtc ttg aac cct tac tat tcg cag     1536
Cys Ala Ser Gly Thr Thr Cys Gln Val Leu Asn Pro Tyr Tyr Ser Gln
480                 485                 490                 495

tgt ctc taa                                                         1545
Cys Leu
```

<210> SEQ ID NO 34
<211> LENGTH: 514
<212> TYPE: PRT
<213> ORGANISM: Trichoderma reesei

<400> SEQUENCE: 34

```
Met Tyr Arg Lys Leu Ala Val Ile Ser Ala Phe Leu Ala Thr Ala Arg
        -15                 -10                 -5

Ala Gln Ser Ala Cys Thr Leu Gln Ser Glu Thr His Pro Pro Leu Thr
-1  1               5                   10                  15

Trp Gln Lys Cys Ser Ser Gly Gly Thr Cys Thr Gln Gln Thr Gly Ser
                20                  25                  30

Val Val Ile Asp Ala Asn Trp Arg Trp Thr His Ala Thr Asn Ser Ser
            35                  40                  45

Thr Asn Cys Tyr Asp Gly Asn Thr Trp Ser Ser Thr Leu Cys Pro Asp
    50                  55                  60

Asn Glu Thr Cys Ala Lys Asn Cys Cys Leu Asp Gly Ala Ala Tyr Ala
65                  70                  75

Ser Thr Tyr Gly Val Thr Thr Ser Gly Asn Ser Leu Ser Ile Gly Phe
80                  85                  90                  95

Val Thr Gln Ser Ala Gln Lys Asn Val Gly Ala Arg Leu Tyr Leu Met
                100                 105                 110

Ala Ser Asp Thr Thr Tyr Gln Glu Phe Thr Leu Leu Gly Asn Glu Phe
            115                 120                 125

Ser Phe Asp Val Asp Val Ser Gln Leu Pro Cys Gly Leu Asn Gly Ala
        130                 135                 140

Leu Tyr Phe Val Ser Met Asp Ala Asp Gly Gly Val Ser Lys Tyr Pro
    145                 150                 155

Thr Asn Thr Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190

Trp Glu Pro Ser Ser Ala Asn Ala Ala Thr Gly Ile Gly Gly His Gly
            195                 200                 205

Ser Cys Cys Ser Glu Met Asp Ile Trp Glu Ala Asn Ser Ile Ser Glu
        210                 215                 220

Ala Leu Thr Pro His Pro Cys Thr Thr Val Gly Gln Glu Ile Cys Glu
    225                 230                 235

Gly Asp Gly Cys Gly Gly Thr Tyr Ser Asp Asn Arg Tyr Gly Gly Thr
240                 245                 250                 255

Cys Asp Pro Asp Gly Cys Asp Trp Asn Pro Tyr Arg Leu Gly Asn Thr
                260                 265                 270

Ser Phe Tyr Gly Pro Gly Ser Ser Phe Thr Leu Asp Thr Thr Lys Lys
            275                 280                 285

Leu Thr Val Val Thr Gln Phe Glu Thr Ser Gly Ala Ile Asn Arg Tyr
        290                 295                 300

Tyr Val Gln Asn Gly Val Thr Phe Gln Gln Pro Asn Ala Glu Leu Gly
    305                 310                 315

Ser Tyr Ser Gly Asn Glu Leu Asn Asp Asp Tyr Cys Thr Ala Glu Glu
320                 325                 330                 335

Ala Glu Phe Gly Gly Ser Ser Phe Ser Asp Lys Gly Gly Leu Thr Gln
                340                 345                 350

Phe Lys Lys Ala Thr Ser Gly Gly Met Val Leu Val Met Ser Leu Trp
            355                 360                 365

Asp Asp Tyr Tyr Ala Asn Met Leu Trp Leu Asp Ser Thr Tyr Pro Thr
        370                 375                 380

Asn Glu Thr Ser Ser Thr Pro Gly Ala Val Arg Gly Ser Cys Ser Thr
    385                 390                 395

Ser Ser Gly Val Pro Ala Gln Val Glu Ser Gln Ser Pro Asn Ala Lys
```

```
400                 405                 410                 415

Val Thr Phe Ser Asn Ile Lys Phe Gly Pro Ile Gly Ser Thr Gly Asn
                420                 425                 430

Pro Ser Gly Gly Asn Pro Pro Gly Gly Asn Pro Pro Gly Thr Thr Thr
            435                 440                 445

Thr Arg Arg Pro Ala Thr Thr Thr Gly Ser Ser Pro Gly Pro Thr Gln
        450                 455                 460

Ser His Tyr Gly Gln Cys Gly Gly Ile Gly Tyr Ser Gly Pro Thr Val
    465                 470                 475

Cys Ala Ser Gly Thr Thr Cys Gln Val Leu Asn Pro Tyr Tyr Ser Gln
480                 485                 490                 495

Cys Leu


<210> SEQ ID NO 35
<211> LENGTH: 1599
<212> TYPE: DNA
<213> ORGANISM: Aspergillus fumigatus
<220> FEATURE:
<221> NAME/KEY: sig_peptide
<222> LOCATION: (1)..(26)
<220> FEATURE:
<221> NAME/KEY: CDS
<222> LOCATION: (1)..(1596)
<220> FEATURE:
<221> NAME/KEY: mat_peptide
<222> LOCATION: (79)..(1596)

<400> SEQUENCE: 35

atg ctg gcc tcc acc ttc tcc tac cgc atg tac aag acc gcg ctc atc       48
Met Leu Ala Ser Thr Phe Ser Tyr Arg Met Tyr Lys Thr Ala Leu Ile
    -25                 -20                 -15

ctg gcc gcc ctt ctg ggc tct ggc cag gct cag cag gtc ggt act tcc       96
Leu Ala Ala Leu Leu Gly Ser Gly Gln Ala Gln Gln Val Gly Thr Ser
-10                 -5                  -1  1               5

cag gcg gaa gtg cat ccg tcc atg acc tgg cag agc tgc acg gct ggc      144
Gln Ala Glu Val His Pro Ser Met Thr Trp Gln Ser Cys Thr Ala Gly
            10                  15                  20

ggc agc tgc acc acc aac aac ggc aag gtg gtc atc gac gcg aac tgg      192
Gly Ser Cys Thr Thr Asn Asn Gly Lys Val Val Ile Asp Ala Asn Trp
        25                  30                  35

cgt tgg gtg cac aaa gtc ggc gac tac acc aac tgc tac acc ggc aac      240
Arg Trp Val His Lys Val Gly Asp Tyr Thr Asn Cys Tyr Thr Gly Asn
    40                  45                  50

acc tgg gac acg act atc tgc cct gac gat gcg acc tgc gca tcc aac      288
Thr Trp Asp Thr Thr Ile Cys Pro Asp Asp Ala Thr Cys Ala Ser Asn
55                  60                  65                  70

tgc gcc ctt gag ggt gcc aac tac gaa tcc acc tat ggt gtg acc gcc      336
Cys Ala Leu Glu Gly Ala Asn Tyr Glu Ser Thr Tyr Gly Val Thr Ala
                75                  80                  85

agc ggc aat tcc ctc cgc ctc aac ttc gtc acc acc agc cag cag aag      384
Ser Gly Asn Ser Leu Arg Leu Asn Phe Val Thr Thr Ser Gln Gln Lys
            90                  95                  100

aac att ggc tcg cgt ctg tac atg atg aag gac gac tcg acc tac gag      432
Asn Ile Gly Ser Arg Leu Tyr Met Met Lys Asp Asp Ser Thr Tyr Glu
        105                 110                 115

atg ttt aag ctg ctg aac cag gag ttc acc ttc gat gtc gat gtc tcc      480
Met Phe Lys Leu Leu Asn Gln Glu Phe Thr Phe Asp Val Asp Val Ser
    120                 125                 130

aac ctc ccc tgc ggt ctc aac ggt gct ctg tac ttt gtc gcc atg gac      528
Asn Leu Pro Cys Gly Leu Asn Gly Ala Leu Tyr Phe Val Ala Met Asp
135                 140                 145                 150
```

```
gcc gac ggt ggc atg tcc aag tac cca acc aac aag gcc ggt gcc aag      576
Ala Asp Gly Gly Met Ser Lys Tyr Pro Thr Asn Lys Ala Gly Ala Lys
            155                 160                 165

tac ggt act gga tac tgt gac tcg cag tgc cct cgc gac ctc aag ttc      624
Tyr Gly Thr Gly Tyr Cys Asp Ser Gln Cys Pro Arg Asp Leu Lys Phe
        170                 175                 180

atc aac ggt cag gcc aac gtc gaa ggg tgg cag ccc tcc tcc aac gat      672
Ile Asn Gly Gln Ala Asn Val Glu Gly Trp Gln Pro Ser Ser Asn Asp
    185                 190                 195

gcc aat gcg ggt acc ggc aac cac ggg tcc tgc tgc gcg gag atg gat      720
Ala Asn Ala Gly Thr Gly Asn His Gly Ser Cys Cys Ala Glu Met Asp
    200                 205                 210

atc tgg gag gcc aac agc atc tcc acg gcc ttc acc ccc cat ccg tgc      768
Ile Trp Glu Ala Asn Ser Ile Ser Thr Ala Phe Thr Pro His Pro Cys
215                 220                 225                 230

gac acg ccc ggc cag gtg atg tgc acc ggt gat gcc tgc ggt ggc acc      816
Asp Thr Pro Gly Gln Val Met Cys Thr Gly Asp Ala Cys Gly Gly Thr
            235                 240                 245

tac agc tcc gac cgc tac ggc ggc acc tgc gac ccc gac gga tgt gat      864
Tyr Ser Ser Asp Arg Tyr Gly Gly Thr Cys Asp Pro Asp Gly Cys Asp
        250                 255                 260

ttc aac tcc ttc cgc cag ggc aac aag acc ttc tac ggc cct ggc atg      912
Phe Asn Ser Phe Arg Gln Gly Asn Lys Thr Phe Tyr Gly Pro Gly Met
    265                 270                 275

acc gtc gac acc aag agc aag ttt acc gtc gtc acc cag ttc atc acc      960
Thr Val Asp Thr Lys Ser Lys Phe Thr Val Val Thr Gln Phe Ile Thr
    280                 285                 290

gac gac ggc acc tcc agc ggc acc ctc aag gag atc aag cgc ttc tac     1008
Asp Asp Gly Thr Ser Ser Gly Thr Leu Lys Glu Ile Lys Arg Phe Tyr
295                 300                 305                 310

gtg cag aac ggc aag gtg atc ccc aac tcg gag tcg acc tgg acc ggc     1056
Val Gln Asn Gly Lys Val Ile Pro Asn Ser Glu Ser Thr Trp Thr Gly
            315                 320                 325

gtc agc ggc aac tcc atc acc acc gag tac tgc acc gcc cag aag agc     1104
Val Ser Gly Asn Ser Ile Thr Thr Glu Tyr Cys Thr Ala Gln Lys Ser
        330                 335                 340

ctg ttc cag gac cag aac gtc ttc gaa aag cac ggc ggc ctc gag ggc     1152
Leu Phe Gln Asp Gln Asn Val Phe Glu Lys His Gly Gly Leu Glu Gly
    345                 350                 355

atg ggt gct gcc ctc gcc cag ggt atg gtt ctc gtc atg tcc ctg tgg     1200
Met Gly Ala Ala Leu Ala Gln Gly Met Val Leu Val Met Ser Leu Trp
    360                 365                 370

gat gat cac tcg gcc aac atg ctc tgg ctc gac agc aac tac ccg acc     1248
Asp Asp His Ser Ala Asn Met Leu Trp Leu Asp Ser Asn Tyr Pro Thr
375                 380                 385                 390

act gcc tct tcc acc act ccc ggc gtc gcc cgt ggt acc tgc gac atc     1296
Thr Ala Ser Ser Thr Thr Pro Gly Val Ala Arg Gly Thr Cys Asp Ile
            395                 400                 405

tcc tcc ggc gtc cct gcg gat gtc gag gcg aac cac ccc gac gcc tac     1344
Ser Ser Gly Val Pro Ala Asp Val Glu Ala Asn His Pro Asp Ala Tyr
            410                 415                 420

gtc gtc tac tcc aac atc aag gtc ggc ccc atc ggc tcg acc ttc aac     1392
Val Val Tyr Ser Asn Ile Lys Val Gly Pro Ile Gly Ser Thr Phe Asn
        425                 430                 435

agc ggt ggc tcg aac ccc ggt ggc gga acc acc acg aca act acc acc     1440
Ser Gly Gly Ser Asn Pro Gly Gly Gly Thr Thr Thr Thr Thr Thr Thr
    440                 445                 450

cag cct act acc acc acg acc acg gct gga aac cct ggc ggc acc gga     1488
Gln Pro Thr Thr Thr Thr Thr Thr Ala Gly Asn Pro Gly Gly Thr Gly
```

```
455                 460                 465                 470

gtc gca cag cac tat ggc cag tgt ggt gga atc gga tgg acc gga ccc     1536
Val Ala Gln His Tyr Gly Gln Cys Gly Gly Ile Gly Trp Thr Gly Pro
                475                 480                 485

aca acc tgt gcc agc cct tat acc tgc cag aag ctg aat gat tat tac     1584
Thr Thr Cys Ala Ser Pro Tyr Thr Cys Gln Lys Leu Asn Asp Tyr Tyr
            490                 495                 500

tct cag tgc ctg tag                                                 1599
Ser Gln Cys Leu
        505


<210> SEQ ID NO 36
<211> LENGTH: 532
<212> TYPE: PRT
<213> ORGANISM: Aspergillus fumigatus

<400> SEQUENCE: 36

Met Leu Ala Ser Thr Phe Ser Tyr Arg Met Tyr Lys Thr Ala Leu Ile
    -25                 -20                 -15

Leu Ala Ala Leu Leu Gly Ser Gly Gln Ala Gln Gln Val Gly Thr Ser
-10                 -5                  -1  1               5

Gln Ala Glu Val His Pro Ser Met Thr Trp Gln Ser Cys Thr Ala Gly
            10                  15                  20

Gly Ser Cys Thr Thr Asn Asn Gly Lys Val Val Ile Asp Ala Asn Trp
        25                  30                  35

Arg Trp Val His Lys Val Gly Asp Tyr Thr Asn Cys Tyr Thr Gly Asn
    40                  45                  50

Thr Trp Asp Thr Thr Ile Cys Pro Asp Asp Ala Thr Cys Ala Ser Asn
55                  60                  65                  70

Cys Ala Leu Glu Gly Ala Asn Tyr Glu Ser Thr Tyr Gly Val Thr Ala
                75                  80                  85

Ser Gly Asn Ser Leu Arg Leu Asn Phe Val Thr Thr Ser Gln Gln Lys
            90                  95                  100

Asn Ile Gly Ser Arg Leu Tyr Met Met Lys Asp Asp Ser Thr Tyr Glu
        105                 110                 115

Met Phe Lys Leu Leu Asn Gln Glu Phe Thr Phe Asp Val Asp Val Ser
    120                 125                 130

Asn Leu Pro Cys Gly Leu Asn Gly Ala Leu Tyr Phe Val Ala Met Asp
135                 140                 145                 150

Ala Asp Gly Gly Met Ser Lys Tyr Pro Thr Asn Lys Ala Gly Ala Lys
                155                 160                 165

Tyr Gly Thr Gly Tyr Cys Asp Ser Gln Cys Pro Arg Asp Leu Lys Phe
            170                 175                 180

Ile Asn Gly Gln Ala Asn Val Glu Gly Trp Gln Pro Ser Ser Asn Asp
        185                 190                 195

Ala Asn Ala Gly Thr Gly Asn His Gly Ser Cys Cys Ala Glu Met Asp
    200                 205                 210

Ile Trp Glu Ala Asn Ser Ile Ser Thr Ala Phe Thr Pro His Pro Cys
215                 220                 225                 230

Asp Thr Pro Gly Gln Val Met Cys Thr Gly Asp Ala Cys Gly Gly Thr
                235                 240                 245

Tyr Ser Ser Asp Arg Tyr Gly Gly Thr Cys Asp Pro Asp Gly Cys Asp
            250                 255                 260

Phe Asn Ser Phe Arg Gln Gly Asn Lys Thr Phe Tyr Gly Pro Gly Met
        265                 270                 275
```

```
Thr Val Asp Thr Lys Ser Lys Phe Thr Val Val Thr Gln Phe Ile Thr
    280                 285                 290

Asp Asp Gly Thr Ser Ser Gly Thr Leu Lys Glu Ile Lys Arg Phe Tyr
295                 300                 305                 310

Val Gln Asn Gly Lys Val Ile Pro Asn Ser Glu Ser Thr Trp Thr Gly
                315                 320                 325

Val Ser Gly Asn Ser Ile Thr Thr Glu Tyr Cys Thr Ala Gln Lys Ser
            330                 335                 340

Leu Phe Gln Asp Gln Asn Val Phe Glu Lys His Gly Gly Leu Glu Gly
        345                 350                 355

Met Gly Ala Ala Leu Ala Gln Gly Met Val Leu Val Met Ser Leu Trp
    360                 365                 370

Asp Asp His Ser Ala Asn Met Leu Trp Leu Asp Ser Asn Tyr Pro Thr
375                 380                 385                 390

Thr Ala Ser Ser Thr Thr Pro Gly Val Ala Arg Gly Thr Cys Asp Ile
                395                 400                 405

Ser Ser Gly Val Pro Ala Asp Val Glu Ala Asn His Pro Asp Ala Tyr
            410                 415                 420

Val Val Tyr Ser Asn Ile Lys Val Gly Pro Ile Gly Ser Thr Phe Asn
        425                 430                 435

Ser Gly Gly Ser Asn Pro Gly Gly Gly Thr Thr Thr Thr Thr Thr Thr
    440                 445                 450

Gln Pro Thr Thr Thr Thr Thr Thr Ala Gly Asn Pro Gly Gly Thr Gly
455                 460                 465                 470

Val Ala Gln His Tyr Gly Gln Cys Gly Gly Ile Gly Trp Thr Gly Pro
                475                 480                 485

Thr Thr Cys Ala Ser Pro Tyr Thr Cys Gln Lys Leu Asn Asp Tyr Tyr
            490                 495                 500

Ser Gln Cys Leu
        505


<210> SEQ ID NO 37
<211> LENGTH: 1374
<212> TYPE: DNA
<213> ORGANISM: Thermoascus aurantiacus
<220> FEATURE:
<221> NAME/KEY: sig_peptide
<222> LOCATION: (1)..(17)
<220> FEATURE:
<221> NAME/KEY: CDS
<222> LOCATION: (1)..(1371)
<220> FEATURE:
<221> NAME/KEY: mat_peptide
<222> LOCATION: (52)..(1371)

<400> SEQUENCE: 37

atg tat cag cgc gct ctt ctc ttc tct ttc ttc ctc tcc gcc gcc cgc      48
Met Tyr Gln Arg Ala Leu Leu Phe Ser Phe Phe Leu Ser Ala Ala Arg
        -15                 -10                 -5

gcg cag cag gcc ggt acc cta acc gca gag aat cac cct tcc ctg acc      96
Ala Gln Gln Ala Gly Thr Leu Thr Ala Glu Asn His Pro Ser Leu Thr
-1  1               5                   10                  15

tgg cag caa tgc tcc agc ggc ggt agt tgt acc acg cag aat gga aaa     144
Trp Gln Gln Cys Ser Ser Gly Gly Ser Cys Thr Thr Gln Asn Gly Lys
                20                  25                  30

gtc gtt atc gat gcg aac tgg cgt tgg gtc cat acc acc tct gga tac     192
Val Val Ile Asp Ala Asn Trp Arg Trp Val His Thr Thr Ser Gly Tyr
            35                  40                  45

acc aac tgc tac acg ggc aat acg tgg gac acc agt atc tgt ccc gac     240
```

```
Thr Asn Cys Tyr Thr Gly Asn Thr Trp Asp Thr Ser Ile Cys Pro Asp
        50                  55                  60

gac gtg acc tgc gct cag aat tgt gcc ttg gat gga gcg gat tac agt      288
Asp Val Thr Cys Ala Gln Asn Cys Ala Leu Asp Gly Ala Asp Tyr Ser
    65                  70                  75

ggc acc tat ggt gtt acg acc agt ggc aac gcc ctg aga ctg aac ttt      336
Gly Thr Tyr Gly Val Thr Thr Ser Gly Asn Ala Leu Arg Leu Asn Phe
80                  85                  90                  95

gtc acc caa agc tca ggg aag aac att ggc tcg cgc ctg tac ctg ctg      384
Val Thr Gln Ser Ser Gly Lys Asn Ile Gly Ser Arg Leu Tyr Leu Leu
                100                 105                 110

cag gac gac acc act tat cag atc ttc aag ctg ctg ggt cag gag ttt      432
Gln Asp Asp Thr Thr Tyr Gln Ile Phe Lys Leu Leu Gly Gln Glu Phe
            115                 120                 125

acc ttc gat gtc gac gtc tcc aat ctc cct tgc ggg ctg aac ggc gcc      480
Thr Phe Asp Val Asp Val Ser Asn Leu Pro Cys Gly Leu Asn Gly Ala
        130                 135                 140

ctc tac ttt gtg gcc atg gac gcc gac ggc gga ttg tcc aaa tac cct      528
Leu Tyr Phe Val Ala Met Asp Ala Asp Gly Gly Leu Ser Lys Tyr Pro
    145                 150                 155

ggc aac aag gca ggc gct aag tat ggc act ggt tac tgc gac tct cag      576
Gly Asn Lys Ala Gly Ala Lys Tyr Gly Thr Gly Tyr Cys Asp Ser Gln
160                 165                 170                 175

tgc cct cgg gat ctc aag ttc atc aac ggt cag gcc aac gtt gaa ggc      624
Cys Pro Arg Asp Leu Lys Phe Ile Asn Gly Gln Ala Asn Val Glu Gly
                180                 185                 190

tgg cag ccg tct gcc aac gac cca aat gcc ggc gtt ggt aac cac ggt      672
Trp Gln Pro Ser Ala Asn Asp Pro Asn Ala Gly Val Gly Asn His Gly
            195                 200                 205

tcc tgc tgc gct gag atg gat gtc tgg gaa gcc aac agc atc tct act      720
Ser Cys Cys Ala Glu Met Asp Val Trp Glu Ala Asn Ser Ile Ser Thr
        210                 215                 220

gcg gtg acg cct cac cca tgc gac acc ccc ggc cag acc atg tgc cag      768
Ala Val Thr Pro His Pro Cys Asp Thr Pro Gly Gln Thr Met Cys Gln
    225                 230                 235

gga gac gac tgt ggt gga acc tac tcc tcc act cga tat gct ggt acc      816
Gly Asp Asp Cys Gly Gly Thr Tyr Ser Ser Thr Arg Tyr Ala Gly Thr
240                 245                 250                 255

tgc gac cct gat ggc tgc gac ttc aat cct tac cgc cag ggc aac cac      864
Cys Asp Pro Asp Gly Cys Asp Phe Asn Pro Tyr Arg Gln Gly Asn His
                260                 265                 270

tcg ttc tac ggc ccc ggg aag atc gtc gac act agc tcc aaa ttc acc      912
Ser Phe Tyr Gly Pro Gly Lys Ile Val Asp Thr Ser Ser Lys Phe Thr
            275                 280                 285

gtc gtc acc cag ttc atc acc gac gac ggg acc ccc tcc ggc acc ctg      960
Val Val Thr Gln Phe Ile Thr Asp Asp Gly Thr Pro Ser Gly Thr Leu
        290                 295                 300

acg gag atc aaa cgc ttc tac gtc cag aac ggc aag gtg atc ccc cag     1008
Thr Glu Ile Lys Arg Phe Tyr Val Gln Asn Gly Lys Val Ile Pro Gln
    305                 310                 315

tcg gag tcg acg atc agc ggc gtc acc ggc aac tca atc acc acc gag     1056
Ser Glu Ser Thr Ile Ser Gly Val Thr Gly Asn Ser Ile Thr Thr Glu
320                 325                 330                 335

tat tgc acg gcc cag aag gcc gcc ttc ggc gac aac acc ggc ttc ttc     1104
Tyr Cys Thr Ala Gln Lys Ala Ala Phe Gly Asp Asn Thr Gly Phe Phe
                340                 345                 350

acg cac ggc ggg ctt cag aag atc agt cag gct ctg gct cag ggc atg     1152
Thr His Gly Gly Leu Gln Lys Ile Ser Gln Ala Leu Ala Gln Gly Met
            355                 360                 365
```

```
gtc ctc gtc atg agc ctg tgg gac gat cac gcc gcc aac atg ctc tgg     1200
Val Leu Val Met Ser Leu Trp Asp Asp His Ala Ala Asn Met Leu Trp
        370                 375                 380

ctg gac agc acc tac ccg act gat gcg gac ccg gac acc cct ggc gtc     1248
Leu Asp Ser Thr Tyr Pro Thr Asp Ala Asp Pro Asp Thr Pro Gly Val
    385                 390                 395

gcg cgc ggt acc tgc ccc acg acc tcc ggc gtc ccg gcc gac gtt gag     1296
Ala Arg Gly Thr Cys Pro Thr Thr Ser Gly Val Pro Ala Asp Val Glu
400                 405                 410                 415

tcg cag aac ccc aat tca tat gtt atc tac tcc aac atc aag gtc gga     1344
Ser Gln Asn Pro Asn Ser Tyr Val Ile Tyr Ser Asn Ile Lys Val Gly
                420                 425                 430

ccc atc aac tcg acc ttc acc gcc aac taa                             1374
Pro Ile Asn Ser Thr Phe Thr Ala Asn
            435                 440
```

<210> SEQ ID NO 38
<211> LENGTH: 457
<212> TYPE: PRT
<213> ORGANISM: Thermoascus aurantiacus

<400> SEQUENCE: 38

```
Met Tyr Gln Arg Ala Leu Leu Phe Ser Phe Phe Leu Ser Ala Ala Arg
        -15                 -10                 -5

Ala Gln Gln Ala Gly Thr Leu Thr Ala Glu Asn His Pro Ser Leu Thr
-1  1               5                   10                  15

Trp Gln Gln Cys Ser Ser Gly Gly Ser Cys Thr Thr Gln Asn Gly Lys
                20                  25                  30

Val Val Ile Asp Ala Asn Trp Arg Trp Val His Thr Thr Ser Gly Tyr
            35                  40                  45

Thr Asn Cys Tyr Thr Gly Asn Thr Trp Asp Thr Ser Ile Cys Pro Asp
        50                  55                  60

Asp Val Thr Cys Ala Gln Asn Cys Ala Leu Asp Gly Ala Asp Tyr Ser
    65                  70                  75

Gly Thr Tyr Gly Val Thr Thr Ser Gly Asn Ala Leu Arg Leu Asn Phe
80                  85                  90                  95

Val Thr Gln Ser Ser Gly Lys Asn Ile Gly Ser Arg Leu Tyr Leu Leu
                100                 105                 110

Gln Asp Asp Thr Thr Tyr Gln Ile Phe Lys Leu Leu Gly Gln Glu Phe
            115                 120                 125

Thr Phe Asp Val Asp Val Ser Asn Leu Pro Cys Gly Leu Asn Gly Ala
        130                 135                 140

Leu Tyr Phe Val Ala Met Asp Ala Asp Gly Gly Leu Ser Lys Tyr Pro
    145                 150                 155

Gly Asn Lys Ala Gly Ala Lys Tyr Gly Thr Gly Tyr Cys Asp Ser Gln
160                 165                 170                 175

Cys Pro Arg Asp Leu Lys Phe Ile Asn Gly Gln Ala Asn Val Glu Gly
                180                 185                 190

Trp Gln Pro Ser Ala Asn Asp Pro Asn Ala Gly Val Gly Asn His Gly
            195                 200                 205

Ser Cys Cys Ala Glu Met Asp Val Trp Glu Ala Asn Ser Ile Ser Thr
        210                 215                 220

Ala Val Thr Pro His Pro Cys Asp Thr Pro Gly Gln Thr Met Cys Gln
    225                 230                 235

Gly Asp Asp Cys Gly Gly Thr Tyr Ser Ser Thr Arg Tyr Ala Gly Thr
240                 245                 250                 255
```

```
Cys Asp Pro Asp Gly Cys Asp Phe Asn Pro Tyr Arg Gln Gly Asn His
                260                 265                 270

Ser Phe Tyr Gly Pro Gly Lys Ile Val Asp Thr Ser Ser Lys Phe Thr
            275                 280                 285

Val Val Thr Gln Phe Ile Thr Asp Asp Gly Thr Pro Ser Gly Thr Leu
        290                 295                 300

Thr Glu Ile Lys Arg Phe Tyr Val Gln Asn Gly Lys Val Ile Pro Gln
    305                 310                 315

Ser Glu Ser Thr Ile Ser Gly Val Thr Gly Asn Ser Ile Thr Thr Glu
320                 325                 330                 335

Tyr Cys Thr Ala Gln Lys Ala Ala Phe Gly Asp Asn Thr Gly Phe Phe
                340                 345                 350

Thr His Gly Gly Leu Gln Lys Ile Ser Gln Ala Leu Ala Gln Gly Met
            355                 360                 365

Val Leu Val Met Ser Leu Trp Asp Asp His Ala Ala Asn Met Leu Trp
        370                 375                 380

Leu Asp Ser Thr Tyr Pro Thr Asp Ala Asp Pro Asp Thr Pro Gly Val
    385                 390                 395

Ala Arg Gly Thr Cys Pro Thr Thr Ser Gly Val Pro Ala Asp Val Glu
400                 405                 410                 415

Ser Gln Asn Pro Asn Ser Tyr Val Ile Tyr Ser Asn Ile Lys Val Gly
                420                 425                 430

Pro Ile Asn Ser Thr Phe Thr Ala Asn
            435                 440


<210> SEQ ID NO 39
<211> LENGTH: 1428
<212> TYPE: DNA
<213> ORGANISM: Penicillium emersonii
<220> FEATURE:
<221> NAME/KEY: exon
<222> LOCATION: (1)..(603)
<220> FEATURE:
<221> NAME/KEY: CDS
<222> LOCATION: (1)..(603)
<220> FEATURE:
<221> NAME/KEY: sig_peptide
<222> LOCATION: (1)..(18)
<220> FEATURE:
<221> NAME/KEY: mat_peptide
<222> LOCATION: (55)..(1425)
<220> FEATURE:
<221> NAME/KEY: Intron
<222> LOCATION: (604)..(663)
<220> FEATURE:
<221> NAME/KEY: exon
<222> LOCATION: (664)..(1425)
<220> FEATURE:
<221> NAME/KEY: CDS
<222> LOCATION: (664)..(1425)

<400> SEQUENCE: 39

atg ctt cga cgg gct ctt ctt cta tcc tct tcc gcc atc ctt gct gtc       48
Met Leu Arg Arg Ala Leu Leu Leu Ser Ser Ser Ala Ile Leu Ala Val
            -15                 -10                 -5

aag gca cag cag gcc ggc acg gcg acg gca gag aac cac ccg ccc ctg       96
Lys Ala Gln Gln Ala Gly Thr Ala Thr Ala Glu Asn His Pro Pro Leu
    -1  1               5                   10

aca tgg cag gaa tgc acc gcc cct ggg agc tgc acc acc cag aac ggg      144
Thr Trp Gln Glu Cys Thr Ala Pro Gly Ser Cys Thr Thr Gln Asn Gly
15                  20                  25                  30

gcg gtc gtt ctt gat gcg aac tgg cgt tgg gtg cac gat gtg aac gga      192
Ala Val Val Leu Asp Ala Asn Trp Arg Trp Val His Asp Val Asn Gly
```

```
                35                  40                  45

tac acc aac tgc tac acg ggc aat acc tgg aac ccc acg tac tgc cct       240
Tyr Thr Asn Cys Tyr Thr Gly Asn Thr Trp Asn Pro Thr Tyr Cys Pro
            50                  55                  60

gac gac gaa acc tgc gcc cag aac tgt gcg ctg gac ggc gcg gat tac       288
Asp Asp Glu Thr Cys Ala Gln Asn Cys Ala Leu Asp Gly Ala Asp Tyr
        65                  70                  75

gag ggc acc tac ggc gtg act tcg tcg ggc agc tcc ttg aag ctc aat       336
Glu Gly Thr Tyr Gly Val Thr Ser Ser Gly Ser Ser Leu Lys Leu Asn
    80                  85                  90

ttc gtc acc ggg tcg aac gtc gga tcc cgt ctc tac ctg ctg cag gac       384
Phe Val Thr Gly Ser Asn Val Gly Ser Arg Leu Tyr Leu Leu Gln Asp
95                  100                 105                 110

gac tcg acc tat cag atc ttc aag ctt ctg aac cgc gag ttt acc ttt       432
Asp Ser Thr Tyr Gln Ile Phe Lys Leu Leu Asn Arg Glu Phe Thr Phe
                115                 120                 125

gac gtc gat gtc tcc aat ctt ccg tgc gga ttg aac ggc gct ctg tac       480
Asp Val Asp Val Ser Asn Leu Pro Cys Gly Leu Asn Gly Ala Leu Tyr
            130                 135                 140

ttt gtc gcc atg gac gcc gac ggc ggc gtg tcc aag tac ccg aac aac       528
Phe Val Ala Met Asp Ala Asp Gly Gly Val Ser Lys Tyr Pro Asn Asn
        145                 150                 155

aag gct ggt gcc aag tac gga acc ggg tat tgc gac tcc caa tgc cca       576
Lys Ala Gly Ala Lys Tyr Gly Thr Gly Tyr Cys Asp Ser Gln Cys Pro
    160                 165                 170

cgg gac ctc aag ttc atc gac ggc gag gtatgtccag tggtaaaatc             623
Arg Asp Leu Lys Phe Ile Asp Gly Glu
175                 180

gatcgtctcg tgaacttctg ctgacaggtt cgatctacag gcc aac gtc gag ggc       678
                                            Ala Asn Val Glu Gly
                                                185

tgg cag ccg tct tcg aac aac gcc aac acc gga att ggc gac cat ggc       726
Trp Gln Pro Ser Ser Asn Asn Ala Asn Thr Gly Ile Gly Asp His Gly
    190                 195                 200

tcc tgc tgt gcg gag atg gat gtc tgg gaa gcc aac agc atc tcc aat       774
Ser Cys Cys Ala Glu Met Asp Val Trp Glu Ala Asn Ser Ile Ser Asn
205                 210                 215                 220

gcg gtc act ccg cac ccg tgc gac acg cca ggc cag acg atg tgc tct       822
Ala Val Thr Pro His Pro Cys Asp Thr Pro Gly Gln Thr Met Cys Ser
                225                 230                 235

ggc gat gac tgc ggt ggc aca tac tct aac gat cgc tac gcg gga acc       870
Gly Asp Asp Cys Gly Gly Thr Tyr Ser Asn Asp Arg Tyr Ala Gly Thr
            240                 245                 250

tgc gat cct gac ggc tgt gac ttc aac cct tac cgc atg ggc aac act       918
Cys Asp Pro Asp Gly Cys Asp Phe Asn Pro Tyr Arg Met Gly Asn Thr
        255                 260                 265

tct ttc tac ggg cct ggc aag atc atc gat acc acc aag cct ttc act       966
Ser Phe Tyr Gly Pro Gly Lys Ile Ile Asp Thr Thr Lys Pro Phe Thr
    270                 275                 280

gtc gtg acg cag ttc ctc act gat gat ggt acg gat act gga act ctc      1014
Val Val Thr Gln Phe Leu Thr Asp Asp Gly Thr Asp Thr Gly Thr Leu
285                 290                 295                 300

agc gag atc aag cgc ttc tac gtc cag aac ggc aac gtc att ccg cag      1062
Ser Glu Ile Lys Arg Phe Tyr Val Gln Asn Gly Asn Val Ile Pro Gln
                305                 310                 315

ccc aac tcg gac atc agt ggc gtg acc ggc aac tcg atc acg acg gag      1110
Pro Asn Ser Asp Ile Ser Gly Val Thr Gly Asn Ser Ile Thr Thr Glu
            320                 325                 330

ttc tgt act gct cag aag cag gcc ttt ggc gac acg gac gac ttc tct      1158
```

```
Phe Cys Thr Ala Gln Lys Gln Ala Phe Gly Asp Thr Asp Asp Phe Ser
        335                 340                 345

cag cac ggt ggc ctg gcc aag atg gga gcg gcc atg cag cag ggt atg     1206
Gln His Gly Gly Leu Ala Lys Met Gly Ala Ala Met Gln Gln Gly Met
    350                 355                 360

gtc ctg gtg atg agt ttg tgg gac gac tac gcc gcg cag atg ctg tgg     1254
Val Leu Val Met Ser Leu Trp Asp Asp Tyr Ala Ala Gln Met Leu Trp
365                 370                 375                 380

ctg gat tcc gac tac ccg acg gat gcg gac ccc acg acc cct ggt att     1302
Leu Asp Ser Asp Tyr Pro Thr Asp Ala Asp Pro Thr Thr Pro Gly Ile
                385                 390                 395

gcc cgt gga acg tgt ccg acg gac tcg ggc gtc cca tcg gat gtc gag     1350
Ala Arg Gly Thr Cys Pro Thr Asp Ser Gly Val Pro Ser Asp Val Glu
            400                 405                 410

tcg cag agc ccc aac tcc tac gtg acc tac tcg aac atc aag ttt ggt     1398
Ser Gln Ser Pro Asn Ser Tyr Val Thr Tyr Ser Asn Ile Lys Phe Gly
        415                 420                 425

ccg atc aac tcg acc ttc acc gct tcg tga                             1428
Pro Ile Asn Ser Thr Phe Thr Ala Ser
    430                 435


<210> SEQ ID NO 40
<211> LENGTH: 455
<212> TYPE: PRT
<213> ORGANISM: Penicillium emersonii

<400> SEQUENCE: 40

Met Leu Arg Arg Ala Leu Leu Leu Ser Ser Ser Ala Ile Leu Ala Val
            -15                 -10                 -5

Lys Ala Gln Gln Ala Gly Thr Ala Thr Ala Glu Asn His Pro Pro Leu
    -1  1               5                   10

Thr Trp Gln Glu Cys Thr Ala Pro Gly Ser Cys Thr Thr Gln Asn Gly
15                  20                  25                  30

Ala Val Val Leu Asp Ala Asn Trp Arg Trp Val His Asp Val Asn Gly
                35                  40                  45

Tyr Thr Asn Cys Tyr Thr Gly Asn Thr Trp Asn Pro Thr Tyr Cys Pro
            50                  55                  60

Asp Asp Glu Thr Cys Ala Gln Asn Cys Ala Leu Asp Gly Ala Asp Tyr
        65                  70                  75

Glu Gly Thr Tyr Gly Val Thr Ser Ser Gly Ser Ser Leu Lys Leu Asn
    80                  85                  90

Phe Val Thr Gly Ser Asn Val Gly Ser Arg Leu Tyr Leu Leu Gln Asp
95                  100                 105                 110

Asp Ser Thr Tyr Gln Ile Phe Lys Leu Leu Asn Arg Glu Phe Thr Phe
                115                 120                 125

Asp Val Asp Val Ser Asn Leu Pro Cys Gly Leu Asn Gly Ala Leu Tyr
            130                 135                 140

Phe Val Ala Met Asp Ala Asp Gly Gly Val Ser Lys Tyr Pro Asn Asn
        145                 150                 155

Lys Ala Gly Ala Lys Tyr Gly Thr Gly Tyr Cys Asp Ser Gln Cys Pro
    160                 165                 170

Arg Asp Leu Lys Phe Ile Asp Gly Glu Ala Asn Val Glu Gly Trp Gln
175                 180                 185                 190

Pro Ser Ser Asn Asn Ala Asn Thr Gly Ile Gly Asp His Gly Ser Cys
                195                 200                 205

Cys Ala Glu Met Asp Val Trp Glu Ala Asn Ser Ile Ser Asn Ala Val
            210                 215                 220
```

```
Thr Pro His Pro Cys Asp Thr Pro Gly Gln Thr Met Cys Ser Gly Asp
        225                 230                 235

Asp Cys Gly Gly Thr Tyr Ser Asn Asp Arg Tyr Ala Gly Thr Cys Asp
    240                 245                 250

Pro Asp Gly Cys Asp Phe Asn Pro Tyr Arg Met Gly Asn Thr Ser Phe
255                 260                 265                 270

Tyr Gly Pro Gly Lys Ile Ile Asp Thr Thr Lys Pro Phe Thr Val Val
                275                 280                 285

Thr Gln Phe Leu Thr Asp Asp Gly Thr Asp Thr Gly Thr Leu Ser Glu
            290                 295                 300

Ile Lys Arg Phe Tyr Val Gln Asn Gly Asn Val Ile Pro Gln Pro Asn
        305                 310                 315

Ser Asp Ile Ser Gly Val Thr Gly Asn Ser Ile Thr Thr Glu Phe Cys
    320                 325                 330

Thr Ala Gln Lys Gln Ala Phe Gly Asp Thr Asp Asp Phe Ser Gln His
335                 340                 345                 350

Gly Gly Leu Ala Lys Met Gly Ala Ala Met Gln Gln Gly Met Val Leu
                355                 360                 365

Val Met Ser Leu Trp Asp Asp Tyr Ala Ala Gln Met Leu Trp Leu Asp
            370                 375                 380

Ser Asp Tyr Pro Thr Asp Ala Asp Pro Thr Thr Pro Gly Ile Ala Arg
        385                 390                 395

Gly Thr Cys Pro Thr Asp Ser Gly Val Pro Ser Asp Val Glu Ser Gln
    400                 405                 410

Ser Pro Asn Ser Tyr Val Thr Tyr Ser Asn Ile Lys Phe Gly Pro Ile
415                 420                 425                 430

Asn Ser Thr Phe Thr Ala Ser
                435


<210> SEQ ID NO 41
<211> LENGTH: 1599
<212> TYPE: DNA
<213> ORGANISM: Talaromyces leycettanus
<220> FEATURE:
<221> NAME/KEY: sig_peptide
<222> LOCATION: (1)..(25)
<220> FEATURE:
<221> NAME/KEY: CDS
<222> LOCATION: (1)..(1596)
<220> FEATURE:
<221> NAME/KEY: mat_peptide
<222> LOCATION: (76)..(1596)

<400> SEQUENCE: 41

atg gcc agc ctc ttc tct ttc aag atg tac aag gcc gct ctg gtc ctc       48
Met Ala Ser Leu Phe Ser Phe Lys Met Tyr Lys Ala Ala Leu Val Leu
-25                 -20                 -15                 -10

tcc tct ctc ctt gcg gcc acc cag gcc cag cag gcc ggc acc ctg acc       96
Ser Ser Leu Leu Ala Ala Thr Gln Ala Gln Gln Ala Gly Thr Leu Thr
                -5                  -1  1               5

acc gaa acc cat cct tct ctg acc tgg cag caa tgc tct gcc ggc ggc      144
Thr Glu Thr His Pro Ser Leu Thr Trp Gln Gln Cys Ser Ala Gly Gly
        10                  15                  20

agc tgc acc act cag aac ggc aag gtc gtc atc gac gcc aac tgg cgc      192
Ser Cys Thr Thr Gln Asn Gly Lys Val Val Ile Asp Ala Asn Trp Arg
    25                  30                  35

tgg gtt cac agc acc agc ggc tcg aac aac tgc tac act ggc aac act      240
Trp Val His Ser Thr Ser Gly Ser Asn Asn Cys Tyr Thr Gly Asn Thr
40                  45                  50                  55
```

```
tgg gat gct act ctc tgc cct gac gac gtg act tgc gct gcc aac tgc      288
Trp Asp Ala Thr Leu Cys Pro Asp Asp Val Thr Cys Ala Ala Asn Cys
                60                  65                  70

gcc ctg gac ggc gct gac tac tcg ggc acc tac ggt gtc acc acc agc      336
Ala Leu Asp Gly Ala Asp Tyr Ser Gly Thr Tyr Gly Val Thr Thr Ser
            75                  80                  85

ggc aac tct ctg cgc ctg aac ttc gtc acc cag gcg tcg cag aag aac      384
Gly Asn Ser Leu Arg Leu Asn Phe Val Thr Gln Ala Ser Gln Lys Asn
        90                  95                  100

gtc ggc tct cgt ctc tat ctg atg gag aat gac aca acc tac cag atc      432
Val Gly Ser Arg Leu Tyr Leu Met Glu Asn Asp Thr Thr Tyr Gln Ile
    105                 110                 115

ttc aag ttg ctg aac cag gag ttc acc ttt gac gtt gat gtc tcc aac      480
Phe Lys Leu Leu Asn Gln Glu Phe Thr Phe Asp Val Asp Val Ser Asn
120                 125                 130                 135

ctt ccc tgc ggt ctc aac ggt gct ctc tac ctg gtt gcc atg gat gcc      528
Leu Pro Cys Gly Leu Asn Gly Ala Leu Tyr Leu Val Ala Met Asp Ala
                140                 145                 150

gac ggc ggc atg gcc aag tac cca acc aac aag gct ggt gcg aag tac      576
Asp Gly Gly Met Ala Lys Tyr Pro Thr Asn Lys Ala Gly Ala Lys Tyr
            155                 160                 165

gga acc ggt tac tgc gac tcc cag tgc cct cgc gac ctg aag ttc atc      624
Gly Thr Gly Tyr Cys Asp Ser Gln Cys Pro Arg Asp Leu Lys Phe Ile
        170                 175                 180

aac ggt gag gcc aat gtt gag gga tgg cag cct tct tcc aat gac ccc      672
Asn Gly Glu Ala Asn Val Glu Gly Trp Gln Pro Ser Ser Asn Asp Pro
    185                 190                 195

aac tct ggc att ggc aac cac ggc tct tgc tgt gct gag atg gac atc      720
Asn Ser Gly Ile Gly Asn His Gly Ser Cys Cys Ala Glu Met Asp Ile
200                 205                 210                 215

tgg gag gcc aac agc atc tcc aat gca gtc act cct cac cct tgc gac      768
Trp Glu Ala Asn Ser Ile Ser Asn Ala Val Thr Pro His Pro Cys Asp
                220                 225                 230

acc ccg gga cag gtc atg tgc acc ggc aac aac tgt ggt ggc act tac      816
Thr Pro Gly Gln Val Met Cys Thr Gly Asn Asn Cys Gly Gly Thr Tyr
            235                 240                 245

agc act act cgc tat gct ggc act tgc gat cct gat ggc tgc gac ttc      864
Ser Thr Thr Arg Tyr Ala Gly Thr Cys Asp Pro Asp Gly Cys Asp Phe
        250                 255                 260

aac ccc tac cgc atg ggc aac cac tcc ttc tac ggc ccc aaa cag atc      912
Asn Pro Tyr Arg Met Gly Asn His Ser Phe Tyr Gly Pro Lys Gln Ile
    265                 270                 275

gtc gac acc agc tcc aag ttc act gtt gtt act cag ttc ctc acc gat      960
Val Asp Thr Ser Ser Lys Phe Thr Val Val Thr Gln Phe Leu Thr Asp
280                 285                 290                 295

gat ggc acc tcc acc ggc acc ctc agc gag atc agg cgc ttc tac gtt     1008
Asp Gly Thr Ser Thr Gly Thr Leu Ser Glu Ile Arg Arg Phe Tyr Val
                300                 305                 310

cag aac ggc cag gtc atc ccc aac tcc gtg tcc acg atc agc ggc gtc     1056
Gln Asn Gly Gln Val Ile Pro Asn Ser Val Ser Thr Ile Ser Gly Val
            315                 320                 325

tcc ggc aac tcc atc acc acc gag ttc tgc acg gcc cag aag cag gct     1104
Ser Gly Asn Ser Ile Thr Thr Glu Phe Cys Thr Ala Gln Lys Gln Ala
        330                 335                 340

ttc ggc gac act gat gac ttc agc aag cac ggc ggt ctg tct ggc atg     1152
Phe Gly Asp Thr Asp Asp Phe Ser Lys His Gly Gly Leu Ser Gly Met
    345                 350                 355

tcc gcc gcc ctc tcc cag ggt atg gtt ctc gtc atg agc ttg tgg gac     1200
Ser Ala Ala Leu Ser Gln Gly Met Val Leu Val Met Ser Leu Trp Asp
```

```
360                 365                 370                 375

gac cac gcc gcc aac atg ctc tgg ctt gac agc acc tac ccg acc aac      1248
Asp His Ala Ala Asn Met Leu Trp Leu Asp Ser Thr Tyr Pro Thr Asn
                380                 385                 390

gcc acc tct tcc acc ccc ggt gcc gcc cgt ggt act tgc gac atc tcc      1296
Ala Thr Ser Ser Thr Pro Gly Ala Ala Arg Gly Thr Cys Asp Ile Ser
            395                 400                 405

tcc ggt gtc ccc gcc gat gtt gag tcc aac gac ccc aac gcc tac gtc      1344
Ser Gly Val Pro Ala Asp Val Glu Ser Asn Asp Pro Asn Ala Tyr Val
        410                 415                 420

gtc tac tcc aac atc aag gtc ggc ccg atc ggc tct acc ttc agc agc      1392
Val Tyr Ser Asn Ile Lys Val Gly Pro Ile Gly Ser Thr Phe Ser Ser
    425                 430                 435

tct ggc tct ggc tct agc tcc agc tcc agc acc acc acc acc acc acc      1440
Ser Gly Ser Gly Ser Ser Ser Ser Ser Ser Thr Thr Thr Thr Thr Thr
440                 445                 450                 455

gct tcc cca acc acg acc acc tcc agc gct tcc agc acc ggc act ggc      1488
Ala Ser Pro Thr Thr Thr Thr Ser Ser Ala Ser Ser Thr Gly Thr Gly
                460                 465                 470

gtt gct cag cac tgg ggt cag tgc ggt ggc cag gga tgg acc ggt ccg      1536
Val Ala Gln His Trp Gly Gln Cys Gly Gly Gln Gly Trp Thr Gly Pro
            475                 480                 485

acc acc tgc gtt agc ccc tac acc tgc cag gag ctg aac ccc tac tac      1584
Thr Thr Cys Val Ser Pro Tyr Thr Cys Gln Glu Leu Asn Pro Tyr Tyr
        490                 495                 500

tac cag tgc ctg taa                                                  1599
Tyr Gln Cys Leu
    505


<210> SEQ ID NO 42
<211> LENGTH: 532
<212> TYPE: PRT
<213> ORGANISM: Talaromyces leycettanus

<400> SEQUENCE: 42

Met Ala Ser Leu Phe Ser Phe Lys Met Tyr Lys Ala Ala Leu Val Leu
-25                 -20                 -15                 -10

Ser Ser Leu Leu Ala Ala Thr Gln Ala Gln Gln Ala Gly Thr Leu Thr
                -5                  -1  1               5

Thr Glu Thr His Pro Ser Leu Thr Trp Gln Gln Cys Ser Ala Gly Gly
        10                  15                  20

Ser Cys Thr Thr Gln Asn Gly Lys Val Val Ile Asp Ala Asn Trp Arg
    25                  30                  35

Trp Val His Ser Thr Ser Gly Ser Asn Asn Cys Tyr Thr Gly Asn Thr
40                  45                  50                  55

Trp Asp Ala Thr Leu Cys Pro Asp Asp Val Thr Cys Ala Ala Asn Cys
                60                  65                  70

Ala Leu Asp Gly Ala Asp Tyr Ser Gly Thr Tyr Gly Val Thr Thr Ser
            75                  80                  85

Gly Asn Ser Leu Arg Leu Asn Phe Val Thr Gln Ala Ser Gln Lys Asn
        90                  95                  100

Val Gly Ser Arg Leu Tyr Leu Met Glu Asn Asp Thr Thr Tyr Gln Ile
    105                 110                 115

Phe Lys Leu Leu Asn Gln Glu Phe Thr Phe Asp Val Asp Val Ser Asn
120                 125                 130                 135

Leu Pro Cys Gly Leu Asn Gly Ala Leu Tyr Leu Val Ala Met Asp Ala
                140                 145                 150
```

```
Asp Gly Gly Met Ala Lys Tyr Pro Thr Asn Lys Ala Gly Ala Lys Tyr
            155                 160                 165

Gly Thr Gly Tyr Cys Asp Ser Gln Cys Pro Arg Asp Leu Lys Phe Ile
        170                 175                 180

Asn Gly Glu Ala Asn Val Glu Gly Trp Gln Pro Ser Ser Asn Asp Pro
    185                 190                 195

Asn Ser Gly Ile Gly Asn His Gly Ser Cys Cys Ala Glu Met Asp Ile
200                 205                 210                 215

Trp Glu Ala Asn Ser Ile Ser Asn Ala Val Thr Pro His Pro Cys Asp
                220                 225                 230

Thr Pro Gly Gln Val Met Cys Thr Gly Asn Asn Cys Gly Gly Thr Tyr
            235                 240                 245

Ser Thr Thr Arg Tyr Ala Gly Thr Cys Asp Pro Asp Gly Cys Asp Phe
        250                 255                 260

Asn Pro Tyr Arg Met Gly Asn His Ser Phe Tyr Gly Pro Lys Gln Ile
    265                 270                 275

Val Asp Thr Ser Ser Lys Phe Thr Val Val Thr Gln Phe Leu Thr Asp
280                 285                 290                 295

Asp Gly Thr Ser Thr Gly Thr Leu Ser Glu Ile Arg Arg Phe Tyr Val
                300                 305                 310

Gln Asn Gly Gln Val Ile Pro Asn Ser Val Ser Thr Ile Ser Gly Val
            315                 320                 325

Ser Gly Asn Ser Ile Thr Thr Glu Phe Cys Thr Ala Gln Lys Gln Ala
        330                 335                 340

Phe Gly Asp Thr Asp Asp Phe Ser Lys His Gly Gly Leu Ser Gly Met
    345                 350                 355

Ser Ala Ala Leu Ser Gln Gly Met Val Leu Val Met Ser Leu Trp Asp
360                 365                 370                 375

Asp His Ala Ala Asn Met Leu Trp Leu Asp Ser Thr Tyr Pro Thr Asn
                380                 385                 390

Ala Thr Ser Ser Thr Pro Gly Ala Ala Arg Gly Thr Cys Asp Ile Ser
            395                 400                 405

Ser Gly Val Pro Ala Asp Val Glu Ser Asn Asp Pro Asn Ala Tyr Val
        410                 415                 420

Val Tyr Ser Asn Ile Lys Val Gly Pro Ile Gly Ser Thr Phe Ser Ser
    425                 430                 435

Ser Gly Ser Gly Ser Ser Ser Ser Ser Ser Thr Thr Thr Thr Thr Thr
440                 445                 450                 455

Ala Ser Pro Thr Thr Thr Thr Ser Ser Ala Ser Ser Thr Gly Thr Gly
                460                 465                 470

Val Ala Gln His Trp Gly Gln Cys Gly Gly Gln Gly Trp Thr Gly Pro
            475                 480                 485

Thr Thr Cys Val Ser Pro Tyr Thr Cys Gln Glu Leu Asn Pro Tyr Tyr
        490                 495                 500

Tyr Gln Cys Leu
    505
```

<210> SEQ ID NO 43
<211> LENGTH: 1599
<212> TYPE: DNA
<213> ORGANISM: Talaromyces leycettanus
<220> FEATURE:
<221> NAME/KEY: sig_peptide
<222> LOCATION: (1)..(25)
<220> FEATURE:
<221> NAME/KEY: CDS

```
<222> LOCATION: (1)..(1596)
<220> FEATURE:
<221> NAME/KEY: mat_peptide
<222> LOCATION: (76)..(1596)

<400> SEQUENCE: 43

atg gcg tcc tct ctc tct tac agg atc tac aag aat gct ctc atc ttc       48
Met Ala Ser Ser Leu Ser Tyr Arg Ile Tyr Lys Asn Ala Leu Ile Phe
-25                 -20                 -15                 -10

tct tct ctc ctg gcc gct gcc cag ggt cag cag att ggt acc tac cag       96
Ser Ser Leu Leu Ala Ala Ala Gln Gly Gln Gln Ile Gly Thr Tyr Gln
                -5                  -1  1               5

acg gag acc cat ccg cct ctg acc tgg cag aca tgc acc agc ggc ggc      144
Thr Glu Thr His Pro Pro Leu Thr Trp Gln Thr Cys Thr Ser Gly Gly
        10                  15                  20

agt tgc acg acc aac caa ggc tcc atc gtc ctc gat gcc aac tgg cgc      192
Ser Cys Thr Thr Asn Gln Gly Ser Ile Val Leu Asp Ala Asn Trp Arg
    25                  30                  35

tgg gtg cac gag gtc ggc agc acc acc aac tgc tac acc ggc aat acc      240
Trp Val His Glu Val Gly Ser Thr Thr Asn Cys Tyr Thr Gly Asn Thr
40                  45                  50                  55

tgg gac acc tcc atc tgc agc acg gat acg acc tgc gct cag caa tgt      288
Trp Asp Thr Ser Ile Cys Ser Thr Asp Thr Thr Cys Ala Gln Gln Cys
                60                  65                  70

gcc gtc gat ggt gcc gac tac gag ggc acc tat ggt atc acg acc agc      336
Ala Val Asp Gly Ala Asp Tyr Glu Gly Thr Tyr Gly Ile Thr Thr Ser
            75                  80                  85

ggc agc cag gtc cgc atc aac ttc gtc acc aac aac tcg aac gga aag      384
Gly Ser Gln Val Arg Ile Asn Phe Val Thr Asn Asn Ser Asn Gly Lys
        90                  95                  100

aac gtc ggc gcg cgt gtc tac atg atg gcg gac aac acc cac tac caa      432
Asn Val Gly Ala Arg Val Tyr Met Met Ala Asp Asn Thr His Tyr Gln
    105                 110                 115

att tac cag ctg ctg aac cag gag ttc acc ttt gat gtc gac gtg tcc      480
Ile Tyr Gln Leu Leu Asn Gln Glu Phe Thr Phe Asp Val Asp Val Ser
120                 125                 130                 135

aac ctg cct tgc ggc ctc aac ggt gcc ctc tac ttt gtg gtc atg gac      528
Asn Leu Pro Cys Gly Leu Asn Gly Ala Leu Tyr Phe Val Val Met Asp
                140                 145                 150

gcc gat ggt ggt gtc tcc aag tat ccc aac aac aag gct ggt gcc cag      576
Ala Asp Gly Gly Val Ser Lys Tyr Pro Asn Asn Lys Ala Gly Ala Gln
            155                 160                 165

tac ggt gtc ggt tac tgc gac tcc cag tgt ccc aga gac ctc aaa ttc      624
Tyr Gly Val Gly Tyr Cys Asp Ser Gln Cys Pro Arg Asp Leu Lys Phe
        170                 175                 180

atc cag gga cag gcc aac gtc gag ggc tgg caa ccg tcg tcc aac aac      672
Ile Gln Gly Gln Ala Asn Val Glu Gly Trp Gln Pro Ser Ser Asn Asn
    185                 190                 195

gcc aat acc ggc ctg ggc aac cac ggc tcc tgc tgt gct gaa ctg gac      720
Ala Asn Thr Gly Leu Gly Asn His Gly Ser Cys Cys Ala Glu Leu Asp
200                 205                 210                 215

gtc tgg gag tcg aac agc atc tcc cag gcc ctc act ccc cac ccc tgc      768
Val Trp Glu Ser Asn Ser Ile Ser Gln Ala Leu Thr Pro His Pro Cys
                220                 225                 230

gac act ccc acc aat acc ctg tgc acc ggt gat agc tgc ggt ggc aca      816
Asp Thr Pro Thr Asn Thr Leu Cys Thr Gly Asp Ser Cys Gly Gly Thr
            235                 240                 245

tac agc agc aac cgt tat gcg ggc act tgc gat cct gac ggc tgc gat      864
Tyr Ser Ser Asn Arg Tyr Ala Gly Thr Cys Asp Pro Asp Gly Cys Asp
        250                 255                 260
```

```
ttc aac ccc tac cgc ttg ggc aac acc acc ttc tac ggt cct ggc aag      912
Phe Asn Pro Tyr Arg Leu Gly Asn Thr Thr Phe Tyr Gly Pro Gly Lys
    265                 270                 275

act att gac acc acc aaa ccc ttc acg gtt gtg acg cag ttc atc acg      960
Thr Ile Asp Thr Thr Lys Pro Phe Thr Val Val Thr Gln Phe Ile Thr
280                 285                 290                 295

gat gac ggc act tcc agc ggc acc ctg tcc gaa att agg cgt ttc tat     1008
Asp Asp Gly Thr Ser Ser Gly Thr Leu Ser Glu Ile Arg Arg Phe Tyr
                300                 305                 310

gtc cag aac ggt gtt acg tac gcc cag ccc aac tct gac gtc agc ggt     1056
Val Gln Asn Gly Val Thr Tyr Ala Gln Pro Asn Ser Asp Val Ser Gly
            315                 320                 325

atc agc ggc aat gcc atc aac agt gct tac tgc act gcg gag aac acc     1104
Ile Ser Gly Asn Ala Ile Asn Ser Ala Tyr Cys Thr Ala Glu Asn Thr
        330                 335                 340

gtc ttc aac ggt gcc ggc acc ttc gcg cag cac ggc ggc ctg gct ggc     1152
Val Phe Asn Gly Ala Gly Thr Phe Ala Gln His Gly Gly Leu Ala Gly
    345                 350                 355

atg agc cag gcc atg tcc acc ggt atg gtc ttg gtg atg agc ctg tgg     1200
Met Ser Gln Ala Met Ser Thr Gly Met Val Leu Val Met Ser Leu Trp
360                 365                 370                 375

gat gat tac tat gcc gac atg ctc tgg ctc gac agc acc tac cca acc     1248
Asp Asp Tyr Tyr Ala Asp Met Leu Trp Leu Asp Ser Thr Tyr Pro Thr
                380                 385                 390

aac gac acc gca agc acg ccc ggt gcg gtc cgt gga acc tgc tct acg     1296
Asn Asp Thr Ala Ser Thr Pro Gly Ala Val Arg Gly Thr Cys Ser Thr
            395                 400                 405

tcg tcc ggt gtc ccc agc cag gtc gaa tcc gcc agc ccg aac gcc tac     1344
Ser Ser Gly Val Pro Ser Gln Val Glu Ser Ala Ser Pro Asn Ala Tyr
        410                 415                 420

gtg acc tac tcg aac atc aag gtt ggt ccc att ggc tcg act ttc aac     1392
Val Thr Tyr Ser Asn Ile Lys Val Gly Pro Ile Gly Ser Thr Phe Asn
    425                 430                 435

tct ggc ggc tct ggc tct ggc agc agc tcc agc act acc acg acc act     1440
Ser Gly Gly Ser Gly Ser Gly Ser Ser Ser Ser Thr Thr Thr Thr Thr
440                 445                 450                 455

cac gcc agc acc acg acg acg tcc tcc gcc tcg tct acg gga act ggc     1488
His Ala Ser Thr Thr Thr Thr Ser Ser Ala Ser Ser Thr Gly Thr Gly
                460                 465                 470

gtg gcc caa cac tgg ggc cag tgt ggt gga cag ggc tgg acc ggc cca     1536
Val Ala Gln His Trp Gly Gln Cys Gly Gly Gln Gly Trp Thr Gly Pro
            475                 480                 485

aca acc tgc gtt tcc ccg tac act tgc cag gag ctg aac ccg tac tac     1584
Thr Thr Cys Val Ser Pro Tyr Thr Cys Gln Glu Leu Asn Pro Tyr Tyr
        490                 495                 500

tac cag tgt ctg tag                                                 1599
Tyr Gln Cys Leu
    505


<210> SEQ ID NO 44
<211> LENGTH: 532
<212> TYPE: PRT
<213> ORGANISM: Talaromyces leycettanus

<400> SEQUENCE: 44

Met Ala Ser Ser Leu Ser Tyr Arg Ile Tyr Lys Asn Ala Leu Ile Phe
-25                 -20                 -15                 -10

Ser Ser Leu Leu Ala Ala Ala Gln Gly Gln Gln Ile Gly Thr Tyr Gln
                -5                  -1  1               5

Thr Glu Thr His Pro Pro Leu Thr Trp Gln Thr Cys Thr Ser Gly Gly
```

```
        10                  15                  20

Ser Cys Thr Thr Asn Gln Gly Ser Ile Val Leu Asp Ala Asn Trp Arg
    25                  30                  35

Trp Val His Glu Val Gly Ser Thr Thr Asn Cys Tyr Thr Gly Asn Thr
40                  45                  50                  55

Trp Asp Thr Ser Ile Cys Ser Thr Asp Thr Thr Cys Ala Gln Gln Cys
                60                  65                  70

Ala Val Asp Gly Ala Asp Tyr Glu Gly Thr Tyr Gly Ile Thr Thr Ser
            75                  80                  85

Gly Ser Gln Val Arg Ile Asn Phe Val Thr Asn Asn Ser Asn Gly Lys
        90                  95                  100

Asn Val Gly Ala Arg Val Tyr Met Met Ala Asp Asn Thr His Tyr Gln
    105                 110                 115

Ile Tyr Gln Leu Leu Asn Gln Glu Phe Thr Phe Asp Val Asp Val Ser
120                 125                 130                 135

Asn Leu Pro Cys Gly Leu Asn Gly Ala Leu Tyr Phe Val Val Met Asp
                140                 145                 150

Ala Asp Gly Gly Val Ser Lys Tyr Pro Asn Asn Lys Ala Gly Ala Gln
            155                 160                 165

Tyr Gly Val Gly Tyr Cys Asp Ser Gln Cys Pro Arg Asp Leu Lys Phe
        170                 175                 180

Ile Gln Gly Gln Ala Asn Val Glu Gly Trp Gln Pro Ser Ser Asn Asn
    185                 190                 195

Ala Asn Thr Gly Leu Gly Asn His Gly Ser Cys Cys Ala Glu Leu Asp
200                 205                 210                 215

Val Trp Glu Ser Asn Ser Ile Ser Gln Ala Leu Thr Pro His Pro Cys
                220                 225                 230

Asp Thr Pro Thr Asn Thr Leu Cys Thr Gly Asp Ser Cys Gly Gly Thr
            235                 240                 245

Tyr Ser Ser Asn Arg Tyr Ala Gly Thr Cys Asp Pro Asp Gly Cys Asp
        250                 255                 260

Phe Asn Pro Tyr Arg Leu Gly Asn Thr Thr Phe Tyr Gly Pro Gly Lys
    265                 270                 275

Thr Ile Asp Thr Thr Lys Pro Phe Thr Val Val Thr Gln Phe Ile Thr
280                 285                 290                 295

Asp Asp Gly Thr Ser Ser Gly Thr Leu Ser Glu Ile Arg Arg Phe Tyr
                300                 305                 310

Val Gln Asn Gly Val Thr Tyr Ala Gln Pro Asn Ser Asp Val Ser Gly
            315                 320                 325

Ile Ser Gly Asn Ala Ile Asn Ser Ala Tyr Cys Thr Ala Glu Asn Thr
        330                 335                 340

Val Phe Asn Gly Ala Gly Thr Phe Ala Gln His Gly Gly Leu Ala Gly
    345                 350                 355

Met Ser Gln Ala Met Ser Thr Gly Met Val Leu Val Met Ser Leu Trp
360                 365                 370                 375

Asp Asp Tyr Tyr Ala Asp Met Leu Trp Leu Asp Ser Thr Tyr Pro Thr
                380                 385                 390

Asn Asp Thr Ala Ser Thr Pro Gly Ala Val Arg Gly Thr Cys Ser Thr
            395                 400                 405

Ser Ser Gly Val Pro Ser Gln Val Glu Ser Ala Ser Pro Asn Ala Tyr
        410                 415                 420

Val Thr Tyr Ser Asn Ile Lys Val Gly Pro Ile Gly Ser Thr Phe Asn
    425                 430                 435
```

```
Ser Gly Gly Ser Gly Ser Gly Ser Ser Ser Ser Thr Thr Thr Thr Thr
440                 445                 450                 455

His Ala Ser Thr Thr Thr Thr Ser Ser Ala Ser Ser Thr Gly Thr Gly
                460                 465                 470

Val Ala Gln His Trp Gly Gln Cys Gly Gly Gln Gly Trp Thr Gly Pro
            475                 480                 485

Thr Thr Cys Val Ser Pro Tyr Thr Cys Gln Glu Leu Asn Pro Tyr Tyr
        490                 495                 500

Tyr Gln Cys Leu
    505


<210> SEQ ID NO 45
<211> LENGTH: 1507
<212> TYPE: DNA
<213> ORGANISM: Talaromyces byssochlamydoides
<220> FEATURE:
<221> NAME/KEY: exon
<222> LOCATION: (1)..(603)
<220> FEATURE:
<221> NAME/KEY: CDS
<222> LOCATION: (1)..(603)
<220> FEATURE:
<221> NAME/KEY: sig_peptide
<222> LOCATION: (1)..(18)
<220> FEATURE:
<221> NAME/KEY: mat_peptide
<222> LOCATION: (55)..(1504)
<220> FEATURE:
<221> NAME/KEY: Intron
<222> LOCATION: (604)..(667)
<220> FEATURE:
<221> NAME/KEY: exon
<222> LOCATION: (668)..(1235)
<220> FEATURE:
<221> NAME/KEY: CDS
<222> LOCATION: (668)..(1235)
<220> FEATURE:
<221> NAME/KEY: Intron
<222> LOCATION: (1236)..(1310)
<220> FEATURE:
<221> NAME/KEY: exon
<222> LOCATION: (1311)..(1504)
<220> FEATURE:
<221> NAME/KEY: CDS
<222> LOCATION: (1311)..(1504)

<400> SEQUENCE: 45

atg ttt cga cgg gct ctt ttc ctg tcc tct tcc gcc ttc ctt gct gtc       48
Met Phe Arg Arg Ala Leu Phe Leu Ser Ser Ser Ala Phe Leu Ala Val
            -15                 -10                 -5

aaa gcc cag cag atc ggc acg gtc agt ccg gag aac cat ccg ccc ctg       96
Lys Ala Gln Gln Ile Gly Thr Val Ser Pro Glu Asn His Pro Pro Leu
    -1  1               5                   10

gca tgg gag cag tgc act gcc cct ggg agt tgc acg act gtg aat ggt      144
Ala Trp Glu Gln Cys Thr Ala Pro Gly Ser Cys Thr Thr Val Asn Gly
15                  20                  25                  30

gcg gtc gtc ctt gat gcg aac tgg cgt tgg gtc cac aat gtt ggg gga      192
Ala Val Val Leu Asp Ala Asn Trp Arg Trp Val His Asn Val Gly Gly
                35                  40                  45

tac acc aac tgc tac act ggc aat acc tgg gac acc acg tac tgc cct      240
Tyr Thr Asn Cys Tyr Thr Gly Asn Thr Trp Asp Thr Thr Tyr Cys Pro
            50                  55                  60

gac gac gtg acc tgc gca gag aat tgt gcg ctg gat ggc gca gat tac      288
Asp Asp Val Thr Cys Ala Glu Asn Cys Ala Leu Asp Gly Ala Asp Tyr
        65                  70                  75

gag ggc acc tac ggc gtg acc acc tcg ggc agc tcc ctg aag ctc gat      336
```

-continued

```
Glu Gly Thr Tyr Gly Val Thr Thr Ser Gly Ser Ser Leu Lys Leu Asp
    80                  85                  90

ttc gtc acc ggg tct aac gtc gga tct cgt ctc tac ctg ttg gag aat      384
Phe Val Thr Gly Ser Asn Val Gly Ser Arg Leu Tyr Leu Leu Glu Asn
95                  100                 105                 110

gat tcg acc tat cag atc ttc aag ctt ctg aac cag gaa ttc acc ttt      432
Asp Ser Thr Tyr Gln Ile Phe Lys Leu Leu Asn Gln Glu Phe Thr Phe
                115                 120                 125

gac gtc gac gtt tcc aat ctt ccg tgc gga tta aac ggc gct ctg tac      480
Asp Val Asp Val Ser Asn Leu Pro Cys Gly Leu Asn Gly Ala Leu Tyr
            130                 135                 140

ctt gtt acc atg gct gct gac ggc ggg gtg tct cag tac ccg aat aac      528
Leu Val Thr Met Ala Ala Asp Gly Gly Val Ser Gln Tyr Pro Asn Asn
        145                 150                 155

aag gcc ggc gca gcg tat gga acc ggt tat tgc gat tcc cag tgt cca      576
Lys Ala Gly Ala Ala Tyr Gly Thr Gly Tyr Cys Asp Ser Gln Cys Pro
    160                 165                 170

agg gac ttg aag ttt atc gat ggc cag gtatgtagag ctgtaatcac            623
Arg Asp Leu Lys Phe Ile Asp Gly Gln
175                 180

ccatgttgtg aaatcactct cctactgaca tggtcgattt atag gcc aac gtt gag     679
                                                 Ala Asn Val Glu
                                                     185

ggc tgg cag ccg tct tcg aac aac gcc aat aca ggt att ggc aac cat      727
Gly Trp Gln Pro Ser Ser Asn Asn Ala Asn Thr Gly Ile Gly Asn His
        190                 195                 200

ggc tcc tgc tgt gcg gag atg gat atc tgg gaa gcc aac agc atc tcc      775
Gly Ser Cys Cys Ala Glu Met Asp Ile Trp Glu Ala Asn Ser Ile Ser
    205                 210                 215

aat gcg gtg act ccg cac cca tgc gac aca ccc ggc cag aca atg tgc      823
Asn Ala Val Thr Pro His Pro Cys Asp Thr Pro Gly Gln Thr Met Cys
220                 225                 230                 235

gag ggg aac gac tgt ggt ggc acg tat tcc acc aat cgc tat gca ggc      871
Glu Gly Asn Asp Cys Gly Gly Thr Tyr Ser Thr Asn Arg Tyr Ala Gly
                240                 245                 250

acc tgc gat cct gac ggc tgc gac ttc aac ccc tac cgc atg ggc aac      919
Thr Cys Asp Pro Asp Gly Cys Asp Phe Asn Pro Tyr Arg Met Gly Asn
            255                 260                 265

cat tct ttc tac ggc cct ggg gag att gtc gat act acc cag ccc ttc      967
His Ser Phe Tyr Gly Pro Gly Glu Ile Val Asp Thr Thr Gln Pro Phe
        270                 275                 280

act gtc gtg aca cag ttc ctt acc gat gat ggc acg gat act ggc act     1015
Thr Val Val Thr Gln Phe Leu Thr Asp Asp Gly Thr Asp Thr Gly Thr
    285                 290                 295

ctc agc gag atc aaa cgc ttc tac gtc caa aac ggg aaa gtc att cct     1063
Leu Ser Glu Ile Lys Arg Phe Tyr Val Gln Asn Gly Lys Val Ile Pro
300                 305                 310                 315

cag ccg aac tcc gac att gcc ggc gtg act ggc aac tcg atc acc agc     1111
Gln Pro Asn Ser Asp Ile Ala Gly Val Thr Gly Asn Ser Ile Thr Ser
                320                 325                 330

gag ttt tgc gat gcc cag aag acg gct ttc ggc gac att aac aac ttt     1159
Glu Phe Cys Asp Ala Gln Lys Thr Ala Phe Gly Asp Ile Asn Asn Phe
            335                 340                 345

gat aca cac ggc ggt ctg gcc agt atg gga gct gcg ctg cag cag ggt     1207
Asp Thr His Gly Gly Leu Ala Ser Met Gly Ala Ala Leu Gln Gln Gly
        350                 355                 360

atg gtt ctg gtg atg agt ctg tgg gac g gtaggtcctt gggagacacc         1255
Met Val Leu Val Met Ser Leu Trp Asp
    365                 370
```

```
cggacgttct atatcaacca gaactgccag aactgacgaa ttaaaacact tttag at      1312
                                                            Asp

tac gcg gca aac atg ctg tgg ttg gac agc att tat cca aca aat gca      1360
Tyr Ala Ala Asn Met Leu Trp Leu Asp Ser Ile Tyr Pro Thr Asn Ala
    375                 380                 385

tct gct agc act cct ggt gct gct cgt gga acc tgt tcg acg agc tcc      1408
Ser Ala Ser Thr Pro Gly Ala Ala Arg Gly Thr Cys Ser Thr Ser Ser
390                 395                 400                 405

ggt gtc cca tcg caa gtc gag tcg cag agc ccc aac gcc tac gtg acg      1456
Gly Val Pro Ser Gln Val Glu Ser Gln Ser Pro Asn Ala Tyr Val Thr
                410                 415                 420

tac tcc aac att aaa gtt gga cca atc aac tcg acc ttc acc act tcg      1504
Tyr Ser Asn Ile Lys Val Gly Pro Ile Asn Ser Thr Phe Thr Thr Ser
            425                 430                 435

taa                                                                  1507


<210> SEQ ID NO 46
<211> LENGTH: 455
<212> TYPE: PRT
<213> ORGANISM: Talaromyces byssochlamydoides

<400> SEQUENCE: 46

Met Phe Arg Arg Ala Leu Phe Leu Ser Ser Ser Ala Phe Leu Ala Val
            -15                 -10                 -5

Lys Ala Gln Gln Ile Gly Thr Val Ser Pro Glu Asn His Pro Pro Leu
    -1  1               5                   10

Ala Trp Glu Gln Cys Thr Ala Pro Gly Ser Cys Thr Thr Val Asn Gly
15                  20                  25                  30

Ala Val Val Leu Asp Ala Asn Trp Arg Trp Val His Asn Val Gly Gly
                35                  40                  45

Tyr Thr Asn Cys Tyr Thr Gly Asn Thr Trp Asp Thr Thr Tyr Cys Pro
            50                  55                  60

Asp Asp Val Thr Cys Ala Glu Asn Cys Ala Leu Asp Gly Ala Asp Tyr
        65                  70                  75

Glu Gly Thr Tyr Gly Val Thr Thr Ser Gly Ser Ser Leu Lys Leu Asp
    80                  85                  90

Phe Val Thr Gly Ser Asn Val Gly Ser Arg Leu Tyr Leu Leu Glu Asn
95                  100                 105                 110

Asp Ser Thr Tyr Gln Ile Phe Lys Leu Leu Asn Gln Glu Phe Thr Phe
                115                 120                 125

Asp Val Asp Val Ser Asn Leu Pro Cys Gly Leu Asn Gly Ala Leu Tyr
            130                 135                 140

Leu Val Thr Met Ala Ala Asp Gly Gly Val Ser Gln Tyr Pro Asn Asn
        145                 150                 155

Lys Ala Gly Ala Ala Tyr Gly Thr Gly Tyr Cys Asp Ser Gln Cys Pro
    160                 165                 170

Arg Asp Leu Lys Phe Ile Asp Gly Gln Ala Asn Val Glu Gly Trp Gln
175                 180                 185                 190

Pro Ser Ser Asn Asn Ala Asn Thr Gly Ile Gly Asn His Gly Ser Cys
                195                 200                 205

Cys Ala Glu Met Asp Ile Trp Glu Ala Asn Ser Ile Ser Asn Ala Val
            210                 215                 220

Thr Pro His Pro Cys Asp Thr Pro Gly Gln Thr Met Cys Glu Gly Asn
        225                 230                 235

Asp Cys Gly Gly Thr Tyr Ser Thr Asn Arg Tyr Ala Gly Thr Cys Asp
    240                 245                 250
```

```
Pro Asp Gly Cys Asp Phe Asn Pro Tyr Arg Met Gly Asn His Ser Phe
255                 260                 265                 270

Tyr Gly Pro Gly Glu Ile Val Asp Thr Thr Gln Pro Phe Thr Val Val
                275                 280                 285

Thr Gln Phe Leu Thr Asp Asp Gly Thr Asp Thr Gly Thr Leu Ser Glu
            290                 295                 300

Ile Lys Arg Phe Tyr Val Gln Asn Gly Lys Val Ile Pro Gln Pro Asn
        305                 310                 315

Ser Asp Ile Ala Gly Val Thr Gly Asn Ser Ile Thr Ser Glu Phe Cys
    320                 325                 330

Asp Ala Gln Lys Thr Ala Phe Gly Asp Ile Asn Asn Phe Asp Thr His
335                 340                 345                 350

Gly Gly Leu Ala Ser Met Gly Ala Ala Leu Gln Gln Gly Met Val Leu
                355                 360                 365

Val Met Ser Leu Trp Asp Asp Tyr Ala Ala Asn Met Leu Trp Leu Asp
            370                 375                 380

Ser Ile Tyr Pro Thr Asn Ala Ser Ala Ser Thr Pro Gly Ala Ala Arg
        385                 390                 395

Gly Thr Cys Ser Thr Ser Ser Gly Val Pro Ser Gln Val Glu Ser Gln
    400                 405                 410

Ser Pro Asn Ala Tyr Val Thr Tyr Ser Asn Ile Lys Val Gly Pro Ile
415                 420                 425                 430

Asn Ser Thr Phe Thr Thr Ser
                435


<210> SEQ ID NO 47
<211> LENGTH: 1353
<212> TYPE: DNA
<213> ORGANISM: Myceliophthora thermophila
<220> FEATURE:
<221> NAME/KEY: sig_peptide
<222> LOCATION: (1)..(20)
<220> FEATURE:
<221> NAME/KEY: CDS
<222> LOCATION: (1)..(1350)
<220> FEATURE:
<221> NAME/KEY: mat_peptide
<222> LOCATION: (61)..(1350)

<400> SEQUENCE: 47

atg aag cag tac ctc cag tac ctc gcg gcg acc ctg ccc ctg gtg ggc       48
Met Lys Gln Tyr Leu Gln Tyr Leu Ala Ala Thr Leu Pro Leu Val Gly
-20                 -15                 -10                 -5

ctg gcc acg gcc cag cag gcg ggt aac ctg cag acc gag act cac ccc       96
Leu Ala Thr Ala Gln Gln Ala Gly Asn Leu Gln Thr Glu Thr His Pro
            -1  1               5                   10

agg ctc act tgg tcc aag tgc acg gcc ccg gga tcc tgc caa cag gtc      144
Arg Leu Thr Trp Ser Lys Cys Thr Ala Pro Gly Ser Cys Gln Gln Val
        15                  20                  25

aac ggc gag gtc gtc atc gac tcc aac tgg cgc tgg gtg cac gac gag      192
Asn Gly Glu Val Val Ile Asp Ser Asn Trp Arg Trp Val His Asp Glu
    30                  35                  40

aac gcg cag aac tgc tac gac ggc aac cag tgg acc aac gct tgc agc      240
Asn Ala Gln Asn Cys Tyr Asp Gly Asn Gln Trp Thr Asn Ala Cys Ser
45                  50                  55                  60

tct gcc acc gac tgc gcc gag aat tgc gcg ctc gag ggt gcc gac tac      288
Ser Ala Thr Asp Cys Ala Glu Asn Cys Ala Leu Glu Gly Ala Asp Tyr
                65                  70                  75

cag ggc acc tat ggc gcc tcg acc agc ggc aat gcc ctg acg ctc acc      336
```

-continued

```
Gln Gly Thr Tyr Gly Ala Ser Thr Ser Gly Asn Ala Leu Thr Leu Thr
            80                  85                  90

ttc gtc act aag cac gag tac ggc acc aac att ggc tcg cgc ctc tac      384
Phe Val Thr Lys His Glu Tyr Gly Thr Asn Ile Gly Ser Arg Leu Tyr
        95                  100                 105

ctc atg aac ggc gcg aac aag tac cag atg ttc acc ctc aag ggc aac      432
Leu Met Asn Gly Ala Asn Lys Tyr Gln Met Phe Thr Leu Lys Gly Asn
    110                 115                 120

gag ctg gcc ttc gac gtc gac ctc tcg gcc gtc gag tgc ggc ctc aac      480
Glu Leu Ala Phe Asp Val Asp Leu Ser Ala Val Glu Cys Gly Leu Asn
125                 130                 135                 140

agc gcc ctc tac ttc gtg gcc atg gag gag gat ggc ggt gtg tcg agc      528
Ser Ala Leu Tyr Phe Val Ala Met Glu Glu Asp Gly Gly Val Ser Ser
                145                 150                 155

tac ccg acc aac acg gcc ggt gct aag ttc ggc act ggg tac tgc gac      576
Tyr Pro Thr Asn Thr Ala Gly Ala Lys Phe Gly Thr Gly Tyr Cys Asp
            160                 165                 170

gcc caa tgc gca cgc gac ctc aag ttc gtc ggc ggc aag ggc aac atc      624
Ala Gln Cys Ala Arg Asp Leu Lys Phe Val Gly Gly Lys Gly Asn Ile
        175                 180                 185

gag ggc tgg aag ccg tcc acc aac gat gcc aat gcc ggt gtc ggt cct      672
Glu Gly Trp Lys Pro Ser Thr Asn Asp Ala Asn Ala Gly Val Gly Pro
    190                 195                 200

tat ggc ggg tgc tgc gct gag atc gac gtc tgg gag tcg aac aag tat      720
Tyr Gly Gly Cys Cys Ala Glu Ile Asp Val Trp Glu Ser Asn Lys Tyr
205                 210                 215                 220

gct ttc gct ttc acc ccg cac ggt tgc gag aac cct aaa tac cac gtc      768
Ala Phe Ala Phe Thr Pro His Gly Cys Glu Asn Pro Lys Tyr His Val
                225                 230                 235

tgc gag acc acc aac tgc ggt ggc acc tac tcc gag gac cgc ttc gct      816
Cys Glu Thr Thr Asn Cys Gly Gly Thr Tyr Ser Glu Asp Arg Phe Ala
            240                 245                 250

ggt gac tgc gat gcc aac ggc tgc gac tac aac ccc tac cgc atg ggc      864
Gly Asp Cys Asp Ala Asn Gly Cys Asp Tyr Asn Pro Tyr Arg Met Gly
        255                 260                 265

aac cag gac ttc tac ggt ccc ggc ttg acg gtc gat acc agc aag aag      912
Asn Gln Asp Phe Tyr Gly Pro Gly Leu Thr Val Asp Thr Ser Lys Lys
    270                 275                 280

ttc acc gtc gtc agc cag ttc gag gag aac aag ctc acc cag ttc ttc      960
Phe Thr Val Val Ser Gln Phe Glu Glu Asn Lys Leu Thr Gln Phe Phe
285                 290                 295                 300

gtc cag gac ggc aag aag att gag atc ccc ggc ccc aag gtc gag ggc     1008
Val Gln Asp Gly Lys Lys Ile Glu Ile Pro Gly Pro Lys Val Glu Gly
                305                 310                 315

atc gat gcg gac agc gcc gct atc acc cct gag ctg tgc agt gcc ctg     1056
Ile Asp Ala Asp Ser Ala Ala Ile Thr Pro Glu Leu Cys Ser Ala Leu
            320                 325                 330

ttc aag gcc ttc gat gac cgt gac cgc ttc tcg gag gtt ggc ggc ttc     1104
Phe Lys Ala Phe Asp Asp Arg Asp Arg Phe Ser Glu Val Gly Gly Phe
        335                 340                 345

gat gcc atc aac acg gcc ctc agc act ccc atg gtc ctc gtc atg tcc     1152
Asp Ala Ile Asn Thr Ala Leu Ser Thr Pro Met Val Leu Val Met Ser
    350                 355                 360

atc tgg gat gat cac tac gcc aat atg ctc tgg ctc gac tcg agc tac     1200
Ile Trp Asp Asp His Tyr Ala Asn Met Leu Trp Leu Asp Ser Ser Tyr
365                 370                 375                 380

ccc cct gag aag gct ggc cag cct ggc ggt gac cgt ggc ccg tgt cct     1248
Pro Pro Glu Lys Ala Gly Gln Pro Gly Gly Asp Arg Gly Pro Cys Pro
                385                 390                 395
```

```
cag gac tct ggc gtc ccg gcc gac gtt gag gct cag tac cct aat gcc     1296
Gln Asp Ser Gly Val Pro Ala Asp Val Glu Ala Gln Tyr Pro Asn Ala
            400                 405                 410

aag gtc atc tgg tcc aac atc cgc ttc ggc ccc atc ggc tcg act gtc     1344
Lys Val Ile Trp Ser Asn Ile Arg Phe Gly Pro Ile Gly Ser Thr Val
        415                 420                 425

aac gtc taa                                                         1353
Asn Val
    430


<210> SEQ ID NO 48
<211> LENGTH: 450
<212> TYPE: PRT
<213> ORGANISM: Myceliophthora thermophila

<400> SEQUENCE: 48

Met Lys Gln Tyr Leu Gln Tyr Leu Ala Ala Thr Leu Pro Leu Val Gly
-20                 -15                 -10                 -5

Leu Ala Thr Ala Gln Gln Ala Gly Asn Leu Gln Thr Glu Thr His Pro
            -1  1               5                   10

Arg Leu Thr Trp Ser Lys Cys Thr Ala Pro Gly Ser Cys Gln Gln Val
        15                  20                  25

Asn Gly Glu Val Val Ile Asp Ser Asn Trp Arg Trp Val His Asp Glu
    30                  35                  40

Asn Ala Gln Asn Cys Tyr Asp Gly Asn Gln Trp Thr Asn Ala Cys Ser
45                  50                  55                  60

Ser Ala Thr Asp Cys Ala Glu Asn Cys Ala Leu Glu Gly Ala Asp Tyr
                65                  70                  75

Gln Gly Thr Tyr Gly Ala Ser Thr Ser Gly Asn Ala Leu Thr Leu Thr
            80                  85                  90

Phe Val Thr Lys His Glu Tyr Gly Thr Asn Ile Gly Ser Arg Leu Tyr
        95                  100                 105

Leu Met Asn Gly Ala Asn Lys Tyr Gln Met Phe Thr Leu Lys Gly Asn
    110                 115                 120

Glu Leu Ala Phe Asp Val Asp Leu Ser Ala Val Glu Cys Gly Leu Asn
125                 130                 135                 140

Ser Ala Leu Tyr Phe Val Ala Met Glu Glu Asp Gly Gly Val Ser Ser
                145                 150                 155

Tyr Pro Thr Asn Thr Ala Gly Ala Lys Phe Gly Thr Gly Tyr Cys Asp
            160                 165                 170

Ala Gln Cys Ala Arg Asp Leu Lys Phe Val Gly Gly Lys Gly Asn Ile
        175                 180                 185

Glu Gly Trp Lys Pro Ser Thr Asn Asp Ala Asn Ala Gly Val Gly Pro
    190                 195                 200

Tyr Gly Gly Cys Cys Ala Glu Ile Asp Val Trp Glu Ser Asn Lys Tyr
205                 210                 215                 220

Ala Phe Ala Phe Thr Pro His Gly Cys Glu Asn Pro Lys Tyr His Val
                225                 230                 235

Cys Glu Thr Thr Asn Cys Gly Gly Thr Tyr Ser Glu Asp Arg Phe Ala
            240                 245                 250

Gly Asp Cys Asp Ala Asn Gly Cys Asp Tyr Asn Pro Tyr Arg Met Gly
        255                 260                 265

Asn Gln Asp Phe Tyr Gly Pro Gly Leu Thr Val Asp Thr Ser Lys Lys
    270                 275                 280

Phe Thr Val Val Ser Gln Phe Glu Glu Asn Lys Leu Thr Gln Phe Phe
285                 290                 295                 300
```

```
Val Gln Asp Gly Lys Lys Ile Glu Ile Pro Gly Pro Lys Val Glu Gly
                305                 310                 315

Ile Asp Ala Asp Ser Ala Ala Ile Thr Pro Glu Leu Cys Ser Ala Leu
            320                 325                 330

Phe Lys Ala Phe Asp Asp Arg Asp Arg Phe Ser Glu Val Gly Gly Phe
        335                 340                 345

Asp Ala Ile Asn Thr Ala Leu Ser Thr Pro Met Val Leu Val Met Ser
    350                 355                 360

Ile Trp Asp Asp His Tyr Ala Asn Met Leu Trp Leu Asp Ser Ser Tyr
365                 370                 375                 380

Pro Pro Glu Lys Ala Gly Gln Pro Gly Gly Asp Arg Gly Pro Cys Pro
                385                 390                 395

Gln Asp Ser Gly Val Pro Ala Asp Val Glu Ala Gln Tyr Pro Asn Ala
            400                 405                 410

Lys Val Ile Trp Ser Asn Ile Arg Phe Gly Pro Ile Gly Ser Thr Val
        415                 420                 425

Asn Val
    430


<210> SEQ ID NO 49
<211> LENGTH: 1590
<212> TYPE: DNA
<213> ORGANISM: Chaetomium thermophilum
<220> FEATURE:
<221> NAME/KEY: sig_peptide
<222> LOCATION: (1)..(18)
<220> FEATURE:
<221> NAME/KEY: CDS
<222> LOCATION: (1)..(1587)
<220> FEATURE:
<221> NAME/KEY: mat_peptide
<222> LOCATION: (55)..(1587)

<400> SEQUENCE: 49

atg atg tac aag aag ttc gcc gct ctc gcc gcc ctc gtg gct ggc gcc       48
Met Met Tyr Lys Lys Phe Ala Ala Leu Ala Ala Leu Val Ala Gly Ala
            -15                 -10                 -5

gcc gcc cag cag gct tgc tcc ctc acc act gag acc cac ccc aga ctc       96
Ala Ala Gln Gln Ala Cys Ser Leu Thr Thr Glu Thr His Pro Arg Leu
    -1  1               5                   10

act tgg aag cgc tgc acc tct ggc ggc aac tgc tcg acc gtg aac ggc      144
Thr Trp Lys Arg Cys Thr Ser Gly Gly Asn Cys Ser Thr Val Asn Gly
15                  20                  25                  30

gcc gtc acc atc gat gcc aac tgg cgc tgg act cac acc gtt tcc ggc      192
Ala Val Thr Ile Asp Ala Asn Trp Arg Trp Thr His Thr Val Ser Gly
                35                  40                  45

tcg acc aac tgc tac acc ggc aac gag tgg gat acc tcc atc tgc tct      240
Ser Thr Asn Cys Tyr Thr Gly Asn Glu Trp Asp Thr Ser Ile Cys Ser
            50                  55                  60

gat ggc aag agc tgc gcc cag acc tgc tgc gtc gac ggc gct gac tac      288
Asp Gly Lys Ser Cys Ala Gln Thr Cys Cys Val Asp Gly Ala Asp Tyr
        65                  70                  75

tct tcg acc tat ggt atc acc acc agc ggt gac tcc ctg aac ctc aag      336
Ser Ser Thr Tyr Gly Ile Thr Thr Ser Gly Asp Ser Leu Asn Leu Lys
    80                  85                  90

ttc gtc acc aag cac cag tac ggc acc aat gtc ggc tct cgt gtc tac      384
Phe Val Thr Lys His Gln Tyr Gly Thr Asn Val Gly Ser Arg Val Tyr
95                  100                 105                 110

ctg atg gag aac gac acc aag tac cag atg ttc gag ctc ctc ggc aac      432
Leu Met Glu Asn Asp Thr Lys Tyr Gln Met Phe Glu Leu Leu Gly Asn
```

```
            115                 120                 125

gag ttc acc ttc gat gtc gat gtc tct aac ctg ggc tgc ggt ctc aac      480
Glu Phe Thr Phe Asp Val Asp Val Ser Asn Leu Gly Cys Gly Leu Asn
                130                 135                 140

ggt gcc ctc tac ttc gtc tcc atg gac gct gat ggt ggt atg agc aag      528
Gly Ala Leu Tyr Phe Val Ser Met Asp Ala Asp Gly Gly Met Ser Lys
        145                 150                 155

tac tct ggc aac aag gct ggc gcc aag tac ggt acc ggc tac tgc gat      576
Tyr Ser Gly Asn Lys Ala Gly Ala Lys Tyr Gly Thr Gly Tyr Cys Asp
    160                 165                 170

gct cag tgc ccg cgc gac ctt aag ttc atc aac ggc gag gcc aac att      624
Ala Gln Cys Pro Arg Asp Leu Lys Phe Ile Asn Gly Glu Ala Asn Ile
175                 180                 185                 190

gag aac tgg acc cct tcg acc aat gat gcc aac gcc ggt ttc ggc cgc      672
Glu Asn Trp Thr Pro Ser Thr Asn Asp Ala Asn Ala Gly Phe Gly Arg
                195                 200                 205

tat ggc agc tgc tgc tct gag atg gat atc tgg gag gcc aac aac atg      720
Tyr Gly Ser Cys Cys Ser Glu Met Asp Ile Trp Glu Ala Asn Asn Met
                210                 215                 220

gct act gcc ttc act cct cac cct tgc acc att atc ggc cag agc cgc      768
Ala Thr Ala Phe Thr Pro His Pro Cys Thr Ile Ile Gly Gln Ser Arg
        225                 230                 235

tgc gag ggc aac agc tgc ggt ggc acc tac agc tct gag cgc tat gct      816
Cys Glu Gly Asn Ser Cys Gly Gly Thr Tyr Ser Ser Glu Arg Tyr Ala
    240                 245                 250

ggt gtt tgc gat cct gat ggc tgc gac ttc aac gcc tac cgc cag ggc      864
Gly Val Cys Asp Pro Asp Gly Cys Asp Phe Asn Ala Tyr Arg Gln Gly
255                 260                 265                 270

gac aag acc ttc tac ggc aag ggc atg acc gtc gac acc acc aag aag      912
Asp Lys Thr Phe Tyr Gly Lys Gly Met Thr Val Asp Thr Thr Lys Lys
                275                 280                 285

atg acc gtc gtc acc cag ttc cac aag aac tcg gct ggc gtc ctc agc      960
Met Thr Val Val Thr Gln Phe His Lys Asn Ser Ala Gly Val Leu Ser
                290                 295                 300

gag atc aag cgc ttc tac gtt cag gac ggc aag atc att gcc aac gcc     1008
Glu Ile Lys Arg Phe Tyr Val Gln Asp Gly Lys Ile Ile Ala Asn Ala
        305                 310                 315

gag tcc aag atc ccc ggc aac ccc ggc aac tcc atc acc cag gag tgg     1056
Glu Ser Lys Ile Pro Gly Asn Pro Gly Asn Ser Ile Thr Gln Glu Trp
    320                 325                 330

tgc gat gcc cag aag gtc gcc ttc ggt gac atc gat gac ttc aac cgc     1104
Cys Asp Ala Gln Lys Val Ala Phe Gly Asp Ile Asp Asp Phe Asn Arg
335                 340                 345                 350

aag ggc ggt atg gct cag atg agc aag gcc ctc gag ggc cct atg gtc     1152
Lys Gly Gly Met Ala Gln Met Ser Lys Ala Leu Glu Gly Pro Met Val
                355                 360                 365

ctg gtc atg tcc gtc tgg gat gac cac tac gcc aac atg ctc tgg ctc     1200
Leu Val Met Ser Val Trp Asp Asp His Tyr Ala Asn Met Leu Trp Leu
                370                 375                 380

gac tcg acc tac ccc atc gac aag gcc ggc acc ccc ggc gcc gag cgc     1248
Asp Ser Thr Tyr Pro Ile Asp Lys Ala Gly Thr Pro Gly Ala Glu Arg
        385                 390                 395

ggt gct tgc ccg acc acc tcc ggt gtc cct gcc gag att gag gcc cag     1296
Gly Ala Cys Pro Thr Thr Ser Gly Val Pro Ala Glu Ile Glu Ala Gln
    400                 405                 410

gtc ccc aac agc aac gtc atc ttc tcc aac atc cgc ttc ggc ccc atc     1344
Val Pro Asn Ser Asn Val Ile Phe Ser Asn Ile Arg Phe Gly Pro Ile
415                 420                 425                 430

ggc tcg acc gtc cct ggc ctc gac ggc agc act ccc agc aac ccg acc     1392
```

```
Gly Ser Thr Val Pro Gly Leu Asp Gly Ser Thr Pro Ser Asn Pro Thr
                435                 440                 445

gcc acc gtt gct cct ccc act tct acc acc agc gtg aga agc agc act      1440
Ala Thr Val Ala Pro Pro Thr Ser Thr Thr Ser Val Arg Ser Ser Thr
            450                 455                 460

act cag att tcc acc ccg act agc cag ccc ggc ggc tgc acc acc cag      1488
Thr Gln Ile Ser Thr Pro Thr Ser Gln Pro Gly Gly Cys Thr Thr Gln
        465                 470                 475

aag tgg ggc cag tgc ggt ggt atc ggc tac acc ggc tgc act aac tgc      1536
Lys Trp Gly Gln Cys Gly Gly Ile Gly Tyr Thr Gly Cys Thr Asn Cys
    480                 485                 490

gtt gct ggc act acc tgc act gag ctc aac ccc tgg tac agc cag tgc      1584
Val Ala Gly Thr Thr Cys Thr Glu Leu Asn Pro Trp Tyr Ser Gln Cys
495                 500                 505                 510

ctg taa                                                              1590
Leu


<210> SEQ ID NO 50
<211> LENGTH: 529
<212> TYPE: PRT
<213> ORGANISM: Chaetomium thermophilum

<400> SEQUENCE: 50

Met Met Tyr Lys Lys Phe Ala Ala Leu Ala Ala Leu Val Ala Gly Ala
            -15                 -10                 -5

Ala Ala Gln Gln Ala Cys Ser Leu Thr Thr Glu Thr His Pro Arg Leu
    -1  1               5                   10

Thr Trp Lys Arg Cys Thr Ser Gly Gly Asn Cys Ser Thr Val Asn Gly
15                  20                  25                  30

Ala Val Thr Ile Asp Ala Asn Trp Arg Trp Thr His Thr Val Ser Gly
                35                  40                  45

Ser Thr Asn Cys Tyr Thr Gly Asn Glu Trp Asp Thr Ser Ile Cys Ser
            50                  55                  60

Asp Gly Lys Ser Cys Ala Gln Thr Cys Cys Val Asp Gly Ala Asp Tyr
        65                  70                  75

Ser Ser Thr Tyr Gly Ile Thr Thr Ser Gly Asp Ser Leu Asn Leu Lys
    80                  85                  90

Phe Val Thr Lys His Gln Tyr Gly Thr Asn Val Gly Ser Arg Val Tyr
95                  100                 105                 110

Leu Met Glu Asn Asp Thr Lys Tyr Gln Met Phe Glu Leu Leu Gly Asn
                115                 120                 125

Glu Phe Thr Phe Asp Val Asp Val Ser Asn Leu Gly Cys Gly Leu Asn
            130                 135                 140

Gly Ala Leu Tyr Phe Val Ser Met Asp Ala Asp Gly Gly Met Ser Lys
        145                 150                 155

Tyr Ser Gly Asn Lys Ala Gly Ala Lys Tyr Gly Thr Gly Tyr Cys Asp
    160                 165                 170

Ala Gln Cys Pro Arg Asp Leu Lys Phe Ile Asn Gly Glu Ala Asn Ile
175                 180                 185                 190

Glu Asn Trp Thr Pro Ser Thr Asn Asp Ala Asn Ala Gly Phe Gly Arg
                195                 200                 205

Tyr Gly Ser Cys Cys Ser Glu Met Asp Ile Trp Glu Ala Asn Asn Met
            210                 215                 220

Ala Thr Ala Phe Thr Pro His Pro Cys Thr Ile Ile Gly Gln Ser Arg
        225                 230                 235

Cys Glu Gly Asn Ser Cys Gly Gly Thr Tyr Ser Ser Glu Arg Tyr Ala
```

```
    240                 245                 250

Gly Val Cys Asp Pro Asp Gly Cys Asp Phe Asn Ala Tyr Arg Gln Gly
255                 260                 265                 270

Asp Lys Thr Phe Tyr Gly Lys Gly Met Thr Val Asp Thr Thr Lys Lys
                275                 280                 285

Met Thr Val Val Thr Gln Phe His Lys Asn Ser Ala Gly Val Leu Ser
            290                 295                 300

Glu Ile Lys Arg Phe Tyr Val Gln Asp Gly Lys Ile Ile Ala Asn Ala
        305                 310                 315

Glu Ser Lys Ile Pro Gly Asn Pro Gly Asn Ser Ile Thr Gln Glu Trp
    320                 325                 330

Cys Asp Ala Gln Lys Val Ala Phe Gly Asp Ile Asp Asp Phe Asn Arg
335                 340                 345                 350

Lys Gly Gly Met Ala Gln Met Ser Lys Ala Leu Glu Gly Pro Met Val
                355                 360                 365

Leu Val Met Ser Val Trp Asp Asp His Tyr Ala Asn Met Leu Trp Leu
            370                 375                 380

Asp Ser Thr Tyr Pro Ile Asp Lys Ala Gly Thr Pro Gly Ala Glu Arg
        385                 390                 395

Gly Ala Cys Pro Thr Thr Ser Gly Val Pro Ala Glu Ile Glu Ala Gln
    400                 405                 410

Val Pro Asn Ser Asn Val Ile Phe Ser Asn Ile Arg Phe Gly Pro Ile
415                 420                 425                 430

Gly Ser Thr Val Pro Gly Leu Asp Gly Ser Thr Pro Ser Asn Pro Thr
                435                 440                 445

Ala Thr Val Ala Pro Pro Thr Ser Thr Thr Ser Val Arg Ser Ser Thr
            450                 455                 460

Thr Gln Ile Ser Thr Pro Thr Ser Gln Pro Gly Gly Cys Thr Thr Gln
        465                 470                 475

Lys Trp Gly Gln Cys Gly Gly Ile Gly Tyr Thr Gly Cys Thr Asn Cys
    480                 485                 490

Val Ala Gly Thr Thr Cys Thr Glu Leu Asn Pro Trp Tyr Ser Gln Cys
495                 500                 505                 510

Leu


<210> SEQ ID NO 51
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 51

cccttgtcga tgcgatgtat c                                              21


<210> SEQ ID NO 52
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 52

atcctcaatt ccgtcggtcg a                                              21


<210> SEQ ID NO 53
<211> LENGTH: 1570
```

```
<212> TYPE: DNA
<213> ORGANISM: Rasamsonia emersonii

<400> SEQUENCE: 53

gaatcgatgc tcaattcggg atggagatgt cgatcagatg gagtataaaa gggcagggtg     60

aatccagggt ccaggccatc tgccatcact cagactcaaa cactccatca gcagcttcga    120

aagcggtctt tttgctatca tcatgcttcg acgggctctt cttctatcct cttccgccat    180

ccttgctgtc aaggcacagc aggccggcac ggcgacggca gagaaccacc cgcccctgac    240

atggcaggaa tgcaccgccc ctgggagctg caccacccag aacggggcgg tcgttcttga    300

tgcgaactgg cgttgggtgc acgatgtgaa cggatacacc aactgctaca cgggcaatac    360

ctggaacccc acgtactgcc ctgacgacga aacctgcgcc cagaactgtg cgctggacgg    420

cgcggattac gagggcacct acggcgtgac ttcgtcgggc agctccttga agctcaattt    480

cgtcaccggg tcgaacgtcg gatcccgtct ctacctgctg caggacgact cgacctatca    540

gatcttcaag cttctgaacc gcgagtttac ctttgacgtc gatgtctcca atcttccgtg    600

cggattgaac ggcgctctgt actttgtcgc catggacgcc gacggcggcg tgtccaagta    660

cccgaacaac aaggctggtg ccaagtacgg aaccgggtat tgcgactccc aatgcccacg    720

ggacctcaag ttcatcgacg gcgaggtatg tccagtggta aaatcgatcg tctcgtgaac    780

ttctgctgac aggttcgatc tacaggccaa cgtcgagggc tggcagccgt cttcgaacaa    840

cgccaacacc ggaattggcg accatggctc ctgctgtgcg gagatggatg tctgggaagc    900

caacagcatc tccaatgcgg tcactccgca cccgtgcgac acgccaggcc agacgatgtg    960

ctctggcgat gactgcggtg gcacatactc taacgatcgc tacgcgggaa cctgcgatcc   1020

tgacggctgt gacttcaacc cttaccgcat gggcaacact tctttctacg ggcctggcaa   1080

gatcatcgat accaccaagc ctttcactgt cgtgacgcag ttcctcactg atgatggtac   1140

ggatactgga actctcagcg agatcaagcg cttctacgtc cagaacggca acgtcattcc   1200

gcagcccaac tcggacatca gtggcgtgac cggcaactcg atcacgacgg agttctgtac   1260

tgctcagaag caggcctttg gcgacacgga cgacttctct cagcacggtg gcctggccaa   1320

gatgggagcg gccatgcagc agggtatggt cctggtgatg agtttgtggg acgactacgc   1380

cgcgcagatg ctgtggctgg attccgacta cccgacggat gcggacccca cgacccctgg   1440

tattgcccgt ggaacgtgtc cgacggactc gggcgtccca tcggatgtcg agtcgcagag   1500

ccccaactcc tacgtgacct actcgaacat caagtttggt ccgatcaact cgaccttcac   1560

cgcttcgtga                                                          1570

<210> SEQ ID NO 54
<211> LENGTH: 1368
<212> TYPE: DNA
<213> ORGANISM: Rasamsonia emersonii

<400> SEQUENCE: 54

atgttgcgaa gggccttgtt gctctcgtcc tccgcaatct tggcggtcaa ggcacagcag     60

gcaggcaccg caaccgcaga gaaccatcct ccgctcactt ggcaggaatg tacagcacct    120

ggctcctgta caacccagaa cggagcggtc gtgctcgatg cgaactggcg ctgggtgcac    180

gatgtcaacg gatacacaaa ctgttataca ggtaacacgt ggaaccctac gtattgtccc    240

gacgacgaaa cgtgtgccca gaactgtgcg ttggatggag cagactacga gggaacgtat    300

ggcgtgacct cgtccggctc ctccttgaag ctcaacttcg tcacgggctc gaacgtcggc    360
```

```
tcccgcttgt acctcctcca ggacgactcg acctaccaga tcttcaagct cctcaacagg    420

gagttcacct tcgacgtcga tgtctccaac ttgccctgtg gtctcaacgg agccttgtac    480

ttcgtcgcga tggatgcaga cggaggtgtc tcgaagtacc ccaacaacaa ggcaggtgcc    540

aagtatggta ctggctactg tgattcgcag tgtcctcgcg atctcaagtt cattgacggt    600

gaggcgaacg tggaaggatg gcagccctcg tccaacaacg cgaacactgg catcggtgat    660

cacggttcgt gttgtgccga gatggacgtc tgggaagcca actccatctc gaacgcggtc    720

acaccgcacc cgtgtgatac tcctggccag actatgtgtt ccggagatga ttgtggaggc    780

acctattcga acgaccggta tgcaggcacg tgtgacccgg atggctgtga cttcaacccg    840

taccgcatgg gcaacacctc cttctatgga ccgggtaaga tcatcgatac aactaagccc    900

ttcaccgtcg tcacgcagtt cctcacagat gacggcacgg acacaggtac tttgtcggag    960

atcaaacgct tctacgtcca gaacggaaac gtcatccccc agccgaactc cgacatttcg   1020

ggagtcacag gcaactcgat tacgaccgag ttctgtacag cccagaaaca ggcattcggt   1080

gacacggatg atttctccca gcacggagga ttggcgaaaa tgggagccgc aatgcagcag   1140

ggaatggtcc tcgtgatgtc gctctgggac gactatgcag cccagatgtt gtggctcgac   1200

tcggactacc ccacagacgc cgatcccacg acacccggta tcgcacgagg cacttgtccg   1260

acagattccg gagtcccgtc ggacgtcgag tcccagtccc ccaactcgta cgtcacctat   1320

tcgaacatca aattcggtcc catcaactcg acattcacag cctcgtaa                1368
```

```
<210> SEQ ID NO 55
<211> LENGTH: 1560
<212> TYPE: DNA
<213> ORGANISM: Rasamsonia emersonii

<400> SEQUENCE: 55

atgttgcgaa gggccttgtt gctctcgtcc tccgcaatct tggcggtcaa ggcacagcag     60

gcaggcaccg caaccgcaga gaaccatcct ccgctcactt ggcaggaatg tacagcacct    120

ggctcctgta caacccagaa cggagcggtc gtgctcgatg cgaactggcg ctgggtgcac    180

gatgtcaacg gatacacaaa ctgttataca ggtaacacgt ggaaccctac gtattgtccc    240

gacgacgaaa cgtgtgccca gaactgtgcg ttggatggag cagactacga gggaacgtat    300

ggcgtgacct cgtccggctc ctccttgaag ctcaacttcg tcacgggctc gaacgtcggc    360

tcccgcttgt acctcctcca ggacgactcg acctaccaga tcttcaagct cctcaacagg    420

gagttcacct tcgacgtcga tgtctccaac ttgccctgtg gtctcaacgg agccttgtac    480

ttcgtcgcga tggatgcaga cggaggtgtc tcgaagtacc ccaacaacaa ggcaggtgcc    540

aagtatggta ctggctactg tgattcgcag tgtcctcgcg atctcaagtt cattgacggt    600

gaggcgaacg tggaaggatg gcagccctcg tccaacaacg cgaacactgg catcggtgat    660

cacggttcgt gttgtgccga gatggacgtc tgggaagcca actccatctc gaacgcggtc    720

acaccgcacc cgtgtgatac tcctggccag actatgtgtt ccggagatga ttgtggaggc    780

acctattcga acgaccggta tgcaggcacg tgtgacccgg atggctgtga cttcaacccg    840

taccgcatgg gcaacacctc cttctatgga ccgggtaaga tcatcgatac aactaagccc    900

ttcaccgtcg tcacgcagtt cctcacagat gacggcacgg acacaggtac tttgtcggag    960

atcaaacgct tctacgtcca gaacggaaac gtcatccccc agccgaactc cgacatttcg   1020

ggagtcacag gcaactcgat tacgaccgag ttctgtacag cccagaaaca ggcattcggt   1080

gacacggatg atttctccca gcacggagga ttggcgaaaa tgggagccgc aatgcagcag   1140
```

```
ggaatggtcc tcgtgatgtc gctctgggac gactatgcag cccagatgtt gtggctcgac   1200

tcggactacc ccacagacgc cgatcccacg acacccggta tcgcacgagg cacttgtccg   1260

acagattccg gagtcccgtc ggacgtcgag tcccagtccc ccaactcgta cgtcacctat   1320

tcgaacatca aattcggtcc catcaactcg acattcacag cctcgggtgg aaaccctcct   1380

ggcggaaacc ctcctggcac aactacaaca cgacggcctg cgactacaac gggttcgtcc   1440

cctggaccga cccagtccca ctacggacag tgtggaggca tcggttattc cggtccgacc   1500

gtctgtgcgt ccggcacaac ctgtcaggtc ttgaaccctt actattcgca gtgtctctaa   1560
```

```
<210> SEQ ID NO 56
<211> LENGTH: 519
<212> TYPE: PRT
<213> ORGANISM: Rasamsonia emersonii

<400> SEQUENCE: 56

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asn Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Thr Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300
```

```
Thr Gln Phe Leu Thr Asp Asp Gly Thr Asp Thr Gly Thr Leu Ser Glu
305                 310                 315                 320

Ile Lys Arg Phe Tyr Val Gln Asn Gly Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Gly Gly Asn Pro Pro Gly Gly Asn Pro
    450                 455                 460

Pro Gly Thr Thr Thr Thr Arg Arg Pro Ala Thr Thr Thr Gly Ser Ser
465                 470                 475                 480

Pro Gly Pro Thr Gln Ser His Tyr Gly Gln Cys Gly Gly Ile Gly Tyr
                485                 490                 495

Ser Gly Pro Thr Val Cys Ala Ser Gly Thr Thr Cys Gln Val Leu Asn
            500                 505                 510

Pro Tyr Tyr Ser Gln Cys Leu
        515
```

<210> SEQ ID NO 57
<211> LENGTH: 58
<212> TYPE: DNA
<213> ORGANISM: Artificial Sequence
<220> FEATURE:
<223> OTHER INFORMATION: Artificial DNA Primer

<400> SEQUENCE: 57
ggtcccatca actcgacatt cacagcctcg ggtggaaacc ctcctggcgg aaaccctc 58

<210> SEQ ID NO 58
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 58
atcctcaatt ccgtcggtcg a 21

<210> SEQ ID NO 59
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 59
ccacacttct cttccttcct caatcctc 28

<210> SEQ ID NO 60
<211> LENGTH: 1560
<212> TYPE: DNA
<213> ORGANISM: Rasamsonia emersonii

<400> SEQUENCE: 60

```
atgttgcgaa gggccttgtt gctctcgtcc tccgcaatct tggcggtcaa ggcacagcag      60
gcaggcaccg caaccgcaga gaaccatcct ccgctcactt ggcaggaatg tacagcacct     120
ggctcctgta caacccagaa cggagcggtc gtgctcgatg cgaactggcg ctgggtgcac     180
gatgtcaacg gatacacaaa ctgttataca ggtaacacgt ggaaccctac gtattgtccc     240
gacgacgaaa cgtgtgccca gaactgtgcg ttggatggag cagactacga gggaacgtat     300
ggcgtgacct cgtccggctc ctccttgaag ctcaacttcg tcacgggctc gaacgtcggc     360
tcccgcttgt acctcctcca ggacgactcg acctaccaga tcttcaagct cctcaacagg     420
gagttcacct tcgacgtcga tgtctccaac ttgccctgtg gtctcaacgg agccttgtac     480
ttcgtcgcga tggatgcaga cggaggtgtc tcgaagtacc ccaacaacaa ggcaggtgcc     540
aagtatggta ctggctactg tgattcgcag tgtcctcgcg atctcaagtt cattgacggt     600
gaggcgaacg tggaaggatg gcagccctcg tccaacaacg cgaacactgg catcggtgat     660
cacggttcgt gttgtgccga gatggacgtc tgggaagcca actccatctc gaacgcggtc     720
acaccgcacc cgtgtgatac tcctggccag actatgtgtt ccggagatga ttgtggaggc     780
acctattcga acgaccggta tgcaggcacg tgtgacccgg atggctgtga cttcaacccg     840
taccgcatgg gcaacacctc cttctatgga ccgggtaaga tcatcgatac aactaagccc     900
ttcaccgtcg tcacgcagtt cctcacagat gacggcacgg acacaggtac tttgtcggag     960
atcaaacgct tctacgtcca gaacggaaac gtcatccccc agccgaactc cgacatttcg    1020
ggagtcacag gcaactcgat tacgaccgag ttctgtacag cccagaaaca ggcattcggt    1080
gacacggatg atttctccca gcacggagga ttggcgaaaa tgggagccgc aatgcagcag    1140
ggaatggtcc tcgtgatgtc gctctgggac gactatgcag cccagatgtt gtggctcgac    1200
tcggactacc ccacagacgc cgatcccacg acacccggta tcgcacgagg cacttgtccg    1260
acagattccg gagtcccgtc ggacgtcgag tcccagtccc ccaactcgta cgtcacctat    1320
tcgaacatca aattcggtcc catcaactcg acattcacag cctcgggtgg aaaccctcct    1380
ggcggaaacc ctcctggcac aactacaaca cgacggcctg cgactacaac gggttcgtcc    1440
cctggaccga cccagtccca ctacggacag tgtggaggca tcggttattc cggtccgacc    1500
gtctgtgcgt ccggcacaac ctgtcaggtc ttgaaccctt actggtcgca gtgtctctaa    1560
```

<210> SEQ ID NO 61
<211> LENGTH: 519
<212> TYPE: PRT
<213> ORGANISM: Rasamsonia emersonii

<400> SEQUENCE: 61

```
Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60
```

```
Tyr Thr Asn Cys Tyr Thr Gly Asn Thr Trp Asn Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Thr Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Val Gln Asn Gly Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Gly Gly Asn Pro Pro Gly Gly Asn Pro
    450                 455                 460

Pro Gly Thr Thr Thr Thr Arg Arg Pro Ala Thr Thr Thr Gly Ser Ser
465                 470                 475                 480
```

```
Pro Gly Pro Thr Gln Ser His Tyr Gly Gln Cys Gly Gly Ile Gly Tyr
                485                 490                 495

Ser Gly Pro Thr Val Cys Ala Ser Gly Thr Thr Cys Gln Val Leu Asn
            500                 505                 510

Pro Tyr Trp Ser Gln Cys Leu
        515
```

<210> SEQ ID NO 62
<211> LENGTH: 1560
<212> TYPE: DNA
<213> ORGANISM: Rasamsonia emersonii

<400> SEQUENCE: 62

```
atgttgcgaa gggccttgtt gctctcgtcc tccgcaatct tggcggtcaa ggcacagcag      60

gcaggcaccg caaccgcaga gaaccatcct ccgctcactt ggcaggaatg tacagcacct     120

ggctcctgta caacccagaa cggagcggtc gtgctcgatg cgaactggcg ctgggtgcac     180

gatgtcaacg gatacacaaa ctgttataca ggtaacacgt ggaaccctac gtattgtccc     240

gacgacgaaa cgtgtgccca gaactgtgcg ttggatggag cagactacga gggaacgtat     300

ggcgtgacct cgtccggctc ctccttgaag ctcaacttcg tcacgggctc gaacgtcggc     360

tcccgcttgt acctcctcca ggacgactcg acctaccaga tcttcaagct cctcaacagg     420

gagttcacct tcgacgtcga tgtctccaac ttgccctgtg gtctcaacgg agccttgtac     480

ttcgtcgcga tggatgcaga cggaggtgtc tcgaagtacc ccaacaacaa ggcaggtgcc     540

aagtatggta ctggctactg tgattcgcag tgtcctcgcg atctcaagtt cattgacggt     600

gaggcgaacg tggaaggatg gcagccctcg tccaacaacg cgaacactgg catcggtgat     660

cacggttcgt gttgtgccga gatggacgtc tgggaagcca actccatctc gaacgcggtc     720

acaccgcacc cgtgtgatac tcctggccag actatgtgtt ccggagatga ttgtggaggc     780

acctattcga acgaccggta tgcaggcacg tgtgacccgg atggctgtga cttcaacccg     840

taccgcatgg gcaacacctc cttctatgga ccgggtaaga tcatcgatac aactaagccc     900

ttcaccgtcg tcacgcagtt cctcacagat gacggcacgg acacaggtac tttgtcggag     960

atcaaacgct tctacgtcca gaacggaaac gtcatccccc agccgaactc cgacatttcg    1020

ggagtcacag gcaactcgat tacgaccgag ttctgtacag cccagaaaca ggcattcggt    1080

gacacggatg atttctccca gcacggagga ttggcgaaaa tgggagccgc aatgcagcag    1140

ggaatggtcc tcgtgatgtc gctctgggac gactatgcag cccagatgtt gtggctcgac    1200

tcggactacc ccacagacgc cgatcccacg acacccggta tcgcacgagg cacttgtccg    1260

acagattccg gagtcccgtc ggacgtcgag tcccagtccc ccaactcgta cgtcacctat    1320

tcgaacatca aattcggtcc catcaactcg acattcacag cctcgggtgg aaaccctcct    1380

ggcggaaacc ctcctggcac aactacaaca cgacggcctg cgactacaac gggttcgtcc    1440

cctggaccga cccagtccca ctggggacag tgtggaggca tcggttattc cggtccgacc    1500

gtctgtgcgt ccggcacaac ctgtcaggtc ttgaaccctt actattcgca gtgtctctaa    1560
```

<210> SEQ ID NO 63
<211> LENGTH: 519
<212> TYPE: PRT
<213> ORGANISM: Rasamsonia emersonii

<400> SEQUENCE: 63

```
Met Leu Arg Arg Ala Leu Leu Leu Ser Ser Ser Ala Ile Leu Ala Val
1               5                   10                  15
```

```
Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asn Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Thr Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Val Gln Asn Gly Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430
```

```
Ser Pro Asn Ser Tyr Val Thr Tyr Ser Asn Ile Lys Phe Gly Pro Ile
        435                 440                 445

Asn Ser Thr Phe Thr Ala Ser Gly Gly Asn Pro Pro Gly Gly Asn Pro
    450                 455                 460

Pro Gly Thr Thr Thr Thr Arg Arg Pro Ala Thr Thr Thr Gly Ser Ser
465                 470                 475                 480

Pro Gly Pro Thr Gln Ser His Trp Gly Gln Cys Gly Gly Ile Gly Tyr
                485                 490                 495

Ser Gly Pro Thr Val Cys Ala Ser Gly Thr Thr Cys Gln Val Leu Asn
            500                 505                 510

Pro Tyr Tyr Ser Gln Cys Leu
        515


<210> SEQ ID NO 64
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 64

ctgtcaggtc ttgaaccctt actggtcgca gtgtctctaa g                          41


<210> SEQ ID NO 65
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 65

gtaagggttc aagacctgac aggttgtgcc gg                                    32


<210> SEQ ID NO 66
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 66

ctggaccgac ccagtcccac tggggacagt gtggaggcat cgg                        43


<210> SEQ ID NO 67
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 67

gtgggactgg gtcggtccag gggacgaacc                                       30


<210> SEQ ID NO 68
<211> LENGTH: 28
<212> TYPE: DNA
<213> ORGANISM: Artificial Sequence
<220> FEATURE:
<223> OTHER INFORMATION: Artificial DNA Primer

<400> SEQUENCE: 68

ccacacttct cttccttcct caatcctc                                         28
```

<210> SEQ ID NO 69
<211> LENGTH: 22
<212> TYPE: DNA
<213> ORGANISM: Artificial Sequence
<220> FEATURE:
<223> OTHER INFORMATION: Artificial DNA Primer

<400> SEQUENCE: 69
gtgaggcgaa cgtggaagga tg 22

<210> SEQ ID NO 70
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 70
gtacctgtgt ccgtgccgtc atctg 25

<210> SEQ ID NO 71
<211> LENGTH: 21
<212> TYPE: DNA
<213> ORGANISM: Artificial Sequence
<220> FEATURE:
<223> OTHER INFORMATION: Artificial DNA Primer

<400> SEQUENCE: 71
atcctcaatt ccgtcggtcg a 21

<210> SEQ ID NO 72
<211> LENGTH: 1560
<212> TYPE: DNA
<213> ORGANISM: Rasamsonia emersonii

<400> SEQUENCE: 72
atgttgcgaa gggccttgtt gctctcgtcc tccgcaatct tggcggtcaa ggcacagcag 60
gcaggcaccg caaccgcaga gaaccatcct ccgctcactt ggcaggaatg tacagcacct 120
ggctcctgta caacccagaa cggagcggtc gtgctcgatg cgaactggcg ctgggtgcac 180
gatgtcaacg gatacacaaa ctgttataca ggtaacacgt ggaaccctac gtattgtccc 240
gacgacgaaa cgtgtgccca gaactgtgcg ttggatggag cagactacga gggaacgtat 300
ggcgtgacct cgtccggctc ctccttgaag ctcaacttcg tcacgggctc gaacgtcggc 360
tcccgcttgt acctcctcca ggacgactcg acctaccaga tcttcaagct cctcaacagg 420
gagttcacct tcgacgtcga tgtctccaac ttgccctgtg gtctcaacgg agccttgtac 480
ttcgtcgcga tggatgcaga cggaggtgtc tcgaagtacc ccaacaacaa ggcaggtgcc 540
aagtatggta ctggctactg tgattcgcag tgtcctcgcg atctcaagtt cattgacggt 600
gaggcgaacg tggaaggatg gcagccctcg tccaacaacg cgaacactgg catcggtgat 660
cacggttcgt gttgtgccga gatggacgtc tgggaagcca actccatctc gaacgcggtc 720
acaccgcacc cgtgtgatac tcctggccag actatgtgtt ccggagatga ttgtggaggc 780
acctattcga acgaccggta tgcaggcacg tgtgacccgg atggctgtga cttcaacccg 840
taccgcatgg gcaacacctc cttctatgga ccgggtaaga tcatcgatac aactaagccc 900
ttcaccgtcg tcacgcagtt cctcacagat gacggcacgg acacaggtac tttgtcggag 960
atcaaacgct tctacgtcca gaacggaaac gtcatccccc agccgaactc cgacatttcg 1020
ggagtcacag gcaactcgat tacgaccgag ttctgtacag cccagaaaca ggcattcggt 1080

```
gacacggatg atttctccca gcacggagga ttggcgaaaa tgggagccgc aatgcagcag   1140

ggaatggtcc tcgtgatgtc gctctgggac gactatgcag cccagatgtt gtggctcgac   1200

tcggactacc ccacagacgc cgatcccacg acacccggta tcgcacgagg cacttgtccg   1260

acagattccg gagtcccgtc ggacgtcgag tcccagtccc ccaactcgta cgtcacctat   1320

tcgaacatca aattcggtcc catcaactcg acattcacag cctcgggtgg aaaccctcct   1380

ggcggaaacc ctcctggcac aactacaaca cgacggcctg cgactacaac gggttcgtcc   1440

cctggaccga cccagtccca ctacggacag tgtggaggca tcggttggtc cggtccgacc   1500

gtctgtgcgt ccggcacaac ctgtcaggtc ttgaaccctt actattcgca gtgtctctaa   1560


<210> SEQ ID NO 73
<211> LENGTH: 519
<212> TYPE: PRT
<213> ORGANISM: Rasamsonia emersonii

<400> SEQUENCE: 73

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asn Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Thr Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
```

```
    290                 295                 300

Thr Gln Phe Leu Thr Asp Asp Gly Thr Asp Thr Gly Thr Leu Ser Glu
305                 310                 315                 320

Ile Lys Arg Phe Tyr Val Gln Asn Gly Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr Ala Ser Gly Gly Asn Pro Pro Gly Gly Asn Pro
    450                 455                 460

Pro Gly Thr Thr Thr Thr Arg Arg Pro Ala Thr Thr Thr Gly Ser Ser
465                 470                 475                 480

Pro Gly Pro Thr Gln Ser His Tyr Gly Gln Cys Gly Gly Ile Gly Trp
                485                 490                 495

Ser Gly Pro Thr Val Cys Ala Ser Gly Thr Thr Cys Gln Val Leu Asn
            500                 505                 510

Pro Tyr Tyr Ser Gln Cys Leu
        515


<210> SEQ ID NO 74
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 74

ggacagtgtg gaggcatcgg ttggtccggt ccgaccgtct gtgc                    44


<210> SEQ ID NO 75
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 75

accgatgcct ccacactgtc cgtagtggga ct                                 32


<210> SEQ ID NO 76
<211> LENGTH: 1599
<212> TYPE: DNA
<213> ORGANISM: Aspergillus fumigatus

<400> SEQUENCE: 76

atgctggcct ccaccttctc ctaccgcatg tacaagaccg cgctcatcct ggccgcccctt     60

ctgggctctg gccaggctca gcaggtcggt acttcccagg cggaagtgca tccgtccatg    120
```

```
acctggcaga gctgcacggc tggcggcagc tgcaccacca acaacggcaa ggtggtcatc    180

gacgcgaact ggcgttgggt gcacaaagtc ggcgactaca ccaactgcta caccggcaac    240

acctgggaca cgactatctg ccctgacgat gcgacctgcg catccaactg cgcccttgag    300

ggtgccaact acgaatccac ctatggtgtg accgccagcg gcaattccct ccgcctcaac    360

ttcgtcacca ccagccagca gaagaacatt ggctcgcgtc tgtacatgat gaaggacgac    420

tcgacctacg agatgtttaa gctgctgaac caggagttca ccttcgatgt cgatgtctcc    480

aacctcccct gcggtctcaa cggtgctctg tactttgtcg ccatggacgc cgacggtggc    540

atgtccaagt acccaaccaa caaggccggt gccaagtacg gtactggata ctgtgactcg    600

cagtgccctc gcgacctcaa gttcatcaac ggtcaggcca acgttgaagg gtggcagccc    660

tcctccaacg atgccaatgc gggtaccggc aaccacgggt cctgctgcgc ggagatggat    720

atctgggagg ccaacagcat ctccacggcc ttcacccccc atccgtgcga cacgcccggc    780

caggtgatgt gcaccggtga tgcctgcggt ggcacctaca gctccgaccg ctacggcggc    840

acctgcgacc ccgacggatg tgatttcaac tccttccgcc agggcaacaa gaccttctac    900

ggccctggca tgaccgtcga caccaagagc aagtttaccg tcgtcaccca gttcatcacc    960

gacgacggca cctccagcgg caccctcaag gagatcaagc gcttctacgt gcagaacggc   1020

aaggtgatcc ccaactcgga gtcgacctgg accggcgtca gcggcaactc catcaccacc   1080

gagtactgca ccgcccagaa aagcctgttc caggaccaga acgtcttcga aaagcacggc   1140

ggcctcgagg gcatgggtgc tgccctcgcc cagggcatgg ttctcgtcat gtccctgtgg   1200

gatgatcact cggccaacat gctctggctc gacagcaact acccgaccac tgcctcttcc   1260

accactcccg gcgtcgcccg tggtacctgc gacatctcct ccggcgtccc tgcggatgtc   1320

gaggcgaacc accccgacgc ctacgtcgtc tactccaaca tcaaggtcgg ccccatcggc   1380

tcgaccttca acagcggtgg ctcgaacccc ggtggcggaa ccaccacgac aactaccacc   1440

cagcctacta ccaccacgac cacggctgga aaccctggcg gcaccggagt cgcacagcac   1500

tatggccagt gtggtggaat cggatggacc ggacccacaa cctgtgccag cccttatacc   1560

tgccagaagc tgaatgatta ttactctcag tgcctgtag                          1599
```

<210> SEQ ID NO 77
<211> LENGTH: 1599
<212> TYPE: DNA
<213> ORGANISM: Aspergillus fumigatus

<400> SEQUENCE: 77

```
atgctggcct ccaccttctc ctaccgcatg tacaagaccg cgctcatcct ggccgccctt     60

ctgggctctg gccaggctca gcaggtcggt acttcccagg cggaagtgca tccgtccatg    120

acctggcaga gctgcacggc tggcggcagc tgcaccacca acaacggcaa ggtggtcatc    180

gacgcgaact ggcgttgggt gcacaaagtc ggcgactaca ccaactgcta caccggcaac    240

acctgggaca cgactatctg ccctgacgat gcgacctgcg catccaactg cgcccttgag    300

ggtgccaact acgaatccac ctatggtgtg accgccagcg gcaattccct ccgcctcaac    360

ttcgtcacca ccagccagca gaagaacatt ggctcgcgtc tgtacatgat gaaggacgac    420

tcgacctacg agatgtttaa gctgctgaac caggagttca ccttcgatgt cgatgtctcc    480

aacctcccct gcggtctcaa cggtgctctg tactttgtcg ccatggacgc cgacggtggc    540

atgtccaagt acccaaccaa caaggccggt gccaagtacg gtactggata ctgtgactcg    600
```

```
cagtgccctc gcgacctcaa gttcatcaac ggtcaggcca acgttgaagg gtggcagccc     660

tcctccaacg atgccaatgc gggtaccggc aaccacgggt cctgctgcgc ggagatggat     720

atctgggagg ccaacagcat ctccacggcc ttcacccccc atccgtgcga cacgcccggc     780

caggtgatgt gcaccggtga tgcctgcggt ggcacctaca gctccgaccg ctacggcggc     840

acctgcgacc ccgacggatg tgatttcaac tccttccgcc agggcaacaa gaccttctac     900

ggccctggca tgaccgtcga caccaagagc aagtttaccg tcgtcaccca gttcatcacc     960

gacgacggca cctccagcgg caccctcaag gagatcaagc gcttctacgt gcagaacggc    1020

aaggtgatcc ccaactcgga gtcgacctgg accggcgtca gcggcaactc catcaccacc    1080

gagtactgca ccgcccagaa aagcctgttc caggaccaga acgtcttcga aaagcacggc    1140

ggcctcgagg gcatgggtgc tgccctcgcc cagggcatgg ttctcgtcat gtccctgtgg    1200

gatgatcact cggccaacat gctctggctc gacagcaact acccgaccac tgcctcttcc    1260

accactcccg gcgtcgcccg tggtacctgc gacatctcct ccggcgtccc tgcggatgtc    1320

gaggcgaacc accccgacgc ctacgtcgtc tactccaaca tcaaggtcgg ccccatcggc    1380

tcgaccttca acagcggtgg ctcgaacccc ggtggcggaa ccaccacgac aactaccacc    1440

cagcctacta ccaccacgac cacggctgga aaccctggcg gcaccggagt cgcacagcac    1500

tatggccagt gtggtggaat cggatggacc ggacccacaa cctgtgccag cccttatacc    1560

tgccagaagc tgaatgatta ttactctcag tgcctgtag                           1599
```

```
<210> SEQ ID NO 78
<211> LENGTH: 532
<212> TYPE: PRT
<213> ORGANISM: Aspergillus fumigatus

<400> SEQUENCE: 78

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
```

```
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530


<210> SEQ ID NO 79
<211> LENGTH: 1599
<212> TYPE: DNA
<213> ORGANISM: Aspergillus fumigatus

<400> SEQUENCE: 79

atgttggcct ccacgttctc ctatcgcatg tacaaaacag cgctcatctt ggcagccctc      60

ttgggctcgg gacaggcaca gcaggtcgga acctcgcagg ccgaggtcca tccttccatg     120

acgtggcagt cgtgtacagc gggtggttcg tgtaccacaa acaacggtaa agtcgtgatc     180
```

gatgcaaact ggaggtgggt gcacaaggtc ggcgactaca ccaactgtta cacaggcaac 240
acatgggata caaccatctg tcccgacgat gccacttgtg catccaactg tgcactcgag 300
ggtgccaact atgagtcgac gtacggagtg accgcctccg gaaactcgct caggctcaac 360
ttcgtcacaa cttcccagca gaagaacatc ggctcgcggt tgtatatgat gaaagacgat 420
tccacttacg agatgttcaa gctcctcaac caggaattca ctttcgatgt cgacgtctcc 480
aacctccctt gtggcttgaa cggagcgctc tacttcgtcg ccatggatgc ggatggaggc 540
atgtccaagt atcctaccaa caaagcagga gccaagtatg gtacaggtta ctgtgattcc 600
cagtgtccca gggatctcaa gttcatcaac ggtcaggcca acgtcgaggg ttggcagcct 660
tcgtcgaacg atgccaacgc aggtaccggc aaccacggtt cctgttgtgc cgaaatggac 720
atttgggaag cgaactcgat ctcgacggcg ttcactcctc acccgtgtga tacacccgga 780
caggtgatgt gtacaggcga cgcctgtggc ggaacctact cgtcggatcg atatggcggt 840
acgtgtgacc ccgacggctg tgacttcaac tccttcaggc agggcaacaa aacattctat 900
ggacctggca tgacggtgga tacaaagtcg aaattcacag tcgtcactca gttcatcacc 960
gacgatggta cgtcctcggg taccttgaag gagatcaaaa ggttctatgt ccagaacgga 1020
aaggtcatcc cgaactcgga gtccacgtgg acaggagtgt cgggtaactc catcactacg 1080
gagtattgta cagcccagaa gtcgctcttc caggatcaga acgtcttcga gaaacatgga 1140
ggcttggaag gaatgggtgc cgcattggcc cagggtatgg tcctcgtcat gtccttgtgg 1200
gacgaccact cggccaacat gctctggttg gattccaact accccaccac tgcctcgtcc 1260
acgacaccgg gtgtcgcacg cggaacttgt gatatctcct cgggagtgcc tgcagacgtc 1320
gaggcgaacc atcccgacgc ctacgtggtc tactcgaaca ttaaggtggg acccatcggt 1380
tcgacattca actccggagg ctcgaaccct ggaggcggaa cgaccactac tacaacgact 1440
cagccgacaa caacaactac cacagcaggc aaccctggag gtacaggtgt ggcccagcac 1500
tacggacagt gtggcggtat cggatggaca ggacctacta cttgtgcatc gccttatacc 1560
tgtcagaaat tgaacgacta ctactcgcag tgtttgtaa 1599

<210> SEQ ID NO 80
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 80
gtgatacacc cggacaggtg atgtg 25

<210> SEQ ID NO 81
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 81
ccatatcgat ccgacgagta ggttc 25

<210> SEQ ID NO 82
<211> LENGTH: 1507
<212> TYPE: DNA
<213> ORGANISM: Talaromyces byssochlamydoides

<400> SEQUENCE: 82

```
atgtttcgac gggctctttt cctgtcctct tccgccttcc ttgctgtcaa agcccagcag     60

atcggcacgg tcagtccgga gaaccatccg cccctggcat gggagcagtg cactgcccct    120

gggagttgca cgactgtgaa tggtgcggtc gtccttgatg cgaactggcg ttgggtccac    180

aatgttgggg gatacaccaa ctgctacact ggcaatacct gggacaccac gtactgccct    240

gacgacgtga cctgcgcaga gaattgtgcg ctggatggcg cagattacga gggcacctac    300

ggcgtgacca cctcgggcag ctccctgaag ctcgatttcg tcaccgggtc taacgtcgga    360

tctcgtctct acctgttgga gaatgattcg acctatcaga tcttcaagct tctgaaccag    420

gaattcacct ttgacgtcga cgtttccaat cttccgtgcg gattaaacgg cgctctgtac    480

cttgttacca tggctgctga cggcggggtg tctcagtacc cgaataacaa ggccggcgca    540

gcgtatggaa ccggttattg cgattcccag tgtccaaggg acttgaagtt tatcgatggc    600

caggtatgta gagctgtaat cacccatgtt gtgaaatcac tctcctactg acatggtcga    660

tttataggcc aacgttgagg gctggcagcc gtcttcgaac aacgccaata caggtattgg    720

caaccatggc tcctgctgtg cggagatgga tatctgggaa gccaacagca tctccaatgc    780

ggtgactccg cacccatgcg acacacccgg ccagacaatg tgcgagggga acgactgtgg    840

tggcacgtat tccaccaatc gctatgcagg cacctgcgat cctgacggct gcgacttcaa    900

cccctaccgc atgggcaacc attctttcta cggccctggg gagattgtcg atactaccca    960

gcccttcact gtcgtgacac agttccttac cgatgatggc acggatactg gcactctcag   1020

cgagatcaaa cgcttctacg tccaaaacgg gaaagtcatt cctcagccga actccgacat   1080

tgccggcgtg actggcaact cgatcaccag cgagttttgc gatgcccaga agacggcttt   1140

cggcgacatt aacaactttg atacacacgg cggtctggcc agtatgggag ctgcgctgca   1200

gcagggtatg gttctggtga tgagtctgtg ggacggtagg tccttgggag acacccggac   1260

gttctatatc aaccagaact gccagaactg acgaattaaa acacttttag attacgcggc   1320

aaacatgctg tggttggaca gcatttatcc aacaaatgca tctgctagca ctcctggtgc   1380

tgctcgtgga acctgttcga cgagctccgg tgtcccatcg caagtcgagt cgcagagccc   1440

caacgcctac gtgacgtact ccaacattaa agttggacca atcaactcga ccttcaccac   1500

ttcgtaa                                                             1507
```

<210> SEQ ID NO 83
<211> LENGTH: 455
<212> TYPE: PRT
<213> ORGANISM: Talaromyces byssochlamydoides

<400> SEQUENCE: 83

```
Met Phe Arg Arg Ala Leu Phe Leu Ser Ser Ser Ala Phe Leu Ala Val
1               5                   10                  15

Lys Ala Gln Gln Ile Gly Thr Val Ser Pro Glu Asn His Pro Pro Leu
            20                  25                  30

Ala Trp Glu Gln Cys Thr Ala Pro Gly Ser Cys Thr Thr Val Asn Gly
        35                  40                  45

Ala Val Val Leu Asp Ala Asn Trp Arg Trp Val His Asn Val Gly Gly
    50                  55                  60

Tyr Thr Asn Cys Tyr Thr Gly Asn Thr Trp Asp Thr Thr Tyr Cys Pro
65                  70                  75                  80

Asp Asp Val Thr Cys Ala Glu Asn Cys Ala Leu Asp Gly Ala Asp Tyr
                85                  90                  95
```

```
Glu Gly Thr Tyr Gly Val Thr Thr Ser Gly Ser Ser Leu Lys Leu Asp
            100                 105                 110

Phe Val Thr Gly Ser Asn Val Gly Ser Arg Leu Tyr Leu Leu Glu Asn
        115                 120                 125

Asp Ser Thr Tyr Gln Ile Phe Lys Leu Leu Asn Gln Glu Phe Thr Phe
    130                 135                 140

Asp Val Asp Val Ser Asn Leu Pro Cys Gly Leu Asn Gly Ala Leu Tyr
145                 150                 155                 160

Leu Val Thr Met Ala Ala Asp Gly Gly Val Ser Gln Tyr Pro Asn Asn
                165                 170                 175

Lys Ala Gly Ala Ala Tyr Gly Thr Gly Tyr Cys Asp Ser Gln Cys Pro
            180                 185                 190

Arg Asp Leu Lys Phe Ile Asp Gly Gln Ala Asn Val Glu Gly Trp Gln
        195                 200                 205

Pro Ser Ser Asn Asn Ala Asn Thr Gly Ile Gly Asn His Gly Ser Cys
    210                 215                 220

Cys Ala Glu Met Asp Ile Trp Glu Ala Asn Ser Ile Ser Asn Ala Val
225                 230                 235                 240

Thr Pro His Pro Cys Asp Thr Pro Gly Gln Thr Met Cys Glu Gly Asn
                245                 250                 255

Asp Cys Gly Gly Thr Tyr Ser Thr Asn Arg Tyr Ala Gly Thr Cys Asp
            260                 265                 270

Pro Asp Gly Cys Asp Phe Asn Pro Tyr Arg Met Gly Asn His Ser Phe
        275                 280                 285

Tyr Gly Pro Gly Glu Ile Val Asp Thr Thr Gln Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Val Gln Asn Gly Lys Val Ile Pro Gln Pro Asn
                325                 330                 335

Ser Asp Ile Ala Gly Val Thr Gly Asn Ser Ile Thr Ser Glu Phe Cys
            340                 345                 350

Asp Ala Gln Lys Thr Ala Phe Gly Asp Ile Asn Asn Phe Asp Thr His
        355                 360                 365

Gly Gly Leu Ala Ser Met Gly Ala Ala Leu Gln Gln Gly Met Val Leu
    370                 375                 380

Val Met Ser Leu Trp Asp Asp Tyr Ala Ala Asn Met Leu Trp Leu Asp
385                 390                 395                 400

Ser Ile Tyr Pro Thr Asn Ala Ser Ala Ser Thr Pro Gly Ala Ala Arg
                405                 410                 415

Gly Thr Cys Ser Thr Ser Ser Gly Val Pro Ser Gln Val Glu Ser Gln
            420                 425                 430

Ser Pro Asn Ala Tyr Val Thr Tyr Ser Asn Ile Lys Val Gly Pro Ile
        435                 440                 445

Asn Ser Thr Phe Thr Thr Ser
    450                 455
```

<210> SEQ ID NO 84
<211> LENGTH: 1705
<212> TYPE: DNA
<213> ORGANISM: Talaromyces byssochlamydoides

<400> SEQUENCE: 84

```
atgtttcgac gggctctttt cctgtcctct tccgccttcc ttgctgtcaa agcccagcag     60
```

```
atcggcacgg tcagtccgga gaaccatccg cccctggcat gggagcagtg cactgcccct    120
gggagttgca cgactgtgaa tggtgcggtc gtccttgatg cgaactggcg ttgggtccac    180
aatgttgggg gatacaccaa ctgctacact ggcaatacct gggacaccac gtactgccct    240
gacgacgtga cctgcgcaga gaattgtgcg ctggatggcg cagattacga gggcacctac    300
ggcgtgacca cctcgggcag ctccctgaag ctcgatttcg tcaccgggtc taacgtcgga    360
tctcgtctct acctgttgga gaatgattcg acctatcaga tcttcaagct tctgaaccag    420
gaattcacct ttgacgtcga cgtttccaat cttccgtgcg gattaaacgg cgctctgtac    480
cttgttacca tggctgctga cggcggggtg tctcagtacc cgaataacaa ggccggcgca    540
gcgtatggaa ccggttattg cgattcccag tgtccaaggg acttgaagtt tatcgatggc    600
caggtatgta gagctgtaat cacccatgtt gtgaaatcac tctcctactg acatggtcga    660
tttataggcc aacgttgagg gctggcagcc gtcttcgaac aacgccaata caggtattgg    720
caaccatggc tcctgctgtg cggagatgga tatctgggaa gccaacagca tctccaatgc    780
ggtgactccg cacccatgcg acacacccgg ccagacaatg tgcgagggga acgactgtgg    840
tggcacgtat tccaccaatc gctatgcagg cacctgcgat cctgacggct gcgacttcaa    900
cccctaccgc atgggcaacc attctttcta cggccctggg gagattgtcg atactaccca    960
gcccttcact gtcgtgacac agttccttac cgatgatggc acggatactg gcactctcag   1020
cgagatcaaa cgcttctacg tccaaaacgg gaaagtcatt cctcagccga actccgacat   1080
tgccggcgtg actggcaact cgatcaccag cgagttttgc gatgcccaga agacggcttt   1140
cggcgacatt aacaactttg atacacacgg cggtctggcc agtatgggag ctgcgctgca   1200
gcagggtatg gttctggtga tgagtctgtg ggacggtagg tccttgggag acacccggac   1260
gttctatatc aaccagaact gccagaactg acgaattaaa acacttttag attacgcggc   1320
aaacatgctg tggttggaca gcatttatcc aacaaatgca tctgctagca ctcctggtgc   1380
tgctcgtgga acctgttcga cgagctccgg tgtcccatcg caagtcgagt cgcagagccc   1440
caacgcctac gtgacgtact ccaacattaa agttggacca atcaactcga ccttcaccac   1500
ttcgggctcg aaccctggag gcggaacgac cactactaca acgactcagc cgacaacaac   1560
aactaccaca gcaggcaacc ctggaggtac aggtgtggcc cagcactacg gacagtgtgg   1620
cggtatcgga tggacaggac ctactacttg tgcatcgcct tatacctgtc agaaattgaa   1680
cgactactac tcgcagtgtt tgtaa                                         1705
```

```
<210> SEQ ID NO 85
<211> LENGTH: 521
<212> TYPE: PRT
<213> ORGANISM: Talaromyces byssochlamydoides

<400> SEQUENCE: 85

Met Phe Arg Arg Ala Leu Phe Leu Ser Ser Ser Ala Phe Leu Ala Val
1               5                   10                  15

Lys Ala Gln Gln Ile Gly Thr Val Ser Pro Glu Asn His Pro Pro Leu
            20                  25                  30

Ala Trp Glu Gln Cys Thr Ala Pro Gly Ser Cys Thr Thr Val Asn Gly
        35                  40                  45

Ala Val Val Leu Asp Ala Asn Trp Arg Trp Val His Asn Val Gly Gly
    50                  55                  60

Tyr Thr Asn Cys Tyr Thr Gly Asn Thr Trp Asp Thr Thr Tyr Cys Pro
65                  70                  75                  80
```

-continued

```
Asp Asp Val Thr Cys Ala Glu Asn Cys Ala Leu Asp Gly Ala Asp Tyr
                85                  90                  95

Glu Gly Thr Tyr Gly Val Thr Thr Ser Gly Ser Ser Leu Lys Leu Asp
            100                 105                 110

Phe Val Thr Gly Ser Asn Val Gly Ser Arg Leu Tyr Leu Leu Glu Asn
        115                 120                 125

Asp Ser Thr Tyr Gln Ile Phe Lys Leu Leu Asn Gln Glu Phe Thr Phe
    130                 135                 140

Asp Val Asp Val Ser Asn Leu Pro Cys Gly Leu Asn Gly Ala Leu Tyr
145                 150                 155                 160

Leu Val Thr Met Ala Ala Asp Gly Gly Val Ser Gln Tyr Pro Asn Asn
                165                 170                 175

Lys Ala Gly Ala Ala Tyr Gly Thr Gly Tyr Cys Asp Ser Gln Cys Pro
            180                 185                 190

Arg Asp Leu Lys Phe Ile Asp Gly Gln Ala Asn Val Glu Gly Trp Gln
        195                 200                 205

Pro Ser Ser Asn Asn Ala Asn Thr Gly Ile Gly Asn His Gly Ser Cys
    210                 215                 220

Cys Ala Glu Met Asp Ile Trp Glu Ala Asn Ser Ile Ser Asn Ala Val
225                 230                 235                 240

Thr Pro His Pro Cys Asp Thr Pro Gly Gln Thr Met Cys Glu Gly Asn
                245                 250                 255

Asp Cys Gly Gly Thr Tyr Ser Thr Asn Arg Tyr Ala Gly Thr Cys Asp
            260                 265                 270

Pro Asp Gly Cys Asp Phe Asn Pro Tyr Arg Met Gly Asn His Ser Phe
        275                 280                 285

Tyr Gly Pro Gly Glu Ile Val Asp Thr Thr Gln Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Val Gln Asn Gly Lys Val Ile Pro Gln Pro Asn
                325                 330                 335

Ser Asp Ile Ala Gly Val Thr Gly Asn Ser Ile Thr Ser Glu Phe Cys
            340                 345                 350

Asp Ala Gln Lys Thr Ala Phe Gly Asp Ile Asn Asn Phe Asp Thr His
        355                 360                 365

Gly Gly Leu Ala Ser Met Gly Ala Ala Leu Gln Gln Gly Met Val Leu
    370                 375                 380

Val Met Ser Leu Trp Asp Asp Tyr Ala Ala Asn Met Leu Trp Leu Asp
385                 390                 395                 400

Ser Ile Tyr Pro Thr Asn Ala Ser Ala Ser Thr Pro Gly Ala Ala Arg
                405                 410                 415

Gly Thr Cys Ser Thr Ser Ser Gly Val Pro Ser Gln Val Glu Ser Gln
            420                 425                 430

Ser Pro Asn Ala Tyr Val Thr Tyr Ser Asn Ile Lys Val Gly Pro Ile
        435                 440                 445

Asn Ser Thr Phe Thr Thr Ser Gly Ser Asn Pro Gly Gly Gly Thr Thr
    450                 455                 460

Thr Thr Thr Thr Thr Gln Pro Thr Thr Thr Thr Thr Thr Ala Gly Asn
465                 470                 475                 480

Pro Gly Gly Thr Gly Val Ala Gln His Tyr Gly Gln Cys Gly Gly Ile
                485                 490                 495

Gly Trp Thr Gly Pro Thr Thr Cys Ala Ser Pro Tyr Thr Cys Gln Lys
```

500 505 510

Leu Asn Asp Tyr Tyr Ser Gln Cys Leu
515 520

<210> SEQ ID NO 86
<211> LENGTH: 50
<212> TYPE: DNA
<213> ORGANISM: Artificial Sequence
<220> FEATURE:
<223> OTHER INFORMATION: Artificial DNA Primer

<400> SEQUENCE: 86
caatcaactc gaccttcacc acttcgggct cgaaccctgg aggcggaacg 50

<210> SEQ ID NO 87
<211> LENGTH: 34
<212> TYPE: DNA
<213> ORGANISM: Artificial Sequence
<220> FEATURE:
<223> OTHER INFORMATION: Artificial DNA Primer

<400> SEQUENCE: 87
ctagatctcg agttacaaac actgcgagta gtag 34

<210> SEQ ID NO 88
<211> LENGTH: 26
<212> TYPE: DNA
<213> ORGANISM: Artificial Sequence
<220> FEATURE:
<223> OTHER INFORMATION: Artificial DNA Primer

<400> SEQUENCE: 88
cgaagtggtg aaggtcgagt tgattg 26

<210> SEQ ID NO 89
<211> LENGTH: 1599
<212> TYPE: DNA
<213> ORGANISM: Aspergillus fumigatus

<400> SEQUENCE: 89
atgttggcct ccacgttctc ctatcgcatg tacaaaacag cgctcatctt ggcagccctc 60
ttgggctcgg gacaggcaca gcaggtcgga acctcgcagg ccgaggtcca tccttccatg 120
acgtggcagt cgtgtacagc gggtggttcg tgtaccacaa acaacggtaa agtcgtgatc 180
gatgcaaact ggaggtgggt gcacaaggtc ggcgactaca ccaactgtta cacaggcaac 240
acatgggata caaccatctg tcccgacgat gccacttgtg catccaactg tgcactcgag 300
ggtgccaact atgagtcgac gtacggagtg accgcctccg gaaactcgct caggctcaac 360
ttcgtcacaa cttcccagca gaagaacatc ggctcgcggt tgtatatgat gaaagacgat 420
tccacttacg agatgttcaa gctcctcaac caggaattca ctttcgatgt cgacgtctcc 480
aacctccctt gtggcttgaa cggagcgctc tacttcgtcg ccatggatgc ggatggaggc 540
atgtccaagt atcctaccaa caaagcagga gccaagtatg gtacaggtta ctgtgattcc 600
cagtgtccca gggatctcaa gttcatcaac ggtcaggcca acgtcgaggg ttggcagcct 660
tcgtcgaacg atgccaacgc aggtaccggc aaccacggtt cctgttgtgc cgaaatggac 720
atttgggaag cgaactcgat ctcgacggcg ttcactcctc acccgtgtga tacacccgga 780
caggtgatgt gtacaggcga cgcctgtggc ggaacctact cgtcggatcg atatggcggt 840
acgtgtgacc ccgacggctg tgacttcaac tccttcaggc agggcaacaa aacattctat 900

```
ggacctggca tgacggtgga tacaaagtcg aaattcacag tcgtcactca gttcatcacc    960

gacgatggta cgtcctcggg taccttgaag gagatcaaaa ggttctatgt ccagaacgga   1020

aaggtcatcc cgaactcgga gtccacgtgg acaggagtgt cgggtaactc catcactacg   1080

gagtattgta cagcccagaa gtcgctcttc caggatcaga acgtcttcga gaaacatgga   1140

ggcttggaag gaatgggtgc cgcattggcc cagggtatgg tcctcgtcat gtccttgtgg   1200

gacgaccact cggccaacat gctctggttg gattccaact accccaccac tgcctcgtcc   1260

acgacaccgg gtgtcgcacg cggaacttgt gatatctcct cgggagtgcc tgcagacgtc   1320

gaggcgaacc atcccgacgc ctacgtggtc tactcgaaca ttaaggtggg acccatcggt   1380

tcgacattca actccggagg ctcgaaccct ggaggcggaa cgaccactac tacaacgact   1440

cagccgacaa caacaactac cacagcaggc aaccctggag gtacaggtgt ggcccagcac   1500

tggggacagt gtggcggtat cggatggaca ggacctacta cttgtgcatc gccttatacc   1560

tgtcagaaat tgaacgacta ctactcgcag tgtttgtaa                          1599


<210> SEQ ID NO 90
<211> LENGTH: 532
<212> TYPE: PRT
<213> ORGANISM: Aspergillus fumigatus

<400> SEQUENCE: 90

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255
```

```
Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Trp Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
        515                 520                 525

Ser Gln Cys Leu
    530
```

<210> SEQ ID NO 91
<211> LENGTH: 1599
<212> TYPE: DNA
<213> ORGANISM: Aspergillus fumigatus

<400> SEQUENCE: 91

```
atgttggcct ccacgttctc ctatcgcatg tacaaaacag cgctcatctt ggcagccctc      60

ttgggctcgg gacaggcaca gcaggtcgga acctcgcagg ccgaggtcca tccttccatg     120

acgtggcagt cgtgtacagc gggtggttcg tgtaccacaa acaacggtaa agtcgtgatc     180

gatgcaaact ggaggtgggt gcacaaggtc ggcgactaca ccaactgtta cacaggcaac     240

acatgggata caaccatctg tcccgacgat gccacttgtg catccaactg tgcactcgag     300

ggtgccaact atgagtcgac gtacggagtg accgcctccg gaaactcgct caggctcaac     360

ttcgtcacaa cttcccagca gaagaacatc ggctcgcggt tgtatatgat gaaagacgat     420

tccacttacg agatgttcaa gctcctcaac caggaattca ctttcgatgt cgacgtctcc     480
```

```
aacctccctt gtggcttgaa cggagcgctc tacttcgtcg ccatggatgc ggatggaggc    540

atgtccaagt atcctaccaa caaagcagga gccaagtatg gtacaggtta ctgtgattcc    600

cagtgtccca gggatctcaa gttcatcaac ggtcaggcca acgtcgaggg ttggcagcct    660

tcgtcgaacg atgccaacgc aggtaccggc aaccacggtt cctgttgtgc cgaaatggac    720

atttgggaag cgaactcgat ctcgacggcg ttcactcctc acccgtgtga tacacccgga    780

caggtgatgt gtacaggcga cgcctgtggc ggaacctact cgtcggatcg atatggcggt    840

acgtgtgacc ccgacggctg tgacttcaac tccttcaggc agggcaacaa aacattctat    900

ggacctggca tgacggtgga tacaaagtcg aaattcacag tcgtcactca gttcatcacc    960

gacgatggta cgtcctcggg taccttgaag gagatcaaaa ggttctatgt ccagaacgga   1020

aaggtcatcc cgaactcgga gtccacgtgg acaggagtgt cgggtaactc catcactacg   1080

gagtattgta cagcccagaa gtcgctcttc caggatcaga acgtcttcga gaaacatgga   1140

ggcttggaag gaatgggtgc cgcattggcc cagggtatgg tcctcgtcat gtccttgtgg   1200

gacgaccact cggccaacat gctctggttg gattccaact accccaccac tgcctcgtcc   1260

acgacaccgg gtgtcgcacg cggaacttgt gatatctcct cgggagtgcc tgcagacgtc   1320

gaggcgaacc atcccgacgc ctacgtggtc tactcgaaca ttaaggtggg acccatcggt   1380

tcgacattca actccggagg ctcgaaccct ggaggcggaa cgaccactac tacaacgact   1440

cagccgacaa caacaactac cacagcaggc aaccctggag gtacaggtgt ggcccagcac   1500

tacggacagt gtggcggtat cggatggaca ggacctacta cttgtgcatc gccttatacc   1560

tgtcagaaat tgaacgactg gtactcgcag tgtttgtaa                          1599
```

```
<210> SEQ ID NO 92
<211> LENGTH: 532
<212> TYPE: PRT
<213> ORGANISM: Aspergillus fumigatus

<400> SEQUENCE: 92

Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175
```

```
Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Trp Tyr
        515                 520                 525

Ser Gln Cys Leu
    530
```

<210> SEQ ID NO 93
<211> LENGTH: 1705
<212> TYPE: DNA
<213> ORGANISM: Talaromyces byssochlamydoides

<400> SEQUENCE: 93

```
atgtttcgac gggctctttt cctgtcctct tccgccttcc ttgctgtcaa agcccagcag      60
```

```
atcggcacgg tcagtccgga gaaccatccg cccctggcat gggagcagtg cactgcccct    120

gggagttgca cgactgtgaa tggtgcggtc gtccttgatg cgaactggcg ttgggtccac    180

aatgttgggg gatacaccaa ctgctacact ggcaatacct gggacaccac gtactgccct    240

gacgacgtga cctgcgcaga gaattgtgcg ctggatggcg cagattacga gggcacctac    300

ggcgtgacca cctcgggcag ctccctgaag ctcgatttcg tcaccgggtc taacgtcgga    360

tctcgtctct acctgttgga gaatgattcg acctatcaga tcttcaagct tctgaaccag    420

gaattcacct ttgacgtcga cgtttccaat cttccgtgcg gattaaacgg cgctctgtac    480

cttgttacca tggctgctga cggcggggtg tctcagtacc cgaataacaa ggccggcgca    540

gcgtatggaa ccggttattg cgattcccag tgtccaaggg acttgaagtt tatcgatggc    600

caggtatgta gagctgtaat cacccatgtt gtgaaatcac tctcctactg acatggtcga    660

tttataggcc aacgttgagg gctggcagcc gtcttcgaac aacgccaata caggtattgg    720

caaccatggc tcctgctgtg cggagatgga tatctgggaa gccaacagca tctccaatgc    780

ggtgactccg cacccatgcg acacacccgg ccagacaatg tgcgaggggga acgactgtgg    840

tggcacgtat tccaccaatc gctatgcagg cacctgcgat cctgacggct gcgacttcaa    900

cccctaccgc atgggcaacc attctttcta cggccctggg gagattgtcg atactaccca    960

gcccttcact gtcgtgacac agttccttac cgatgatggc acggatactg gcactctcag   1020

cgagatcaaa cgcttctacg tccaaaacgg gaaagtcatt cctcagccga actccgacat   1080

tgccggcgtg actggcaact cgatcaccag cgagttttgc gatgcccaga agacggcttt   1140

cggcgacatt aacaactttg atacacacgg cggtctggcc agtatgggag ctgcgctgca   1200

gcagggtatg gttctggtga tgagtctgtg ggacggtagg tccttgggag acacccggac   1260

gttctatatc aaccagaact gccagaactg acgaattaaa acacttttag attacgcggc   1320

aaacatgctg tggttggaca gcatttatcc aacaaatgca tctgctagca ctcctggtgc   1380

tgctcgtgga acctgttcga cgagctccgg tgtcccatcg caagtcgagt cgcagagccc   1440

caacgcctac gtgacgtact ccaacattaa agttggacca atcaactcga ccttcaccac   1500

ttcgggctcg aaccctggag gcggaacgac cactactaca acgactcagc cgacaacaac   1560

aactaccaca gcaggcaacc ctggaggtac aggtgtggcc cagcactacg gacagtgtgg   1620

cggtatcgga tggacaggac ctactacttg tgcatcgcct tatacctgtc agaaattgaa   1680

cgactggtac tcgcagtgtt tgtaa                                          1705
```

```
<210> SEQ ID NO 94
<211> LENGTH: 521
<212> TYPE: PRT
<213> ORGANISM: Talaromyces byssochlamydoides

<400> SEQUENCE: 94

Met Phe Arg Arg Ala Leu Phe Leu Ser Ser Ser Ala Phe Leu Ala Val
1               5                   10                  15

Lys Ala Gln Gln Ile Gly Thr Val Ser Pro Glu Asn His Pro Pro Leu
            20                  25                  30

Ala Trp Glu Gln Cys Thr Ala Pro Gly Ser Cys Thr Thr Val Asn Gly
        35                  40                  45

Ala Val Val Leu Asp Ala Asn Trp Arg Trp Val His Asn Val Gly Gly
    50                  55                  60

Tyr Thr Asn Cys Tyr Thr Gly Asn Thr Trp Asp Thr Thr Tyr Cys Pro
65                  70                  75                  80
```

```
Asp Asp Val Thr Cys Ala Glu Asn Cys Ala Leu Asp Gly Ala Asp Tyr
                85                  90                  95

Glu Gly Thr Tyr Gly Val Thr Thr Ser Gly Ser Ser Leu Lys Leu Asp
            100                 105                 110

Phe Val Thr Gly Ser Asn Val Gly Ser Arg Leu Tyr Leu Leu Glu Asn
        115                 120                 125

Asp Ser Thr Tyr Gln Ile Phe Lys Leu Leu Asn Gln Glu Phe Thr Phe
    130                 135                 140

Asp Val Asp Val Ser Asn Leu Pro Cys Gly Leu Asn Gly Ala Leu Tyr
145                 150                 155                 160

Leu Val Thr Met Ala Ala Asp Gly Gly Val Ser Gln Tyr Pro Asn Asn
                165                 170                 175

Lys Ala Gly Ala Ala Tyr Gly Thr Gly Tyr Cys Asp Ser Gln Cys Pro
            180                 185                 190

Arg Asp Leu Lys Phe Ile Asp Gly Gln Ala Asn Val Glu Gly Trp Gln
        195                 200                 205

Pro Ser Ser Asn Asn Ala Asn Thr Gly Ile Gly Asn His Gly Ser Cys
    210                 215                 220

Cys Ala Glu Met Asp Ile Trp Glu Ala Asn Ser Ile Ser Asn Ala Val
225                 230                 235                 240

Thr Pro His Pro Cys Asp Thr Pro Gly Gln Thr Met Cys Glu Gly Asn
                245                 250                 255

Asp Cys Gly Gly Thr Tyr Ser Thr Asn Arg Tyr Ala Gly Thr Cys Asp
            260                 265                 270

Pro Asp Gly Cys Asp Phe Asn Pro Tyr Arg Met Gly Asn His Ser Phe
        275                 280                 285

Tyr Gly Pro Gly Glu Ile Val Asp Thr Thr Gln Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Val Gln Asn Gly Lys Val Ile Pro Gln Pro Asn
                325                 330                 335

Ser Asp Ile Ala Gly Val Thr Gly Asn Ser Ile Thr Ser Glu Phe Cys
            340                 345                 350

Asp Ala Gln Lys Thr Ala Phe Gly Asp Ile Asn Asn Phe Asp Thr His
        355                 360                 365

Gly Gly Leu Ala Ser Met Gly Ala Ala Leu Gln Gln Gly Met Val Leu
    370                 375                 380

Val Met Ser Leu Trp Asp Asp Tyr Ala Ala Asn Met Leu Trp Leu Asp
385                 390                 395                 400

Ser Ile Tyr Pro Thr Asn Ala Ser Ala Ser Thr Pro Gly Ala Ala Arg
                405                 410                 415

Gly Thr Cys Ser Thr Ser Ser Gly Val Pro Ser Gln Val Glu Ser Gln
            420                 425                 430

Ser Pro Asn Ala Tyr Val Thr Tyr Ser Asn Ile Lys Val Gly Pro Ile
        435                 440                 445

Asn Ser Thr Phe Thr Thr Ser Gly Ser Asn Pro Gly Gly Gly Thr Thr
    450                 455                 460

Thr Thr Thr Thr Thr Gln Pro Thr Thr Thr Thr Thr Thr Ala Gly Asn
465                 470                 475                 480

Pro Gly Gly Thr Gly Val Ala Gln His Tyr Gly Gln Cys Gly Gly Ile
                485                 490                 495

Gly Trp Thr Gly Pro Thr Thr Cys Ala Ser Pro Tyr Thr Cys Gln Lys
```

```
            500                 505                 510

Leu Asn Asp Trp Tyr Ser Gln Cys Leu
        515                 520


<210> SEQ ID NO 95
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 95

gtacaggtgt ggcccagcac tggggacagt gtggcggtat cgg                        43


<210> SEQ ID NO 96
<211> LENGTH: 31
<212> TYPE: DNA
<213> ORGANISM: Artificial Sequence
<220> FEATURE:
<223> OTHER INFORMATION: Artificial DNA Primer

<400> SEQUENCE: 96

gtgctgggcc acacctgtac ctccagggtt g                                     31


<210> SEQ ID NO 97
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 97

atacctgtca gaaattgaac gactggtact cgcagtgttt gtaagcttc                  49


<210> SEQ ID NO 98
<211> LENGTH: 32
<212> TYPE: DNA
<213> ORGANISM: Artificial Sequence
<220> FEATURE:
<223> OTHER INFORMATION: Artificial DNA Primer

<400> SEQUENCE: 98

gtcgttcaat ttctgacagg tataaggcga tg                                    32


<210> SEQ ID NO 99
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 99

cctcagccga actccgacat tgc                                              23


<210> SEQ ID NO 100
<211> LENGTH: 23
<212> TYPE: DNA
<213> ORGANISM: Artificial Sequence
<220> FEATURE:
<223> OTHER INFORMATION: Artificial DNA Primer

<400> SEQUENCE: 100

gcaatgtcgg agttcggctg agg                                              23
```

POLYPEPTIDES HAVING CELLOBIOHYDROLASE ACTIVITY AND POLYNUCLEOTIDES ENCODING SAME

CROSS-REFERENCE TO RELATED APPLICATIONS

This application is a 35 U.S.C. § 371 national application of PCT/US2015/048620 filed Sep. 4, 2015, which claims priority or the benefit under 35 U.S.C. § 119 of U.S. Provisional Application No. 62/046,344 filed Sep. 5, 2014, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides comprising carbohydrate binding module variants, polynucleotides encoding the variants, methods of producing the variants, and methods of using the variants.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

Modified carbohydrate binding modules with reduced binding to lignin have been described (WO 2011/097713 A1; Linder et al., 1995, *Protein Science* 4: 1056-1064; and Linder et al., 1999, *FEBS* 447: 13-16). Additional variants of carbohydrate binding modules have been described in WO 2012/135719.

Hybrid polypeptides comprising a cellobiohydrolase catalytic domain and a carbohydrate binding module are described in e.g., WO 2010/060056, WO2013/091577, and WO2014/138672.

It would be an advantage in the art to provide polypeptides comprising carbohydrate binding module variants, e.g., cellobiohydrolase variants, with improved properties, such as increased binding affinity, for converting cellulosic materials to monosaccharides, disaccharides, and polysaccharides.

The present invention provides polypeptides comprising carbohydrate binding module variants with improved properties compared to their parents.

SUMMARY OF THE INVENTION

The present invention relates to carbohydrate binding module variants, comprising a substitution at one or more (e.g., several) positions corresponding to positions 5, 13, 31 and 32 of the carbohydrate binding module of SEQ ID NO: 4, wherein the variants have carbohydrate binding activity. In one aspect, a cellulolytic enzyme comprises a carbohydrate binding module variant of the present invention. In some embodiments, the carbohydrate binding module variants have improved binding activity.

The present invention also relates to isolated cellobiohydrolase variants, comprising a substitution at one or more (e.g., several) positions corresponding to positions 483, 491, 509 and 510 of SEQ ID NO: 2, wherein the variants have cellobiohydrolase activity.

The present invention also relates to isolated hybrid polypeptides comprising a carbohydrate binding module variant described herein and a heterologous catalytic domain of a cellulolytic enzyme. In one aspect, the catalytic domain is a cellobiohydrolase catalytic domain.

The present invention also relates to hybrid polypeptides comprising a carbohydrate binding module variant described herein and a heterologous catalytic domain of a cellulolytic enzyme. In one aspect, the catalytic domain is a cellobiohydrolase catalytic domain.

The present invention also relates to isolated polynucleotides encoding the variants and hybrid polypeptides; nucleic acid constructs, vectors, and host cells comprising the polynucleotides; and methods of producing the variants and hybrid polypeptides.

The present invention also relates to methods for degrading or converting a cellulosic material, comprising: treating the cellulosic material with an enzyme composition in the presence of a cellobiohydrolase variant or a hybrid polypeptide of the present invention. In one aspect, the method further comprises recovering the degraded or converted cellulosic material.

The present invention also relates to methods of producing a fermentation product, comprising: (a) saccharifying a cellulosic material with an enzyme composition in the presence of a cellobiohydrolase variant or a hybrid polypeptide of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a cellobiohydrolase variant or a hybrid polypeptide of the present invention. In one aspect, the fermenting of the cellulosic material produces a fermentation product. In another aspect, the method further comprises recovering the fermentation product from the fermentation.

BRIEF DESCRIPTION OF THE FIGURES

FIG. 1 shows the cDNA sequence (SEQ ID NO: 31) and the deduced amino acid sequence (SEQ ID NO: 2) of a

*Trichoderma reesei* cellobiohydrolase I gene. The signal peptide is shown in italics. The carbohydrate binding module is underlined.

Figure 2:
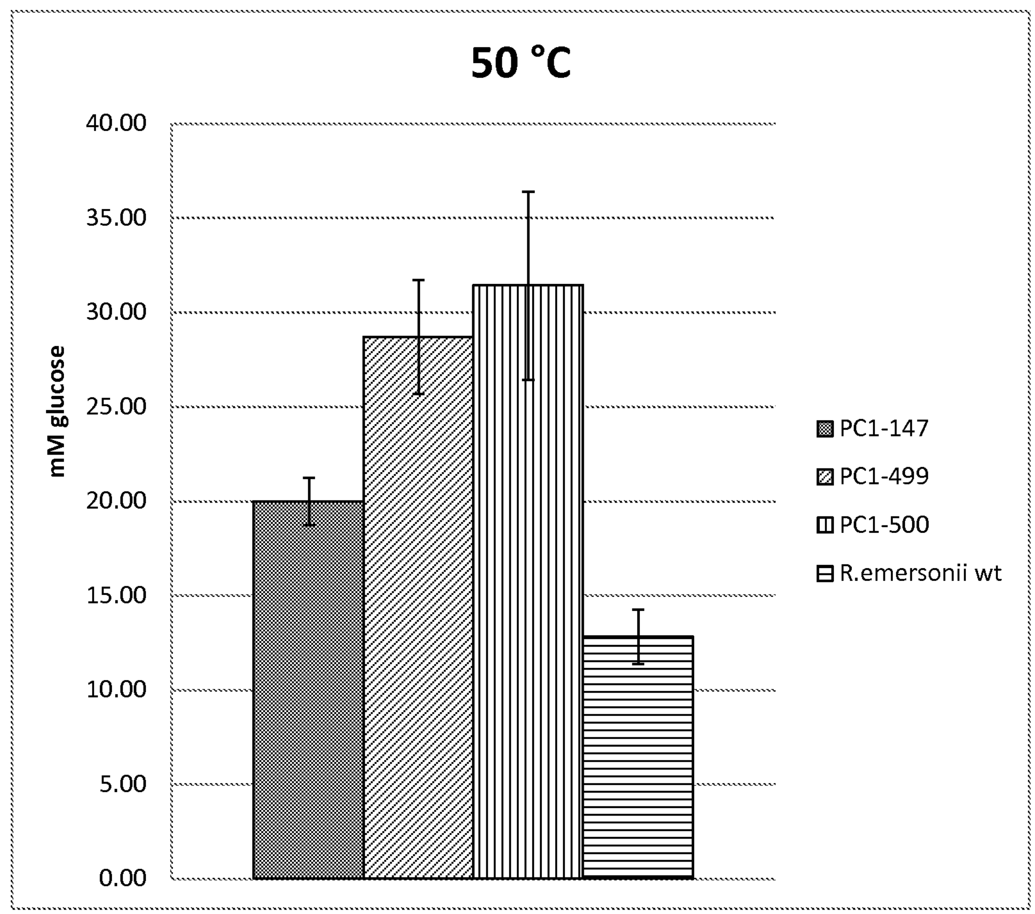

FIG. 2 shows hydrolysis of microcrystalline cellulose by *R. emersonii* wild-type cellobiohydrolase I, and hybrid polypeptides PC1-147, PC1-499 and PC1-500. Values are shown in mM released cellobiose after 24 hours at pH 5 and 50° C.

Figure 3:
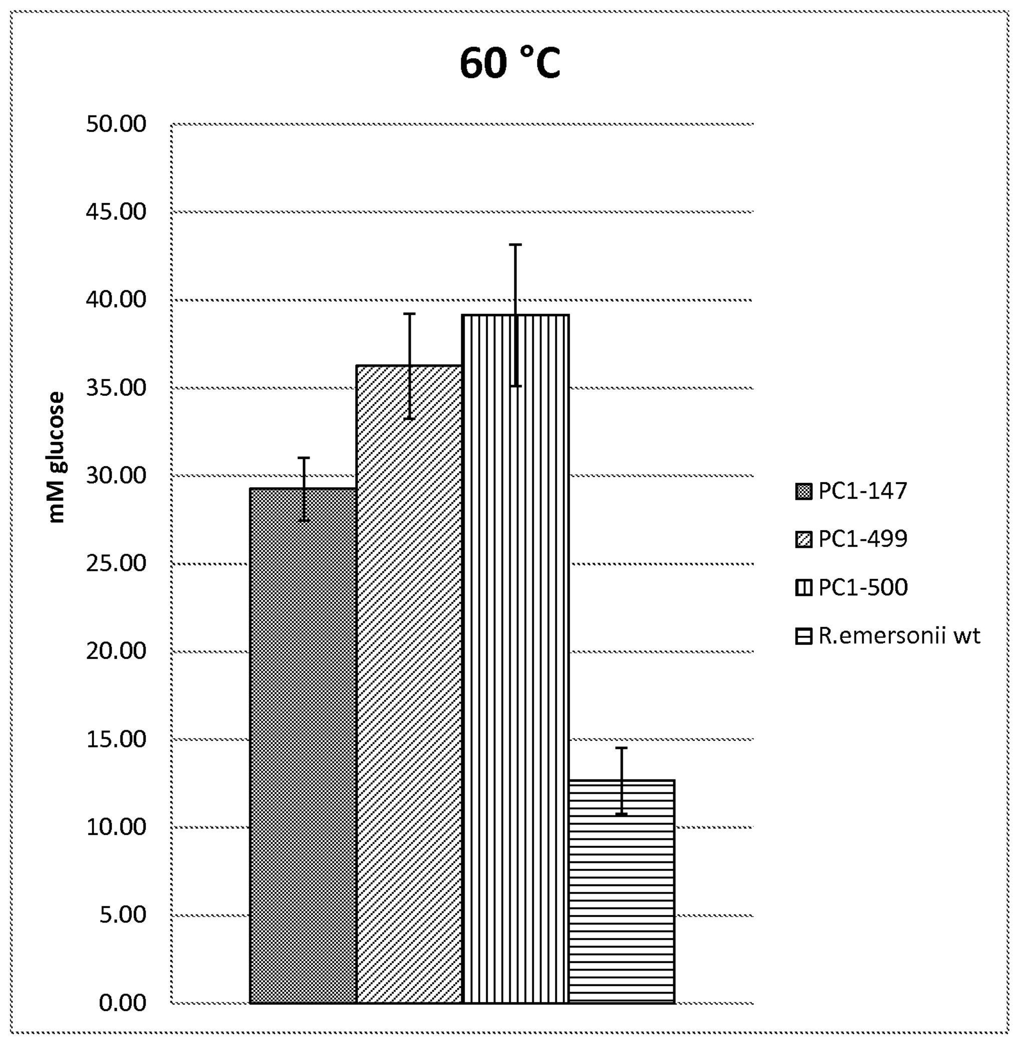

FIG. 3 shows hydrolysis of microcrystalline cellulose by *R. emersonii* wild-type cellobiohydrolase I, and hybrid polypeptides PC1-147, PC1-499 and PC1-500. Values are shown in mM released cellobiose after 24 hours at pH 5 and 60° C.

Figure 4:
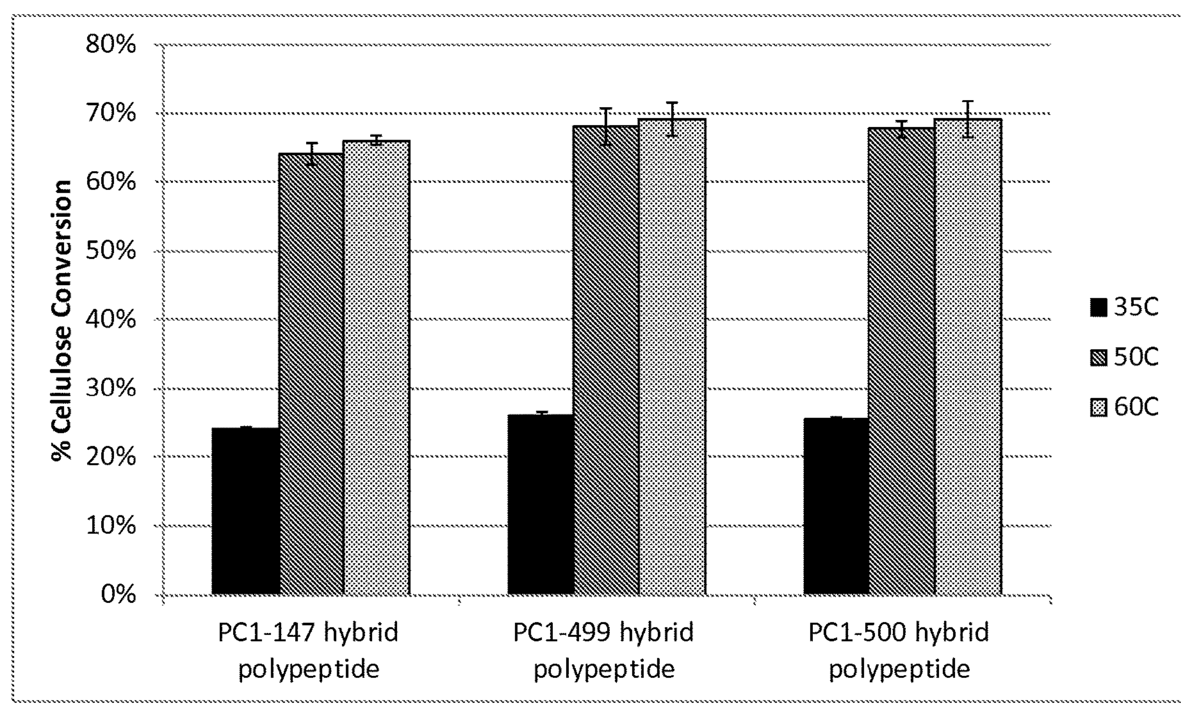

FIG. 4 shows a comparison of percent cellulose conversion of pretreated corn stover at 35° C., 50° C., and 60° C. by enzyme compositions comprising hybrid polypeptides PC1-147, PC1-499 or PC1-500.

Figure 5:
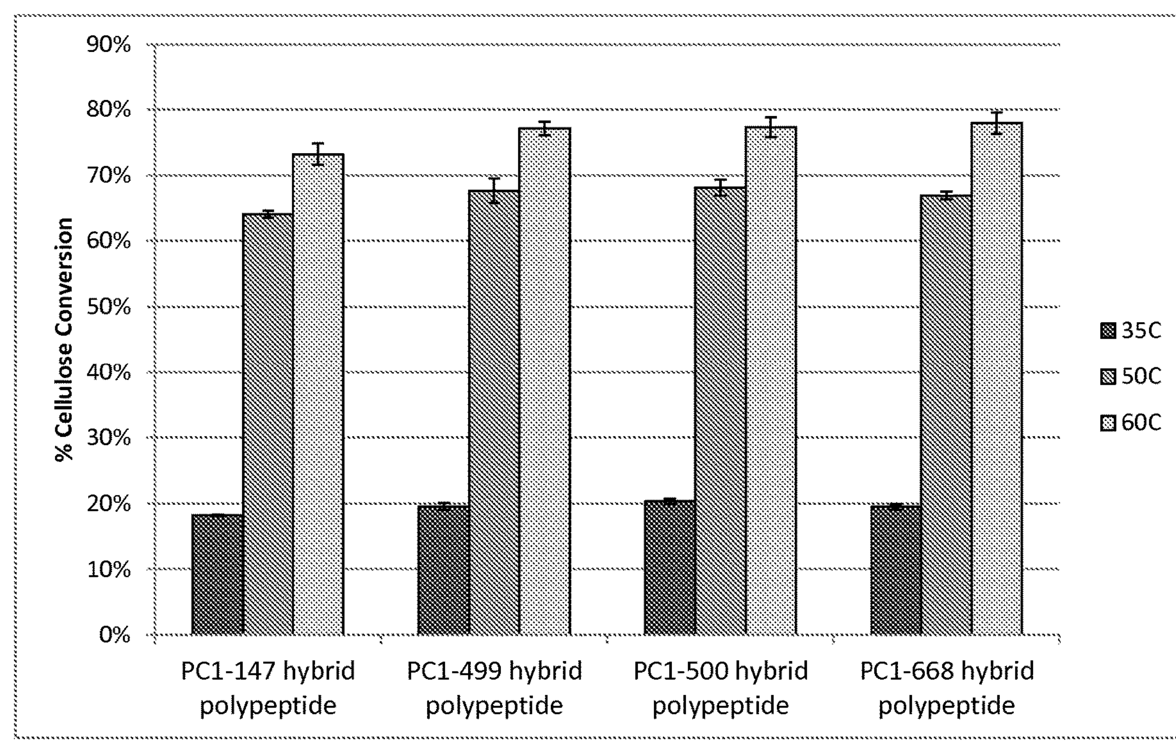

FIG. 5 shows a comparison of percent cellulose conversion of pretreated corn stover at 35° C., 50° C., and 60° C. by enzyme compositions comprising hybrid polypeptides PC1-147, PC1-499, PC1-500, or PC1-668.

Figure 6:
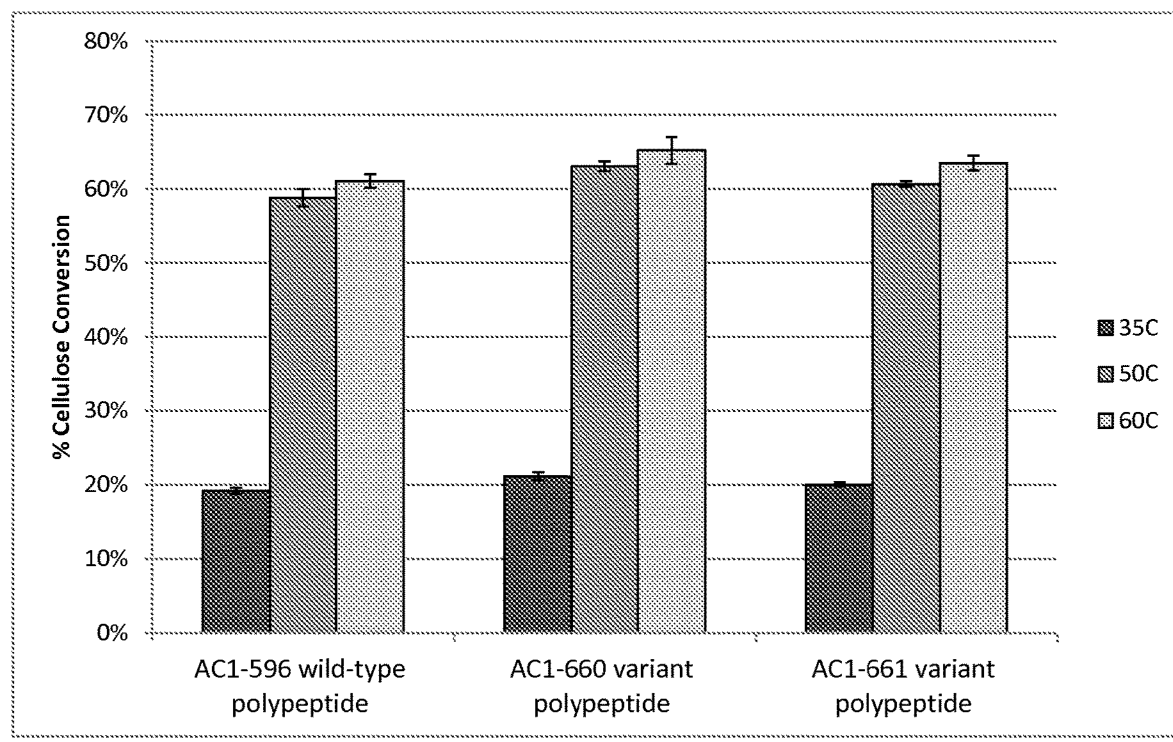

FIG. 6 shows a comparison of percent cellulose conversion of pretreated corn stover at 35° C., 50° C., and 60° C. by enzyme compositions comprising polypeptides AC1-596, AC1-660, or AC1-661.

Figure 7:
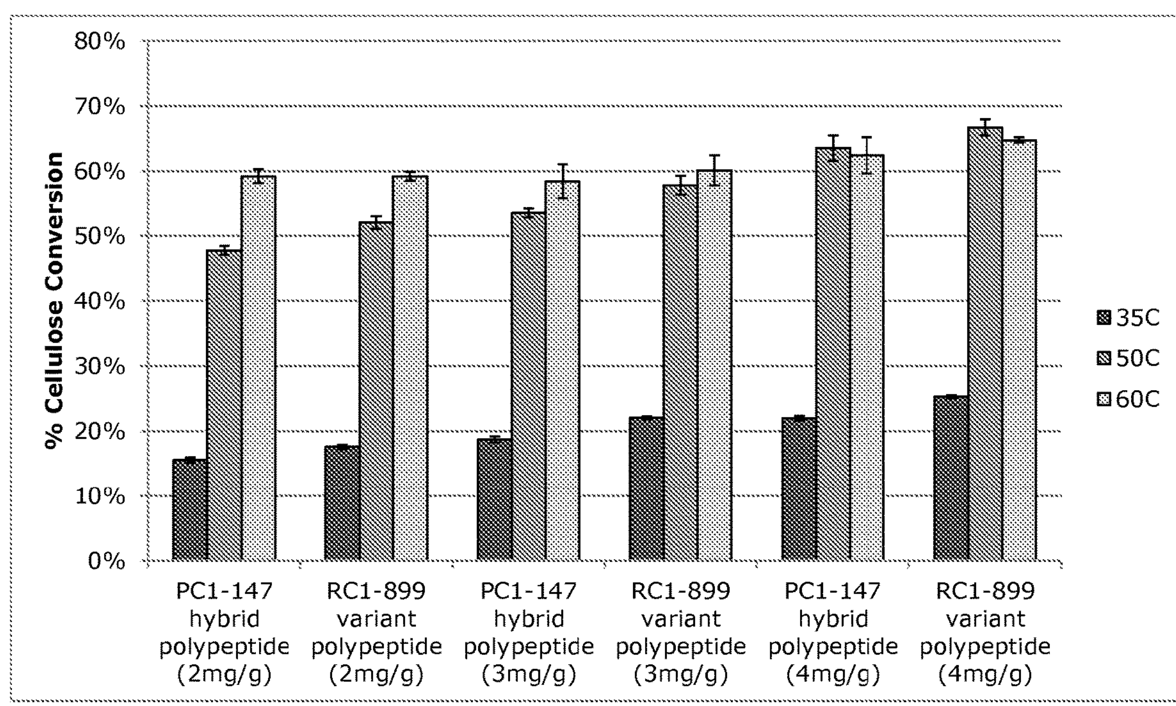

FIG. 7 shows a comparison of percent cellulose conversion of pretreated corn stover at 35° C., 50° C., and 60° C. by enzyme compositions comprising polypeptides PC1-147 or RC1-899.

DEFINITIONS

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)-and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C. and a suitable pH, such as 4-9, e.g., 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST™ 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can also be used in the presence of a soluble activating divalent metal cation according to WO 2008/151043 or WO 2012/122518, e.g., manganese or copper.

The AA9 polypeptide can be used in the presence of a dioxy compound, a bicyclic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Carbohydrate binding module: The term "carbohydrate binding module" means a domain within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalase: The term "catalase" means a hydrogen-peroxide:hydrogen-peroxide oxidoreductase (EC 1.11.1.6) that catalyzes the conversion of $2H_2O_2$ to $O_2$+2 $H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Catalytic domain: The term "catalytic domain" means the region of an enzyme containing the catalytic machinery of the enzyme. In one aspect, the catalytic domain is amino acids 1 to 429 of SEQ ID NO: 30. In another aspect, the catalytic domain is amino acids 1 to 437 of SEQ ID NO: 36. In another aspect, the catalytic domain is amino acids 1 to 440 of SEQ ID NO: 38. In another aspect, the catalytic domain is amino acids 1 to 437 of SEQ ID NO: 40. In another aspect, the catalytic domain is amino acids 1 to 437 of SEQ ID NO: 42. In another aspect, the catalytic domain is amino acids 1 to 438 of SEQ ID NO: 44. In another aspect, the catalytic domain is amino acids 1 to 437 of SEQ ID NO: 46. In another aspect, the catalytic domain is amino acids 1 to 430 of SEQ ID NO: 48. In another aspect, the catalytic domain is amino acids 1 to 433 of SEQ ID NO: 50.

Catalytic domain coding sequence: The term "catalytic domain coding sequence" means a polynucleotide that encodes a catalytic domain having catalytic activity. In one aspect, the catalytic domain coding sequence is nucleotides 52 to 1469 of SEQ ID NO: 29. In another aspect, the catalytic domain coding sequence is nucleotides 52 to 1389 of SEQ ID NO: 31. In another aspect, the catalytic domain coding sequence is nucleotides 52 to 1389 of SEQ ID NO: 32. In another aspect, the catalytic domain coding sequence is nucleotides 79 to 1389 of SEQ ID NO: 35 In another aspect, the catalytic domain coding sequence is nucleotides 52 to 1371 of SEQ ID NO: 37. In another aspect, the catalytic domain coding sequence is nucleotides 55 to 1482 of SEQ ID NO: 39. In another aspect, the catalytic domain coding sequence is nucleotides 76 to 1386 of SEQ ID NO: 41. In another aspect, the catalytic domain is nucleotides 76 to 1386 of SEQ ID NO: 43. In another aspect, the catalytic domain coding sequence is nucleotides 55 to 1504 of SEQ ID NO: 45. In another aspect, the catalytic domain coding sequence is nucleotides 61 to 1350 of SEQ ID NO: 47. In another aspect, the catalytic domain coding sequence is nucleotides 55 to 1353 of SEQ ID NO: 49.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is *arundo*, bagasse, bamboo, corn cob, corn fiber, corn stover, *miscanthus*, rice straw, sugar cane straw, switchgrass, or wheat straw.

In another embodiment, the cellulosic material is aspen, *eucalyptus*, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellobiohydrolase activity. In one aspect, a fragment contains at least 425 amino acid residues, e.g., at least 450 amino acid residues or at least 475 amino acid residues of the mature polypeptide of SEQ ID NO: 2. In another aspect, a fragment contains at least 425 amino acid residues, e.g., at least 450 amino acid residues or at least 475 amino acid residues of the mature polypeptide of SEQ ID NO: 6. In another aspect, a fragment contains at least 425 amino acid residues, e.g., at least 450 amino acid residues or at least 475 amino acid residues of the mature polypeptide of SEQ ID NO: 10. In another aspect, a fragment contains at least 425 amino acid residues, e.g., at least 450 amino acid residues or at least 475 amino acid residues of the mature polypeptide of SEQ ID NO: 14. In another aspect, a fragment contains at least 425 amino acid residues, e.g., at least 450 amino acid residues or at least 475 amino acid residues of the mature polypeptide of SEQ ID NO: 18. In another aspect, a fragment contains at least 425 amino acid residues, e.g., at least 450 amino acid residues or at least 475 amino acid residues of the mature polypeptide of SEQ ID NO: 22. In another aspect, a fragment contains at least 425 amino acid residues, e.g., at least 450 amino acid residues or at least 475 amino acid residues of the mature polypeptide of SEQ ID NO: 26.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 40° C., 45° C., 50° C., 55° C., 60° C., 65° C., 70° C., 75° C., or 80° C., and a suitable pH such as 4-9, e.g., 4.0, 4.5, 5.0, 5.5, 6.0, 6.5, 7.0, 7.5, 8.0, 8.5, or 9.0.

Hemicellulosic material: The term "hemicellulosic material" means any material comprising hemicelluloses. Hemicelluloses include xylan, glucuronoxylan, arabinoxylan, glucomannan, and xyloglucan. These polysaccharides contain many different sugar monomers. Sugar monomers in hemicellulose can include xylose, mannose, galactose, rhamnose, and arabinose. Hemicelluloses contain most of the D-pentose sugars. Xylose is in most cases the sugar monomer present in the largest amount, although in softwoods mannose can be the most abundant sugar. Xylan contains a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono) arabinoxylans, arabinoxylans, and complex heteroxylans. See, for example, Ebringerova et al., 2005, *Adv. Polym. Sci.* 186: 1-67. Hemicellulosic material is also known herein as "xylan-containing material".

Sources for hemicellulosic material are essentially the same as those for cellulosic material described herein.

In the processes of the present invention, any material containing hemicellulose may be used. In a preferred aspect, the hemicellulosic material is lignocellulose.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide in which a region of one polypeptide is fused at the N-terminus or the C-terminus of a region of another (heterologous) polypeptide.

Increased specific performance: The term "increased specific performance" by a variant of the present invention means improved conversion of a cellulosic material to a product, as compared to the same level of conversion by the parent. Increased specific performance is determined per unit protein (e.g., mg protein, or μmole protein). The increased specific performance of the variant relative to the parent can be assessed, for example, under one or more (e.g., several) conditions of pH, temperature, and substrate concentration. In one aspect, the product is glucose. In another aspect, the product is cellobiose. In another aspect, the product is glucose+cellobiose.

In one aspect, the condition is pH. For example, the pH can be any pH in the range of 3 to 7, e.g., 3.0, 3.5, 4.0, 4.5, 5.0, 5.5, 6.0, 6.5, or 7.0 (or in between). Any suitable buffer for achieving the desired pH can be used.

In another aspect, the condition is temperature. For example, the temperature can be any temperature in the range of 25° C. to 90° C., e.g., 25, 30, 35, 40, 45, 50, 55, 60, 65, 70, 75, 80, 85, or 90° C. (or in between).

In another aspect, the condition is substrate concentration. Any cellulosic material defined herein can be used as the substrate. In one aspect, the substrate concentration is measured as the dry solids content. The dry solids content is preferably in the range of about 1 to about 50 wt %, e.g., about 5 to about 45 wt %, about 10 to about 40 wt %, or about 20 to about 30 wt %. In another aspect, the substrate concentration is measured as the insoluble glucan content. The insoluble glucan content is preferably in the range of about 2.5 to about 25 wt %, e.g., about 5 to about 20 wt % or about 10 to about 15 wt %.

In another aspect, a combination of two or more (e.g., several) of the above conditions are used to determine the increased specific performance of the variant relative to the parent, such as any temperature in the range of 25° C. to 90° C., e.g., 25, 30, 35, 40, 45, 50, 55, 60, 65, 70, 75, 80, 85, or 90° C. (or in between) at a pH in the range of 3 to 7, e.g., 3.0, 3.5, 4.0, 4.5, 5.0, 5.5, 6.0, 6.5, or 7.0 (or in between).

The increased specific performance of the variant relative to the parent can be determined using any enzyme assay known in the art for cellobiohydrolases as described herein. Alternatively, the increased specific performance of the variant relative to the parent can be determined using the assays described in Examples 9 and 12.

In another aspect, the specific performance of the variant is at least 1.01-fold, e.g., at least 1.02-fold, at least 1.03-fold, at least 1.04-fold, at least 1.05-fold, at least 1.06-fold, at least 1.07-fold, at least 1.08-fold, at least 1.09-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 5-fold, at least 10-fold, at least 15-fold, at least 20-fold, at least 25-fold, and at least 50-fold higher than the specific performance of the parent.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). Any of the carbohydrate binding module variants, cellobiohydrolase variants, or hybrid polypeptides described herein may be in isolated form.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 514 of SEQ ID NO: 2, amino acids 19 to 525 of SEQ ID NO: 6, amino acids 19 to 530 of SEQ ID NO: 10, amino acids 26 to 537 of SEQ ID NO: 14, amino acids 27 to 532 of SEQ ID NO: 18, amino acids 18 to 526 of SEQ ID NO: 22, amino acids 18 to 525 of SEQ ID NO: 26, amino acids 19 to 519 of SEQ ID NO: 61, amino acids 19 to 519 of SEQ ID NO: 63, amino acids 19 to 519 of SEQ ID NO: 73, amino acids 27 to 532 of SEQ ID NO: 78, amino acids 27 to 532 of SEQ ID NO: 90, amino acids 27 to 532 of SEQ ID NO: 92, amino acids 19 to 521 of SEQ ID NO: 94 based on the SignalP program (Nielsen et al., 1997, *Protein Engineering* 10: 1-6) that predicts amino acids 1 to 17 of SEQ ID NO: 2, amino acids 1 to 18 of SEQ ID NO: 6, amino acids 1 to 18 of SEQ ID NO: 10, amino acids 1 to 25 of SEQ ID NO: 14, amino acids 1 to 26 of SEQ ID NO: 18, amino acids 1 to 17 of SEQ ID NO: 22, and amino acids 1 to 17 of SEQ ID NO: 26, amino acids 1 to 18 of SEQ ID NO: 61, amino acids 1 to 18 of SEQ ID NO: 63, amino acids 1 to 18 of SEQ ID NO: 73, amino acids 1 to 26 of SEQ ID NO: 78, amino acids 1 to 26 of SEQ ID NO: 90, amino acids 1 to 26 of SEQ ID NO: 92, amino acids 1 to 18 of SEQ ID NO: 94, respectively, are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellobiohydrolase activity. In one aspect, the mature polypeptide coding sequence is nucleotides 52 to 1542 of SEQ ID NO: 1, nucleotides 55 to 1635 of SEQ ID NO: 5, nucleotides 55 to 1590 of SEQ ID NO: 9, nucleotides 76 to 1614 of SEQ ID NO: 13, nucleotides 79 to 1596 of SEQ ID NO: 17, nucleotides 52 to 1578 of SEQ ID NO: 21, and nucleotides 52 to 1575 of SEQ ID NO: 25, or the genomic DNA or cDNA sequence thereof, based on the SignalP program (Nielsen et al., supra) that predicts nucleotides 1 to 51 of SEQ ID NO: 1, nucleotides 1 to 54 of SEQ ID NO: 5, nucleotides 1 to 54 of SEQ ID NO: 9, nucleotides 1 to 75 of SEQ ID NO: 13, nucleotides 1 to 78 of SEQ ID NO: 17, nucleotides 1 to 51 of SEQ ID NO: 21, and nucleotides 1 to 51 of SEQ ID NO: 25, respectively, encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent cellobiohydrolase: The term "parent cellobiohydrolase" means a cellobiohydrolase to which an alteration is made to produce the enzyme variants of the present invention. The parent may be a naturally occurring (wild-type) polypeptide or a variant or fragment thereof. The parent cellobiohydrolase may include a carbohydrate binding module.

Parent carbohydrate binding module: The term "parent carbohydrate binding module" means a carbohydrate binding module to which an alteration is made to produce the carbohydrate binding module variants of the present invention. The parent may be a naturally occurring (wild-type) polypeptide or a variant or fragment thereof.

Pretreated cellulosic or hemicellulosic material: The term "pretreated cellulosic or hemicellulosic material" means a cellulosic or hemicellulosic material derived from biomass by treatment with heat and dilute sulfuric acid, alkaline pretreatment, neutral pretreatment, or any pretreatment known in the art.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellobiohydrolase activity. In one aspect, a subsequence contains at least 1275 nucleotides, e.g., at least 1350 nucleotides or at least 1425 nucleotides of the mature polypeptide coding sequence of SEQ ID NO: 1. In another aspect, a subsequence contains at least 1275 nucleotides, e.g., at least 1350 nucleotides or at least 1425 nucleotides of the mature polypeptide coding sequence of SEQ ID NO: 5. In another aspect, a subsequence contains at least 1275 nucleotides, e.g., at least 1350 nucleotides or at least 1425 nucleotides of the mature polypeptide coding sequence of SEQ ID NO: 9. In another aspect, a subsequence contains at least 1275 nucleotides, e.g., at least 1350 nucleotides or at least 1425 nucleotides of the mature polypeptide coding sequence of SEQ ID NO: 13. In another aspect, a subsequence contains at least 1275 nucleotides, e.g., at least 1350 nucleotides or at least 1425 nucleotides of the mature polypeptide coding sequence of SEQ ID NO: 17. In another aspect, a subsequence contains at least 1275 nucleotides, e.g., at least 1350 nucleotides or at least 1425 nucleotides of the mature polypeptide coding sequence of SEQ ID NO: 21. In another aspect, a subsequence contains at least 1275 nucleotides, e.g., at least 1350 nucleotides or at least 1425 nucleotides of the mature polypeptide coding sequence of SEQ ID NO: 25.

Variant: The term "variant" means a polypeptide having cellobiohydrolase activity or a carbohydrate binding module comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

A cellobiohydrolase variant of the present invention has at least 20%, e.g., at least 40%, at least 50%, at least 60%, at least 70%, at least 80%, at least 90%, at least 95%, or at least 100% of the cellobiohydrolase activity of the mature polypeptide of SEQ ID NO: 2, SEQ ID NO: 6, SEQ ID NO: 10, SEQ ID NO: 14, SEQ ID NO: 18, SEQ ID NO: 22, or SEQ ID NO: 26. A carbohydrate binding module variant of the present invention has at least 20%, e.g., at least 40%, at least 50%, at least 60%, at least 70%, at least 80%, at least 90%, at least 95%, or at least 100% of the carbohydrate binding activity of SEQ ID NO: 4, SEQ ID NO: 8, SEQ ID NO: 12, SEQ ID NO: 16, SEQ ID NO: 20, SEQ ID NO: 24, or SEQ ID NO: 28.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Wild-type cellobiohydrolase: The term "wild-type" cellobiohydrolase means a cellobiohydrolase expressed by a naturally occurring microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrimann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION OF THE INVENTION

The present invention relates to carbohydrate binding module variants, comprising a substitution at one or more (e.g., several) positions corresponding to positions 5, 13, 31 and 32 of the carbohydrate binding module of SEQ ID NO: 4, wherein the variants have carbohydrate binding activity. In one aspect, a cellulolytic enzyme comprises a carbohydrate binding module variant of the present invention (e.g., a hybrid polypeptide).

The present invention also relates to isolated cellobiohydrolase variants, comprising a substitution at one or more (e.g., several) positions corresponding to positions 483, 491, 509 and 510 of SEQ ID NO: 2, wherein the variants have cellobiohydrolase activity.

Conventions for Designation of Variants

For purposes of the present invention, the polypeptide sequence disclosed in SEQ ID NO: 2 or the carbohydrate binding module (CBM) disclosed in SEQ ID NO: 4 is used to determine the corresponding amino acid residue in another cellobiohydrolase or CBM, respectively. The amino acid sequence of another cellobiohydrolase or CBM is aligned with SEQ ID NO: 2 or SEQ ID NO: 4, respectively, and based on the alignment, the amino acid position number corresponding to any amino acid residue in the polypeptide disclosed in SEQ ID NO: 2 or the CBM disclosed in SEQ ID NO: 4 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another cellobiohydrolase or CBM can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 2 or the other CBM has diverged from SEQ ID NO: 4 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195<br>G | 195 195a 195b<br>G-K-A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Carbohydrate Binding Module Variants

The present invention relates to variants of a parent carbohydrate binding module comprising a substitution at one or more (e.g., several) positions corresponding to positions 5, 13, 31 and 32 of the carbohydrate binding module of SEQ ID NO: 4, wherein the variant has carbohydrate binding activity.

In one aspect, the carbohydrate binding module variant has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent carbohydrate binding module.

In another aspect, the carbohydrate binding module variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4, SEQ ID NO: 8, SEQ ID NO: 12, SEQ ID NO: 16, SEQ ID NO: 20, SEQ ID NO: 24, or SEQ ID NO: 28.

In one aspect, the number of substitutions in the carbohydrate binding module variants of the present invention is 1-4, such as 1, 2, 3, or 4 substitutions.

In one aspect, the carbohydrate binding module variant comprises or consists of a substitution at a position corresponding to position 5 of SEQ ID NO: 4. In one embodiment, the amino acid at a position corresponding to position 5 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 5 of SEQ ID NO: 4 is substituted with Trp. In another embodiment, the amino acid at a position corresponding to position 5 of SEQ ID NO: 4 is Tyr substituted with Trp (e.g., Y5W of SEQ ID NO: 4).

In another aspect, the carbohydrate binding module variant comprises or consists of a substitution at a position corresponding to position 13 of SEQ ID NO: 4. In one embodiment, the amino acid at a position corresponding to position 13 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 13 of SEQ ID NO: 4 is substituted with Trp. In another embodiment, the amino acid at a position corresponding to position 13 of SEQ ID NO: 4 is Tyr substituted with Trp (e.g., Y13W of SEQ ID NO: 4).

In another aspect, the carbohydrate binding module variant comprises or consists of a substitution at a position corresponding to position 31 of SEQ ID NO: 4. In one embodiment, the amino acid at a position corresponding to position 31 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 31 of SEQ ID NO: 4 is substituted with Trp. In another embodiment, the amino acid at a position corresponding to position 31 of SEQ ID NO: 4 is Tyr substituted with Trp (e.g., Y31W of SEQ ID NO: 4).

In another aspect, the carbohydrate binding module variant comprises or consists of a substitution at a position corresponding to position 32 of SEQ ID NO: 4. In one embodiment, the amino acid at a position corresponding to position 32 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 32 of SEQ ID NO: 4 is substituted with Trp. In another embodiment, the amino acid at a position corresponding to position 32 of SEQ ID NO: 4 is Tyr substituted with Trp (e.g., Y32W of SEQ ID NO: 4).

In another aspect, the carbohydrate binding module variant comprises or consists of a substitution at two positions corresponding to positions 5, 13, 31 and 32 of SEQ ID NO: 4, such as those described above. In one embodiment, the carbohydrate binding module variant comprises or consists of a substitution at positions corresponding to positions 5 and 13 (e.g., substituted with Trp at positions corresponding to positions 5 and 13, such as Y5W and/or Y13W). In another embodiment, the carbohydrate binding module variant comprises or consists of a substitution at positions corresponding to positions 5 and 31 (e.g., substituted with Trp at positions corresponding to positions 5 and 31, such as Y5W and/or Y31W). In another embodiment, the carbohydrate binding module variant comprises or consists of a substitution at positions corresponding to positions 5 and 32 (e.g., substituted with Trp at positions corresponding to positions 5 and 32, such as Y5W and/or Y32W). In another embodiment, the carbohydrate binding module variant comprises or consists of a substitution at positions corresponding to positions 13 and 31 (e.g., substituted with Trp at positions corresponding to positions 13 and 31, such as Y13W and/or Y31W). In another embodiment, the carbohydrate binding module variant comprises or consists of a substitution at positions corresponding to positions 13 and 32 (e.g., substituted with Trp at positions corresponding to positions 13 and 32, such as Y13W and/or Y32W). In another embodiment, the carbohydrate binding module variant comprises or consists of a substitution at positions corresponding to positions 31 and 32 (e.g., substituted with Trp at positions corresponding to positions 31 and 32, such as Y31W and/or Y32W).

In another aspect, the carbohydrate binding module variant comprises or consists of a substitution at three positions corresponding to positions 5, 13, 31 and 32 of SEQ ID NO: 4, such as those described above. In one embodiment, the carbohydrate binding module variant comprises or consists of a substitution at positions corresponding to positions 5, 13, and 31 (e.g., substituted with Trp at positions corresponding to positions 5, 13, and 31, such as Y5W, Y13W, and/or Y31W). In another embodiment, the carbohydrate binding module variant comprises or consists of a substitution at positions corresponding to positions 5, 13, and 32 (e.g., substituted with Trp at positions corresponding to positions 5, 13, and 32, such as Y5W, Y13W, and/or Y32W). In another embodiment, the carbohydrate binding module variant comprises or consists of a substitution at positions corresponding to positions 5, 31, and 32 (e.g., substituted with Trp at positions corresponding to positions 5, 31, and 32, such as Y5W, Y31W, and/or Y32W). In another embodiment, the carbohydrate binding module variant comprises or consists of a substitution at positions corresponding to positions 13, 31, and 32 (e.g., substituted with Trp at positions corresponding to positions 13, 31, and 32, such as Y13W, Y31W, and/or Y32W).

In another aspect, the carbohydrate binding module variant comprises or consists of a substitution at all four positions corresponding to positions 5, 13, 31 and 32 of SEQ ID NO: 4, such as those described above. In one embodiment, the carbohydrate binding module variant comprises or consists of a Trp substitution at one or more positions corresponding to positions 5, 13, 31 and 32, such as Y5W, Y13W, Y31W and/or Y32W).

The carbohydrate binding module variants may further comprise a substitution, a deletion, and/or an insertion at one or more (e.g., several) other positions, such as one or more (e.g., several) substitutions at positions corresponding to positions disclosed in WO 2012/135719, which is incorporated herein by reference. For example, in one aspect, the carbohydrate binding module variant further comprises a substitution at one or more (e.g., several) positions corresponding to positions 4, 6, and 29 of SEQ ID NO: 4. In another aspect, the carbohydrate binding module variant further comprises a substitution at two positions corresponding to any of positions 4, 6, and 29. In another aspect, the carbohydrate binding module variant further comprises a substitution at each position corresponding to positions 4, 6, and 29.

In another aspect, the carbohydrate binding module variant further comprises or consists of a substitution at a position corresponding to position 4. In another aspect, the amino acid at a position corresponding to position 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Leu, Lys, Phe, or Trp. In another aspect, the carbohydrate binding module variant further comprises or consists of the substitution H4L of SEQ ID NO: 4. In another aspect, the carbohydrate binding module variant further comprises or consists of the substitution H4K of SEQ ID NO: 4. In another aspect, the carbohydrate binding module variant further comprises or consists of the substitution H4E of SEQ ID NO: 4. In another aspect, the carbohydrate binding module variant further comprises or consists of the substitution H4F of SEQ ID NO: 4. In another aspect, the carbohydrate binding module variant further comprises or consists of the substitution H4W of SEQ ID NO: 4.

In another aspect, the carbohydrate binding module variant further comprises or consists of a substitution at a position corresponding to position 6. In another aspect, the amino acid at a position corresponding to position 6 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the carbohydrate binding module variant further comprises or consists of the substitution G6A of SEQ ID NO: 4.

In another aspect, the carbohydrate binding module variant further comprises or consists of a substitution at a position corresponding to position 29. In another aspect, the amino acid at a position corresponding to position 29 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the carbohydrate binding module variant further comprises or consists of the substitution N29D of SEQ ID NO: 4.

In another aspect, the carbohydrate binding module variant further comprises or consists of a substitution at positions corresponding to positions 4 and 6, such as those described above.

In another aspect, the carbohydrate binding module variant further comprises or consists of substitutions at positions corresponding to positions 4 and 29, such as those described above.

In another aspect, the carbohydrate binding module variant further comprises or consists of substitutions at positions corresponding to positions 6 and 29, such as those described above.

In another aspect, the carbohydrate binding module variant further comprises or consists of substitutions at positions corresponding to positions 4, 6, and 29, such as those described above.

In another aspect, the carbohydrate binding module variant further comprises or consists of one or more (e.g., several) substitutions selected from the group consisting of H4L,K,E,F,W, G6A, and N29D or the one or more (e.g., several) substitutions selected from the group consisting of H4L,K,E,F,W, G6A, and N29D corresponding to SEQ ID NO: 4 in other cellulose binding modules described herein.

In another aspect, the carbohydrate binding module variant further comprises or consists of the substitutions H4L+G6A of SEQ ID NO: 4.

In another aspect, the carbohydrate binding module variant further comprises or consists of the substitutions H4K+G6A of SEQ ID NO: 4.

In another aspect, the carbohydrate binding module variant further comprises or consists of the substitutions H4E+G6A of SEQ ID NO: 4.

In another aspect, the carbohydrate binding module variant further comprises or consists of the substitutions H4F+G6A of SEQ ID NO: 4.

In another aspect, the carbohydrate binding module variant further comprises or consists of the substitutions H4W+G6A of SEQ ID NO: 4.

In another aspect, the carbohydrate binding module variant further comprises or consists of the substitutions H4L+N29D of SEQ ID NO: 4.

In another aspect, the carbohydrate binding module variant further comprises or consists of the substitutions H4K+N29D of SEQ ID NO: 4.

In another aspect, the carbohydrate binding module variant further comprises or consists of the substitutions H4E+N29D of SEQ ID NO: 4.

In another aspect, the carbohydrate binding module variant further comprises or consists of the substitutions H4F+N29D of SEQ ID NO: 4.

In another aspect, the carbohydrate binding module variant further comprises or consists of the substitutions H4W+N29D of SEQ ID NO: 4.

In another aspect, the carbohydrate binding module variant further comprises or consists of the substitutions G6A+N29D of SEQ ID NO: 4.

In another aspect, the carbohydrate binding module variant further comprises or consists of the substitutions H4L+G6A+N29D of SEQ ID NO: 4.

In another aspect, the carbohydrate binding module variant further comprises or consists of the substitutions H4K+G6A+N29D of SEQ ID NO: 4.

In another aspect, the carbohydrate binding module variant further comprises or consists of the substitutions H4E+G6A+N29D of SEQ ID NO: 4.

In another aspect, the carbohydrate binding module variant further comprises or consists of the substitutions H4F+G6A+N29D of SEQ ID NO: 4.

In another aspect, the carbohydrate binding module variant further comprises or consists of the substitutions H4W+G6A+N29D of SEQ ID NO: 4.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding module.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In some aspects, the carbohydrate binding module variants may consist of 28 to 36 amino acids, inclusive, e.g., 28, 29, 30, 31, 32, 33, 34, 35, or 36 amino acids.

As described in more detail below, the present invention also relates to a polypeptide having cellulolytic activity, comprising a carbohydrate binding module variant as described above. In one aspect, the polypeptide is derived from a "wild-type" cellulolytic enzyme (such as a "wild-type" cellobiohydrolase) having a carbohydrate binding module, wherein the carbohydrate binding module comprises a substitution at one or more (e.g., several) positions corresponding to positions 5, 13, 31 and 32 of SEQ ID NO: 4. In one aspect, a carbohydrate binding module variant of the present invention may be fused to a polypeptide lacking a carbohydrate binding module. In another aspect, a carbohydrate binding module contained in a polypeptide may be replaced with a carbohydrate binding module variant of the present invention. In another aspect, the polypeptide is a cellulolytic enzyme selected from the group consisting of an endoglucanase, a cellobiohydrolase, and a GH61 polypeptide. In one embodiment, the cellulolytic enzyme is an endoglucanase. In another embodiment, the cellulolytic enzyme is a cellobiohydrolase. In another embodiment, the cellulolytic enzyme is a GH61 polypeptide.

In some aspects, the carbohydrate binding module variants have improved binding activity. In some embodiments, carbohydrate binding module variants do not have decreased binding activity compared to the parent. In some embodiments, the carbohydrate binding module variant has at least 1.01-fold, e.g., at least 1.02-fold, at least 1.03-fold, at least 1.04-fold, at least 1.05-fold, at least 1.06-fold, at least 1.07-fold, at least 1.08-fold, at least 1.09-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, at least 2.2-fold, at least 2.3-fold, at least 2.4-fold, at least 2.5-fold, at least 5-fold, at least 10-fold, at least 15-fold, at least 20-fold, at least 25-fold, and at least 50-fold higher binding activity compared to the parent.

Cellobiohydrolase Variants

The present invention also relates to variants of a parent cellobiohydrolase comprising a carbohydrate binding module wherein the carbohydrate binding module comprises a substitution at one or more (e.g., several) positions corresponding to positions 5, 13, 31 and 32 of SEQ ID NO: 4. For example, in one aspect is a variant of a parent cellobiohydrolase comprising a substitution at one or more (e.g., several) positions corresponding to positions 483, 491, 509 and 510 of SEQ ID NO: 2, wherein the variant has cellobiohydrolase activity.

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent cellobiohydrolase.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

In one aspect, the number of substitutions in the variants of the present invention is 1-3, such as 1, 2, or 3 substitutions.

In another aspect, the variant comprises or consists of a substitution at a position corresponding to position 483 of SEQ ID NO: 2. In one embodiment, the amino acid at a position corresponding to position 483 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 483 of SEQ ID NO: 2 is substituted with Trp. In another embodiment, the amino acid at a position corresponding to position 483 of SEQ ID NO: 2 is Tyr substituted with Trp (e.g., Y483W of SEQ ID NO: 4).

In another aspect, the variant comprises or consists of a substitution at a position corresponding to position 491 of SEQ ID NO: 2. In one embodiment, the amino acid at a position corresponding to position 491 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 491 of SEQ ID NO: 2 is substituted with Trp. In another embodiment, the amino acid at a position corresponding to position 491 of SEQ ID NO: 2 is Tyr substituted with Trp (e.g., Y491W of SEQ ID NO: 4).

In another aspect, the variant comprises or consists of a substitution at a position corresponding to position 509 of SEQ ID NO: 2. In one embodiment, the amino acid at a position corresponding to position 509 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 509 of SEQ ID NO: 2 is substituted with Trp. In another embodiment, the amino acid at a position corresponding to position 509 of SEQ ID NO: 2 is Tyr substituted with Trp (e.g., Y509W of SEQ ID NO: 4).

In another aspect, the variant comprises or consists of a substitution at a position corresponding to position 510 of SEQ ID NO: 2. In one embodiment, the amino acid at a position corresponding to position 510 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 510 of SEQ ID NO: 2 is substituted with Trp. In another embodiment, the amino acid at a position corresponding to position 510 of SEQ ID NO: 2 is Tyr substituted with Trp (e.g., Y510W of SEQ ID NO: 4).

In another aspect, the variant comprises or consists of a substitution at two positions corresponding to positions 483, 491, 509 and 510 of SEQ ID NO: 2, such as those described above. In one embodiment, the variant comprises or consists of a substitution at positions corresponding to positions 483 and 491 (e.g., substituted with Trp at positions corresponding to positions 483 and 491, such as Y483W and/or Y491W). In another embodiment, the variant comprises or consists of a substitution at positions corresponding to positions 483 and 509 (e.g., substituted with Trp at positions corresponding to positions 483 and 509, such as Y483W and/or Y509W). In another embodiment, the variant comprises or consists of a substitution at positions corresponding to positions 483 and 510 (e.g., substituted with Trp at positions corresponding to positions 483 and 510, such as Y483W and/or Y510W). In another embodiment, the variant comprises or consists of a substitution at positions corresponding to positions 491 and 509 (e.g., substituted with Trp at positions corresponding to positions 491 and 509, such as Y491W and/or Y509W). In another embodiment, the variant comprises or consists of a substitution at positions corresponding to positions 491 and 510 (e.g., substituted with Trp at positions corresponding to positions 491 and 510, such as Y491W and/or Y32W). In another embodiment, the variant comprises or consists of a substitution at positions corresponding to positions 509 and 510 (e.g., substituted with Trp at positions corresponding to positions 509 and 510, such as Y509W and/or Y510W).

In another aspect, the variant comprises or consists of a substitution at three positions corresponding to positions 483, 491, 509 and 32 of SEQ ID NO: 2, such as those described above. In one embodiment, the variant comprises or consists of a substitution at positions corresponding to positions 483, 491, and 509 (e.g., substituted with Trp at positions corresponding to positions 483, 491, and 509, such as Y483W, Y491W, and/or Y509W). In another embodiment, the variant comprises or consists of a substitution at positions corresponding to positions 483, 491, and 510 (e.g., substituted with Trp at positions corresponding to positions 483, 491, and 510, such as Y5W, Y491W, and/or Y510W). In another embodiment, the variant comprises or consists of a substitution at positions corresponding to positions 483, 509, and 510 (e.g., substituted with Trp at positions corresponding to positions 483, 509, and 510, such as Y483W, Y509W, and/or Y510W). In another embodiment, the variant comprises or consists of a substitution at positions corresponding to positions 491, 509, and 510 (e.g., substituted with Trp at positions corresponding to positions 491, 509, and 510, such as Y491W, Y509W, and/or Y510W).

In another aspect, the variant comprises or consists of a substitution at all four positions corresponding to positions 483, 491, 509 and 510 of SEQ ID NO: 2, such as those described above. In one embodiment, the variant comprises or consists of a Trp substitution at one or more positions corresponding to positions 483, 491, 509 and 510, such as Y483W, Y491W, Y509W and/or Y510W).

In one aspect, the variant comprises or consists of SEQ ID NO: 90 or SEQ ID NO: 92, or the mature polypeptide sequence thereof.

The cellobiohydrolase variants may further comprise a substitution, a deletion, and/or an insertion at one or more (e.g., several) other positions, such as an alteration at one or more (e.g., several) positions corresponding to positions disclosed in PCT/US2014/022068, WO 2011/050037, WO 2005/028636, WO 2005/001065, WO 2004/016760, and U.S. Pat. No. 7,375,197, which are incorporated herein in their entireties.

For example, in one aspect, a variant comprises an alteration at one or more positions corresponding to positions 214, 215, 216, and 217 of SEQ ID NO: 2 (corresponding to positions 197, 198, 199, and 200 of the mature polypeptide sequence), wherein the alteration at the one or more positions corresponding to positions 214, 215, and 217 is a substitution and the alteration at the position corresponding to position 216 is a deletion. In another aspect, a variant comprises an alteration at two positions corresponding to any of positions 214, 215, 216, and 217 of SEQ ID NO: 2, wherein the alteration at the one or more positions corresponding to positions 214, 215, and 217 is a substitution and the alteration at the position corresponding to position 216 is a deletion. In another aspect, a variant comprises an alteration at three positions corresponding to any of positions 214, 215, 216, and 217 of SEQ ID NO: 2, wherein the alteration at the one or more positions corresponding to positions 214, 215, and 217 is a substitution and the alteration at the position corresponding to position 216 is a deletion. In another aspect, a variant comprises a substitution at each position corresponding to positions 214, 215, and 217 and a deletion at a position corresponding to position 216.

In another aspect, the variant comprises or consists of a substitution at a position corresponding to position 214. In another aspect, the amino acid at a position corresponding to position 214 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution N214A of SEQ ID NO: 2.

In another aspect, the variant comprises or consists of a substitution at a position corresponding to position 215. In another aspect, the amino acid at a position corresponding to position 215 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution N215A of SEQ ID NO: 2.

In another aspect, the variant comprises or consists of a deletion at a position corresponding to position 216. In another aspect, the amino acid at a position corresponding to position 216 is Ala, Arg, Asn, Asp, Cys, Gin, Glu, Gly, His, Ile, Leu, Lys, Met, Phe, Pro, Ser, Thr, Trp, Tyr, or Val, preferably Ala. In another aspect, the variant comprises or consists of the deletion A216* of SEQ ID NO: 2.

In another aspect, the variant comprises or consists of a substitution at a position corresponding to position 217. In another aspect, the amino acid at a position corresponding to position 217 is substituted with Ala, Arg, Asn, Asp, Cys, Gin, Glu, Gly, His, Ile, Leu, Lys, Met, Phe, Pro, Ser, Thr, Trp, Tyr, or Val, preferably with Ala, Gly, or Trp. In another aspect, the variant comprises or consists of the substitution N217A,G,W of SEQ ID NO: 2.

In another aspect, the variant comprises or consists of an alteration at positions corresponding to positions 214 and 215, such as those described above.

In another aspect, the variant comprises or consists of alterations at positions corresponding to positions 214 and 216, such as those described above.

In another aspect, the variant comprises or consists of alterations at positions corresponding to positions 214 and 217, such as those described above.

In another aspect, the variant comprises or consists of alterations at positions corresponding to positions 215 and 216, such as those described above.

In another aspect, the variant comprises or consists of alterations at positions corresponding to positions 215 and 217, such as those described above.

In another aspect, the variant comprises or consists of alterations at positions corresponding to positions 216 and 217, such as those described above.

In another aspect, the variant comprises or consists of alterations at positions corresponding to positions 214, 215, and 216, such as those described above.

In another aspect, the variant comprises or consists of alterations at positions corresponding to positions 214, 215, and 217, such as those described above.

In another aspect, the variant comprises or consists of alterations at positions corresponding to positions 214, 216, and 217, such as those described above.

In another aspect, the variant comprises or consists of alterations at positions corresponding to positions 215, 216, and 217, such as those described above.

In another aspect, the variant comprises or consists of alterations at positions corresponding to positions 214, 215, 216, and 217, such as those described above.

In another aspect, the variant comprises or consists of one or more alterations selected from the group consisting of N214A, N215A, A216*, and N217A,G,W.

In another aspect, the variant comprises or consists of the alterations N214A+N215A of SEQ ID NO: 2.

In another aspect, the variant comprises or consists of the alterations N214A+A216* of SEQ ID NO: 2.

In another aspect, the variant comprises or consists of the alterations N214A+N217A,G,W of SEQ ID NO: 2.

In another aspect, the variant comprises or consists of the alterations N215A+A216* of SEQ ID NO: 2.

In another aspect, the variant comprises or consists of the alterations N215A+N217A,G,W of SEQ ID NO: 2.

In another aspect, the variant comprises or consists of the alterations A216*+N217A,G,W of SEQ ID NO: 2.

In another aspect, the variant comprises or consists of the alterations N214A+N215A+A216* of SEQ ID NO: 2.

In another aspect, the variant comprises or consists of the alterations N214A+N215A+N217A,G,W of SEQ ID NO: 2.

In another aspect, the variant comprises or consists of the alterations N214A+A216*+N217A,G,W of SEQ ID NO: 2.

In another aspect, the variant comprises or consists of the alterations N215A+A216*+N217A,G,W of SEQ ID NO: 2.

In another aspect, the variant comprises or consists of the alterations N214A+N215A+A216*+N217A,G,W of SEQ ID NO: 2.

Essential amino acids in a parent can be identified according to procedures known in the art, as described herein.

In some aspects, the cellobiohydrolase variants may consist of 310 to 537 amino acids, inclusive, e.g., 310 to 320, 320 to 330, 330 to 340, 340 to 350, 350 to 360, 360 to 370, 370 to 380, 380 to 390, 390 to 400, 400 to 415, 415 to 425, 425 to 435, 435 to 445, 445 to 455, 455 to 465, 465 to 475, 475 to 485, 485 to 495, 495 to 505, 505 to 515, 515 to 525, or 525 to 537 amino acids.

Parent Cellobiohydrolases and Carbohydrate Binding Modules

The parent carbohydrate binding module may be (a) a carbohydrate binding module having at least 60% sequence identity to the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28; (b) a carbohydrate binding module encoded by a polynucleotide that hybridizes under at least low stringency conditions with the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof; or (c) a carbohydrate binding module encoded by a polynucleotide having at least 60% sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27.

The parent cellobiohydrolase may be (a) a polypeptide having at least 60% sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78; (b) a polypeptide encoded by a polynucleotide that hybridizes under at least low stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii); (c) a polypeptide encoded by a polynucleotide having at least 60% sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; or (d) a fragment of (a), (b), or (c), which has cellobiohydrolase activity.

In a first aspect, the parent carbohydrate binding module has a sequence identity to the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have carbohydrate binding activity. In one embodiment, the amino acid sequence of the parent carbohydrate binding module differs by up to 10 amino acids, e.g., 1, 2, 3, 4, 5, 6, 7, 8, 9, or 10, from the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28.

In another embodiment, the parent carbohydrate binding module comprises or consists of the amino acid sequence of SEQ ID NO: 4, SEQ ID NO: 8, SEQ ID NO: 12, SEQ ID NO: 16, SEQ ID NO: 20, SEQ ID NO: 24, or SEQ ID NO: 28.

In another embodiment, the parent carbohydrate binding module is a fragment of the mature polypeptide of SEQ ID NO: 4, SEQ ID NO: 8, SEQ ID NO: 12, SEQ ID NO: 16, SEQ ID NO: 20, SEQ ID NO: 24, or SEQ ID NO: 28 containing at least 28 amino acid residues, e.g., at least 30, at least 32, or at least 34 amino acid residues.

In another embodiment, the parent carbohydrate binding module is an allelic variant of the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28.

In another first aspect, the parent cellobiohydrolase has a sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In one embodiment, the amino acid sequence of the parent cellobiohydrolase differs by up to 10 amino acids, e.g., 1, 2, 3, 4, 5, 6, 7, 8, 9, or 10, from the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

In another embodiment, the parent cellobiohydrolase comprises or consists of the amino acid sequence of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78. In another embodiment, the parent cellobiohydrolase comprises or consists of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78. In another embodiment, the parent cellobiohydrolase comprises or consists of amino acids 18 to 514 of SEQ ID NO: 2, amino acids 19 to 525 of SEQ ID NO: 6, amino acids 19 to 530 of SEQ ID NO: 10, amino acids 26 to 537 of SEQ ID NO: 14, amino acids 27 to 532 of SEQ ID NO: 18, amino acids 18 to 526 of SEQ ID NO: 22, or amino acids 18 to 525 of SEQ ID NO: 26.

In another embodiment, the parent cellobiohydrolase is a fragment containing at least 85% of the amino acid residues, e.g., at least 90% of the amino acid residues or at least 95% of the amino acid residues of the mature polypeptide of the parent cellobiohydrolase.

In another embodiment, the parent cellobiohydrolase is an allelic variant of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

In a second aspect, the parent carbohydrate binding module is encoded by a polynucleotide that hybridizes under very low stringency conditions, low stringency conditions, medium stringency conditions, medium-high stringency conditions, high stringency conditions, or very high stringency conditions with the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof (Sambrook et al., 1989, *Molecular Cloning, A Laboratory Manual, 2d edition*, Cold Spring Harbor, N.Y.).

In another second aspect, the parent cellobiohydrolase is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii) (Sambrook et al., 1989, supra).

The polynucleotide of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, SEQ ID NO: 77, SEQ ID NO: 3, SEQ ID NO: 7, SEQ ID NO: 11, SEQ ID NO: 15, SEQ ID NO: 19, SEQ ID NO: 23, or SEQ ID NO: 27, or a subsequence thereof, as well as the polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78, SEQ ID NO: 4, SEQ ID NO: 8, SEQ ID NO: 12, SEQ ID NO: 16, SEQ ID NO: 20, SEQ ID NO: 24, or SEQ ID NO: 28, or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, SEQ ID NO: 3, SEQ ID NO: 7, SEQ ID NO: 11, SEQ ID NO: 15, SEQ ID NO: 19, SEQ ID NO: 23, or SEQ ID NO: 27, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; (ii) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; (iii) the genomic DNA or cDNA sequence thereof; (iv) the full-length complement thereof; or (v) a subsequence thereof; or (i) SEQ ID NO: 3, SEQ ID NO: 7, SEQ ID NO: 11, SEQ ID NO: 15, SEQ ID NO: 19, SEQ ID NO: 23, or SEQ ID NO: 27; (ii) the full-length complement thereof; or (iii) a subsequence thereof; under very low to very high stringency conditions. Molecules to which the nucleic acid probe hybridizes under these conditions can be detected using, for example, X-ray film or any other detection means known in the art.

In one embodiment, the nucleic acid probe is the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77. In another embodiment, the nucleic acid probe is nucleotides 52 to 1542 of SEQ ID NO: 1, nucleotides 55 to 1635 of SEQ ID NO: 5, nucleotides 55 to 1590 of SEQ ID NO: 9, nucleotides 76 to 1614 of SEQ ID NO: 13, nucleotides 79 to 1596 of SEQ ID NO: 17, nucleotides 52 to 1578 of SEQ ID NO: 21, or nucleotides 52 to 1575 of SEQ ID NO: 25. In another embodiment, the nucleic acid probe is a polynucleotide that encodes the polypeptide of SEQ ID NO: 2, SEQ ID NO: 6, SEQ ID NO:

10, SEQ ID NO: 14, SEQ ID NO: 18, SEQ ID NO: 22, SEQ ID NO: 26, SEQ ID NO: 42, SEQ ID NO: 44, or SEQ ID NO: 78; the mature polypeptide thereof; or a fragment thereof. In another embodiment, the nucleic acid probe is SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77 or the genomic DNA or cDNA sequence thereof.

In another embodiment, the nucleic acid probe is SEQ ID NO: 3, SEQ ID NO: 7, SEQ ID NO: 11, SEQ ID NO: 15, SEQ ID NO: 19, SEQ ID NO: 23, or SEQ ID NO: 27. In another embodiment, the nucleic acid probe is a polynucleotide that encodes the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28, or a fragment thereof.

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a third aspect, the parent carbohydrate binding module is encoded by a polynucleotide having a sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encodes a polypeptide having carbohydrate binding activity. In one embodiment, the carbohydrate binding module coding sequence is SEQ ID NO: 3, SEQ ID NO: 7, SEQ ID NO: 11, SEQ ID NO: 15, SEQ ID NO: 19, SEQ ID NO: 23, or SEQ ID NO: 27. In another embodiment, the parent is encoded by a polynucleotide comprising or consisting of SEQ ID NO: 3, SEQ ID NO: 7, SEQ ID NO: 11, SEQ ID NO: 15, SEQ ID NO: 19, SEQ ID NO: 23, or SEQ ID NO: 27.

In another third aspect, the parent cellobiohydrolase is encoded by a polynucleotide having a sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77 or the genomic DNA or cDNA sequence thereof, of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encodes a polypeptide having cellobiohydrolase activity. In one aspect, the mature polypeptide coding sequence is nucleotides 52 to 1542 of SEQ ID NO: 1, nucleotides 55 to 1635 of SEQ ID NO: 5, nucleotides 55 to 1590 of SEQ ID NO: 9, nucleotides 76 to 1614 of SEQ ID NO: 13, nucleotides 79 to 1596 of SEQ ID NO: 17, nucleotides 52 to 1578 of SEQ ID NO: 21, or nucleotides 52 to 1575 of SEQ ID NO: 25, or the genomic DNA or cDNA sequence thereof. In another aspect, the parent cellobiohydrolase is encoded by a polynucleotide comprising or consisting of SEQ ID NO: 1, SEQ ID NO: 5, SEQ ID NO: 9, SEQ ID NO: 13, SEQ ID NO: 17, SEQ ID NO: 21, or SEQ ID NO: 25 or the genomic DNA or cDNA sequence thereof.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial cellobiohydrolase or carbohydrate binding module. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* cellobiohydrolase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* polypeptide.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another aspect, the parent is a *Streptococcus equisimilis, Streptococcus pyogenes, Streptococcus uberis*, or *Streptococcus equi* subsp. *Zooepidemicus* polypeptide.

In another aspect, the parent is a *Streptomyces achromogenes, Streptomyces avermitilis, Streptomyces coelicolor, Streptomyces griseus*, or *Streptomyces lividans* polypeptide.

The parent may be a fungal cellobiohydrolase or carbohydrate binding module. For example, the parent may be a yeast cellobiohydrolase or carbohydrate binding module such as a *Candida, Kluyveromyces, Pichia, Saccharomyces, Schizosaccharomyces*, or *Yarrowia* polypeptide. For example, the parent may be a filamentous fungal cellobiohydrolase or carbohydrate binding module such as an *Acremonium, Agaricus, Alternaria, Aspergillus, Aureobasidium, Botryosphaeria, Ceriporiopsis, Chaetomium, Chrysosporium, Claviceps, Cochliobolus, Coprinopsis, Coptotermes, Corynascus, Cryphonectria, Cryptococcus, Diplodia, Exidia, Fennellia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chtysosporium inops, Chtysosporium keratinophilum,*

*Chrysosporium lucknowense, Chtysosporium merdarium, Chtysosporium pannicola, Chtysosporium queenslandicum, Chtysosporium tropicum, Chtysosporium zonatum, Corynascus thermophilus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Talaromyces byssochlamydoides, Talaromyces emersonii, Thermoascus aurantiacus, Thermoascus crustaceus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* polypeptide.

In another aspect, the parent is a *Trichoderma reesei* cellobiohydrolase, e.g., the cellobiohydrolase of SEQ ID NO: 2 or the mature polypeptide thereof, or a *Trichoderma reesei* carbohydrate binding module, e.g., the carbohydrate binding module of SEQ ID NO: 4.

In another aspect, the parent is *Humicola insolens* cellobiohydrolase, e.g., the cellobiohydrolase of SEQ ID NO: 6 or the mature polypeptide thereof, or a *Humicola insolens* carbohydrate binding module, e.g., the carbohydrate binding module of SEQ ID NO: 8.

In another aspect, the parent is a *Chaetomium thermophilum* cellobiohydrolase, e.g., the cellobiohydrolase of SEQ ID NO: 10 or the mature polypeptide thereof, or a *Chaetomium thermophilum* carbohydrate binding module, e.g., the carbohydrate binding module of SEQ ID NO: 12.

In another aspect, the parent is a *Talaromyces byssochlamydoides* cellobiohydrolase, e.g., the cellobiohydrolase of SEQ ID NO: 14 or the mature polypeptide thereof, or a *Talaromyces byssochlamydoides* carbohydrate binding module, e.g., the carbohydrate binding module of SEQ ID NO: 16.

In another aspect, the parent is a *Talaromyces leycettanus* cellobiohydrolase, e.g., the cellobiohydrolase of SEQ ID NO: 42, SEQ ID NO: 44 or the mature polypeptide thereof, or a *Talaromyces leycettanus* carbohydrate binding module, e.g., the carbohydrate binding module of amino acids 472 to 507 of SEQ ID NO: 42 or amino acids 472 to 507 of SEQ ID NO: 44.

In another aspect, the parent is an *Aspergillus fumigatus* cellobiohydrolase, e.g., the cellobiohydrolase of SEQ ID NO: 18, SEQ ID NO: 78, or the mature polypeptide thereof, or an *Aspergillus fumigatus* carbohydrate binding module, e.g., the carbohydrate binding module of SEQ ID NO: 20.

In another aspect, the parent is a *Thielavia terrestris* cellobiohydrolase, e.g., the cellobiohydrolase of SEQ ID NO: 22 or the mature polypeptide thereof, or a *Thielavia terrestris* carbohydrate binding module, e.g., the carbohydrate binding module of SEQ ID NO: 24.

In another aspect, the parent is a *Myceliophthora thermophilum* cellobiohydrolase, e.g., the cellobiohydrolase of SEQ ID NO: 26 or the mature polypeptide thereof, or a *Myceliophthora thermophilum* carbohydrate binding module, e.g., the carbohydrate binding module of SEQ ID NO: 28.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having cellobiohydrolase activity, comprising: (a) introducing into a parent cellobiohydrolase a substitution at one or more (e.g., several) positions corresponding to positions 483, 491, 509 and 510 of SEQ ID NO: 2, wherein the variant has cellobiohydrolase activity; and (b) recovering the variant.

The present invention also relates to methods for obtaining a carbohydrate binding module variant, comprising: (a) introducing into a parent carbohydrate binding module a substitution at one or more (e.g., several) positions corresponding to positions 5, 13, 31 and 32 of the carbohydrate binding module of SEQ ID NO: 4, wherein the variant has carbohydrate binding activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Hybrid Polypeptides

The present invention also relates to hybrid polypeptides comprising a carbohydrate binding module variant described herein and a heterologous catalytic domain of a cellulolytic enzyme. In some embodiments, the hybrid polypeptide has carbohydrate binding activity. In some embodiments, the hybrid polypeptide has cellulolytic activity (e.g., cellobiohydrolase activity). In some embodiments, the hybrid polypeptide has both carbohydrate binding activity and cellulolytic activity (e.g., cellobiohydrolase activity).

The hybrid polypeptide may be formed by fusing a catalytic domain of a cellulolytic enzyme lacking a carbohydrate binding module to a carbohydrate binding module variant described herein, or by replacing an existing catalytic domain of a cellulolytic enzyme comprising the carbohydrate binding module variant (such as a cellobiohydrolase variant described herein) with a catalytic domain of a different cellulolytic enzyme.

In one aspect, the carbohydrate binding module variant is fused to the N-terminus of a heterologous catalytic domain. In another aspect, the carbohydrate binding module variant is fused to the C-terminus of a heterologous catalytic domain.

In one aspect is a hybrid polypeptide having cellulolytic activity, comprising:

(a) a fragment at the N-terminal end of the hybrid polypeptide comprising the heterologous catalytic domain of a cellulolytic enzyme; and (b) a fragment at the C-terminal end of the first polypeptide fragment comprising a carbohydrate binding module variant, wherein the variant comprises a substitution at one or more (e.g., several) positions corresponding to positions 5, 13, 31 and 32 of the carbohydrate binding module of SEQ ID NO: 4.

The catalytic domain used in the hybrid polypeptides may be any suitable catalytic domain of any cellulolytic enzyme described herein (such as the catalytic domain of any cellulolytic enzyme described in the enzyme composition section below), and may be obtained from microorganisms of any genus, as described supra.

For example, the catalytic domain may be obtained from an endoglucanase, a cellobiohydrolase, or a GH61 polypeptide, inter alia. In one embodiment, the catalytic domain is from an endoglucanase. In another embodiment, the catalytic domain is from a cellobiohydrolase. In another embodiment, the catalytic domain is from a GH61 polypeptide.

In one aspect, the catalytic domain of the hybrid polypeptide is a cellobiohydrolase catalytic domain and the hybrid polypeptide has cellobiohydrolase activity.

The catalytic domain of the hybrid polypeptide may be a filamentous fungal cellobiohydrolase. For example, the parent may be a filamentous fungal cellobiohydrolase such as an *Aspergillus, Chaetomium, Chrysosporium, Myceliophthora, Penicillium, Talaromyces, Thermoascus*, or *Trichoderma* cellobiohydrolase.

In one aspect, the catalytic domain of the hybrid polypeptide is an *Aspergillus aculeatus, Aspergillus awamori, Aspergillus foetidus, Aspergillus fumigatus, Aspergillus japonicus, Aspergillus nidulans, Aspergillus niger, Aspergillus oryzae, Chaetomium thermophilum, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Myceliophthora thermophila, Penicillium emersonii, Penicillium funiculosum, Penicillium purpurogenum, Talaromyces byssochlamydoides, Talaromyces emersonii, Talaromyces leycettanus, Trichoderma harzianum, Trichoderma koningii, Trichoderma longibrachiatum, Trichoderma reesei*, or *Trichoderma viride* cellobiohydrolase catalytic domain.

In one embodiment, the catalytic domain is a heterologous catalytic domain of a *Trichoderma reesei* cellobiohydrolase, e.g., the catalytic domain of SEQ ID NO: 30, such as amino acids 1 to 429 of SEQ ID NO: 30

In another embodiment, the catalytic domain is a heterologous catalytic domain of an *Aspergillus fumigatus* cellobiohydrolase, e.g., the catalytic domain of SEQ ID NO: 36, such as amino acids 1 to 437 of SEQ ID NO: 36.

In another embodiment, the catalytic domain is a heterologous catalytic domain of a *Thermoascus aurantiacus* cellobiohydrolase, e.g., the catalytic domain of SEQ ID NO: 38, such as amino acids 1 to 440 of SEQ ID NO: 38.

In another embodiment, the catalytic domain is a heterologous catalytic domain of a *Penicillium emersonii*

(*Rasamsonia emersonii*) cellobiohydrolase, e.g., the catalytic domain of SEQ ID NO: 40, such as amino acids 1 to 437 of SEQ ID NO: 40

In another embodiment, the catalytic domain is a heterologous catalytic domain of a *Talaromyces leycettanus* cellobiohydrolase, e.g., the catalytic domain of SEQ ID NO: 42, such as amino acids 1 to 437 of SEQ ID NO: 42 or the catalytic domain of SEQ ID NO: 44 such as amino acids 1 to 438 of SEQ ID NO: 44.

In another embodiment, the catalytic domain is a heterologous catalytic domain of a *Talaromyces byssochlamydoides* cellobiohydrolase, e.g., the catalytic domain of SEQ ID NO: 46, such as amino acids 1 to 437 of SEQ ID NO: 46.

In another embodiment, the catalytic domain is a heterologous catalytic domain of a *Myceliophthora thermophila* cellobiohydrolase, e.g., the catalytic domain of SEQ ID NO: 48, such as amino acids 1 to 430 of SEQ ID NO: 48.

In another embodiment, the catalytic domain is a heterologous catalytic domain of a *Chaetomium thermophilum* cellobiohydrolase, e.g., the catalytic domain of SEQ ID NO: 50, such as amino acids 1 to 433 of SEQ ID NO: 50

In another aspect is a hybrid polypeptide having cellulolytic activity, comprising:

(a) a fragment at the N-terminal end of the hybrid polypeptide comprising the heterologous catalytic domain of a cellulolytic enzyme, wherein the fragment (i) has at least 60% identity to amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, (ii) is encoded by catalytic domain coding sequence that hybridizes under low stringency condition with nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; the cDNA sequence thereof; or the full-length complement of the foregoing;

(iii) is encoded by catalytic domain coding sequence having at least 60% identity to nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; or cDNA sequence thereof;

(iv) is a variant of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, comprising a substitution, deletion, and/or insertion at one or more (e.g., several) positions; or (v) comprises or consists of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50; and (b) a fragment at the C-terminal end of the first polypeptide fragment comprising a carbohydrate binding module variant, wherein the variant comprises a substitution at one or more (e.g., several) positions corresponding to positions 5, 13, 31 and 32 of the carbohydrate binding module of SEQ ID NO: 4.

In one embodiment, the fragment at the N-terminal end of the hybrid polypeptide comprising the heterologous catalytic domain (i) has at least 60% identity to amino acids 1 to 429 of SEQ ID NO: 30; (ii) is encoded by catalytic domain coding sequence that hybridizes under low stringency condition with nucleotides 52 to 1469 of SEQ ID NO: 29, nucleotides 52 to 1389 of SEQ ID NO: 31, or nucleotides 52 to 1389 of SEQ ID NO: 32; the cDNA sequence thereof; or the full-length complement of the foregoing; or (iii) is encoded by catalytic domain coding sequence having at least 60% identity to nucleotides 52 to 1469 of SEQ ID NO: 29, nucleotides 52 to 1389 of SEQ ID NO: 31, or nucleotides 52 to 1389 of SEQ ID NO: 32.

In another embodiment, the fragment at the N-terminal end of the hybrid polypeptide comprising the heterologous catalytic domain (i) has at least 60% identity to amino acids 1 to 437 of SEQ ID NO: 36; (ii) is encoded by catalytic domain coding sequence that hybridizes under low stringency condition with nucleotides 79 to 1389 of SEQ ID NO: 35; the cDNA sequence thereof; or the full-length complement of the foregoing; or (iii) is encoded by catalytic domain coding sequence having at least 60% identity to nucleotides 79 to 1389 of SEQ ID NO: 35.

In another embodiment, the fragment at the N-terminal end of the hybrid polypeptide comprising the heterologous catalytic domain (i) has at least 60% identity to amino acids 1 to 440 of SEQ ID NO: 38; (ii) is encoded by catalytic domain coding sequence that hybridizes under low stringency condition with nucleotides 52 to 1371 of SEQ ID NO: 37; the cDNA sequence thereof; or the full-length complement of the foregoing; or (iii) is encoded by catalytic domain coding sequence having at least 60% identity to nucleotides 52 to 1371 of SEQ ID NO: 37.

In another embodiment, the fragment at the N-terminal end of the hybrid polypeptide comprising the heterologous catalytic domain (i) has at least 60% identity to amino acids 1 to 437 of SEQ ID NO: 40; (ii) is encoded by catalytic domain coding sequence that hybridizes under low stringency condition with nucleotides 55 to 1482 of SEQ ID NO: 39; the cDNA sequence thereof; or the full-length complement of the foregoing; or (iii) is encoded by catalytic domain coding sequence having at least 60% identity to nucleotides 55 to 1482 of SEQ ID NO: 39.

In another embodiment, the fragment at the N-terminal end of the hybrid polypeptide comprising the heterologous catalytic domain (i) has at least 60% identity to amino acids 1 to 437 of SEQ ID NO: 42; (ii) is encoded by catalytic domain coding sequence that hybridizes under low stringency condition with nucleotides 76 to 1386 of SEQ ID NO: 41; the cDNA sequence thereof; or the full-length complement of the foregoing; or (iii) is encoded by catalytic domain coding sequence having at least 60% identity to nucleotides 76 to 1386 of SEQ ID NO: 41.

In another embodiment, the fragment at the N-terminal end of the hybrid polypeptide comprising the heterologous catalytic domain (i) has at least 60% identity to amino acids 1 to 438 of SEQ ID NO: 44; (ii) is encoded by catalytic domain coding sequence that hybridizes under low stringency condition with nucleotides 76 to 1386 of SEQ ID NO: 43; the cDNA sequence thereof; or the full-length complement of the foregoing; or (iii) is encoded by catalytic domain coding sequence having at least 60% identity to nucleotides 76 to 1386 of SEQ ID NO: 43.

In another embodiment, the fragment at the N-terminal end of the hybrid polypeptide comprising the heterologous catalytic domain (i) has at least 60% identity to amino acids 1 to 437 of SEQ ID NO: 46; (ii) is encoded by catalytic domain coding sequence that hybridizes under low stringency condition with nucleotides 55 to 1504 of SEQ ID NO: 45; the cDNA sequence thereof; or the full-length complement of the foregoing; or (iii) is encoded by catalytic domain coding sequence having at least 60% identity to nucleotides 55 to 1504 of SEQ ID NO: 45.

In another embodiment, the fragment at the N-terminal end of the hybrid polypeptide comprising the heterologous catalytic domain (i) has at least 60% identity to amino acids 1 to 430 of SEQ ID NO: 48; (ii) is encoded by catalytic domain coding sequence that hybridizes under low stringency condition with nucleotides 61 to 1350 of SEQ ID NO: 47; the cDNA sequence thereof; or the full-length complement of the foregoing; or (iii) is encoded by catalytic domain coding sequence having at least 60% identity to nucleotides 61 to 1350 of SEQ ID NO: 47.

In another embodiment, the fragment at the N-terminal end of the hybrid polypeptide comprising the heterologous catalytic domain (i) has at least 60% identity to amino acids 1 to 433 of SEQ ID NO: 50; (ii) is encoded by catalytic domain coding sequence that hybridizes under low stringency condition with nucleotides 55 to 1353 of SEQ ID NO: 49; the cDNA sequence thereof; or the full-length complement of the foregoing; or (iii) is encoded by catalytic domain coding sequence having at least 60% identity to nucleotides 55 to 1353 of SEQ ID NO: 49.

In another embodiment, the fragment at the N-terminal end of the hybrid polypeptide comprising the heterologous catalytic domain has a sequence identity to amino acids 1 to 429 of SEQ ID NO: 30 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 429 of SEQ ID NO: 30. In another embodiment, the fragment at the N-terminal end of the hybrid polypeptide comprising the heterologous catalytic domain comprises or consists of amino acids 1 to 429 of SEQ ID NO: 30.

In another embodiment, the fragment at the N-terminal end of the hybrid polypeptide comprising the heterologous catalytic domain has a sequence identity to amino acids 1 to 437 of SEQ ID NO: 36 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 36. In another embodiment, the fragment at the N-terminal end of the hybrid polypeptide comprising the heterologous catalytic domain comprises or consists of amino acids 1 to 437 of SEQ ID NO: 36.

In another embodiment, the fragment at the N-terminal end of the hybrid polypeptide comprising the heterologous catalytic domain has a sequence identity to amino acids 1 to 440 of SEQ ID NO: 38 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 440 of SEQ ID NO: 38. In another embodiment, the fragment at the N-terminal end of the hybrid polypeptide comprising the heterologous catalytic domain comprises or consists of amino acids 1 to 440 of SEQ ID NO: 38.

In another embodiment, the fragment at the N-terminal end of the hybrid polypeptide comprising the heterologous catalytic domain has a sequence identity to amino acids 1 to 437 of SEQ ID NO: 40 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 40. In another embodiment, the fragment at the N-terminal end of the hybrid polypeptide comprising the heterologous catalytic domain comprises or consists of amino acids 1 to 437 of SEQ ID NO: 40.

In another embodiment, the fragment at the N-terminal end of the hybrid polypeptide comprising the heterologous catalytic domain has a sequence identity to amino acids 1 to 437 of SEQ ID NO: 42 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 42. In another embodiment, the fragment at the N-terminal end of the hybrid polypeptide comprising the heterologous catalytic domain comprises or consists of amino acids 1 to 437 of SEQ ID NO: 42.

In another embodiment, the fragment at the N-terminal end of the hybrid polypeptide comprising the heterologous catalytic domain has a sequence identity to amino acids 1 to 438 of SEQ ID NO: 44 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 438 of SEQ ID NO: 44. In another embodiment, the fragment at the N-terminal end of the hybrid polypeptide comprising the heterologous catalytic domain comprises or consists of amino acids 1 to 438 of SEQ ID NO: 44.

In another embodiment, the fragment at the N-terminal end of the hybrid polypeptide comprising the heterologous catalytic domain has a sequence identity to amino acids 1 to 437 of SEQ ID NO: 46 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 437 of SEQ ID NO: 46. In another embodiment, the fragment at the N-terminal end of the hybrid polypeptide comprising the heterologous catalytic domain comprises or consists of amino acids 1 to 437 of SEQ ID NO: 46.

In another embodiment, the fragment at the N-terminal end of the hybrid polypeptide comprising the heterologous catalytic domain has a sequence identity to amino acids 1 to 430 of SEQ ID NO: 48 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 430 of SEQ ID NO: 48. In another embodiment, the fragment at the N-terminal end of the hybrid polypeptide comprising the heterologous catalytic domain comprises or consists of amino acids 1 to 430 of SEQ ID NO: 48. In some embodiments, the hybrid polypeptide comprises or consists of SEQ ID NO: 61. In other embodiments, the hybrid polypeptide comprises or consists of SEQ ID NO: 63.

In another embodiment, the fragment at the N-terminal end of the hybrid polypeptide comprising the heterologous catalytic domain has a sequence identity to amino acids 1 to 433 of SEQ ID NO: 50 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have cellobiohydrolase activity. In another aspect, the amino acid sequence of the parent differs by up to 10 amino acids, e.g., 1, 2, 3, 4, 5, 6, 7, 8, 9, or 10, from amino acids 1 to 433 of SEQ ID NO: 50. In another embodiment, the fragment at the N-terminal end of the hybrid polypeptide comprising the heterologous catalytic domain comprises or consists of amino acids 1 to 433 of SEQ ID NO: 50.

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 52 to 1469 of SEQ ID NO: 29, nucleotides 52 to 1389 of SEQ ID NO: 31, nucleotides 52 to 1389 of SEQ ID NO: 32; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 79 to 1389 of SEQ ID NO: 35; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 52 to 1371 of SEQ ID NO: 37; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 55 to 1482 of SEQ ID NO: 39; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 76 to 1386 of SEQ ID NO: 41; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 76 to 1386 of SEQ ID NO: 43; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 55 to 1504 of SEQ ID NO: 45; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 61 to 1350 of SEQ ID NO: 47; the cDNA sequence thereof; or the full-length complement of the foregoing (Sambrook et al., 1989, supra).

In another aspect, the fragment at the N-terminal end of the hybrid polypeptide comprising the heterologous catalytic domain hybridizes under low stringency conditions, medium stringency conditions, medium-high stringency conditions, high stringency conditions, or very high stringency conditions with nucleotides 55 to 1353 of SEQ ID NO: 49; the cDNA sequence thereof; or the full-length complement of the foregoing (Sambrook et al., 1989, supra).

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 52 to 1469 of SEQ ID NO: 29, nucleotides 52 to 1389 of SEQ ID NO: 31, nucleotides 52 to 1389 of SEQ ID NO: 32; or the cDNA sequence thereof. In another embodiment, the fragment at the N-terminal end of the hybrid polypeptide comprising the heterologous catalytic domain comprises or consists of nucleotides 52 to 1469 of SEQ ID NO: 29, nucleotides 52 to 1389 of SEQ ID NO: 31, nucleotides 52 to 1389 of SEQ ID NO: 32; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 79 to 1389 of SEQ ID NO: 35; or the cDNA sequence thereof. In another embodiment, the fragment at the N-terminal end of the hybrid polypeptide comprising the heterologous catalytic domain comprises or consists of nucleotides 79 to 1389 of SEQ ID NO: 35; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 52 to 1371 of SEQ ID NO: 37; or the cDNA sequence thereof. In another embodiment, the fragment at the N-terminal end of the hybrid polypeptide comprising the heterologous catalytic domain comprises or consists of nucleotides 52 to 1371 of SEQ ID NO: 37; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 55 to 1482 of SEQ ID NO: 39; or the cDNA sequence thereof. In another embodiment, the fragment at the N-terminal end of the hybrid polypeptide comprising the heterologous catalytic domain comprises or consists of nucleotides 55 to 1482 of SEQ ID NO: 39; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 76 to 1386 of SEQ ID NO: 41; or the cDNA sequence thereof. In another embodiment, the fragment at the N-terminal end of the hybrid polypeptide comprising the heterologous catalytic domain comprises or consists of nucleotides 76 to 1386 of SEQ ID NO: 41; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 76 to 1386 of SEQ ID NO: 43; or the cDNA sequence thereof. In another embodiment, the fragment at the N-terminal end of the hybrid polypeptide comprising the heterologous catalytic domain comprises or consists of nucleotides 76 to 1386 of SEQ ID NO: 43; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 55 to 1504 of SEQ ID NO: 45; or the cDNA sequence thereof. In another embodiment, the fragment at the N-terminal end of the hybrid polypeptide comprising the heterologous catalytic domain comprises or consists of nucleotides 55 to 1504 of SEQ ID NO: 45; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 61 to 1350 of SEQ ID NO: 47; or the cDNA sequence thereof. In another embodiment, the fragment at the N-terminal end of the hybrid polypeptide comprising the heterologous catalytic domain comprises or consists of nucleotides 61 to 1350 of SEQ ID NO: 47; or the cDNA sequence thereof.

In another aspect, the fragment at the N-terminal end of the hybrid polypeptide comprising the heterologous catalytic domain has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nucleotides 55 to 1353 of SEQ ID NO: 49; or the cDNA sequence thereof. In another embodiment, the fragment at the N-terminal end of the hybrid polypeptide comprising the heterologous catalytic domain comprises or consists of nucleotides 55 to 1353 of SEQ ID NO: 49; or the cDNA sequence thereof.

The fragment at the N-terminal end of the hybrid polypeptide comprising the heterologous catalytic domain of the hybrid polypeptide may further comprise a substitution, a deletion, and/or an insertion at one or more (e.g., several) other positions, such as an alteration at one or more (e.g., several) positions corresponding to positions disclosed in PCT/US2014/022068, WO 2011/050037, WO 2005/028636, WO 2005/001065, WO 2004/016760, and U.S. Pat. No. 7,375,197, which are incorporated herein in their entireties.

For example, in one aspect, the fragment at the N-terminal end comprising the heterologous catalytic domain is a cellobiohydrolase comprising an alteration at one or more positions corresponding to positions 197, 198, 199, and 200 of SEQ ID NO: 30, wherein the alteration at the one or more positions corresponding to positions 197, 198, and 200 is a substitution and the alteration at the position corresponding to position 199 is a deletion. In another aspect, the fragment comprises an alteration at two positions corresponding to any of positions 197, 198, 199, and 200 of SEQ ID NO: 30, wherein the alteration at the one or more positions corresponding to positions 197, 198, and 200 is a substitution and the alteration at the position corresponding to position 199 is a deletion. In another aspect, the fragment comprises an alteration at three positions corresponding to any of positions 197, 198, 199, and 200 of SEQ ID NO: 30, wherein the alteration at the one or more positions corresponding to positions 197, 198, and 200 is a substitution and the alteration at the position corresponding to position 199 is a deletion. In another aspect, the fragment comprises a substitution at each position corresponding to positions 197, 198, and 200 and a deletion at a position corresponding to position 199.

In another aspect, the fragment at the N-terminal end comprising the heterologous catalytic domain comprises or consists of a substitution at a position corresponding to position 197 of SEQ ID NO: 30. In another aspect, the amino acid at a position corresponding to position 197 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the fragment comprises or consists of the substitution N197A of SEQ ID NO: 30.

In another aspect, the fragment at the N-terminal end comprising the heterologous catalytic domain comprises or consists of a substitution at a position corresponding to position 198 of SEQ ID NO: 30. In another aspect, the amino acid at a position corresponding to position 198 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the fragment comprises or consists of the substitution N198A of SEQ ID NO: 30.

In another aspect, the fragment at the N-terminal end comprising the heterologous catalytic domain comprises or consists of a deletion at a position corresponding to position 199 of SEQ ID NO: 30. In another aspect, the amino acid at a position corresponding to position 199 is Ala, Arg, Asn, Asp, Cys, Gln, Glu, Gly, His, Ile, Leu, Lys, Met, Phe, Pro, Ser, Thr, Trp, Tyr, or Val, preferably Ala. In another aspect, the variant comprises or consists of the deletion A199* of SEQ ID NO: 30.

In another aspect, the fragment at the N-terminal end comprising the heterologous catalytic domain comprises or consists of a substitution at a position corresponding to position 200 of SEQ ID NO: 30. In another aspect, the amino acid at a position corresponding to position 200 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Gly, or Trp. In another aspect, the fragment comprises or consists of the substitution N200A,G,W of the mature polypeptide of SEQ ID NO: 30.

In another aspect, the fragment at the N-terminal end comprising the heterologous catalytic domain comprises or consists of an alteration at positions corresponding to positions 197 and 198 of SEQ ID NO: 30, such as those described above.

In another aspect, the fragment at the N-terminal end comprising the heterologous catalytic domain comprises or consists of alterations at positions corresponding to positions 197 and 199 of SEQ ID NO: 30, such as those described above.

In another aspect, the fragment at the N-terminal end comprising the heterologous catalytic domain comprises or consists of alterations at positions corresponding to positions 197 and 200 of SEQ ID NO: 30, such as those described above.

In another aspect, the fragment at the N-terminal end comprising the heterologous catalytic domain comprises or consists of alterations at positions corresponding to positions 198 and 199 of SEQ ID NO: 30, such as those described above.

In another aspect, the fragment at the N-terminal end comprising the heterologous catalytic domain comprises or consists of alterations at positions corresponding to positions 198 and 200 of SEQ ID NO: 30, such as those described above.

In another aspect, the fragment at the N-terminal end comprising the heterologous catalytic domain comprises or consists of alterations at positions corresponding to positions 199 and 200 of SEQ ID NO: 30, such as those described above.

In another aspect, the fragment at the N-terminal end comprising the heterologous catalytic domain comprises or consists of alterations at positions corresponding to positions 197, 198, and 199 of SEQ ID NO: 30, such as those described above.

In another aspect, the fragment at the N-terminal end comprising the heterologous catalytic domain comprises or consists of alterations at positions corresponding to positions 197, 198, and 200 of SEQ ID NO: 30, such as those described above.

In another aspect, the fragment at the N-terminal end comprising the heterologous catalytic domain comprises or consists of alterations at positions corresponding to positions 197, 199, and 200 of SEQ ID NO: 30, such as those described above.

In another aspect, the fragment at the N-terminal end comprising the heterologous catalytic domain comprises or consists of alterations at positions corresponding to positions 198, 199, and 200 of SEQ ID NO: 30, such as those described above.

In another aspect, the fragment at the N-terminal end comprising the heterologous catalytic domain comprises or consists of alterations at positions corresponding to positions 197, 198, 199, and 200 of SEQ ID NO: 30, such as those described above.

In another aspect, the fragment at the N-terminal end comprising the heterologous catalytic domain comprises or consists of one or more alterations selected from the group consisting of N197A, N198A, A199*, and N200A,G,W.

In another aspect, the fragment at the N-terminal end comprising the heterologous catalytic domain comprises or consists of the alterations N197A+N198A of SEQ ID NO: 30.

In another aspect, the fragment at the N-terminal end comprising the heterologous catalytic domain comprises or consists of the alterations N197A+A199* of SEQ ID NO: 30.

In another aspect, the fragment at the N-terminal end comprising the heterologous catalytic domain comprises or consists of the alterations N197A+N200A,G,W of SEQ ID NO: 30.

In another aspect, the fragment at the N-terminal end comprising the heterologous catalytic domain comprises or consists of the alterations N198A+A199* of SEQ ID NO: 30.

In another aspect, the fragment at the N-terminal end comprising the heterologous catalytic domain comprises or consists of the alterations N198A+N200A,G,W of SEQ ID NO: 30.

In another aspect, the fragment at the N-terminal end comprising the heterologous catalytic domain comprises or consists of the alterations A199*+N200A,G,W of SEQ ID NO: 30.

In another aspect, the fragment at the N-terminal end comprising the heterologous catalytic domain comprises or consists of the alterations N197A+N198A+A199* of SEQ ID NO: 30.

In another aspect, the fragment at the N-terminal end comprising the heterologous catalytic domain comprises or consists of the alterations N197A+N198A+N200A,G,W of SEQ ID NO: 30.

In another aspect, the fragment at the N-terminal end comprising the heterologous catalytic domain comprises or consists of the alterations N197A+A199*+N200A,G,W of SEQ ID NO: 30.

In another aspect, the fragment at the N-terminal end comprising the heterologous catalytic domain comprises or consists of the alterations N198A+A199*+N200A,G,W of SEQ ID NO: 30.

In another aspect, the fragment at the N-terminal end comprising the heterologous catalytic domain comprises or consists of the alterations N197A+N198A+A199*+N200A, G,W of SEQ ID NO: 30.

The carbohydrate binding module variant of the hybrid polypeptides may be any suitable carbohydrate binding module variant described supra.

In one aspect, the carbohydrate binding module variant of the hybrid polypeptide has sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent carbohydrate binding module.

In another aspect, the carbohydrate binding module variant of the hybrid polypeptide has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4, SEQ ID NO: 8, SEQ ID NO: 12, SEQ ID NO: 16, SEQ ID NO: 20, SEQ ID NO: 24, or SEQ ID NO: 28.

In one aspect, the number of substitutions in the carbohydrate binding module variants of the hybrid polypeptide is 1-4, such as 1, 2, 3, or 4 substitutions.

In one aspect, the carbohydrate binding module variant of the hybrid polypeptide comprises or consists of a substitution at a position corresponding to position 5 of SEQ ID NO: 4. In one embodiment, the amino acid at a position corresponding to position 5 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 5 of SEQ ID NO: 4 is substituted with Trp. In another embodiment, the amino acid at a position corresponding to position 5 of SEQ ID NO: 4 is Tyr substituted with Trp (e.g., Y5W of SEQ ID NO: 4).

In another aspect, the carbohydrate binding module variant of the hybrid polypeptide comprises or consists of a substitution at a position corresponding to position 13 of SEQ ID NO: 4. In one embodiment, the amino acid at a position corresponding to position 13 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 13 of SEQ ID NO: 4 is substituted with Trp. In another embodiment, the amino acid at a position corresponding to position 13 of SEQ ID NO: 4 is Tyr substituted with Trp (e.g., Y13W of SEQ ID NO: 4).

In another aspect, the carbohydrate binding module variant of the hybrid polypeptide comprises or consists of a substitution at a position corresponding to position 31 of SEQ ID NO: 4. In one embodiment, the amino acid at a position corresponding to position 31 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 31 of SEQ ID NO: 4 is substituted with Trp. In another embodiment, the amino acid at a position corresponding to position 31 of SEQ ID NO: 4 is Tyr substituted with Trp (e.g., Y31W of SEQ ID NO: 4).

In another aspect, the carbohydrate binding module variant of the hybrid polypeptide comprises or consists of a substitution at a position corresponding to position 32 of SEQ ID NO: 4. In one embodiment, the amino acid at a position corresponding to position 32 is substituted with Ala, Arg, Asn, Asp, Cys, Gln, Glu, Gly, His, Ile, Leu, Lys, Met, Phe, Pro, Ser, Thr, Trp, Tyr, or Val, such as with Tyr, Phe, or Trp. In another embodiment, the amino acid at a position corresponding to position 32 of SEQ ID NO: 4 is substituted with Trp. In another embodiment, the amino acid at a position corresponding to position 32 of SEQ ID NO: 4 is Tyr substituted with Trp (e.g., Y5W of SEQ ID NO: 4).

In another aspect, the carbohydrate binding module variant of the hybrid polypeptide comprises or consists of a substitution at two positions corresponding to positions 5, 13, 31 and 32 of SEQ ID NO: 4, such as those described above. In one embodiment, the carbohydrate binding module variant comprises or consists of a substitution at positions corresponding to positions 5 and 13 (e.g., substituted with Trp at positions corresponding to positions 5 and 13, such as Y5W and/or Y13W). In another embodiment, the carbohydrate binding module variant comprises or consists of a substitution at positions corresponding to positions 5 and 31 (e.g., substituted with Trp at positions corresponding to positions 5 and 31, such as Y5W and/or Y31W). In another embodiment, the carbohydrate binding module variant comprises or consists of a substitution at positions corresponding to positions 5 and 32 (e.g., substituted with Trp at positions corresponding to positions 5 and 32, such as Y5W and/or Y32W). In another embodiment, the carbohydrate binding module variant comprises or consists of a substitution at positions corresponding to positions 13 and 31 (e.g., substituted with Trp at positions corresponding to positions 13 and 31, such as Y13W and/or Y31W). In another embodiment, the carbohydrate binding module variant comprises or consists of a substitution at positions corresponding to positions 13 and 32 (e.g., substituted with Trp at positions corresponding to positions 13 and 32, such as Y13W and/or Y32W). In another embodiment, the carbohydrate binding module variant comprises or consists of a substitution at positions corresponding to positions 31 and 32 (e.g., substituted with Trp at positions corresponding to positions 31 and 32, such as Y31W and/or Y32W).

In another aspect, the carbohydrate binding module variant of the hybrid polypeptide comprises or consists of a substitution at three positions corresponding to positions 5, 13, 31 and 32 of SEQ ID NO: 4, such as those described above. In one embodiment, the carbohydrate binding module variant comprises or consists of a substitution at positions corresponding to positions 5, 13, and 31 (e.g., substituted with Trp at positions corresponding to positions 5, 13, and 31, such as Y5W, Y13W, and/or Y31W). In another embodiment, the carbohydrate binding module variant comprises or consists of a substitution at positions corresponding to positions 5, 13, and 32 (e.g., substituted with Trp at positions corresponding to positions 5, 13, and 32, such as Y5W, Y13W, and/or Y32W). In another embodiment, the carbohydrate binding module variant comprises or consists of a substitution at positions corresponding to positions 5, 31, and 32 (e.g., substituted with Trp at positions corresponding to positions 5, 31, and 32, such as Y5W, Y31W, and/or Y32W). In another embodiment, the carbohydrate binding module variant comprises or consists of a substitution at positions corresponding to positions 13, 31, and 32 (e.g., substituted with Trp at positions corresponding to positions 13, 31, and 32, such as Y13W, Y31W, and/or Y32W).

In another aspect, the carbohydrate binding module variant of the hybrid polypeptide comprises or consists of a substitution at all four positions corresponding to positions 5, 13, 31 and 32 of SEQ ID NO: 4, such as those described above. In one embodiment, the carbohydrate binding module variant comprises or consists of a Trp substitution at one or more positions corresponding to positions 5, 13, 31 and 32, such as Y5W, Y13W, Y31W and/or Y32W).

The carbohydrate binding module variant of the hybrid polypeptide may further comprise a substitution, a deletion, and/or an insertion at one or more (e.g., several) other positions, such as one or more (e.g., several) substitutions at positions corresponding to positions disclosed in WO 2012/135719, which is incorporated herein by reference. For example, in one aspect, the carbohydrate binding module variant of the hybrid polypeptide further comprises a substitution at one or more (e.g., several) positions corresponding to positions 4, 6, and 29 of SEQ ID NO: 4. In another aspect, the carbohydrate binding module variant of the hybrid polypeptide further comprises a substitution at two positions corresponding to any of positions 4, 6, and 29. In another aspect, the carbohydrate binding module variant of the hybrid polypeptide further comprises a substitution at each position corresponding to positions 4, 6, and 29.

In another aspect, the carbohydrate binding module variant of the hybrid polypeptide further comprises or consists of a substitution at a position corresponding to position 4. In another aspect, the amino acid at a position corresponding to position 4 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Leu, Lys, Phe, or Trp. In another aspect, the carbohydrate binding module variant of the hybrid polypeptide further comprises or consists of the substitution H4L of SEQ ID NO: 4. In another aspect, the carbohydrate binding module variant of the hybrid polypeptide further comprises or consists of the substitution H4K of SEQ ID NO: 4. In another aspect, the carbohydrate binding module variant of the hybrid polypeptide further comprises or consists of the substitution H4E of SEQ ID NO: 4. In another aspect, the carbohydrate binding module variant of the hybrid polypeptide further comprises or consists of the substitution H4F of SEQ ID NO: 4. In another aspect, the carbohydrate binding module variant of the hybrid polypeptide further comprises or consists of the substitution H4W of SEQ ID NO: 4.

In another aspect, the carbohydrate binding module variant of the hybrid polypeptide further comprises or consists of a substitution at a position corresponding to position 6. In another aspect, the amino acid at a position corresponding to position 6 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the carbohydrate binding module variant of the hybrid polypeptide further comprises or consists of the substitution G6A of SEQ ID NO: 4.

In another aspect, the carbohydrate binding module variant of the hybrid polypeptide further comprises or consists of a substitution at a position corresponding to position 29. In another aspect, the amino acid at a position corresponding to position 29 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the carbohydrate binding module variant of the hybrid polypeptide further comprises or consists of the substitution N29D of SEQ ID NO: 4.

In another aspect, the carbohydrate binding module variant of the hybrid polypeptide further comprises or consists of a substitution at positions corresponding to positions 4 and 6, such as those described above.

In another aspect, the carbohydrate binding module variant of the hybrid polypeptide further comprises or consists of substitutions at positions corresponding to positions 4 and 29, such as those described above.

In another aspect, the carbohydrate binding module variant of the hybrid polypeptide further comprises or consists of substitutions at positions corresponding to positions 6 and 29, such as those described above.

In another aspect, the carbohydrate binding module variant of the hybrid polypeptide further comprises or consists of substitutions at positions corresponding to positions 4, 6, and 29, such as those described above.

In another aspect, the carbohydrate binding module variant of the hybrid polypeptide further comprises or consists of one or more (e.g., several) substitutions selected from the group consisting of H4L,K,E,F,W, G6A, and N29D or the one or more (e.g., several) substitutions selected from the group consisting of H4L,K,E,F,W, G6A, and N29D corresponding to SEQ ID NO: 4 in other cellulose binding modules described herein.

In another aspect, the carbohydrate binding module variant of the hybrid polypeptide further comprises or consists of the substitutions H4L+G6A of SEQ ID NO: 4.

In another aspect, the carbohydrate binding module variant of the hybrid polypeptide further comprises or consists of the substitutions H4K+G6A of SEQ ID NO: 4.

In another aspect, the carbohydrate binding module variant of the hybrid polypeptide further comprises or consists of the substitutions H4E+G6A of SEQ ID NO: 4.

In another aspect, the carbohydrate binding module variant of the hybrid polypeptide further comprises or consists of the substitutions H4F+G6A of SEQ ID NO: 4.

In another aspect, the carbohydrate binding module variant of the hybrid polypeptide further comprises or consists of the substitutions H4W+G6A of SEQ ID NO: 4.

In another aspect, the carbohydrate binding module variant of the hybrid polypeptide further comprises or consists of the substitutions H4L+N29D of SEQ ID NO: 4.

In another aspect, the carbohydrate binding module variant of the hybrid polypeptide further comprises or consists of the substitutions H4K+N29D of SEQ ID NO: 4.

In another aspect, the carbohydrate binding module variant of the hybrid polypeptide further comprises or consists of the substitutions H4E+N29D of SEQ ID NO: 4.

In another aspect, the carbohydrate binding module variant of the hybrid polypeptide further comprises or consists of the substitutions H4F+N29D of SEQ ID NO: 4.

In another aspect, the carbohydrate binding module variant of the hybrid polypeptide further comprises or consists of the substitutions H4W+N29D of SEQ ID NO: 4.

In another aspect, the carbohydrate binding module variant of the hybrid polypeptide further comprises or consists of the substitutions G6A+N29D of SEQ ID NO: 4.

In another aspect, the carbohydrate binding module variant of the hybrid polypeptide further comprises or consists of the substitutions H4L+G6A+N29D of SEQ ID NO: 4.

In another aspect, the carbohydrate binding module variant of the hybrid polypeptide further comprises or consists of the substitutions H4K+G6A+N29D of SEQ ID NO: 4.

In another aspect, the carbohydrate binding module variant of the hybrid polypeptide further comprises or consists of the substitutions H4E+G6A+N29D of SEQ ID NO: 4.

In another aspect, the carbohydrate binding module variant of the hybrid polypeptide further comprises or consists of the substitutions H4F+G6A+N29D of SEQ ID NO: 4.

In another aspect, the carbohydrate binding module variant of the hybrid polypeptide further comprises or consists of the substitutions H4W+G6A+N29D of SEQ ID NO: 4.

In some embodiments, the hybrid polypeptide comprises or consists of SEQ ID NO: 61. In other embodiments, the hybrid polypeptide is encoded by the coding sequence of SEQ ID NO: 60.

In other embodiments, the hybrid polypeptide comprises or consists of SEQ ID NO: 63. In other embodiments, the hybrid polypeptide is encoded by the coding sequence of SEQ ID NO: 62.

In other embodiments, the hybrid polypeptide comprises or consists of SEQ ID NO: 73. In other embodiments, the hybrid polypeptide is encoded by the coding sequence of SEQ ID NO: 72.

In other embodiments, the hybrid polypeptide comprises or consists of SEQ ID NO: 94. In other embodiments, the hybrid polypeptide is encoded by the coding sequence of SEQ ID NO: 93.

Essential amino acids in a parent can be identified according to procedures known in the art, as described herein.

Techniques for producing fusion polypeptides are known in the art, and include ligating the coding sequences encoding the polypeptides so that they are in frame and expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

Polynucleotides

The present invention also relates to isolated polynucleotides encoding the carbohydrate binding module variants, cellobiohydrolase variants, and hybrid polypeptides of the present invention.

Nucleic Acid Constructs

The present invention also relates to nucleic acid constructs comprising a polynucleotide encoding a carbohydrate binding module variant, cellobiohydrolase variant, or hybrid polypeptide of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus maltogenic* amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the variant. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases).

A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a variant and the signal peptide sequence is positioned next to the N-terminus of the propeptide sequence.

It may also be desirable to add regulatory sequences that regulate expression of the variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a carbohydrate binding module variant, cellobiohydrolase variant, or hybrid polypeptide of the present invention, together with a promoter, and transcriptional and translational stop signals. The various nucleotide and control sequences may be joined together to produce a recombinant expression vector that may include one or more convenient restriction sites to allow for insertion or substitution of the polynucleotide encoding the variant sequence at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a carbohydrate binding module variant, cellobiohydrolase variant, or hybrid polypeptide of the present invention operably linked to one or more control sequences that direct the production of the desired variant polypeptide. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a carbohydrate binding module variant, cellobiohydrolase variant, or hybrid polypeptide described herein, comprising: (a) cultivating a recombinant host cell of the present invention under conditions suitable for production of the carbohydrate binding module variant, cellobiohydrolase variant, or hybrid polypeptide; and optionally (b) recovering the carbohydrate binding module variant, cellobiohydrolase variant, or hybrid polypeptide.

The host cells are cultivated in a nutrient medium suitable for production of the variant using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the carbohydrate binding module variant, cellobiohydrolase variant, or hybrid polypeptide described herein to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a carbohydrate binding module variant, cellobiohydrolase variant, or hybrid polypeptide of the present invention. The fermentation broth product further comprises additional ingredients used in the fermentation process, such as, for example, cells (including, the host cells containing the gene encoding a variant of the present invention which are used to produce the variant of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a carbohydrate binding module variant, cellobiohydrolase variant, or hybrid polypeptide of the present invention. Preferably, the compositions are enriched in such a polypeptide. The term "enriched" indicates that the cellobiohydrolase activity or the cellulolytic enzyme activity of the composition has been increased, e.g., with an enrichment factor of at least 1.1.

The composition may comprise a carbohydrate binding module variant, cellobiohydrolase variant, or hybrid polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, expansin, glucoamylase, invertase, laccase, lipase, mannosidase, mutanase, oxidase, pectinolytic enzyme, peroxidase, phytase, polyphenoloxidase, proteolytic enzyme, ribonuclease, swollenin, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following methods for using the cellobiohydrolase variants described herein, or hybrid polypeptides comprising a carbohydrate binding module variant and a heterologous catalytic domain of a cellulolytic enzyme described herein, as well as compositions thereof.

The present invention relates to methods for degrading or converting a cellulosic material, comprising: treating the cellulosic material with an enzyme composition in the presence of a cellobiohydrolase variant or a cellulolytic enzyme comprising a carbohydrate binding module variant of the present invention. In one aspect, the methods further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to methods of producing a fermentation product, comprising: (a) saccharifying a cellulosic material with an enzyme composition in the presence of a cellobiohydrolase variant or a cellulolytic enzyme comprising a carbohydrate binding module variant of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a cellobiohydrolase variant or a cellulolytic enzyme comprising a carbohydrate binding module variant of the present invention. In one aspect, the fermenting of the cellulosic material produces a fermentation product. In another aspect, the method further comprises recovering the fermentation product from the fermentation.

The methods of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment.

In practicing the methods of the present invention, any pretreatment process known in the art can be used to disrupt plant cell wall components of the cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a cellobiohydrolase variant or a cellulolytic enzyme comprising a carbohydrate binding module variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the methods of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and cellobiohydrolase variants or cellulolytic enzymes comprising a carbohydrate binding module variant depend on several factors including, but not limited to, the mixture of component cellulolytic enzymes and/or hemicellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another preferred aspect, an effective amount of a cellobiohydrolase variant or a cellulolytic enzyme comprising a carbohydrate binding module variant to the cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably about 0.025 to about 1.5 mg, more preferably about 0.05 to about 1.25 mg, more preferably about 0.075 to about 1.25 mg, more preferably about 0.1 to about 1.25 mg, even more preferably about 0.15 to about 1.25 mg, and most preferably about 0.25 to about 1.0 mg per g of the cellulosic material.

In another preferred aspect, an effective amount of a cellobiohydrolase variant or a cellulolytic enzyme comprising a carbohydrate binding module variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity, (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus,*

*Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, Gene 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In the methods of the present invention, any GH61 polypeptide having cellulolytic enhancing activity can be used.

In a first aspect, the GH61 polypeptide having cellulolytic enhancing activity comprises the following motifs:

```
                         (SEQ ID NO: 27 or SEQ ID NO: 28)
[ILMV]-P-X(4,5)-G-X-Y-[ILMV]-X-R-X-[EQ]-X(4)-[HNQ]
and

[FW]-[TF]-K-[AIV],
```

wherein X is any amino acid, X(4,5) is any amino acid at 4 or 5 contiguous positions, and X(4) is any amino acid at 4 contiguous positions.

The polypeptide comprising the above-noted motifs may further comprise:

```
                   (SEQ ID NO: 29 or SEQ ID NO: 30),
H-X(1,2)-G-P-X(3)-[YW]-[AILMV],

                                       (SEQ ID NO: 31)
[EQ]-X-Y-X(2)-C-X-[EHQN]-[FILV]-X-[ILV],
or

                     (SEQ ID NO: 32 or SEQ ID NO: 33)
H-X(1,2)-G-P-X(3)-[YW]-[AILMV]
and

                                       (SEQ ID NO: 34)
[EQ]-X-Y-X(2)-C-X-[EHQN]-[FILV]-X-[ILV],
```

wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the GH61 polypeptide having cellulolytic enhancing activity further comprises H-X(1,2)-G-P-X(3)-[YW]-[AILMV] (SEQ ID NO: 29 or SEQ ID NO: 30). In another preferred aspect, the GH61 polypeptide having cellulolytic enhancing activity further comprises [EQ]-X-Y-X(2)-C-X-[EHQN]-[FILV]-X-[ILV] (SEQ ID NO: 31). In another preferred aspect, the GH61 polypeptide having cellulolytic enhancing activity further comprises H-X(1,2)-G-P-X(3)-[YW]-[AILMV] (SEQ ID NO: 32 or SEQ ID NO: 33) and [EQ]-X-Y-X(2)-C-X-[EHQN]-[FILV]-X-[ILV] (SEQ ID NO: 34).

In a second aspect, the GH61 polypeptide having cellulolytic enhancing activity comprises the following motif:

```
                         (SEQ ID NO: 35 or SEQ ID NO: 36)
[ILMV]-P-x(4,5)-G-x-Y-[ILMV]-x-R-x-[EQ]-x(3)-A-

[HNQ],
```

wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

Examples of GH61 polypeptides having cellulolytic enhancing activity useful in the methods of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In another aspect, the GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-6}$ to about 1 g, about $10^{-6}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Peni-* cillium pinophilum (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae.*

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagu-*

*lans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K lactis, K thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis.*

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida* scehatae. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvarum.*

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis.*

Commercially available yeast suitable for ethanol production include, e.g., BIOFERM™ AFT and XR (NABC—North American Bioproducts Corporation, Ga., USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, Wis., USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TALI genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis.*

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in Biomass and *Bioenergy, Vol.* 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to isolated plants, e.g., a transgenic plant, plant part, or plant cell, comprising a polynucleotide of the present invention so as to express and produce the carbohydrate binding module variant, cellobiohydrolase variant, or hybrid polypeptide of the present invention in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The present invention may be further described by the following numbered paragraphs:

[1] An isolated carbohydrate binding module (CBM) variant, comprising a substitution at one or more (e.g., several) positions corresponding to positions 5, 13, 31 and 32 of SEQ ID NO: 4, wherein the variant has carbohydrate binding activity.

[2] The variant of paragraph [1], which is a variant of a parent carbohydrate binding module selected from: (a) a carbohydrate binding module having at least 60% sequence identity to the carbohydrate binding module of SEQ ID NO: 4, SEQ ID NO: 8, SEQ ID NO: 12, SEQ ID NO: 16, SEQ ID NO: 20, SEQ ID NO: 24, or SEQ ID NO: 28; (b) a carbohydrate binding module encoded by a polynucleotide that hybridizes under at least low stringency conditions with the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof; (c) a carbohydrate binding module encoded by a polynucleotide having at least 60% sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27.

[3] The variant of paragraph [2], wherein the parent carbohydrate binding module has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 4, SEQ ID NO: 8, SEQ ID NO: 12, SEQ ID NO: 16, SEQ ID NO: 20, SEQ ID NO: 24, or SEQ ID NO: 28.

[4] The variant of paragraph [2] or [3], wherein the parent carbohydrate binding module is encoded by a polynucleotide that hybridizes under low stringency conditions, medium stringency conditions, medium-high stringency conditions, high stringency conditions, or very high stringency conditions with SEQ ID NO: 3, SEQ ID NO: 7, SEQ ID NO: 11, SEQ ID NO: 15, SEQ ID NO: 19, SEQ ID NO: 23, or SEQ ID NO: 27, or the full-length complement thereof.

[5] The variant of any of paragraphs [2]-[4], wherein the parent carbohydrate binding module is encoded by a polynucleotide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the carbohydrate binding module coding sequence of SEQ ID NO: 3, SEQ ID NO: 7, SEQ ID NO: 11, SEQ ID NO: 15, SEQ ID NO: 19, SEQ ID NO: 23, or SEQ ID NO: 27.

[6] The variant of any of paragraphs [2]-[5], wherein the parent carbohydrate binding module comprises or consists of SEQ ID NO: 4, SEQ ID NO: 8, SEQ ID NO: 12, SEQ ID NO: 16, SEQ ID NO: 20, SEQ ID NO: 24, or SEQ ID NO: 28.

[7] The variant of any of paragraphs [2]-[6], wherein the parent carbohydrate binding module is a fragment of SEQ ID NO: 4, SEQ ID NO: 8, SEQ ID NO: 12, SEQ ID NO: 16, SEQ ID NO: 20, SEQ ID NO: 24, or SEQ ID NO: 28, wherein the fragment has carbohydrate binding activity.

[8] The variant of any of paragraphs [2]-[7], which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the amino acid sequence of the parent carbohydrate binding module.

[9] The variant of any of paragraphs [1]-[8], which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to SEQ ID NO: 4, SEQ ID NO: 8, SEQ ID NO: 12, SEQ ID NO: 16, SEQ ID NO: 20, SEQ ID NO: 24, or SEQ ID NO: 28.

[10] The variant of any of paragraphs [1]-[9], wherein the carbohydrate binding module variant consists of 28 to 36 amino acids, e.g., 28, 29, 30, 31, 32, 33, 34, 35, or 36 amino acids.

[11] The variant of any of paragraphs [1]-[10], wherein the number of substitutions is 1-4, e.g., 1, 2, 3 or 4 substitutions.

[12] The variant of any of paragraphs [1]-[11], which comprises a substitution at the position corresponding to position 5 of SEQ ID NO: 4.

[13] The variant of paragraph [12], wherein the substitution is with Tyr, Phe, or Trp, such as Trp (e.g., Y5W).

[14] The variant of any of paragraphs [1]-[13], which comprises a substitution at the position corresponding to position 13 of SEQ ID NO: 4.

[15] The variant of paragraph [14], wherein the substitution is with Tyr, Phe, or Trp, such as Trp (e.g., Y13W).

[16] The variant of any of paragraphs [1]-[15], which comprises a substitution at the position corresponding to position 31 of SEQ ID NO: 4.

[17] The variant of paragraph [16], wherein the substitution is with Tyr, Phe, or Trp, such as Trp (e.g., Y31W).

[18] The variant of any of paragraphs [1]-[17], which comprises a substitution at a position corresponding to position 32 of SEQ ID NO: 4.

[19] The variant of paragraph [18], wherein the substitution is with Tyr, Phe, or Trp, such as Trp (e.g., Y32W).

[20] The variant of any one of paragraphs [1]-[19], which comprises a substitution at two positions corresponding to positions 5 and 13; 5 and 31; 5 and 32; 13 and 31; 13 and 32; or 31 and 32.

[21] The variant of paragraph [20], which comprises the substitutions Y5W+Y13W; Y5W+Y31W; Y5W+Y32W; Y13W+Y31W; Y13W+Y32W; or Y31W+Y32W.

[22] The variant of any one of paragraphs [1]-[19], which comprises a substitution at three positions corresponding to positions 5, 13, and 31; 5, 13, and 32; 5, 31, and 32; or 13, 31, and 32.

[23] The variant of paragraph [22], which comprises the substitutions Y5W, Y13W, +Y31W; Y5W, Y13W, +Y32W; Y5W, Y31W, +Y32W; or Y13W, Y31W, +Y32W.

[24] The variant of any one of paragraphs [1]-[19], which comprises a substitution at all four positions corresponding to positions 5, 13, 31, and 32.

[25] The variant of paragraph [24], which comprises the substitutions Y5W, Y13W, Y31W, and Y32W.

[26] The variant of any of paragraphs [1]-[25], which further comprises a substitution at one or more (e.g., several) positions corresponding to positions 4, 6, and 29 of SEQ ID NO: 4.

[27] An isolated polypeptide having cellulolytic activity, comprising the carbohydrate binding module variant of any of paragraphs [1]-[26].

[28] The polypeptide of paragraph [27], which is selected from the group consisting of an endoglucanase, a cellobiohydrolase, and a GH61 polypeptide.

[29] A composition comprising the variant of any of paragraphs [1]-[28].

[30] An isolated polynucleotide encoding the variant of any of paragraphs [1]-[28].

[31] A nucleic acid construct comprising the polynucleotide of paragraph [30].

[32] An expression vector comprising the polynucleotide of paragraph [30].

[33] A host cell comprising the polynucleotide of paragraph [30].

[34] A method of producing a variant, comprising: cultivating the host cell of paragraph [33] under conditions suitable for expression of the variant.

[35] The method of paragraph [34], further comprising recovering the variant.

[36] A transgenic plant, plant part or plant cell transformed with the polynucleotide of paragraph [30].

[37] A method of producing the variant of any of paragraphs [1]-[28], comprising: cultivating a transgenic plant, plant part or a plant cell comprising a polynucleotide encoding the variant under conditions conducive for production of the variant.

[38] The method of paragraph [37], further comprising recovering the variant.

[39] A method for obtaining a variant of a parent carbohydrate binding module, comprising introducing into the carbohydrate binding module a substitution at one or more (e.g., several) positions corresponding to positions 5, 13, 31, and 32 of SEQ ID NO: 4, wherein the variant has carbohydrate binding activity; and recovering the variant.

[40] An isolated cellobiohydrolase variant, comprising a substitution at one or more (e.g., several) positions corresponding to positions 483, 491, 509 and 510 of SEQ ID NO: 2, wherein the variant has cellobiohydrolase activity.

[41] The variant of paragraph [40], which is a variant of a parent cellobiohydrolase selected from: (a) a polypeptide having at least 60% sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78; (b) a polypeptide encoded by a polynucleotide that hybridizes under at least low stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii); (c) a polypeptide encoded by a polynucleotide having at least 60% sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77; and (d) a fragment of (a), (b), or (c), which has cellobiohydrolase activity

[42] The variant of paragraph [41], wherein the parent cellobiohydrolase has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

[43] The variant of paragraph [41] or [42], wherein the parent cellobiohydrolase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77, (ii) the genomic DNA or cDNA sequence thereof, or (iii) the full-length complement of (i) or (ii).

[44] The variant of any of paragraphs [41]-[43], wherein the parent cellobiohydrolase is encoded by a polynucleotide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, SEQ ID NO: 5, SEQ ID NO: 9, SEQ ID NO: 13, SEQ ID NO: 17, SEQ ID NO: 21, SEQ ID NO: 25, SEQ ID NO: 41, SEQ ID NO: 43, or SEQ ID NO: 77 or the genomic DNA or cDNA sequence thereof.

[45] The variant of any of paragraphs [41]-[44], wherein the parent cellobiohydrolase comprises or consists of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

[46] The variant of any of paragraphs [41]-[44], wherein the parent cellobiohydrolase is a fragment of the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78, wherein the fragment has cellobiohydrolase activity.

[47] The variant of any of paragraphs [41]-[46], which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the amino acid sequence of the parent cellobiohydrolase.

[48] The variant of any of paragraphs [40]-[47], which has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2, SEQ ID NO: 6, SEQ ID NO: 10, SEQ ID NO: 14, SEQ ID NO: 18, SEQ ID NO: 22, SEQ ID NO: 26, SEQ ID NO: 42, SEQ ID NO: 44, or SEQ ID NO: 78.

[49] The variant of any of paragraphs [40]-[48], wherein the variant consists of 310 to 537 amino acids, e.g., 310 to 320, 320 to 330, 330 to 340, 340 to 350, 350 to 360, 360 to 370, 370 to 380, 380 to 390, 390 to 400, 400 to 415, 415 to 425, 425 to 435, 435 to 445, 445 to 455, 455 to 465, 465 to 475, 475 to 485, 485 to 495, 495 to 505, 505 to 515, 515 to 525, or 525 to 537 amino acids.

[50] The variant of any of paragraphs [40]-[49], wherein the number of substitutions is 1-4, e.g., 1, 2, 3 or 4 substitutions.

[51] The variant of any of paragraphs [40]-[50], which comprises a substitution at a position corresponding to position 483.

[52] The variant of paragraph [51], wherein the substitution is with Tyr, Phe, or Trp, such as Trp (e.g., Y483W).

[53] The variant of any of paragraphs [40]-[52], which comprises a substitution at a position corresponding to position 491.

[54] The variant of paragraph [53], wherein the substitution is with Tyr, Phe, or Trp, such as Trp (e.g., Y491W).

[55] The variant of any of paragraphs [40]-[54], which comprises a substitution at a position corresponding to position 509.

[56] The variant of paragraph [55], wherein the substitution is with Tyr, Phe, or Trp, such as Trp (e.g., Y509W).

[57] The variant of any of paragraphs [40]-[56], which comprises a substitution at a position corresponding to position 510.

[58] The variant of paragraph [57], wherein the substitution is with Tyr, Phe, or Trp, such as Trp (e.g., Y510W).

[59] The variant of paragraph [40]-[58], which comprises a substitution at two positions corresponding to positions 483 and 491; 483 and 509; 483 and 510; 483 and 509; 483 and 510; or 509 and 510.

[60] The variant of paragraph [59], which comprises the substitutions Y483W+Y491W; Y483W+Y509W; Y483W+Y510W; Y483W+Y509W; Y483W+Y510W; or Y509W+Y510W.

[61] The variant of any one of paragraphs [40]-[50], which comprises a substitution at three positions corresponding to positions 483, 491, and 509; 483, 491, and 510; 483, 509, and 510; or 491, 509, and 510.

[62] The variant of paragraph [61], which comprises the substitutions Y483W, Y491W, +Y509W; Y483W, Y491W, +Y510W; Y483W, Y509W, +Y510W; or Y491W, Y509W, +Y510W.

[63] The variant of any one of paragraphs [40]-[58], which comprises a substitution at all four positions corresponding to positions 483, 491, 509, and 510.

[64] The variant of paragraph [63], which comprises the substitutions Y5W, Y13W, Y31W, +Y32W.

[65] The variant of any of paragraphs [40]-[64], which further comprises a substitution at one or more (e.g., several) positions corresponding to positions 214, 215, 216, and 217 of SEQ ID NO: 2.

[66] The variant of any one of paragraphs [40]-[58] comprising or consisting of SEQ ID NO: 90 or SEQ ID NO: 92, or the mature polypeptide sequence thereof.

[67] A composition comprising the variant of any of paragraphs [40]-[66].

[68] An isolated polynucleotide encoding the variant of any of paragraphs [40]-[66].

[69] A nucleic acid construct comprising the polynucleotide of paragraph [68].

[70] An expression vector comprising the polynucleotide of paragraph [68].

[71] A host cell comprising the polynucleotide of paragraph [68].

[72] A method of producing a variant of a parent cellobiohydrolase, comprising: cultivating the host cell of paragraph [71] under conditions suitable for expression of the variant.

[73] The method of paragraph [72], further comprising recovering the variant.

[74] A transgenic plant, plant part or plant cell transformed with the polynucleotide of paragraph [68].

[75] A method of producing the variant of any of paragraphs [40]-[66], comprising: cultivating a transgenic plant, plant part or a plant cell comprising a polynucleotide encoding the variant under conditions conducive for production of the variant.

[76] The method of paragraph [75], further comprising recovering the variant.

[77] A method for obtaining a variant of a parent cellobiohydrolase, comprising introducing into the parent cellobiohydrolase a substitution at one or more (e.g., several) positions corresponding to positions 483, 491, 509, and 510 of the mature polypeptide of SEQ ID NO: 2, wherein the variant has cellobiohydrolase activity; and recovering the variant.

[78] A hybrid polypeptide comprising a carbohydrate binding module variant of any one of paragraphs [1]-[26], and a heterologous catalytic domain of a cellulolytic enzyme.

[79] The hybrid polypeptide of paragraph [78], having cellulolytic activity (e.g., cellobiohydrolase activity).

[80] A hybrid polypeptide having cellulolytic activity, comprising:

(a) a fragment at the N-terminal end of the hybrid polypeptide comprising the heterologous catalytic domain of a cellulolytic enzyme; and (b) a fragment at the C-terminal end of the first polypeptide fragment comprising a carbohydrate binding module variant of any one of paragraphs [1]-[26].

[81] The hybrid polypeptide of any one of paragraphs [78]-[80], having carbohydrate binding activity.

[82] A hybrid polypeptide having cellulolytic activity, comprising:

(a) a fragment at the N-terminal end of the hybrid polypeptide comprising the heterologous catalytic domain of a cellulolytic enzyme, wherein the fragment (i) has at least 60% identity to amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, (ii) is encoded by catalytic domain coding sequence that hybridizes under low stringency condition with nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; the cDNA sequence thereof; or the full-length complement of the foregoing;

(iii) is encoded by catalytic domain coding sequence having at least 60% identity to nucleotides 52 to 1469 of SEQ ID NO: 29, nucleotides 52 to 1389 of SEQ ID NO: 31, nucleotides 52 to 1389 of SEQ ID NO: 32, nucleotides 79 to 1389 of SEQ ID NO: 35, nucleotides 52 to 1371 of SEQ ID NO: 37, nucleotides 55 to 1482 of SEQ ID NO: 39, nucleotides 76 to 1386 of SEQ ID NO: 41, nucleotides 76 to 1386 of SEQ ID NO: 43, nucleotides 55 to 1504 of SEQ ID NO: 45, nucleotides 61 to 1350 of SEQ ID NO: 47, or nucleotides 55 to 1353 of SEQ ID NO: 49; or cDNA sequence thereof;

(iv) is a variant of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50, comprising a substitution, deletion, and/or insertion at one or more (e.g., several) positions; or (v) comprises or consists of amino acids 1 to 429 of SEQ ID NO: 30, amino acids 1 to 437 of SEQ ID NO: 36, amino acids 1 to 440 of SEQ ID NO: 38, amino acids 1 to 437 of SEQ ID NO: 40, amino acids 1 to 437 of SEQ ID NO: 42, amino acids 1 to 438 of SEQ ID NO: 44, amino acids 1 to 437 of SEQ ID NO: 46, amino acids 1 to 430 of SEQ ID NO: 48, or amino acids 1 to 433 of SEQ ID NO: 50; and (b) a fragment at the C-terminal end of the first polypeptide fragment comprising a carbohydrate binding module variant, wherein the variant comprises a substitution at one or more (e.g., several) positions corresponding to positions 5, 13, 31 and 32 of the carbohydrate binding module of SEQ ID NO: 4 (e.g., a carbohydrate binding module variant of any one of paragraphs [1]-[26]).

[83] The hybrid polypeptide of any one of paragraphs [78]-[82] comprising or consisting of SEQ ID NO: 61, SEQ ID NO: 63, SEQ ID NO: 73, or SEQ ID NO: 94, or the mature polypeptide thereof.

[84] The hybrid polypeptide of any of paragraphs [78]-[83], which further comprises a substitution at one or more (e.g., several) positions corresponding to positions 214, 215, 216, and 217 of SEQ ID NO: 2.

[85] A composition comprising the hybrid polypeptide of any of paragraphs [78]-[84].

[86] An isolated polynucleotide encoding the hybrid polypeptide of any of paragraphs [78]-[84].

[87] A nucleic acid construct comprising the polynucleotide of paragraph [86].

[88] An expression vector comprising the polynucleotide of paragraph [86].

[89] A host cell comprising the polynucleotide of paragraph [86].

[90] A method of producing a hybrid polypeptide, comprising: cultivating the host cell of paragraph [89] under conditions suitable for expression of the hybrid polypeptide.

[91] The method of paragraph [90], further comprising recovering the hybrid polypeptide.

[92] A transgenic plant, plant part or plant cell transformed with the polynucleotide of paragraph [86].

[93] A method of producing the hybrid polypeptide of any of paragraphs [78]-[84], comprising: cultivating a transgenic plant, plant part or a plant cell comprising a polynucleotide encoding the hybrid polypeptide under conditions conducive for production of the hybrid polypeptide.

[94] A method for degrading or converting a cellulosic material, comprising: treating the cellulosic material with an enzyme composition in the presence of the variant of any of paragraphs [40]-[66] or the hybrid polypeptide of any of paragraphs [78]-[84].

[95] The method of paragraph [94], wherein the cellulosic material is pretreated.

[96] The method of paragraph [94] or [95], wherein the enzyme composition comprises one or more enzymes selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

[97] The method of paragraph [96], wherein the cellulase is one or more enzymes selected from the group consisting of an endoglucanase, a cellobiohydrolase, and a beta-glucosidase.

[98] The method of paragraph [96], wherein the hemicellulase is one or more enzymes selected from the group consisting of a xylanase, an acetylxylan esterase, a feruloyl esterase, an arabinofuranosidase, a xylosidase, and a glucuronidase.

[99] The method of any of paragraphs [94]-[98], further comprising recovering the degraded cellulosic material.

[100] The method of paragraph [99], wherein the degraded cellulosic material is a sugar.

[101] The method of paragraph [100], wherein the sugar is selected from the group consisting of glucose, xylose, mannose, galactose, and arabinose.

[102] A method for producing a fermentation product, comprising: (a) saccharifying a cellulosic material with an enzyme composition in the presence of the variant of any of paragraphs [40]-[66] or the hybrid polypeptide of any of paragraphs [78]-[84]; (b) fermenting the saccharified cellulosic material with one or more fermenting microorganisms to produce the fermentation product; and (c) recovering the fermentation product from the fermentation.

[103] The method of paragraph [102], wherein the cellulosic material is pretreated.

[104] The method of paragraph [102] or [103], wherein the enzyme composition comprises the enzyme composition comprises one or more enzymes selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

[105] The method of paragraph [104], wherein the cellulase is one or more enzymes selected from the group consisting of an endoglucanase, a cellobiohydrolase, and a beta-glucosidase.

[106] The method of paragraph [104], wherein the hemicellulase is one or more enzymes selected from the group consisting of a xylanase, an acetylxylan esterase, a feruloyl esterase, an arabinofuranosidase, a xylosidase, and a glucuronidase.

[107] The method of any of paragraphs [102]-[106], wherein steps (a) and (b) are performed simultaneously in a simultaneous saccharification and fermentation.

[108] The method of any of paragraphs [102]-[107], wherein the fermentation product is an alcohol, an organic acid, a ketone, an amino acid, an alkane, a cycloalkane, an alkene, isoprene, polyketide, or a gas.

[109] A method of fermenting a cellulosic material, comprising: fermenting the cellulosic material with one or more fermenting microorganisms, wherein the cellulosic material is saccharified with an enzyme composition in the presence of the variant of any of paragraphs [40]-[66] or the hybrid polypeptide of any of paragraphs [78]-[84].

[110] The method of paragraph [109], wherein the fermenting of the cellulosic material produces a fermentation product.

[111] The method of paragraph [110], further comprising recovering the fermentation product from the fermentation.

[112] The method of any of paragraphs [1094111], wherein the cellulosic material is pretreated before saccharification.

[113] The method of any of paragraphs [109]-[112], wherein the enzyme composition comprises one or more enzymes selected from the group consisting of a cellulase, a GH61 polypeptide having cellulolytic enhancing activity, a hemicellulase, an expansin, an esterase, a laccase, a ligninolytic enzyme, a pectinase, a peroxidase, a protease, and a swollenin.

[114] The method of paragraph [113], wherein the cellulase is one or more enzymes selected from the group consisting of an endoglucanase, a cellobiohydrolase, and a beta-glucosidase.

[115] The method of paragraph [113], wherein the hemicellulase is one or more enzymes selected from the group consisting of a xylanase, an acetylxylan esterase, a feruloyl esterase, an arabinofuranosidase, a xylosidase, and a glucuronidase.

[116] The method of any of paragraphs [110]-[115, wherein the fermentation product is an alcohol, an organic acid, a ketone, an amino acid, an alkane, a cycloalkane, an alkene, isoprene, polyketide, or a gas.

[117] A whole broth formulation or cell culture composition comprising the variant of any of paragraphs [40]-[66] or the hybrid polypeptide of any of paragraphs [78]-[84].

The present invention is further described by the following examples that should not be construed as limiting the scope of the invention.

EXAMPLES

Strains

*Aspergillus oryzae* strain MT3568 was used as a host for expression of the carbohydrate binding module variants and hybrid polypeptides thereof. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene.

Media and Solutions

COVE sucrose plates or slants were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and then acetamide to 10 mM, CsCl to 15 mM, and TRITON® X-100 (50 μl/500 ml) were added.

COVE salt solution was composed of 26 g of $MgSO_4.7H_2O$, 26 g of KCl, 26 g of $KH_2PO_4$, 50 ml of COVE trace metals solution, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

DAP-4C medium was composed of 20 g of dextrose, 10 g of maltose, 11 g of $MgSO_4.7H_2O$, 1 g of $KH_2PO_4$, 2 g of citric acid, 5.2 g of $K_3PO_4.H_2O$, 0.5 g of yeast extract (Difco), 1 ml of antifoam, 0.5 ml of KU6 trace metals solution, 2.5 g of $CaCO_3$, and deionized water to 1 liter. The medium was sterilized by autoclaving at 15 psi for 15 minutes (Bacteriological Analytical Manual, 8th Edition, Revision A, 1998). Before use, 3.5 ml of sterile 50% $(NH_4)_2HPO_4$ and 5 ml of sterile 20% lactic acid were added per 150 ml.

G2-Gly medium was composed of 18 g of yeast extract, 24 g of glycerol (86-88%), 1 ml of antifoam, and deionized water to 1 liter.

KU6 trace metals solution was composed of 0.13 g of $NiCl_2$, 2.5 g of $CuSO_4.5H_2O$, 13.9 g of $FeSO_4.7H_2O$, 8.45 g of $MnSO_4$—$H_2O$, 6.8 g of $ZnCl_2$, 3 g of citric acid, and deionized water to 1 liter.

LB medium was composed of 10 g of Bacto-Tryptone, 5 g of yeast extract, 10 g of sodium chloride, and deionized water to 1 liter.

LB plates were composed of 10 g of Bacto-Tryptone, 5 g of yeast extract, 10 g of sodium chloride, 15 g of Bacto-agar, and deionized water to 1 liter.

PDA plates were composed of potato infusion made by boiling 300 g of sliced (washed but unpeeled) potatoes in water for 30 minutes and then decanting or straining the broth through cheesecloth. Distilled water was then added until the total volume of the suspension was 1 liter. Then 20 g of dextrose and 20 g of agar powder were added. The medium was sterilized by autoclaving at 15 psi for 15 minutes (Bacteriological Analytical Manual, 8th Edition, Revision A, 1998).

TAE buffer was composed of 40 mM Tris base, 20 mM sodium acetate, and 1 mM disodium EDTA.

YP+2% glucose medium was composed of 1% yeast extract, 2% peptone, and 2% glucose in deionized water.

YP+2% maltose medium was composed of 10 g of yeast extract, 20 g of peptone, 20 g of maltose, and deionized water to 1 liter.

Example 1: Source of DNA Sequence Information for *Trichoderma reesei* Cellobiohydrolase I The genomic DNA sequence and deduced amino acid sequence of the *Trichoderma reesei* GH7 cellobiohydrolase I gene is shown in SEQ ID NO: 1 and SEQ ID NO: 2, respectively. Genomic sequence information was generated by the U.S. Department of Energy Joint Genome Institute (JGI) and published by Martinez et al., 2008, *Nature Biotechnology* 26 (5): 553-560. The amino acid sequence of the full-length cellobiohydrolase I is publicly available from the National Center for Biotechnology Information (NCBI) and annotated as GenBank: EGR44817.1 (SEQ ID NO: 2). The cDNA sequence of the *Trichoderma reesei* cellobiohydrolase I gene is shown in SEQ ID NO: 31.

Based on the publicly available amino acid sequence, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 32) was synthesized by the GENEART® Gene Synthesis service (Life Technologies Corp., San Diego. Calif., USA) with a 5' Bam HI restriction site, a 3' Hind III restriction site, and a Kozac consensus sequence (CACC) situated between the start codon and the Bam HI restriction site.

Example 2: Construction of an *Aspergillus oryzae* Expression Vector Containing a *Trichoderma reesei* cDNA Sequence Encoding Cellobiohydrolase I The kanamycin-resistant *E. coli* cloning vector provided by GENEART® Gene Synthesis encoding the *T. reesei* cellobiohydrolase I (SEQ ID NO: 2) was digested with Fast Digest Bam HI and Hind III (Fermentas Inc., Glen Burnie, Md., USA) according to manufacturer's instructions. The reaction products were isolated by 1.0% agarose gel electrophoresis using TAE buffer where a 1552 bp product band was excised from the gel and purified using an ILLUSTRA™ GFX™ DNA Purification Kit (GE Healthcare Life Sciences, Brondby, Denmark).

The 1552 bp fragment was then cloned into pDau109 (WO 2005/042735) digested with Bam HI and Hind III using T4 DNA ligase (New England Biolabs, Ipswich, Mass., USA). The Bam HI-Hind III digested pDau109 and the Bam HI/Hind III fragment containing the *T. reesei* cellobiohydrolase I coding sequence were mixed in a molar ratio of 1:3 (i.e., mass ratio approximately 2.5:1 or 20 ng:50 ng) and ligated with 50 units of T4 DNA ligase in 1× T4 DNA ligase buffer (New England Biolabs, Ipswich, Mass., USA) with 1 mM ATP at 16° C. over-night in accordance with the manufacturer's instructions. Cloning of the *T. reesei* cellobiohydrolase I gene into the Bam HI-Hind III digested pDau109 resulted in transcription of the *T. reesei* cellobiohydrolase I gene under the control of a NA2-tpi double promoter. The NA2-tpi promoter is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, colonies were observed growing under selection on the LB ampicillin plates Insertion of the *T. reesei* cellobiohydrolase I gene into pDau109 was verified by PCR on colonies as described below using the following primers.

```
Primer F-pDau109
                                        (SEQ ID NO: 51)
5'-CCCTTGTCGATGCGATGTATC-3'

Primer R-pDau109
                                        (SEQ ID NO: 52)
5'-ATCCTCAATTCCGTCGGTCGA-3'
```

A 1.1× REDDYMIX® Master Mix (Thermo Fisher Scientific, Roskilde, Denmark) was used for the PCR. The PCR solution was composed of 10 μl of 1.1× REDDYMIX® Master Mix, 0.5 μl of primer F-pDau109 (10 μM), and 0.5 μl of primer R-pDau109 (10 μM). A toothpick was used to transfer a small amount of cells to the PCR solution. The PCR was performed using a PTC-200 DNA Engine programmed for 1 cycle at 94° C. for 3 minutes; 30 cycles each at 94° C. for 30 seconds, 50° C. for 1 minute, and 72° C. for 2 minutes; and 1 cycle at 72° C. for 1 minute. The PCR solution was then held at 15° C. until removed from the PCR machine.

The PCR products were analyzed by 1.0% agarose gel electrophoresis using TAE buffer where a 1860 bp PCR product band was observed confirming insertion of the *T. reesei* cellobiohydrolase I coding sequence into pDau109.

An *E. coli* transformant containing the *T. reesei* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pKHJN0036.

Example 3: Source of DNA Sequence Information for *Rasamsonia emersonii* Cellobiohydrolase I The genomic DNA sequence and deduced amino acid sequence of the wild-type *Rasamsonia emersonii* GH7 cellobiohydrolase I gene is shown in SEQ ID NO: 39 and SEQ ID NO: 40, respectively. The gene sequence is 99% identical to Genbank entry AF439935.4. The cDNA sequence and deduced amino acid sequence of the *Rasamsonia emersonii* cellobiohydrolase I gene is shown in SEQ ID NO: 53 and SEQ ID NO: 40, respectively.

Based on the cDNA sequence for *Rasamsonia emersonii* cellobiohydrolase I, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 54) was synthesized by the GENEART® Gene Synthesis service (Life Technologies Corp., San Diego. Calif., USA) with a 5' Bam HI restriction site, a 3' Hind III restriction site, and a Kozac consensus sequence (CACC) situated between the start codon and the Bam HI restriction site.

Example 4: Construction of an *Aspergillus oryzae* Expression Vector Containing a *Rasamsonia emersonii* DNA Sequence Encoding Cellobiohydrolase I The kanamycin-resistant *E. coli* cloning vector provided by GENEART® Gene Synthesis encoding the *Rasamsonia emersonii* cellobiohydrolase I was digested with Fast Digest Bam HI and Hind III (Fermentas Inc., Glen Burnie, Md., USA) according to manufacturer's instructions. The reaction products were isolated by 1.0% agarose gel electrophoresis using TAE buffer where a 1375 bp product band was excised from the gel and purified using an ILLUSTRA™ GFX™ DNA Purification Kit.

The 1375 bp fragment was then cloned into pDau109 digested with Bam HI and Hind III using T4 DNA ligase. The Bam HI-Hind III digested pDau109 and the Bam HI/Hind III fragment containing the *T. reesei* cellobiohydrolase I coding sequence were mixed in a molar ratio of 1:3 (i.e., mass ratio approximately 2.5:1 or 20 ng:50 ng) and ligated with 50 units of T4 DNA ligase in 1× T4 DNA ligase buffer with 1 mM ATP at 16° C. over-night in accordance with the manufacturer's instructions. Cloning of the *Rasamsonia emersonii* cellobiohydrolase I gene into Bam HI-Hind III digested pDau109 resulted in the transcription of the *Rasamsonia emersonii* cellobiohydrolase I gene under the control of a NA2-tpi double promoter.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Insertion of the *Rasamsonia emersonii* cellobiohydrolase I gene into pDau109 was verified by PCR on the transformants as described below using primers F-pDau109 and R-pDau109.

A 1.1× REDDYMIX® Master Mix (Thermo Fisher Scientific, Roskilde, Denmark) was used for the PCR. The PCR solution was composed of 10 μl of 1.1× REDDYMIX® Master Mix, 0.5 μl of primer F-pDau109 (10 μM), and 0.5 μl of primer R-pDau109 (10 μM). A toothpick was used to transfer a small amount of cells to the PCR solution. The PCR was performed using a PTC-200 DNA Engine programmed for 1 cycle at 94° C. for 3 minutes; 30 cycles each at 94° C. for 30 seconds, 50° C. for 1 minute, and 72° C. for 2 minutes; and 1 cycle at 72° C. for 1 minute. The PCR solution was then held at 15° C. until removed from the PCR machine.

The PCR products were analyzed by 1.0% agarose gel electrophoresis using TAE buffer where a 1600 bp PCR product band was observed confirming insertion of the *Rasamsonia emersonii* cellobiohydrolase I coding sequence into pDau109.

An *E. coli* transformant containing the *Rasamsonia emersonii* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pKHJN0135.

Example 5: Construction of a Hybrid Polypeptide of *Rasamsonia emersonii Cellobiohydrolase I with Linker and Carbohydrate Binding Module from Trichoderma reesei* Cellobiohydrolase I (PC1-147)

The codon-optimized synthetic gene encoding the *T. reesei* (*H. jecorina*) cellobiohydrolase I is described in Example 1.

The codon-optimized synthetic gene encoding the *R. emersonii* cellobiohydrolase I is described in Example 3.

To generate a gene encoding a hybrid polypeptide of *R. emersonii* cellobiohydrolase I with linker and carbohydrate binding module (CBM) from *T. reesei* cellobiohydrolase I (SEQ ID NOs: 55 and 56 for the hybrid polypeptide DNA and amino acid sequences, respectively), a DNA fragment encoding *T. reesei* cellobiohydrolase I linker and CBM was assembled to the 3'-end of the gene encoding the *R. emersonii* cellobiohydrolase I using splicing overlap extension (SOE) PCR.

The DNA fragment encoding the *T. reesei* cellobiohydrolase I linker and CBM was amplified using primer F-SOE and primer R-pDau109 shown below.

```
Primer F-SOE:
                                        (SEQ ID NO: 57)
5'-GGTCC CATCA ACTCG ACATT CACAG CCTCG GGTGG AAACC

CTCCT GGCGG AAACC CTC-3'

Primer R-pDau109:
                                        (SEQ ID NO: 58)
5'-ATCCTCAATTCCGTCGGTCGA-3'
```

-continued

```
Primer F-pDau109:
                                          (SEQ ID NO: 59)
5'-CCACACTTCTCTTCCTTCCTCAATCCTC-3'
```

The amplification of the DNA fragment encoding the *T. reesei* cellobiohydrolase I linker and CBM was performed using a PHUSION® High-Fidelity PCR Kit. The PCR solution was composed of 10 μl of 5×HF buffer, 1 μl of dNTPs (10 mM), 0.5 μl of PHUSION® DNA polymerase (0.2 units/μl), 0.25 μl of primer F-SOE (100 μM), 0.25 μl of primer R-pDau109 (100 μM), 10 μl of template DNA (pDAu222-*T. reesei* cellobiohydrolase I, 1 ng/μl), and 28 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 405 bp PCR fragment encoding the *T. reesei* a linker and CBM was excised from the gel and purified using a MinElute Gel Extraction Kit (QIAGEN Inc., Valencia, Calif., USA).

A DNA fragment encoding the *R. emersonii* cellobiohydrolase I was amplified using primer F-pDau109 and primer R-pDau109 above.

The amplification of the DNA fragment encoding the *R. emersonii* wild-type cellobiohydrolase I was performed using a PHUSION® High-Fidelity PCR Kit. The PCR solution was composed of 10 μl of 5×HF buffer, 1 μl of dNTPs (10 mM), 0.5 μl of PHUSION® DNA polymerase (0.2 units/μl), 0.25 μl of primer F-pDAu109 (100 μM), 0.25 μl of primer R-pDau109 (100 μM), 10 μl of template DNA (pDAu222-*R. emersonii* cellobiohydrolase I, 1 ng/μl), and 28 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 1600 bp fragment encoding the *R. emersonii* wild-type cellobiohydrolase I was excised from the gel and purified using a MinElute Gel Extraction Kit.

The two purified DNA fragments were assembled using SOE PCR and a PHUSION® High-Fidelity PCR Kit. The PCR solution was composed of 10 μl of 5×HF buffer, 1 μl of dNTPs (10 mM), 0.5 μl of PHUSION® DNA polymerase (0.2 units/μl), 0.25 μl of primer F-pDAu109 (100 μM), 10 μl of gel purified fragment encoding *T. reesei* cellobiohydrolase 1 linker and CBM, 2 μl of DNA fragment encoding *R. emersonii* cellobiohydrolase 1, and 26 μl of deionized water in a total volume of 50 μl. The PCR was performed using a GeneAmp® PCR System 9700 programmed for 1 cycle at 98° C. for 30 seconds; and 30 cycles each at 98° C. for 20 seconds, 55° C. for 30 seconds, and 72° C. for 1 minute. The PCR solution was then held at 8° C. until removed from the PCR machine.

The PCR generated DNA fragment was then digested with Bam HI (New England Biolabs, Ipswich, Mass., USA) and Hind III (New England Biolabs, Ipswich, Mass., USA) as follows. Forty μl of PCR product were mixed with 5 μl buffer 2 (New England Biolabs, Ipswich, Mass., USA), 1 μl of Bam HI, and 1 μl of Hind III and incubated for 4 hours at 37° C. The resulting DNA product was submitted to 1% agarose gel electrophoresis using TAE buffer. A band of approximately 1567 bp was excised from the gel and purified using a MinElute Gel Extraction Kit.

The purified 1567 bp fragment encoding the *R. emersonii* cellobiohydrolase I with linker and carbohydrate binding module (CBM) from *T. reesei* cellobiohydrolase I was cloned into pDAu109 digested with Bam HI and Hind III using T4 DNA ligase. The Bam HI-Hind III digested pDau109 and the Bam HI/Hind III fragment containing the *R. emersonii* cellobiohydrolase I with linker and carbohydrate binding module (CBM) from *T. reesei* cellobiohydrolase I coding sequence were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Two transformants were cultivated in LB medium supplemented with 0.15 mg of ampicillin per ml and plasmids were isolated using a QIAPREP® Spin Miniprep Kit.

The insertion of the DNA fragment encoding the *R. emersonii* cellobiohydrolase I with linker and carbohydrate binding module (CBM) from *T. reesei* cellobiohydrolase I into pDAu109 was verified by sequencing. The isolated plasmids were sequenced using an Applied Biosystems 3730xl DNA Analyzer with vector primers F-pDau109 and R-pDau109 in order to determine a representative plasmid that was free of PCR errors and contained the correct insertion.

One plasmid clone free of PCR errors and containing the DNA fragment encoding the *R. emersonii* cellobiohydrolase I with linker and carbohydrate binding module (CBM) from *T. reesei* cellobiohydrolase I was chosen and designated plasmid pE147. The corresponding hybrid polypeptide was designated as PC1-147.

Example 6: Site-Directed Mutagenesis of the Hybrid Polypeptide of *Rasamsonia emersonii* Cellobiohydrolase I with Linker and Carbohydrate Binding Module from *Trichoderma reesei* Cellobiohydrolase I (PC1-499, PC1-500)

The plasmid pE147 containing the DNA fragment encoding the hybrid polypeptide of *Rasamsonia emersonii* cellobiohydrolase I with linker and carbohydrate binding module from *Trichoderma reesei* cellobiohydrolase I was described in Example 5.

To generate the hybrid polypeptide PC1-499 containing a Y→W substitution corresponding to Y32W of the carbohydrate binding module of the hybrid polypeptide PC1-147 supra, a TAT codon encoding position 515 of SEQ ID NO: 56 was replaced with a TGG codon in the gene encoding PC1-147. The mutant DNA sequence and corresponding polypeptide sequence are designated as SEQ ID NO: 60 and SEQ ID NO: 61, respectively.

To generate the hybrid polypeptide PC1-500 containing a Y→W substitution corresponding to Y5W of the carbohydrate binding module of the hybrid polypeptide PC1-147 supra, a TAC codon encoding position 488 of SEQ ID NO: 56 was replaced with a TGG codon in the gene encoding PC1-147. The mutant DNA sequence and corresponding polypeptide sequence are designated as SEQ ID NO: 62 and SEQ ID NO: 63, respectively.

Two synthetic primers for each site-directed mutagenesis were designed as shown below using an SOE primer design tool. The introduced site-directed mutation changed a TAT codon encoding position 515 of SEQ ID NO: 56 to a TGG codon and a TAC codon encoding position 488 of SEQ ID NO: 56 to a TGG codon.

```
Primer F-Y497W:
                                        (SEQ ID NO: 64)
5'-CTGTC AGGTC TTGAA CCCTT ACTGG TCGCA GTGTC

TCTAA G-3'

Primer R-Y497W:
                                        (SEQ ID NO: 65)
5'-GTAAG GGTTC AAGAC CTGAC AGGTT GTGCC GG-3'

Primer F-Y470W:
                                        (SEQ ID NO: 66)
5'-CTGGA CCGAC CCAGT CCCAC TGGGG ACAGT GTGGA

GGCAT CGG-3'

Primer R-Y470W:
                                        (SEQ ID NO: 67)
5'-GTGGG ACTGG GTCGG TCCAG GGGAC GAACC-3'
```

Site-directed mutagenesis was facilitated by PCR amplifications of the pDau109 vector containing the coding sequence for the hybrid polypeptide PC1-147. The gene was previously cloned into Bam HI-Hind III digested pDau109 resulting in transcription of the gene under the control of a NA2-tpi double promoter.

The mutations were introduced by PCR using a PHUSION® High-Fidelity PCR Kit. The PCR solution was composed of 10 μl of 5×HF buffer, 1 μl of dNTPs (10 mM), 0.5 μl of PHUSION® DNA polymerase (0.2 units/μl), 0.25 μl of primer F-Y497W (100 μM), 0.25 μl of primer R-Y497W (100 μM), 10 μl of plasmid pE147 DNA (1 ng/μl), and 28 μl of deionized water in a total volume of 50 μl. For the TAC to TGG mutation 0.25 μl of primer F-Y470W (100 μM), 0.25 μl of primer R-Y470W (100 μM) were used. The PCR was performed using a GeneAmp® PCR System 9700 programmed for 1 cycle at 98° C. for 30 seconds; and 19 cycles each at 98° C. for 30 seconds, 55° C. for 1 minute, and 72° C. for 4 minutes. The PCR solution was then held at 8° C. until removed from the PCR machine.

Following the PCR, 10 units of Dpn I were added directly to the PCR solution and incubated at 37° C. for 1 hour. Then 1 μl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.15 mg of ampicillin per ml and plasmids were isolated using a QIAPREP® Spin Miniprep Kit.

The isolated plasmids were sequenced using an Applied Biosystems 3730xl DNA Analyzer with primers F-p147, F-Central1, R-Central2 and R-pDau109, in order to determine a representative plasmid that was free of PCR errors and contained the desired mutations.

```
Primer F-p147
                                        (SEQ ID NO: 68)
5'-CCACACTTCTCTTCCTTCCTCAATCCTC-3'
```

-continued

```
Primer F-Central1
                                        (SEQ ID NO: 69)
5'-GTGAG GCGAA CGTGG AAGGA TG-3'

Primer R-Central2
                                        (SEQ ID NO: 70)
5'-GTACC TGTGT CCGTG CCGTC ATCTG-3'

Primer R-pDau109
                                        (SEQ ID NO: 71)
5'-ATCCT CAATT CCGTC GGTCG A-3'
```

One plasmid clone free of PCR errors and containing the TAT to TGG mutation was chosen and designated plasmid pE499. The corresponding fusion polypeptide was designated as PC1-499.

One plasmid clone free of PCR errors and containing the TAC to TGG mutation was chosen and designated plasmid pE500. The corresponding fusion polypeptide was designated as PC1-500.

Example 7: Expression of Hybrid Polypeptides PC1-147, PC1-499 and PC1-500

The expression plasmids pE147, pE499 and pE500 (supra) were transformed into *Aspergillus oryzae* MT3568 protoplasts according to Christensen et al., 1988, supra and WO 2004/032648. *A. oryzae* MT3568 protoplasts were prepared according to the method of EP 0238023 B1, pages 14-15.

Transformants were purified on COVE sucrose plates without CsCl through single conidia. Spores of the transformants were inoculated into 96 deep well plates containing 0.50 ml of YP+2% maltose+0.5% glucose medium and incubated stationary at 34° C. for 6 days. Production of hybrid polypeptides by the transformants were analyzed from culture supernatants of the 96 deep well cultivations. Expression was verified by measuring released reducing sugars from hydrolysis of microcrystalline cellulose. The hydrolysis was performed in 96 well microtiter plates (NUNC Thermo Fisher Scientific, Roskilde, Denmark) at 25° C. and 1100 rpm. Each hydrolysis reaction mixture contained 167 μl of microcrystalline cellulose at 90 g/liter in 50 mM sodium acetate pH 5.0, 0.01% TRITON® X-100, 20 μl of culture supernatant, and 63 μl of 50 mM sodium acetate pH 5.0, 0.01% TRITON® X-100. The plates were sealed with tape. The hydrolysis reaction was stopped by spinning the plate at 3500 rpm for 3 minutes. Then 50 μl of the reaction supernatant were added to 75 μl of stop solution in a 96 well PCR plate (Thermo Fisher Scientific, Roskilde, Denmark). The stop solution was composed of 15 mg/ml 4-hydroxybenzhydrazide (Sigma Chemical Co., Inc., St. Louis, Mo., USA), 50 mg/ml K—Na-tartrate (Sigma Chemical Co., Inc., St. Louis, Mo., USA) in 2% (w/v) NaOH. The plate was sealed with a lid and the mixture was incubated at 95° C. for 10 minutes and 5 minutes at 20° C. Then 100 μl was transferred to a microtiter plate and absorbance at 410 nm was measured using a SPECTRAMAX® Plus 384 (Molecular Devices, Sunnyvale, Calif., USA). The concentration of reducing sugar was proportional to the absorbance at 410 nm of the oxidized 4-hydroxybenzhydrazide. The reducing sugar content in the culture supernatants was measured by adding 4 μl of culture supernatant to a mixture of 75 μl of stop solution and 46 μl of milliQ water in a 96 well PCR plate. The plate was sealed with a lid and the mixture was incubated at 95° C. for 10 minutes and 5 minutes at 20° C. Then 100 μl was transferred to a microtiter plate and the absorbance at 410 nm was measured. The absorbance at 410 nm from the cell culture supernatant was subtracted from the absorbance at 410 nm of the hydrolysis reaction, to measure the amount of reducing sugar released by the enzymes.

Based on the level of hydrolysis of the microcrystalline cellulose one transformant for each of the hybrid polypeptides PC1-147, PC1-499 and PC1-500 was selected and designated *A. oryzae* PC1-147, *A. oryzae* PC1-499 and *A. oryzae* PC1-500, respectively.

For larger scale production, *A. oryzae* PC1-147 or *A. oryzae* PC1-499 or PC1-500 spores were spread onto COVE sucrose slants and incubated for five days at 37° C. The confluent spore slants were washed twice with 5 ml of G2-Gly medium. The spore suspensions were then used to inoculate 500 ml flasks containing 150 ml of G2-Gly medium. These pre-cultures were incubated at 30° C. with constant shaking at 150 rpm. After one day, each of the pre-cultures was used to inoculate four 500 ml flasks containing 150 ml of DAP-4C medium. At day four post-inoculation, the culture broths were collected by filtration through a bottle top MF75 Supor MachV 0.2 μm PES filter.

Example 8: Purification of Hybrid Polypeptides PC1-147, PC1-499 and PC1-500

The fermentation broths were filtered through a PES Bottle top filter with a 0.22 μm cut-off. Ammonium sulphate was added to the filtered fermentation broths to a concentration of 1.8 M.

The desired hybrid polypeptides were purified from the fermentation broths by HIC/affinity chromatography followed by IEX/affinity chromatography.

In the HIC/affinity chromatographic step, the fermentation broths were applied to a 200 ml Phenyl SEPHAROSE® 6 Fast Flow column (high sub) (GE Healthcare, Piscataway, N.J., USA) which had been pre-equilibrated with 1.8 M ammonium sulphate, 25 mM HEPES pH 7.0. After applying the sample, the column was washed with 2 column volumes of 1.8 M ammonium sulphate followed by 1 column volume of 0.54 M ammonium sulphate. The bound proteins were batch eluted with 25 mM HEPES pH 7.0.

The elution of the protein was monitored at 280 nm. Fractions with high 280 nm absorbance were analyzed on SDS-PAGE using 12-well NUPAGE® 4-12% Bis-Tris gel (GE Healthcare, Piscataway, N.J., USA) for their cellobiohydrolase I content. Fractions with high content of this protein were pooled and collected for further purification. The pooled fractions were desalted on a SEPHADEX™ G-25 (medium) column (GE Healthcare, Piscataway, N.J., USA) equilibrated with 25 mM MES pH 6.0. The elution of the protein was monitored at 280 nm and fractions with high absorbance at 280 nm were chosen for the second chromatographic step.

The pooled fractions were applied to the 60 ml RESOURCE™ 15Q column (GE Healthcare, Piscataway, N.J., USA) equilibrated with 25 mM MES pH 6.0 and bound proteins were eluted with a linear 100-200 mM sodium chloride gradient for 1.5 column volumes followed by 1.5 column volumes of 300 mM sodium chloride, followed by 1.5 column volumes of 1 M sodium chloride. The elution of the protein was monitored at 280 nm and fractions with high absorbance at 280 nm were analyzed on SDS-PAGE.

Fractions with high content of cellobiohydrolase I were pooled.

Example 9: Activity Measurement on Microcrystalline Cellulose of Hybrid Polypeptides PC1-147, PC1-499 and PC1-500

The activities of the purified hybrid polypeptides PC1-147, PC1-499 and PC1-500 (supra) were compared to the purified wild-type *R. emersonii* cellobiohydrolase I using washed microcrystalline cellulose (AVICEL® PH101; Sigma-Aldrich, St. Louis, Mo., USA) as a substrate (see PCT/US2014/022068).

The purified hybrid polypeptides were diluted in 50 mM sodium acetate, 2 mM $CaCl_2$ pH 5. The diluted hybrid polypeptides and β-glucosidase were added to each well (microwell plate 96F 26960 Thermo scientific). Washed AVICEL then was added to each well and the microtiter plate was quickly transferred to a thermomixer (eppendorf) and incubated for 24 hours at 1100 rpm and 50° C. or 60° C. The final concentration of hybrid polypeptides in the reaction was 3 μM and the concentration of AVICEL was 76 g/l. The reaction was stopped by centrifugation at 3500 rpm for 3 min at 5° C. (Hereaus multifuge 3 S-R). The supernatants diluted and transferred to PCR sample tubes (Thermoscientific 0.2 ml non-skirtet 96-well PCR plate AB0600). PAHBAH (4-hydroxy-benzhydrazid) (Sigma, H 9882) was dissolved in buffer (0.18 M K—Na-tartrate (Merck, 1.08087) and 0.5 M NaOH) to make a 15 mg/ml solution. 75 μl of the PAHBAH solution was added to the supernatants in the PCR samples tubes.

The PCR sample tubes were placed in a Peltier Thermal Cycler and incubated at 95° C. for 10 min and 20° C. for 5 min. After incubation 100 μl were transferred to a 96 well microtiter plate (microwell plate 96F 26960 Thermo scientific) and the absorbance was measured at 410 nm. For each run a standard was included. The standard used was glucose diluted in 50 mM sodium acetate, 2 mM $CaCl_2$ pH 5 to a concentration of 0.008, 0.016, 0.0312, 0.0625, 0.125, 0.25, 0.5, 1 mM. In addition to the standard, a blank (without cellobiohydrolase) for each run was included. For all the measurement, the blank measurement was subtracted. The absorbance data were normalized to glucose concentration using the standards.

The results as shown in FIG. 2 demonstrated that at 50° C., the hybrid polypeptides PC1-500 (containing an *R. emersonii* cellobiohydrolase I catalytic domain linked to a *T. reesei* carbohydrate binding module variant with a substitution corresponding to Y5W of the CBM) and PC1-499 (containing an *R. emersonii* cellobiohydrolase I catalytic domain linked to a *T. reesei* carbohydrate binding module variant with a substitution corresponding to Y32W of the CBM) had an approximately 145% and 124% increase, respectively, toward microcrystalline cellulose compared to the wild-type cellobiohydrolase I and an increase of 57% and 44%, respectively, compared with the hybrid polypeptide lacking either substitution corresponding to Y5W or Y32W of the CBM.

The results as shown in FIG. 3 demonstrated that at 60° C., the hybrid polypeptides PC1-500 and PC1-499 showed an increase of 209% and 186%, respectively, compared to the wild-type cellobiohydrolase I and an increase of 34% and 24%, respectively, compared with the hybrid polypeptide lacking either substitution corresponding to Y5W or Y32W of the CBM.

Example 10: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of the PCS to 5.0 by addition of 10 M NaOH with extensive mixing, and then autoclaving for 20 minutes at 120° C. The dry weight of the whole slurry PCS was 29%.

A 96-well plate was generated by machining a teflon plate of depth ¼ inch with 96, cone-shaped wells, diameter ¼ inch at the upper surface and diameter ⅛ inch at the lower surface. The center of each well was at an equivalent position to the center of a corresponding well in a standard 96-well microtiter plate, approximately 23/64 inch on center. The resulting volume of each well was approximately 135 μl. This 96-well aluminum plate is hereinafter referred to as the "fill plate". The pH-adjusted corn stover was used to fill the holes in the fill plate by applying a suitable volume of the corn stover to the upper surface of the plate, then using a spatula to spread the material over the surface and into the holes. Holes were deemed sufficiently full when corn stover was extruded through the hole in the bottom surface, forming noodle-like tubes. A MULTISCREEN® Column Loader Scraper (Millipore) held perpendicular to the fill plate surface was used to scrape excess corn stover from the top and bottom surfaces of the fill plate, leaving the surfaces of the corn stover in each well flush with the surfaces of the fill plate. The fill plate was then placed on the top of a 2.2 ml deep well plate (Axygen, Union City, Calif., USA) with the top surface adjacent to the open end of the well plate (e.g. the top of the well plate), and the wells aligned with the corn stover-filled holes in the fill plate. The fill plate was secured in this position, and the assembly centrifuged at 2500 rpm (1350×g) for 5 minutes in a Sorvall Legend RT+ (Thermo Scientific, Waltham, Mass., USA). Following centrifugation, the corn stover had been transferred to the deep well plate. A 3 mm glass bead (Fisher Scientific, Waltham, Mass., USA) was placed in each well for mixing.

The hydrolysis of PCS was conducted in a total reaction volume of 0.2 ml. The hydrolysis was performed with 50 mg of insoluble PCS solids containing 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 20 μl to 50 μl, for a final volume of 0.2-0.50 ml in each reaction. The plate was then sealed using an ALPS-300™ plate heat sealer (Abgene, Epsom, United Kingdom), mixed thoroughly, and incubated at a specific temperature for 72 hours.

Following hydrolysis, samples were filtered using a 0.45 μm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction.

Glucose and cellobiose were measured individually. Measured sugar concentrations were adjusted for the appropriate dilution factor. The net concentrations of enzymatically-produced sugars from unwashed PCS were determined by adjusting the measured sugar concentrations for corresponding background sugar concentrations in unwashed PCS at zero time point. All HPLC data processing was performed using MICROSOFT EXCEL™ software (Microsoft, Richland, Wash., USA).

The degree of glucose conversion to glucose was calculated using the following equation: % cellulose conversion=(glucose concentration)/(glucose concentration in a limit digest)×100. In order to calculate % glucose conversion, a 100% conversion point was set based on a cellulase control (100 mg of *T. reesei* cellulase supplemented with *Thermoascus aurantiacus* GH61A polypeptide, *Aspergillus fumigatus* GH10 xylanase (xyn3), and *Talaromyces emersonii* beta-xylosidase per gram cellulose). Quadruplicate data points were averaged and standard deviation was calculated.

Example 11: Preparation of an Enzyme Composition without Cellobiohydrolase I

The *Talaromyces leycettanus* GH6 cellobiohydrolase II (GENESEQP:AZY49446) was prepared recombinantly in *Aspergillus oryzae* as described in WO 2012/103288. The filtered broth of the *Talaromyces leycettanus* GH6 cellobiohydrolase II was concentrated and buffer exchanged into 20 mM Tris pH 8.0 using a 400 ml SEPHADEX™ G-25 column (GE Healthcare, United Kingdom). The fractions were pooled, and 3 M ammonia sulfate, 20 mM Tris pH 8.0 was added to the desalted protein to a final concentration of 1.2 M ammonia sulfate, 20 mM Tris pH 8.0. The protein was loaded onto a Phenyl Sepharose™ 6 Fast Flow column (high sub) (GE Healthcare, Piscataway, N.J., USA) equilibrated in 20 mM Tris pH 8.0 with 1.2 M ammonium sulfate, and bound proteins were eluted with 20 mM Tris pH 8.0 with no ammonium sulfate. Fractions were analyzed by 8-16% Tris-HCl SDS-PAGE gels (Bio-Rad, Hercules, Calif., USA), and pooled. The pooled protein was buffer exchanged into 20 mM MES pH 6.0 using a Vivaflow 200 with 10 kDa molecular weight cut-off tangential flow membrane (Sartorius, Bohemia, N.Y., USA).

The *Trichoderma reesei* GH5 endoglucanase II (GENESEQP:AZI04858) was prepared recombinantly according to WO 2011/057140 using *Aspergillus oryzae* as a host. The filtered broth of the *T. reesei* endoglucanase 11 was desalted and buffer-exchanged into 20 mM Tris pH 8.0 using a tangential flow concentrator (Pall Filtron, Northborough, Mass., USA) equipped with a 10 kDa polyethersulfone membrane (Pall Filtron, Northborough, Mass., USA).

*Thermoascus aurantiacus* CGMCC 0583 GH61A polypeptide having cellulolytic enhancing activity (GENESEQP:AEC05922) was recombinantly prepared according to WO 2005/074656 using *Aspergillus oryzae* JaL250 as a host. The broth was filtered using a 0.22 μm EXPRESS™ Plus Membrane (Millipore, Bedford, Mass., USA).

The *Aspergillus fumigatus* GH10 xylanase (xyn3) (GENESEQP:AZI04884) was prepared recombinantly according to WO 2006/078256 using *Aspergillus oryzae* BECh2 (WO 2000/39322) as a host. The filtered broth of the *A. fumigatus* xylanase was desalted and buffer-exchanged into 50 mM sodium acetate pH 5.0 using a HIPREP® 26/10 Desalting Column (GE Healthcare, Piscataway, N.J., USA).

The *Aspergillus fumigatus* Cel3A beta-glucosidase 4M mutant (GENESEQP:AZU67153) was recombinantly prepared according to WO 2012/044915. The filtered broth of *Aspergillus fumigatus* Cel3A beta-glucosidase 4M was concentrated and buffer exchanged using a tangential flow concentrator (Pall Filtron, Northborough, Mass., USA) equipped with a 10 kDa polyethersulfone membrane (Pall Filtron, Northborough, Mass., USA) with 50 mM sodium acetate pH 5.0 containing 100 mM sodium chloride.

The *Talaromyces emersonii* CBS 393.64 beta-xylosidase (GENESEQP:AZI04896) was prepared recombinantly according to Rasmussen et al., 2006, *Biotechnology and Bioengineering* 94: 869-876 using *Aspergillus oryzae* JaL355 as a host (WO 2003/070956). The filtered broth was concentrated and desalted with 50 mM sodium acetate pH 5.0 using a tangential flow concentrator equipped with a 10 kDa polyethersulfone membrane (Pall Filtron, Northborough, Mass., USA).

The protein concentration for each of the monocomponents described above was determined using a Microplate BCA™ Protein Assay Kit (Thermo Fischer Scientific, Waltham, Mass., USA) in which bovine serum albumin was used as a protein standard. An enzyme composition was prepared composed of each monocomponent as follows: 39.7% *Talaromyces leycettanus* GH6 cellobiohydrolase II, 15.9% *Trichoderma reesei* GH5 endoglucanase II, 23.8% *Thermoascus aurantiacus* GH61A polypeptide, 7.9% *Aspergillus fumigatus* GH10 xylanase, 7.9% *Aspergillus fumigatus* beta-glucosidase, and 4.8% *Talaromyces emersonii* beta-xylosidase. The enzyme composition is designated herein as "cellulolytic enzyme composition without cellobiohydrolase I".

Example 12: Comparison of the Effect of Hybrid Polypeptides PC1-147, PC1-499 and PC1-500 on the Hydrolysis of Unwashed PCS by a Cellulase Enzyme Composition The hybrid polypeptides PC1-499 and PC1-500 (containing a substitution corresponding to Y32W and Y5W of the cellulose binding module, respectively) were added to the cellulolytic enzyme composition without cellobiohydrolase I (supra) at 35° C., 50° C. and 60° C. using unwashed PCS as a substrate, and compared against the hybrid polypeptide PC1-147 (lacking either substitution corresponding to Y5W or Y32W of the cellulose binding module). Each cellobiohydrolase I was added individually at 3.33 mg enzyme protein per g cellulose to 5.67 mg enzyme protein of the cellulase enzyme composition without cellobiohydrolase I per g cellulose.

The assay was performed as described in supra. The reactions with unwashed PCS (20% total solids) were conducted for 72 hours at 35° C., 50° C. and 60° C. in 50 mM sodium acetate pH 5.0 buffer containing 1 mM manganese sulfate. All reactions were performed in quadruplicate and shaking at 200 rpm throughout the hydrolysis.

The results shown in FIG. 4 demonstrated that the cellulase enzyme composition containing the hybrid polypeptide PC1-499 (containing an *R. emersonii* cellobiohydrolase I catalytic domain linked to a *T. reesei* carbohydrate binding module (CBM) variant with a substitution corresponding to Y32W of the CBM) had significantly higher cellulose conversion at all temperatures compared to the cellulase enzyme composition that included the hybrid polypeptide PC1-147 lacking either substitution corresponding to Y5W or Y32W of the CBM. In addition, the hybrid polypeptide PC1-500 (containing an *R. emersonii* cellobiohydrolase I catalytic domain linked to a *T. reesei* carbohydrate binding module variant with a substitution corresponding to Y5W of the CBM) had significantly higher cellulose conversion at all temperatures compared to PC1-147.

Example 13: Site-Directed Mutagenesis of the Hybrid Polypeptide of *Rasamsonia emersonii* Cellobiohydrolase I with Linker and Carbohydrate Binding Module from *Trichoderma reesei* Cellobiohydrolase I (PC1-668)

The plasmid pE147 contains the DNA fragment encoding the hybrid polypeptide of *Rasamsonia emersonii* cellobiohydrolase I with linker and carbohydrate binding module from *Trichoderma reesei* cellobiohydrolase I was described in Example 5.

To generate the hybrid polypeptide PC1-668 containing a Y→W substitution corresponding to Y13W of the carbohydrate binding module of the hybrid polypeptide PC1-147 supra, a TAT codon encoding position 496 of SEQ ID NO: 56 was replaced with a TGG codon in the gene encoding PC1-147. The mutant DNA sequence and corresponding polypeptide sequence are designated as SEQ ID NO: 72 and SEQ ID NO: 73, respectively.

Two synthetic primers for each site-directed mutagenesis were designed as shown below using an SOE primer design tool. The introduced site-directed mutation changed a TAT codon encoding position 496 of SEQ ID NO: 56 to a TGG codon.

```
Primer F-Y478W:
                                        (SEQ ID NO: 74)
5'-GGACA GTGTG GAGGC ATCGG TTGGT CCGGT CCGAC

CGTCT GTGC-3'

Primer R-Y478W:
                                        (SEQ ID NO: 75)
5'-ACCGA TGCCT CCACA CTGTC CGTAG TGGGA CT-3'
```

Site-directed mutagenesis was facilitated by PCR amplifications of the pDau109 vector containing the coding sequence for the hybrid polypeptide PC1-147. The gene was previously cloned into Bam HI-Hind III digested pDau109 resulting in transcription of the gene under the control of a NA2-tpi double promoter.

The mutation was introduced by PCR using a PHUSION® High-Fidelity PCR Kit. The PCR solution was composed of 10 μl of 5×HF buffer, 1 μl of dNTPs (10 mM), 0.5 μl of PHUSION® DNA polymerase (0.2 units/p1), 0.25 μl of primer F-Y478W (100 μM), 0.25 μl of primer R-Y478W (100 μM), 10 μl of plasmid pE147 DNA (1 ng/μl), and 28 μl of deionized water in a total volume of 50 μl. The PCR was performed using a GeneAmp® PCR System 9700 programmed for 1 cycle at 98° C. for 30 seconds; and 19 cycles each at 98° C. 15 for 30 seconds, 55° C. for 1 minute, and 72° C. for 4 minutes. The PCR solution was then held at 8° C. until removed from the PCR machine.

Following the PCR, 10 units of Dpn I were added directly to the PCR solution and incubated at 37° C. for 1 hour. Then 1 μl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.15 mg of ampicillin per ml and plasmids were isolated using a QIAPREP® Spin Miniprep Kit.

The isolated plasmids were sequenced using an Applied Biosystems 3730xl DNA Analyzer with primers F-p147, F-Central1, R-Central2 and R-pDau109, in order to determine a representative plasmid that was free of PCR errors and contained the desired mutations.

```
Primer F-p147
                                        (SEQ ID NO: 68)
5'-CCACA CTTCT CTTCC TTCCT CAATC CTC-3'

Primer F-Central1
                                        (SEQ ID NO: 69)
5'-GTGAG GCGAA CGTGG AAGGA TG-3'

Primer R-Central2
                                        (SEQ ID NO: 70)
5'-GTACC TGTGT CCGTG CCGTC ATCTG-3'

Primer R-pDau109
                                        (SEQ ID NO: 71)
5'-ATCCT CAATT CCGTC GGTCG A-3'
```

One plasmid clone free of PCR errors and containing the TAT to TGG mutation was chosen and designated plasmid pE668. The corresponding fusion polypeptide was designated as PC1-668.

Example 14: Source of DNA Sequence Information for *Aspergillus fumigatus* Cellobiohydrolase I The genomic DNA sequence and deduced amino acid sequence of the *Aspergillus fumigatus* Af293 GH7 cellobiohydrolase I gene is shown in SEQ ID NO: 76 and SEQ ID NO: 78, respectively. Genomic sequence information was generated by The Institute for Genomic Research, Rockville, Md. 20850, USA and published by Nierman, W. C. et al., 2005, *Nature* 438 (7071): 1151-1156. The amino acid sequence of the full-length cellobiohydrolase I is publicly available from the National Center for Biotechnology Information (NCBI) and annotated as GenBank: EAL89006.1 The cDNA sequence and deduced amino acid sequence of the *Aspergillus fumigatus* cellobiohydrolase I gene is shown in SEQ ID NO: 77 and SEQ ID NO: 78, respectively.

Based on the publicly available amino acid sequence, a codon-optimized synthetic gene encoding the full-length cellobiohydrolase I was generated for *Aspergillus oryzae* expression based on the algorithm developed by Gustafsson et al., 2004, *Trends in Biotechnology* 22 (7): 346-353. The codon-optimized coding sequence (SEQ ID NO: 79) was synthesized by the GENEART® Gene Synthesis service (Life Technologies Corp., San Diego. Calif., USA) with a 5' Bam HI restriction site, a 3' Hind III restriction site, and a Kozac consensus sequence (CACC) situated between the start codon and the Bam HI restriction site.

Example 15: Construction of an *Aspergillus oryzae* Expression Vector Containing an *Aspergillus fumigatus* DNA Sequence Encoding Cellobiohydrolase I The ampicillin-resistant *E. coli* cloning vector provided by GENEART® Gene Synthesis encoding the *A. fumigatus* cellobiohydrolase I (Example 14) was digested with Bam HI and Hind III (New England Biolabs, Mass., USA) according to manufacturer's instructions. The reaction products were isolated by 1.0% agarose gel electrophoresis using TAE buffer where a 1606 bp product band was excised from the gel and purified using a MinElute Gel Extraction Kit (QIAGEN Inc., Valencia, Calif., USA).

The purified 1606 bp fragment encoding the *A. fumigatus* cellobiohydrolase I was cloned into pDau109 (WO 2005/042735) digested with Bam HI and Hind III using T4 DNA ligase (New England Biolabs, Mass., USA). The Bam HI-Hind III digested pDau109 and the Bam HI/Hind III fragment containing the *A. fumigatus* cellobiohydrolase I were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

Cloning of the *A. fumigatus* cellobiohydrolase I gene into the Bam HI-Hind III digested pDau109 will result in transcription of the *A. fumigatus* cellobiohydrolase I gene under the control of a NA2-tpi double promoter. The NA2-tpi promoter is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, colonies were observed growing under selection on the LB ampicillin plates.

Insertion of the *A. fumigatus* cellobiohydrolase I gene into pDau109 was verified by DNA sequencing. The isolated plasmids were sequenced using an Applied Biosystems 3730xl DNA Analyzer with vector primers and *A. fumigatus* cellobiohydrolase I gene specific primers, shown below, in order to determine a representative plasmid that was free of PCR errors and contained the desired insert.

```
Primer F-pDau109
                                        (SEQ ID NO: 59)
5'-CCCTT GTCGA TGCGA TGTAT C-3'

Primer R-pDau109
                                        (SEQ ID NO: 58)
5'-ATCCT CAATT CCGTC GGTCG A-3'

Primer F-pE596
                                        (SEQ ID NO: 80)
5'-GTGAT ACACC CGGAC AGGTG ATGTG-3'

Primer R-pE596
                                        (SEQ ID NO: 81)
5'-CCATA TCGAT CCGAC GAGTA GGTTC-3'
```

An *E. coli* transformant containing the *A. fumigatus* cellobiohydrolase I plasmid construct was cultivated in LB medium supplemented with 0.1 mg of ampicillin per ml and plasmid DNA was isolated using a QIAPREP® Spin Miniprep Kit. The plasmid was designated pE596 and the corresponding polypeptide was designated as AC1-596.

Example 16: Construction of an *Aspergillus oryzae* Expression Vector Containing a *Rasamsonia byssochlamydoides* DNA Sequence Encoding Cellobiohydrolase I The genomic DNA sequence and deduced amino acid sequence of the *Rasamsonia byssochlamydoides* (*Talaromyces byssochlamydoides*) strain CBS413.71 GH7 cellobiohydrolase I gene is shown in SEQ ID NO: 82 and SEQ ID NO: 83, respectively. The GH7 cellobiohydrolase I gene is 1507 bp including the stop codon with two predicted introns (604 to 667 and 1236 to 1310). Cloning of the *R. byssochlamydoides* GH7 gene into pDau109 vector is described patent WO2012/103300 (the content of which is hereby incorporated by reference). The plasmid of pDau109 containing the *R. byssochlamydoides* GH7 gene was designated pE637.

Example 17: Construction of a Fusion Polypeptide of *Rasamsonia byssochlamydoides* *Cellobiohydrolase I with Linker and Carbohydrate Binding Module from Aspergillus fumigatus* Cellobiohydrolase I (RC1-638)

The codon-optimized synthetic gene encoding the *Aspergillus fumigatus* cellobiohydrolase I is described in Examples 14 and 15.

The gene encoding the *R. byssochlamydoides* cellobiohydrolase I is described in Example 16.

To generate a gene encoding a fusion polypeptide of *R. byssochlamydoides* cellobiohydrolase I with linker and carbohydrate binding module (CBM) from *A. fumigatus* cellobiohydrolase I (SEQ ID NOs: 84 and 85 for the fusion polypeptide DNA and amino acid sequences, respectively), a DNA fragment encoding *A. fumigatus* cellobiohydrolase I linker and CBM was assembled to the 3'-end of the gene encoding the *R. byssochlamydoides* cellobiohydrolase I using splicing overlap extension (50E) PCR.

The DNA fragment encoding the *A. fumigatus* cellobiohydrolase I linker and CBM was amplified using primer F-50E638 and primer R-50E638 shown below.

```
Primer F-SOE638:
                                        (SEQ ID NO: 86)
5'-CAATC AACTC GACCT TCACC ACTTC GGGCT CGAAC

CCTGG AGGCG GAACG-3'

Primer R-SOE638:
                                        (SEQ ID NO: 87)
5'-CTAGA TCTCG AGTTA CAAAC ACTGC GAGTA GTAG-3'
```

The amplification of the DNA fragment encoding the *A. fumigatus* cellobiohydrolase I linker and CBM was performed using a PHUSION® High-Fidelity PCR Kit. The PCR solution was composed of 10 μl of 5×HF buffer, 4 μl of dNTPs (2.5 mM), 0.5 μl of PHUSION® DNA polymerase (0.2 units/μl), 0.25 μl of primer F-50E638 (100 μM), 0.25 μl of primer R-50E638 (100 μM), 10 μl of template DNA (pE596 cellobiohydrolase I, 1 ng/μl), and 25 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 239 bp PCR fragment encoding the *A. fumigatus* cellobiohydrolase I linker and CBM was excised from the gel and purified using a MinElute Gel Extraction Kit (QIAGEN Inc., Valencia, Calif., USA).

A DNA fragment encoding the *R. byssochlamydoides* cellobiohydrolase I was amplified using primer F-pDau109 and primer R-50E637 shown below.

```
Primer F-pDau109:
                                        (SEQ ID NO: 59)
5'-CCACA CTTCT CTTCC TTCCT CAATC CTC-3'

Primer R-SOE637
                                        (SEQ ID NO: 88)
5'-CGAAG TGGTG AAGGT CGAGT TGATT G-3'
```

The amplification of the DNA fragment encoding the *R. byssochlamydoides* wild-type cellobiohydrolase I was performed using a PHUSION® High-Fidelity PCR Kit. The PCR solution was composed of 10 μl of 5×HF buffer, 4 μl of dNTPs (2.5 mM), 0.5 μl of PHUSION® DNA polymerase (0.2 units/μl), 0.25 μl of primer F-pDAu109 (100 μM), 0.25 μl of primer R-50E637 (100 μM), 10 μl of template DNA (pE637-*R. byssochlamydoides* cellobiohydrolase I, 1 ng/μl), and 25 μl of deionized water in a total volume of 50 μl. The PCR was performed using a GeneAmp® PCR System 9700 programmed for 1 cycle at 98° C. for 30 seconds; and 30 cycles each at 98° C. for 10 seconds, 55° C. for 30 seconds, and 72° C. for 1 minute. The PCR solution was then held at 8° C. until removed from the PCR machine.

The PCR solution was submitted to 1% agarose gel electrophoresis using TAE buffer where a 1658 bp fragment encoding the *R. byssochlamydoides* wild-type cellobiohydrolase I was excised from the gel and purified using a MinElute Gel Extraction Kit.

The two purified DNA fragments were assembled using SOE PCR and a PHUSION® High-Fidelity PCR Kit. The PCR solution was composed of 10 μl of 5×HF buffer, 4 μl of dNTPs (2.5 mM), 0.5 μl of PHUSION® DNA polymerase (0.2 units/μl), 0.25 μl of primer F-pDAu109 (100 μM), 0.25 of R-pDAu109 (100 μM), 2 μl of gel purified fragment encoding *A. fumigatus* cellobiohydrolase 1 linker and CBM, 2 μl of DNA fragment encoding *R. byssochlamydoides* cellobiohydrolase I, and 31 μl of deionized water to give a final volume of 50 μl. The PCR was performed using a GeneAmp® PCR System 9700 programmed for 1 cycle at 98° C. for 2 min; then 10 cycles of 98° C. for 20 seconds, 65° C. for 20 seconds, and 72° C. for 4 minutes; then followed by 20 cycles of 98° C. for 20 seconds, 55° C. for 20 seconds, and 72° C. for 6 minutes. The PCR solution was then held at 6° C. until removed from the PCR machine.

The PCR generated DNA fragment was then digested with Bam HI (New England Biolabs, Ipswich, Mass., USA) and XhoI (New England Biolabs, Ipswich, Mass., USA) as follows. Twenty μl of PCR product were mixed with 2.3 μl buffer 3.1 (New England Biolabs, Ipswich, Mass., USA), 0.8 μl of Bam HI, and 0.6 μl of XhoI and incubated at 37° C. overnight. The resulting DNA product was submitted to 1% agarose gel electrophoresis using TAE buffer. A band of approximately 1717 bp was excised from the gel and purified using a MinElute Gel Extraction Kit.

The 1717 bp fragment encoding the *R. byssochlamydoides* cellobiohydrolase I with linker and carbohydrate binding module (CBM) from *A. fumigatus* cellobiohydrolase I was cloned into pDAu109 digested with Bam HI and XhoI using T4 DNA ligase. The Bam HI-XhoI digested pDau109 and the Bam HI/XhoI fragment containing the *R. byssochlamydoides* cellobiohydrolase I with linker and carbohydrate binding module (CBM) from *A. fumigatus* cellobiohydrolase I coding sequence were mixed in a molar ratio of 1:3 (i.e., equal volumes of gel purified products) and ligated with 50 units of T4 DNA ligase in 1× T4 DNA ligase buffer with 1 mM ATP and incubated at 22° C. for 10 minutes.

The ligation mixture was transformed into ONE SHOT® TOP10F' Chemically Competent *E. coli* cells according to the manufacturer's protocol and spread onto LB plates supplemented with 0.1 mg of ampicillin per ml. After incubation at 37° C. overnight, transformants were observed growing under selection on the LB ampicillin plates. Two transformants were cultivated in LB medium supplemented with 0.15 mg of ampicillin per ml and plasmids were isolated using a QIAPREP® Spin Miniprep Kit.

The insertion of the DNA fragment encoding the *R. byssochlamydoides* cellobiohydrolase I with linker and carbohydrate binding module (CBM) from *A. fumigatus* cellobiohydrolase I into pDAu109 was verified by sequencing. The isolated plasmids were sequenced using an Applied Biosystems 3730xl DNA Analyzer with vector primers F-pDau109 and R-pDau109 in order to determine a representative plasmid that was free of PCR errors and contained the correct insertion.

One plasmid clone free of PCR errors and containing the DNA fragment encoding the *R. byssochlamydoides* cellobiohydrolase I with linker and carbohydrate binding module (CBM) from *A. fumigatus* cellobiohydrolase I was chosen and designated plasmid pE638. The corresponding hybrid polypeptide was designated as RC1-638.

Example 18: Site-Directed Mutagenesis of the *Aspergillus fumigatus* Cellobiohydrolase I (AC1-660 and AC1-661) and of the Fusion Polypeptide of *Rasamsonia byssochlamydoides* Cellobiohydrolase I with Linker and Carbohydrate Binding Module from *Aspergillus fumigatus* Cellobiohydrolase I (RC1-899)

Plasmid pE596 (Example 15) was used for the construction of the *A. fumigatus* cellobiohydrolase I variants AC1-660 and AC1-661.

AC1-660 (SEQ ID NO: 89 for the mutant DNA sequence and SEQ ID NO: 90 for the variant) contains a Y→W substitution at position 501 (corresponding to Y5W of the carbohydrate binding module) and was generated by replacing a TAC codon (Y501) with a TGG codon (501W).

AC1-661 (SEQ ID NO: 91 for the mutant DNA sequence and SEQ ID NO: 92 for the variant) contains a Y→W substitution at position 527 (corresponding to Y31W of the carbohydrate binding module) and was generated by replacing a TAC codon (Y527) with a TGG codon (527W).

Plasmid pE638 (Example 17) was used to generate *R. byssochlamydoides*-*A. fumigatus* fusion cellobiohydrolase I variant (RC1-899). RC1-899 (SEQ ID NO: 93 for the mutant DNA sequence and SEQ ID NO: 94 for the variant) contains a Y→W substitution at position 516 (corresponding to Y31W of the carbohydrate binding module) and was generated by replacing a TAC codon (Y516) with a TGG codon (516W).

Two synthetic primers for each site-directed mutagenesis were designed using a SOE primer design tool. Site-directed mutagenesis of the synthetic gene encoding the wild-type *A. fumigatus* cellobiohydrolase I was facilitated by PCR amplifications of pE596 using the primers and procedure described below. Site-directed mutageneis of the fusion gene endcoding *R. byssochlamydoides* cellobiohydrolase I with linker and carbohydrate binding module (CBM) from *A. fumigatus* cellobiohydrolase I was facilitated by PCR amplification of pE638 using primers F-Y527W and R-Y527W and the procedure described below.

```
Primer F-Y501W:
                                        (SEQ ID NO: 95)
5'-GTACA GGTGT GGCCC AGCAC TGGGG ACAGT GTGGC

GGTAT CGG-3'

Primer R-Y501W:
                                        (SEQ ID NO: 96)
5'-GTGCT GGGCC ACACC TGTAC CTCCA GGGTT G-3'

Primer F-Y527W:
                                        (SEQ ID NO: 97)
5'-ATACC TGTCA GAAAT TGAAC GACTG GTACT CGCAG

TGTTT GTAAG CTTC-3'

Primer R-Y527W:
                                        (SEQ ID NO: 98)
5'-GTCGT TCAAT TTCTG ACAGG TATAA GGCGA TG-3'
```

The mutation was introduced by PCR using a PHUSION® High-Fidelity PCR Kit (New England Biolabs Inc. Mass., USA). The PCR solutions were composed of 10 μl of 5×HF buffer, 4 μl of dNTPs (2.5 mM), 0.5 μl of PHUSION® DNA polymerase (0.2 units/μl), 0.25 μl of primer F-Y501W or F-Y527W (100 μM), 0.25 μl of primer R-Y501W or R-Y527W (100 μM), 5 μl of template DNA (pE596, 1 ng/μl or pE638, 1 ng/μl), and 30 μl of deionized water in a total volume of 50 μl. the PCR was performed using an Applied Biosystems® Veriti® 96 well thermal cycler programmed for 1 cycle at 98° C. for 30 seconds; and 19 cycles each at 98° C. for 30 seconds, 55° C. for 1 minute, and 72° C. for 7 minutes. The PCR solution was then held at 8° C. until removed from the PCR machine.

Following the PCR, 10 units of Dpn I were added directly to the PCR solution and incubated at 37° C. for 1 hour. Then 1 μl of the Dpn I treated PCR solution was transformed into ONE SHOT® TOP10F' Chemically Competent *E. coli* cells according to the manufacturer's protocol and spread onto LB plates supplemented with 0.15 mg of ampicillin per ml. After incubation at 37° C. overnight, transformants were observed growing under selection on the LB ampicillin plates. Four transformants were cultivated in LB medium supplemented with 0.10 mg of ampicillin per ml and plasmids were isolated using a QIAPREP® Spin Miniprep Kit (QIAGEN Inc., Valencia, Calif., USA).

The isolated mutant plasmids of pE596 were sequenced using an Applied Biosystems 3730xl DNA Analyzer (Applied Biosystems, Foster City, Calif., USA) with primers F-pDau109 (SEQ ID NO: 59), R-pDau109 (SEQ ID NO: 58), F-pE596 (SEQ ID NO: 80) and R-pE596 (SEQ ID NO: 81), in order to determine a representative plasmid that was free of PCR errors and contained the desired mutations.

```
Primer F-pDau109:
                                        (SEQ ID NO: 59)
5'-CCACACTTCTCTTCCTTCCTCAATCCTC-3'

Primer R-pDau109:
                                        (SEQ ID NO: 58)
5'-ATCCTCAATTCCGTCGGTCGA-3'

Primer F-pE596
                                        (SEQ ID NO: 80)
5'-GTGAT ACACC CGGAC AGGTG ATGTG-3'

Primer R-pE596
                                        (SEQ ID NO: 81)
5'-CCATA TCGAT CCGAC GAGTA GGTTC-3'
```

One plasmid clone free of PCR errors and containing the TAC (Y501) to TGG (501W) mutation (corresponding to Y5W of the carbohydrate binding module) was chosen and designated plasmid pE660 and the corresponding polypeptide was designated as AC1-660.

One plasmid clone free of PCR errors and containing the TAC (Y527) to TGG (527W) mutation corresponding to Y31W of the carbohydrate binding module) was chosen and designated plasmid pE661 and the corresponding polypeptide was designated as AC1-661.

The isolated mutant plasmids of pE638 were sequenced using an Applied Biosystems 3730xl DNA Analyzer (Applied Biosystems, Foster City, Calif., USA) with primers F-pDau109 (SEQ ID NO: 59), R-pDau109 (SEQ ID NO: 58), F-pE638 (SEQ ID NO: 99) and R-pE638 (SEQ ID NO: 100), in order to determine a representative plasmid that was free of PCR errors and contained the desired mutations.

```
Primer F-pDau109:
                                      (SEQ ID NO: 59)
5'-CCACACTTCTCTTCCTTCCTCAATCCTC-3'

Primer R-pDau109:
                                      (SEQ ID NO: 58)
5'-ATCCTCAATTCCGTCGGTCGA-3'

Primer F-pE638:
                                      (SEQ ID NO: 99)
5'-CCTCA GCCGA ACTCC GACAT TGC-3'

Primer R-pE638:
                                     (SEQ ID NO: 100)
5'-GCAAT GTCGG AGTTC GGCTG AGG-3'
```

One plasmid clone free of PCR errors and containing the TAC (Y516) to TGG (516W) mutation (corresponding to Y31W of the carbohydrate binding module) was chosen and designated plasmid pE899 and the corresponding polypeptide was designated as RC1-899.

Example 19: Expression of the Wild Type *A. fumigatus* Cellobiohydrolase I AC1-596, the *A. fumigatus* Variants AC1-660 and AC1-661, *R. emersonii* Fusion Protein Variant PC1-668 and the *R. byssochlamydoides-A. fumigatus* Fusion Protein Variant RC1-899

The expression plasmids pE596 (Example 15), pE660 and pE661 (Example 18), pE668 (Example 13) and pE899 (Example 18) were transformed into *Aspergillus oryzae* MT3568 protoplasts according to Christensen et al., 1988, supra and WO 2004/032648. *A. oryzae* MT3568 protoplasts were prepared according to the method of EP 0238023 B1, pages 14-15.

Transformants were purified on COVE sucrose plates without Triton X-100 through single conidia. Spores of the transformants were inoculated into 96 deep well plates containing 0.50 ml of DAP-4C medium and incubated stationary at 34° C. for 6 days.

Production of the wild type *A. fumigatus* cellobiohydrolase I AC1-596, *A. fumigatus* cellobiohydrolase variants AC1-660 and AC1-661, and *R. byssochlamydoides-A. fumigatus* fusion cellobiohydrolase I variant RC1-899 by the transformants were analyzed from culture supernatants of the 96 deep well cultivations. Expression was verified by measuring released reducing sugars from hydrolysis of microcrystalline cellulose. The hydrolysis was performed in 96 well microtiter plates (NUNC Thermo Fisher Scientific, Roskilde, Denmark) at 32° C. and 1100 rpm. Each hydrolysis reaction mixture contained 170 μl of microcrystalline cellulose at 90 g/liter in 50 mM sodium acetate pH 5.0, 0.01% TRITON® X-100, 20 μl of culture supernatant, and 60 μl of 50 mM sodium acetate pH 5.0, 0.01% TRITON® X-100. The plates were sealed with tape. The hydrolysis reaction was stopped by spinning the plate at 3500 rpm for 3 minutes. Then 12.5 μl of the reaction supernatant were added to 37.5 μl MQ water in a 96 well PCR plate (Thermo Fisher Scientific, Roskilde, Denmark). To this mixture 75 μl of stop solution was added. The stop solution was composed of 15 mg/ml 4-hydroxybenzhydrazide (Sigma Chemical Co., Inc., St. Louis, Mo., USA), 50 mg/ml K—Na-tartrate (Sigma Chemical Co., Inc., St. Louis, Mo., USA) in 2% (w/v) NaOH. The plate was sealed with a lid and the mixture was incubated at 95° C. for 10 minutes and 5 minutes at 20° C. Then 100 μl was transferred to a microtiter plate and absorbance at 410 nm was measured using a SPECTRAMAX® Plus 384 (Molecular Devices, Sunnyvale, Calif., USA). The concentration of reducing sugar was proportional to the absorbance at 410 nm of the oxidized 4-hydroxybenzhydrazide. The reducing sugar content in the culture supernatants was measured by adding 1 μl of culture supernatant to a mixture of 75 μl of stop solution and 49 μl of milliQ water in a 96 well PCR plate. The plate was sealed with a lid and the mixture was incubated at 95° C. for 10 minutes and 5 minutes at 20° C. Then 100 μl was transferred to a microtiter plate and the absorbance at 410 nm was measured. The absorbance at 410 nm from the cell culture supernatant was subtracted from the absorbance at 410 nm of the hydrolysis reaction, to measure the amount of reducing sugar released by the enzymes.

Based on the level of hydrolysis of the microcrystalline cellulose one transformant expressing the wild type *A. fumigatus* cellobiohydrolase I was selected and designated *A. oryzae* AC1-596.

Based on the level of hydrolysis of the microcrystalline cellulose, one transformant expressing the *A. fumigatus* cellobiohydrolase I variant AC1-660 was selected and designated *A. oryzae* AC1-660.

Based on the level of hydrolysis of the microcrystalline cellulose, one transformant expressing the *A. fumigatus* cellobiohydrolase I variant AC1-661 was selected and designated *A. oryzae* AC1-661.

Based on the level of hydrolysis of the microcrystalline cellulose, one transformant expressing the *R. emersonii-T. reesei* fusion cellobiohydrolase I variant PC1-668 was selected and designated *A. oryzae* PC1-668.

Based on the level of hydrolysis of the microcrystalline cellulose, one transformant expressing the *R. byssochiamydoides-A. fumigatus* fusion cellobiohydrolase I variant RC1-899 was selected and designated *A. oryzae* RC1-899.

For larger scale production, *A. oryzae* AC1-596, *A. oryzae* AC1-660, *A. oryzae* AC1-661, *A. oryzae* PC1-668 or *A. oryzae* RC1-899 spores were spread onto COVE sucrose slants and incubated for five days at 37° C. The confluent spore slants were washed twice with 5 ml MQ water with 0.01% TWEEN® 20. The spore suspensions were then used to inoculate a 500 ml flask containing 150 ml of G2-Gly medium. The pre-culture was incubated at 30° C. with constant shaking at 200 rpm. After one day, the pre-culture was used to inoculate four 500 ml flasks containing 200 ml of DAP-4C medium. At day four post-inoculation, the culture broths were collected by filtration through a bottle top MF75 Supor MachV 0.2 μm PES filter.

Example 20: Comparison of the Effect of Hybrid Polypeptides PC1-147, PC1-499, PC1-500, and PC1-688 on the Hydrolysis of Unwashed PCS by a Cellulase Enzyme Composition The hybrid polypeptides PC1-499, PC1-500, and PC1-668 (containing a substitution corresponding to Y32W, Y5W, and Y13W of the cellulose binding module, respectively) were added to the cellulolytic enzyme composition without cellobiohydrolase I (Example 11) at 35° C., 50° C. and 60° C. using unwashed PCS as a substrate, and compared against the hybrid polypeptide PC1-147 (lacking substitutions corresponding to Y5W, Y13W, or Y32W of the CBM). Each cellobiohydrolase I was added individually at 3.33 mg enzyme protein per g cellulose to 5.67 mg enzyme protein of the cellulase enzyme composition without cellobiohydrolase I per g cellulose.

The assay was performed as described in Example 11. The reactions with unwashed PCS (20% total solids) were conducted for 72 hours at 35° C., 50° C. and 60° C. in 71 mM sodium acetate pH 5.0 buffer containing 1 mM manganese sulfate. All reactions were performed in quadruplicate and shaking at 200 rpm throughout the hydrolysis.

The results shown in FIG. 5 demonstrated that the cellulase enzyme composition containing the hybrid polypeptide PC1-668 (containing an *R. emersonii* cellobiohydrolase I catalytic domain linked to a *T. reesei* carbohydrate binding module variant with a substitution corresponding to Y13W of the CBM) had significantly higher cellulose conversion at all temperatures compared to the cellulase enzyme composition that included the hybrid polypeptide PC1-147 lacking either substitution corresponding to Y5W, Y13W, or Y32W of the CBM. As previously observed, the hybrid polypeptide PC1-499 and the hybrid polypeptide PC1-500 (containing an *R. emersonii* cellobiohydrolase I catalytic domain linked to a *T. reesei* carbohydrate binding module variant with a substitution corresponding to Y32W or Y5W of the CBM, respectively) had significantly higher cellulose conversion at all temperatures compared to PC1-147.

Example 21: Comparison of the Effect of Variant Polypeptide AC1-660, Variant Polypeptides AC1-661, and Wild-Type Polypeptide AC1-596 on the Hydrolysis of Unwashed PCS by a Cellulase Enzyme Composition The variant polypeptides AC1-660 and AC1-661 (containing a substitution corresponding to Y5W and Y31W of the cellulose binding module, respectively) were added to the cellulolytic enzyme composition without cellobiohydrolase I (Example 11) at 35° C., 50° C. and 60° C. using unwashed PCS as a substrate, and compared against the wild-type polypeptide AC1-596 (lacking either substitution corresponding to Y5W and Y31W of the CBM). Each cellobiohydrolase I was added individually at 3.33 mg enzyme protein per g cellulose to 5.67 mg enzyme protein of the cellulase enzyme composition without cellobiohydrolase I per g cellulose.

The assay was performed as described in Example 11. The reactions with unwashed PCS (20% total solids) were conducted for 72 hours at 35° C., 50° C. and 60° C. in 71 mM sodium acetate pH 5.0 buffer containing 1 mM manganese sulfate. All reactions were performed in quadruplicate and shaking at 200 rpm throughout the hydrolysis.

The results shown in FIG. 6 demonstrated that the cellulase enzyme composition containing the variant polypeptide AC1-660 (containing an *A. fumigatus* cellobiohydrolase I variant with a substitution corresponding to Y5W of the CBM) had significantly higher cellulose conversion at all temperatures compared to the cellulase enzyme composition that included the wild-type polypeptide AC1-596 lacking either substitution corresponding to Y5W or Y31W of the CBM. In addition, the variant polypeptide AC1-661 (containing an *A. fumigatus* cellobiohydrolase I variant with a substitution corresponding to Y31W of the CBM) had significantly higher cellulose conversion at all temperatures compared to AC1-596.

Example 22: Comparison of the Effect of Variant Polypeptide RC1-899, and Hybrid Polypeptide PC1-147 on the Hydrolysis of Unwashed PCS by a Cellulase Enzyme Composition The variant polypeptides RC1-899 (*R. byssochlamydoides* cellobiohydrolase I catalytic domain linked to the *A. fumigatus* carbohydrate binding module with a substitution corresponding to Y31W of the CBM) was added to the cellulolytic enzyme composition without cellobiohydrolase I (Example 11) at 35° C., 50° C. and 60° C. using unwashed PCS as a substrate, and compared against the hybrid polypeptide PC1-147 (containing an *R. emersonii* cellobiohydrolase I catalytic domain linked to a *T. reesei* carbohydrate binding module variant lacking a substitution corresponding to Y31W of the CBM). Each cellobiohydrolase I was added individually at 2, 3, and 4 mg enzyme protein per g cellulose to 5.108 mg enzyme protein of the cellulase enzyme composition without cellobiohydrolase I per g cellulose.

The assay was performed as described in Example 11. The reactions with unwashed PCS (20% total solids) were conducted for 72 hours at 35° C., 50° C. and 60° C. in 80 mM sodium acetate pH 5.0 buffer containing 1 mM manganese sulfate. All reactions were performed in quadruplicate and shaking at 200 rpm throughout the hydrolysis.

The results shown in FIG. 7 demonstrated that the cellulase enzyme composition containing the variant polypeptide RC1-899 had significantly higher cellulose conversion at 35° C. and 50° C. compared to the cellulase enzyme composition that included the hybrid polypeptide PC1-147.

Example 23: Determination of Td by Differential Scanning Calorimetry of the *R. Byssochlamydoides-A. fumigatus* Fusion Protein Variant RC1-899

The thermostability of RC1-899 was determined by Differential Scanning calorimetry (DSC) using a VP-Capillary Differential Scanning calorimeter (MicroCal Inc., Piscataway, N.J., USA). The thermal denaturation temperature, Td (° C.), was taken as the top of denaturation peak (major endothermic peak) in thermograms (Cp vs. T) obtained after heating enzyme solutions (approx. 0.5 mg/ml) in buffer (50 mM acetate buffer pH 5.0) at a constant programmed heating rate of 200 K/hr.

Sample- and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 100° C. Denaturation temperatures were determined at an accuracy of approximately +/−1° C.

The results demonstrated that the *R. byssochlamydoides-A. fumigatus* fusion cellobiohydrolase I has a Td of approximately 77° C. which is comparable to the improved Td of PC1-147 (within approximately 1 deg C.).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A cellobiohydrolase variant comprising a substitution at two or more positions corresponding to positions 483, 491, 509 and 510 of SEQ ID NO: 2, wherein the substitution at position 483 is with Phe or Trp, the substitution at position 491 is with Tyr or Phe, the substitution at position 509 is with Trp, and the substitution at position 510 is with Phe or Trp, wherein the variant has cellobiohydrolase activity, and wherein the variant has at least 95% sequence identity, but less than 100% sequence identity, to amino acids 27 to 532 of the polypeptide of SEQ ID NO: 78.

2. The variant of claim 1, wherein said variant comprises SEQ ID NO: 90 or amino acids 27 to 532 of SEQ ID NO: 90.

3. The cellobiohydrolase variant of claim 1, wherein said variant comprises SEQ ID NO: 92 or amino acids 27 to 532 of SEQ ID NO: 92.

4. The cellobiohydrolase variant of claim 1, wherein said variant further comprises an alteration at one or more positions corresponding to positions 214, 215, 216, and 217 of SEQ ID NO: 2, wherein the alteration at position 214 is a substitution with Ala, the alteration at position 215 is a substitution with Ala, the alteration at position 216 is a deletion, and the alteration at position 217 is a substitution with Ala, Gly, or Trp.

5. A composition comprising the cellobiohydrolase variant of claim 1.

6. A hybrid polypeptide having cellulolytic activity comprising:

(a) a fragment at the N-terminal end of the hybrid polypeptide comprising a heterologous catalytic domain of a cellulolytic enzyme, wherein the catalytic domain has at least 95% sequence identity to amino acids 1 to 437 of the polypeptide of SEQ ID NO: 36; and (b) a fragment at the C-terminal end of the hybrid polypeptide comprising a carbohydrate binding module (CBM) variant, wherein the CBM variant comprises a substitution at one or more positions corresponding to positions 5, 13, 31 and 32 of SEQ ID NO: 4, wherein the substitution at position 5 is with Tyr, Phe, or Trp, the substitution at position 13 is with Tyr, Phe, or Trp, the substitution at position 31 is with Tyr, Phe, or Trp, and the substitution at position 32 is with Tyr, Phe, or Trp, wherein the CBM variant has at least 95% sequence identity, but less than 100% sequence identity, to the carbohydrate binding module of SEQ ID NO: 20.

7. The hybrid polypeptide of claim 6, wherein the CBM variant has at least 97% sequence identity, but less than 100% sequence identity, to the polypeptide of SEQ ID NO: 20.

8. The hybrid polypeptide of claim 6, wherein the catalytic domain comprises amino acids 1 to 437 of SEQ ID NO: 36.

9. The hybrid polypeptide of claim 6, wherein the CBM variant has at least 96% sequence identity, but less than 100% sequence identity, to the carbohydrate binding module of SEQ ID NO: 20.

10. The hybrid polypeptide of claim 6, wherein the CBM variant has at least 98% sequence identity, but less than 100% sequence identity, to the carbohydrate binding module of SEQ ID NO: 20.

11. The hybrid polypeptide of claim 6, wherein the CBM variant further comprises a substitution at one or more positions corresponding to positions 4, 6, and 29 of SEQ ID NO: 4, wherein the substitution at position 4 is with Glu, Leu, Lys, Phe, or Trp, the substitution at position 6 is with Ala, and the substitution at position 29 is with Asp.

12. A composition comprising the hybrid polypeptide of claim 6.

13. A method for degrading or converting a cellulosic material, said method comprising treating the cellulosic material with an enzyme composition, wherein said composition comprises:

(a) a cellobiohydrolase variant comprising a substitution at two or more positions corresponding to positions 483, 491, 509 and 510 of SEQ ID NO: 2, wherein the substitution at position 483 is with Phe or Trp, the substitution at position 491 is with Tyr or Phe, the substitution at position 509 is with Trp, and the substitution at position 510 is with Phe or Trp, wherein the variant has cellobiohydrolase activity, and wherein the variant has at least 95% sequence identity, but less than 100% sequence identity, to amino acids 27 to 532 of the polypeptide of SEQ ID NO: 78; or (b) a hybrid polypeptide having cellulolytic activity comprising (i) a fragment at the N-terminal end of the hybrid polypeptide comprising a heterologous catalytic domain of a cellulolytic enzyme, wherein the catalytic domain has at least 95% sequence identity to amino acids 1 to 437 of the polypeptide of SEQ ID NO: 36; and (ii) a fragment at the C-terminal end of the hybrid polypeptide comprising a carbohydrate binding module (CBM) variant, wherein the CBM variant comprises a substitution at one or more positions corresponding to positions 5, 13, 31 and 32 of SEQ ID NO: 4, wherein the substitution at position 5 is with Tyr, Phe, or Trp, the substitution at position 13 is with Tyr, Phe, or Trp, the substitution at position 31 is with Tyr, Phe, or Trp, and the substitution at position 32 is with Tyr, Phe, or Trp, wherein the CBM variant has at least 95% sequence identity, but less than 100% sequence identity, to the carbohydrate binding module of SEQ ID NO: 20.

14. A method for producing a fermentation product, said method comprising (I) saccharifying a cellulosic material with an enzyme composition, wherein the composition comprises:

(a) a cellobiohydrolase variant comprising a substitution at two or more positions corresponding to positions 483, 491, 509 and 510 of SEQ ID NO: 2, wherein the substitution at position 483 is with Phe or Trp, the substitution at position 491 is with Tyr or Phe, the substitution at position 509 is with Trp, and the substitution at position 510 is with Phe or Trp, wherein the variant has cellobiohydrolase activity, and wherein the variant has at least 95% sequence identity, but less than 100% sequence identity, to amino acids 27 to 532 of the polypeptide of SEQ ID NO: 78; or (b) a hybrid polypeptide having cellulolytic activity comprising (i) a fragment at the N-terminal end of the hybrid polypeptide comprising a heterologous catalytic domain of a cellulolytic enzyme, wherein the catalytic domain has at least 95% sequence identity to amino acids 1 to 437 of the polypeptide of SEQ ID NO: 36; and (ii) a fragment at the C-terminal end of the hybrid polypeptide comprising a carbohydrate binding module (CBM) variant, wherein the CBM variant comprises a substitution at one or more positions corresponding to positions 5, 13, 31 and 32 of SEQ ID NO: 4, wherein the substitution at position 5 is with Tyr, Phe, or Trp, the substitution at position 13 is with Tyr, Phe, or Trp, the substitution at position 31 is with Tyr, Phe, or Trp, and the substitution at position 32 is with Tyr, Phe, or Trp, wherein the CBM variant has at least 95% sequence identity, but less than 100% sequence identity, to the carbohydrate binding module of SEQ ID NO: 20; and (II) fermenting the saccharified cellulosic material with one or more fermenting microorganisms to produce the fermentation product.

* * * * *